(12) United States Patent
Guo et al.

(10) Patent No.: US 12,157,733 B2
(45) Date of Patent: Dec. 3, 2024

(54) AMINOTRIAZOLOPYRIDINES AS KINASE INHIBITORS

(71) Applicant: BRISTOL-MYERS SQUIBB COMPANY, Princeton, NJ (US)

(72) Inventors: Junqing Guo, Princeton, NJ (US); Amy C. Hart, Ewing, NJ (US); John E. Macor, Washington Crossing, PA (US); Michael E. Mertzman, New Hope, PA (US); William J. Pitts, Newtown, PA (US); Steven H. Spergel, Warrington, PA (US); Scott Hunter Watterson, Pennington, NJ (US); Murugaiah Andappan Murugaiah Subbaiah, Tamil Radu (IN); Jie Chen, Cambridge, MA (US); Carolyn Diane Dzierba, Middletown, CT (US); Guanglin Luo, Newtown, PA (US); Jianliang Shi, Furlong, PA (US); Sing-Yuen Sit, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 947 days.

(21) Appl. No.: 17/116,016

(22) Filed: Dec. 9, 2020

(65) Prior Publication Data
US 2022/0315580 A1    Oct. 6, 2022

Related U.S. Application Data

(62) Division of application No. 16/484,604, filed as application No. PCT/US2018/017755 on Feb. 12, 2018, now Pat. No. 10,913,738.
(Continued)

(51) Int. Cl.
*C07D 471/04*    (2006.01)
(52) U.S. Cl.
CPC ................. *C07D 471/04* (2013.01)
(58) Field of Classification Search
CPC .................................................. C07D 471/04
(Continued)

(56) References Cited

U.S. PATENT DOCUMENTS 10,913,738 B2 *  2/2021  Guo ............... A61P 29/00
11,767,322 B2 *  9/2023  Luo ............... A61P 17/06
                                          514/303
(Continued)

FOREIGN PATENT DOCUMENTS

WO       2008107125  A1    9/2008
WO    WO-2009068482  A1 *  6/2009 ............ A61P 1/00
(Continued)

OTHER PUBLICATIONS

Harris et al., "Discovery of Small Molecule RIP1 Kinase Inhibitors for the Treatment of Pathologies Associated with Necroptosis", Medicinal Chemistry Letters, vol. 4, pp. 1238-1243 (2013).
(Continued)

*Primary Examiner* — Yih-Horng J Shiao
*Assistant Examiner* — Jaret J Crews
(74) *Attorney, Agent, or Firm* — Mary K. VanAtten

(57) ABSTRACT

Compounds having formula (I)-(IX), and enantiomers, and diastereomers, stereoisomers, pharmaceutically acceptable salts and prodrugs thereof, are useful as kinase modulators, including RIPK1 modulation. All the variables are as defined herein.

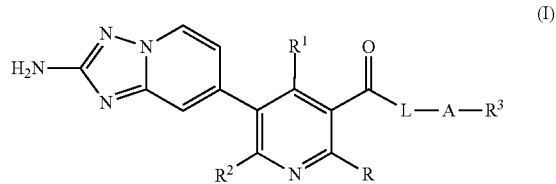

(I)

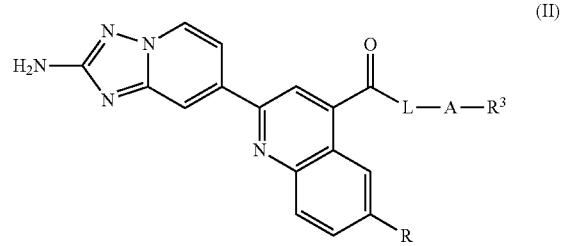

(II)

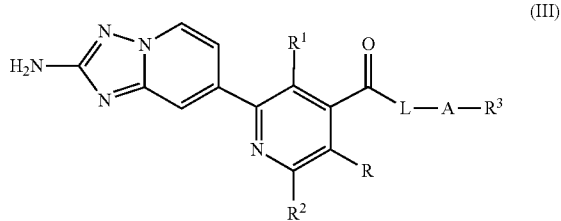

(III)

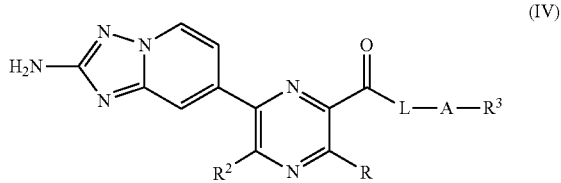

(IV)

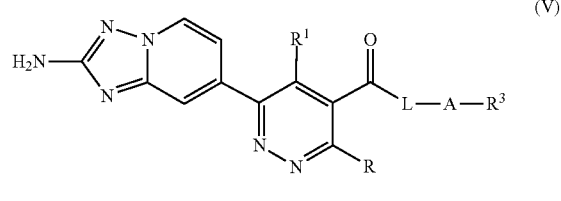

(V)

(Continued)

-continued

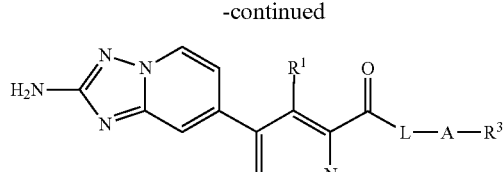
(VI)

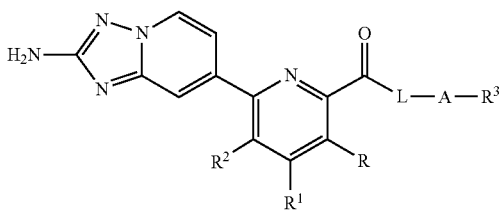

(VII)

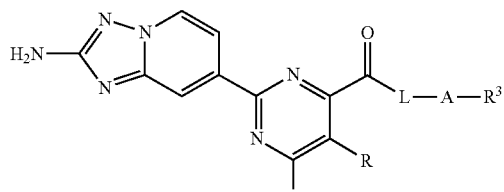

(VIII)

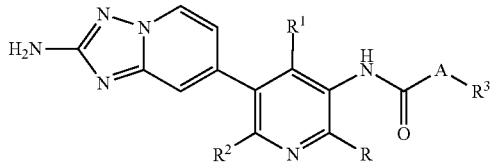

(IX)

6 Claims, No Drawings

Related U.S. Application Data

(60) Provisional application No. 62/458,144, filed on Feb. 13, 2017.

(58) Field of Classification Search
USPC .......................................................... 514/303
See application file for complete search history.

(56) References Cited

U.S. PATENT DOCUMENTS

| | | |
|---|---|---|
| 2005/0288502 A1 | 12/2005 | Andersen et al. |
| 2018/0317492 A1 | 11/2018 | Tanaka et al. |

FOREIGN PATENT DOCUMENTS

| | | | |
|---|---|---|---|
| WO | 2010007100 A1 | 1/2010 | |
| WO | WO-2010057877 A1 * | 5/2010 | ........... C07D 471/04 |
| WO | 2010091067 A2 | 8/2010 | |
| WO | 2014198594 A1 | 12/2014 | |
| WO | 2016027253 A1 | 2/2016 | |
| WO | 2018017435 A1 | 1/2018 | |
| WO | 2018139436 A1 | 8/2018 | |
| WO | 2019089442 A1 | 5/2019 | |
| WO | 2019147782 A1 | 8/2019 | |

OTHER PUBLICATIONS

Li, et al "Combination of 2-methoxy-3 phenylsulfonylaminobenzamide and 2-aminobenzothiazole to discover novel anticancer agents", Bioorganic & Medicinal Chemistry 22 (2014) 3739-3748.

* cited by examiner

AMINOTRIAZOLOPYRIDINES AS KINASE INHIBITORS

CROSS REFERENCE TO RELATED APPLICATION

This application is a divisional of U.S. Ser. No. 16/484,604 filed on Aug. 8, 2019, now allowed, which is a 371 International Application of PCT/US2018/017755, filed Feb. 12, 2018, which in turn claims priority to Provisional Patent Application U.S. Ser. No. 62/458,144 filed Feb. 13, 2017, hereby incorporated by reference in their entireties.

FIELD OF THE INVENTION

The present invention relates to novel compounds that inhibit receptor interacting protein kinases and methods of making and using the same. Specifically, the present invention relates to aminotriazolopyridines as receptor interacting protein kinase 1 (RIPK1) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) Cell Death Differ 16:3-11). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein P & Kroemer G (2007) Trends Biochem. Sci. 32:37-43; Festjens et al. (2006) Biochim. Biophys. Acta 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al. (2000) Nat. Immunol. 1:489-495; Degterev et al. (2008) Nat. Chem. Biol. 4:313-321). This novel mechanism of cell death is termed "programmed necrosis" or "necroptosis" (Degterev et al., (2005) Nat Chem Biol 1:112-119).

Necroptosis can be triggered by a number of mechanisms including of TNF receptor activation, Toll-like receptor engagement, genotoxic stress and viral infection. Downstream of the various stimuli, the signaling pathway that results in necroptosis is dependent on RIPK1 and RIPK3 kinase activity. (He et al., (2009) Cell 137:1100-1111; Cho et. al., (2009) Cell 137:1112-1123; Zhang et al., (2009) Science 325:332-336).

Dysregulation of the necroptosis signaling pathway has been linked to inflammatory diseases such as macrophage necrosis in atheroscelerosis development, virus-induced inflammation, systemic inflammatory response syndrome and ethanol-induced liver injury, neurodegeneration such as detachment of the retina, ischemia, amyotrophic lateral sclerosis (ALS), and Gaucher's disease (Trichonas et al., (2010) Proc. Natl. Acad. Sci. 107, 21695-21700; Lin et al., (2013) Cell Rep. 3, 200-210; Cho et al., (2009) Cell, 137, 1112-1123; Duprez et al., (2011) Immunity 35, 908-918; Roychowdhury et al., Hepatology 57, 1773-1783; Vandenabeele et al., (2010) Nature 10, 700-714; Vandenabeele et al., (2010) Sci. Signalling 3, 1-8; Zhang et al., (2010) Cellular & Mol. Immunology 7, 243-249; Moriwaki et al., (2013) Genes Dev. 27, 1640-1649; Ito et al., (2016) Science 353, 603-608; Vitner et al., (2014) Nature Med. 20, 204-208).

A potent, selective, small molecule inhibitor of RIPK1 activity would block RIPK1-dependent pro-inflammatory signaling and thereby provide a therapeutic benefit in inflammatory diseases characterized by increased and/or dysregulated RIPK1 kinase activity.

SUMMARY OF THE INVENTION

The present invention provides novel aminotriazolopyridines including stereoisomers, tautomers, isotopes, prodrugs, pharmaceutically acceptable salts, salts, or solvates thereof, which are useful as inhibitors of RIPK1.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, isotopes, prodrugs, pharmaceutically acceptable salts, salts, or solvates thereof.

The compounds of the invention may be used in the treatment and/or prophylaxis of conditions associated with aberrant RIPK1 activity.

The compounds of the present invention may be used in therapy.

The compounds of the present invention may be used for the manufacture of a medicament for the treatment and/or prophylaxis of a condition associated with aberrant RIPK1 activity.

In another aspect, the present invention is directed to a method of treating diseases mediated at least partially by RIPK1 including inflammatory diseases, ischemia, neurodegeneration, and Gaucher's disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I)-(IX) or stereoisomers, tautomers, isotopes, salts, pharmaceutically acceptable salts, solvates, or prodrugs thereof, wherein

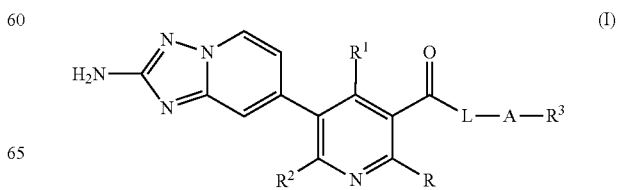

-continued

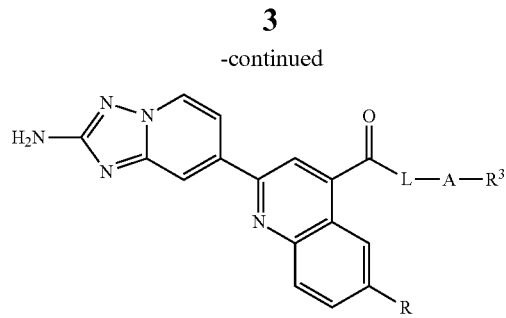 (II)

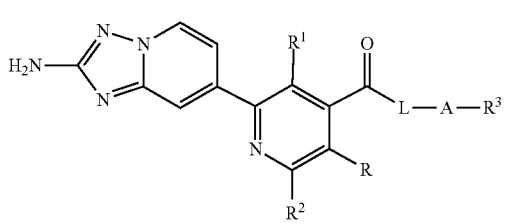 (III)

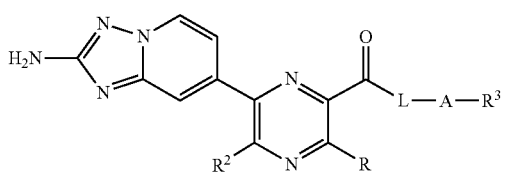 (IV)

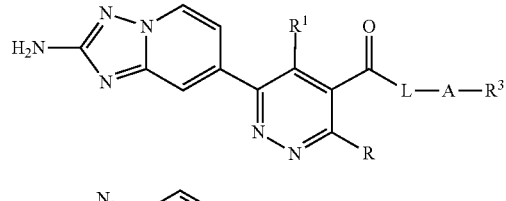 (V)

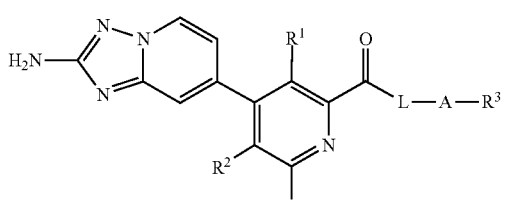 (VI)

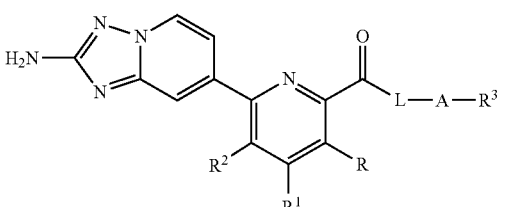 (VII)

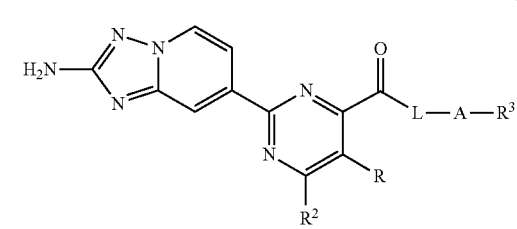 (VIII)

-continued

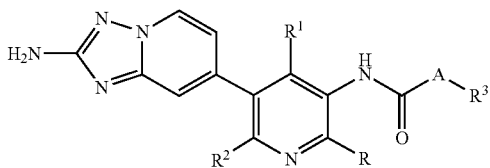 (IX)

$R^1$ is H, $C_{1-4}$ alkyl, $C_{1-4}$ haloalkyl, $C_{1-4}$ deuteroalkyl, or halo;
$R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;
R is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or $N(R^a)_2$:
$R^a$ is H, $C_{1-4}$ alkyl, $C_{1-4}$ deuteroalkyl, or $C_{3-6}$ cycloalkyl;
L is —NH, —$NR^b$,

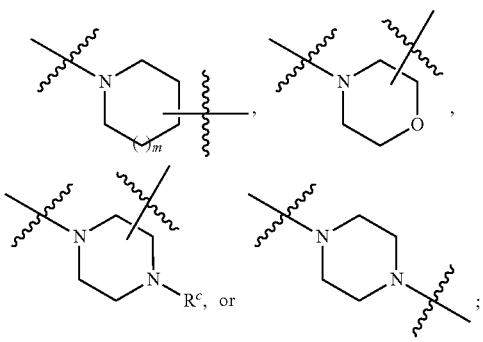

$R^b$ is H, $C_{1-4}$ alkyl, $C_{1-4}$ deuteroalkyl, $C_{3-6}$ cycloalkyl, (phosphonooxy)alkyl, ((phosphonooxy)alkylcarbonyloxy)alkyl, ((amino)alkylcarbonyloxy)alkyl, ((amino)cycloalkylcarbonyloxy)alkyl, ((((phophonooxy)alkyl)carbonyloxy)alkyl)oxycarbonyl (((((phophonooxy) cycloalkyl)carbonyloxy)alkyl)oxycarbonyl; ((((amino) alkyl)carbonyloxy)alkyl)oxycarbonyl, ((((amino) cycloalkyl)carbonyloxy)alkyl)oxycarbonyl, or (((((phosphonooxy)(alkoxy)benzoyl)alkyl)oxycarbonyl;
$R^c$ is $C_{1-3}$ alkyl, or $C_{1-3}$ haloalkyl;
A is absent, —S—, $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ alkyl-O—, $C_{1-6}$ deuteroalkyl-O—, $C_{1-6}$ haloalkyl-O—, $C_{3-6}$ cycloalkyl-$C_{1-3}$-alkyl-, $C_{1-3}$-alkyl-$C_{3-6}$ cycloalkyl-, $C_{1-3}$-alkylcarbonyl, -pyrrolyl-$C_{1-3}$-alkyl-, —$C_{1-3}$-alkyl-pyrrolyl-, pyrrolidinyl-$C_{1-3}$-alkyl-, or —$C_{1-3}$-alkyl-pyrrolidinyl-;
$R^3$ is $C_{6-10}$ aryl, CH(aryl)$_2$, 5—or 6-membered heteroaryl, or 5 to 10 membered heterocycle having 1-4 heteroatoms selected from N, O, and S, wherein any of aryl, heteroaryl, or heterocycle groups are substituted with 0-3 $R^4$;
$R^4$ is halo, $C_{1-6}$ alkyl, $C_{1-6}$ ($C_6$ alkoxy)alkyl, $C_{1-6}$ ($C_{6-10}$ aryl)alkyl, $C_{1-6}$ alkoxy, $C_{1-6}$ ($C_{3-7}$ cycloalkyl)alkoxy, $C_{1-6}$ deuteroalkyl, $C_{1-6}$ deuteroalkoxy, $C_{1-6}$ ($C_{3-7}$ cycloalkyl) deuteroalkoxy, $C_{1-6}$ haloalkyl, $C_{1-6}$ haloalkoxy, $C_{3-7}$ cycloalkoxy, $C_{3-7}$ cycloalkyl, $C_{6-10}$ aryl, $C_{6-10}$ aryloxy, 5—or 6-membered heteroaryl, —S—$C_{1-6}$alkyl, —S—$C_{1-6}$ haloalkyl, —S—$C_{6-10}$ aryl, —$SO_2$—$C_{1-6}$ alkyl, —$SO_2$—$C_{6-10}$ aryl, —$SO_2$-heterocycle, —O-heterocycle, —(CO)-heterocycle, —$(CH_2)_n$-heterocycle, or O—C(O)—$N(R^a)_2$, wherein each heterocycle is independently a 3-10 membered ring having 1-4 heteroatoms selected from N, O, and S, and wherein each heterocycle, aryl, or heteroaryl is substituted with 0-2 $R^5$;

$R^5$, at each occurrence, is independently $C_{1-4}$ alkyl, halo, =O, $C_{1-4}$ hydroxyalkyl;

n is 1-3; and m is 0 or 1.

Another aspect of the invention is a compound of formula (I)-(III)

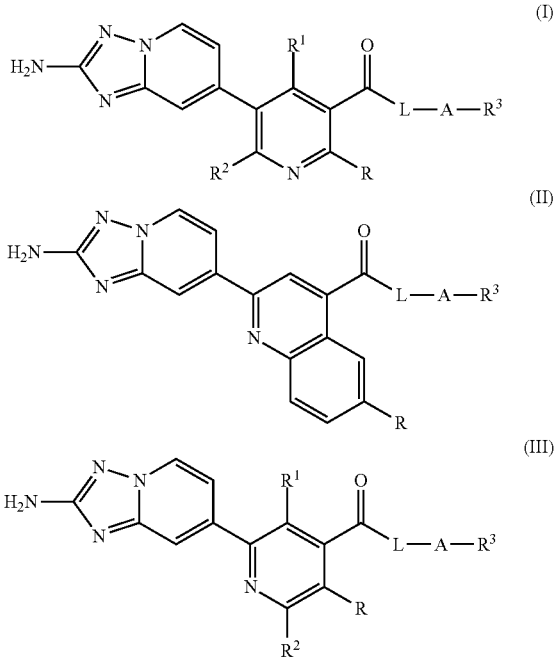

where $R^1$ is H, $C_{1-4}$ alkyl, $C_{1-4}$ haloalkyl, $C_{1-4}$ deuteroalkyl, or halo;

$R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;

R is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or $N(R^a)_2$;

$R^a$ is H, $C_{1-4}$ alkyl, $C_{1-4}$ deuteroalkyl, or $C_{3-6}$ cycloalkyl;

L is —NH, —$NR^a$,

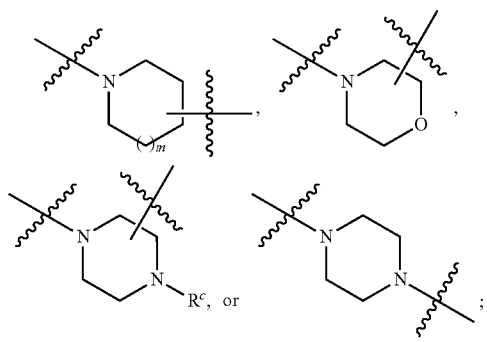

$R^c$ is $C_{1-3}$ alkyl, or $C_{1-3}$ haloalkyl;

A is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ alkyl-O—, $C_{1-6}$ deuteroalkyl-O—, $C_{1-6}$ haloalkyl-O—, $C_{3-6}$ cycloalkyl-$C_{1-3}$-alkyl-, $C_{1-3}$-alkyl-$C_{3-6}$ cycloalkyl-, pyrrolyl-$C_{1-3}$-alkyl-, —$C_{1-3}$-alkyl-pyrrolyl-, -pyrrolidinyl-$C_{1-3}$-alkyl-, or —$C_{1-3}$-alkyl-pyrrolidinyl-;

$R^3$ is $C_{6-10}$ aryl, CH(aryl)$_2$, or a 5 to 10 membered heterocycle having 1-4 heteroatoms selected from N, O, and S, wherein any of aryl or heteroaryl groups are substituted with 0-3 $R^4$;

$R^4$ is halo, $C_{1-6}$ alkyl, $C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-7}$ cycloalkoxy, $C_{3-7}$ cycloalkyl, $C_{6-10}$ aryl, $C_{6-10}$ aryloxy, —S—$C_{1-6}$alkyl, —S—$C_{1-6}$ haloalkyl, —S—$C_{6-10}$ aryl, —$SO_2$—$C_{1-6}$ alkyl, —$SO_2$—$C_{6-10}$ aryl, —$SO_2$-heterocycle, —O-heterocycle, or —$(CH_2)_n$-hetercycle, O—C(O)—$N(R^a)_2$, wherein each heterocycle is independently a 3-10 membered ring having 1-4 heteroatoms selected from N, O, and S, and wherein each heterocycle or aryl is substituted with 0-2 $R^5$;

$R^5$, at each occurrence, is independently $C_{1-4}$ alkyl, halo, =O, or $C_{1-4}$ hydroxyalkyl; and m is 0 or 1.

Another embodiment provides a compound of Formula (I), (II), or (III), or (I)-(IX), stereoisomers, tautomers, isotopes, salts, pharmaceutically acceptable salts, solvates, or prodrugs thereof, wherein L is —NH, —$NR^a$ or alternatively —$NR^aR^b$; wherein $R^a$ and $R^b$ can be taken together to form a 3-10 membered ring optionally substituted with 1-4 heteroatoms selected from N, O, and S, and wherein each heterocycle or aryl is substituted with 0-2 $R^5$.

Another embodiment provides a compound of Formula (I), (II), or (III), or (I)-(IX), or stereoisomers, tautomers, isotopes, salts, pharmaceutically acceptable salts, solvates, or prodrugs thereof, wherein $R^3$ is $C_{6-10}$ aryl, CH(phenyl)$_2$, or a heterocycle having 1-4 heteroatoms selected from N, O, and S, wherein any of aryl or heteroaryl groups are substituted with 0-3 $R^4$, and wherein the heterocycle is selected from pyridyl, pyridinyl, or pyrrolyl.

Another embodiment provides a compound of Formula (I), (II), or (III), or (I)-(IX), or stereoisomers, tautomers, isotopes, salts, pharmaceutically acceptable salts, solvates, or prodrugs thereof, wherein A is $C_{1-4}$ alkyl substituted with 0-1 OH, $C_{1-4}$ deuteroalkyl substituted with 0-1 OH, $C_{1-4}$ haloalkyl substituted with 0-1 OH, $C_{1-4}$ alkyl-O—, $C_{1-4}$ deuteroalkyl-O—, $C_{1-4}$ haloalkyl-O—, $C_{3-6}$ cycloalkyl-$C_{1-3}$-alkyl-, $C_{1-3}$-alkyl-$C_{3-6}$ cycloalkyl-, pyrrolyl-$C_{1-3}$-alkyl-, $C_{1-3}$-alkyl-pyrrolyl-, -pyrrolidinyl-$C_{1-3}$-alkyl-, or $C_{1-3}$-alkyl-pyrrolidinyl-.

Another embodiment provides a compound of Formula (I), (II), or (III), or (I)-(IX), or stereoisomers, tautomers, isotopes, salts, pharmaceutically acceptable salts, solvates, or prodrugs thereof, wherein $R^3$ is phenyl, CH(phenyl)$_2$, or a 5 to 10 membered heterocycle having 1-4 heteroatoms selected from N, O, and S, wherein any of aryl or heteroaryl groups are substituted with 0-3 $R^4$, and wherein the heterocycle is selected from pyridyl, pyridinyl, or pyrrolyl.

Another embodiment provides a compound of Formula (I), (II), or (III), or (I)-(IX), or stereoisomers, tautomers, isotopes, salts, pharmaceutically acceptable salts, solvates, or prodrugs thereof, wherein A is $C_{1-4}$ alkyl substituted with 0-1 OH, $C_{1-4}$ deuteroalkyl, $C_{1-4}$ alkyl-O—, $C_{1-4}$ deuteroalkyl-O—, $C_{3-6}$ cycloalkyl-$C_{1-3}$-alkyl-, -pyrrolyl-$C_{1-3}$-alkyl-, $C_{1-3}$-alkyl-pyrrolyl-, -pyrrolidinyl-$C_{1-3}$-alkyl-, or $C_{1-3}$-alkyl-pyrrolidinyl-.

Another embodiment provides a compound of Formula (I), (II), or (III), or (I)-(IX), or stereoisomers, tautomers, isotopes, salts, pharmaceutically acceptable salts, solvates, or prodrugs thereof, wherein $R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;

R is H, Cl, F, Br, $C_{1-4}$ alkyl, $C_{1-4}$ alkoxy, cyclopropyl, or $NR^a_2$;

$R^a$ is H, $C_{1-4}$ alkyl, or $C_{1-4}$ deuteroalkyl.

Another embodiment provides a compound of Formula (I), (II), or (III), or (I)-(IX), or stereoisomers, tautomers, isotopes, salts, pharmaceutically acceptable salts, solvates, or prodrugs thereof, wherein $R^4$ is halo, $C_{1-6}$ alkyl, $C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-7}$ cycloalkoxy, or $C_{3-7}$ cycloalkyl.

Another embodiment provides a compound of Formula (I), or stereoisomers, tautomers, isotopes, salts, pharmaceutically acceptable salts, solvates, or prodrugs thereof, wherein

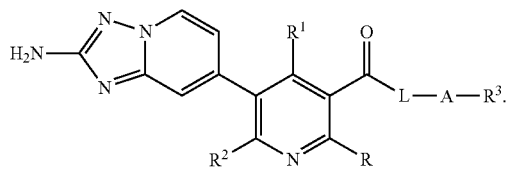

(I)

Another embodiment provides a compound of Formula (II), or stereoisomers, tautomers, isotopes, salts, pharmaceutically acceptable salts, solvates, or prodrugs thereof, wherein

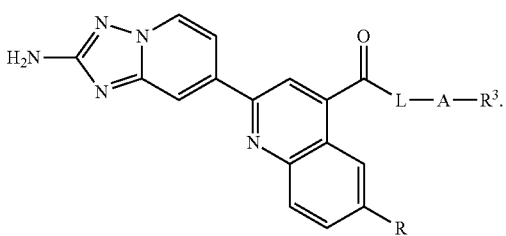

(II)

Another embodiment provides a compound of Formula (III), or stereoisomers, tautomers, isotopes, salts, pharmaceutically acceptable salts, solvates, or prodrugs thereof, wherein

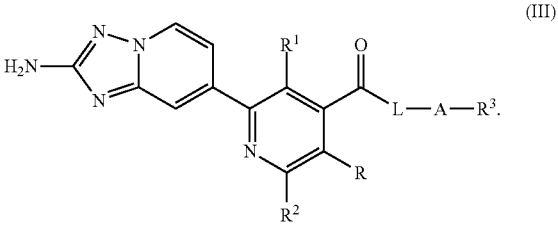

(III)

Another embodiment provides a compound of Formula (I)-(IX), or stereoisomers, tautomers, isotopes, salts, pharmaceutically acceptable salts, solvates, or prodrugs thereof, wherein $R^3$ is phenyl, or pyridinyl each substituted with 0-3 $R^4$.

Another embodiment provides a compound of Formula (I)-(IX), or stereoisomers, tautomers, isotopes, salts, pharmaceutically acceptable salts, solvates, or prodrugs thereof, wherein $R^3$ is pyrazinyl, pyridazinyl, or pyrimidyl each substituted with 0-3 $R^4$.

Another embodiment provides a compound of Formula (I)-(IX), or stereoisomers, tautomers, isotopes, salts, pharmaceutically acceptable salts, solvates, or prodrugs thereof, wherein $R^3$ is a 5-membered ring heterocycle having 1-4 heteroatoms selected from N, O, and S, and wherein each heterocycle is substituted with 0-3 $R^4$.

Another embodiment provides a compound of Formula (I)-(IX), or stereoisomers, tautomers, isotopes, salts, pharmaceutically acceptable salts, solvates, or prodrugs thereof, wherein $R^4$ is halo, $C_{1-6}$ alkyl, $C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-7}$ cycloalkoxy, or $C_{3-7}$ cycloalkyl.

Another embodiment provides a compound of Formula (I)-(IX), or stereoisomers, tautomers, isotopes, salts, pharmaceutically acceptable salts, solvates, or prodrugs thereof, wherein $R^4$ is $C_{6-10}$ aryl, $C_{6-10}$ aryloxy, —S—$C_{1-6}$alkyl, —S—$C_{1-6}$ haloalkyl, —S—$C_{6-10}$ aryl, —$SO_2$—$C_{1-6}$ alkyl, —$SO_2$—$C_{6-10}$ aryl, —$SO_2$-heterocycle, —O-heterocycle, —$(CH_2)_n$-hetercycle, or O—C(O)—N$(R^a)_2$, wherein each heterocycle is a 5-6 membered ring having 1-4 heteroatoms selected from N, O, and S, and wherein each heterocycle or aryl is substituted with 0-2 $R^5$.

The present invention is also directed to pharmaceutical compositions useful in treating diseases associated with kinase modulation, including the modulation of receptor interacting protein kinases such as RIPK1, comprising compounds of formula (I)-(IX), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK1, comprising administering to a patient in need of such treatment a therapeutically-effective amount of a compound according to formula (I)-(IX).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I)-(IX) wherein the disease is inflammatory bowel disease, Crohn's disease or ulcerative colitis, psoriasis, systemic lupus erythematosus (SLE), rheumatoid arthritis, multiple sclerosis (MS), or transplant rejection.

The present invention also provides a method of treating a condition comprising administering to a patient in need of such treatment a therapeutically-effective amount of a compound of formula (I)-(IX), wherein the condition is selected from systemic lupus erythematosus (SLE), multiple sclerosis (MS), transplant rejection, acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris and asthma The present invention also provides a method of treating a condition comprising administering to a patient in need of such treatment a therapeutically-effective amount of a compound of formula (I)-(IX), wherein the condition is selected from macrophage necrosis in atheroscelerosis development, virus-induced inflammation, systemic inflammatory response syndrome and ethanol-induced liver injury, neurodegeneration such as detachment of the retina, retinal degeneration, wet and dry age-related macular degeneration (AMD), ischemia, amyotrophic lateral sclerosis (ALS), NASH, and Gaucher's disease.

The present invention also provides a method of treating a condition comprising administering to a patient in need of such treatment a therapeutically-effective amount of a compound of formula (I)-(IX), wherein the condition is selected from Inflammatory bowel disease, ulcerative colitis, Crohn's disease, psoriasis, rheumatoid arthritis (RA), and heart failure.

The present invention also provides a method of treating a condition comprising administering to a patient in need of such treatment a therapeutically-effective amount of a compound of formula (I)-(IX), wherein the condition is selected from inflammatory bowel disease, Crohn's disease, ulcerative colitis, and psoriasis.

The present invention also provides a method for treating rheumatoid arthritis, comprising administering to a patient in need of such treatment a therapeutically-effective amount of a compound of formula ((I)-(IX).

The present invention also provides a method of treating diseases, comprising administering to a patient in need of such treatment a therapeutically-effective amount of a compound of formula (I)-(IX), or pharmaceutically acceptable salt thereof, in combination with other therapeutic agents.

The present invention also provides the compounds of the present invention or stereoisomers, tautomers, isotopes, salts, pharmaceutically acceptable salts, solvates, or prodrugs thereof, for use in therapy.

In another embodiment, compounds of formula (I)-(IX), are selected from exemplified examples or combinations of exemplified examples or other embodiments herein.

In another embodiment, the $IC_{50}$ value of compounds of formula (I), (II), or (III) in the RIPK1 assays described below is >200 nM.

In another embodiment, the $IC_{50}$ value of compounds of formula (I), (II), or (III) in the RIPK1 assays described below is <200 nM.

In another embodiment, the $IC_{50}$ value of compounds of formula (I), (II), or (III) in the RIPK1 assays described below is <20 nM.

The present invention also provides the use of the compounds of the present invention or stereoisomers, tautomers, isotopes, salts, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula (I), (II), or (III) (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_6$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "carbocyclyl" or "carbocyclic" refers to a saturated or unsaturated, or partially unsaturated, monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Carbocycles, can include cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocyclic", or "heterocyclyl" may be used interchangeably and refer to substituted and unsubstituted non-aromatic 3—to 7-membered monocyclic groups, 7—to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "$CO_2$" is used herein, this is intended to refer to the group

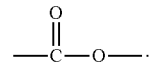

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I)-(IX) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I)-(IX) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I)-(IX) may be formed, for example, by reacting a compound of the formula (I)-(IX) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. In one embodiment, salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, amide NH moieties can be substituted with (phosphonooxy)alkylene, ((phosphonooxy)alkylcarbonyloxy)alkylene, ((amino)alkylcarbonyloxy)alkylene, ((amino)cycloalkylcarbonyloxy)alkylene, ((((phophonooxy)alkyl)carbonyloxy)alkyl)oxycarbonyl ((((phophonooxy)cycloalkyl)carbonyloxy)alkyl)oxycarbonyl; ((((amino)alkyl)carbonyloxy)alkyl)oxycarbonyl, ((((amino)cycloalkyl)carbonyloxy)alkyl)oxycarbonyl, and substituted ((((phosphonooxy)benzoyl)alkyl)oxycarbonyl substituents. Additionally, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

Utility

The compounds of the invention modulate kinase activity, including the modulation of RIPK1. Accordingly, compounds of formula (I)-(IX) have utility in treating conditions associated with the modulation of kinase activity, and particularly the selective inhibition of RIPK1 activity. In another embodiment, compounds of formula (I)-(IX) have advantageous selectivity for RIPK1 activity preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of RIPK1, compounds of Formula (I)-(IX) are useful in treating RIPK1-associated conditions including, but not limited to, inflammatory diseases such as Crohn's disease and ulcerative colitis, inflammatory bowel disease, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, ALS, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from inflammatory bowel disease, Crohn's disease and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK1-associated condition" or "RIPK1-associated disease or disorder" are used herein, each is intended to encompass all of the conditions identified above as if repeated at length, as well as any other condition that is affected by RIPK1 kinase activity.

The present invention thus provides methods for treating such conditions, comprising administering to a subject in need thereof a therapeutically-effective amount of at least one compound of Formula (I)-(IX) or a salt thereof "Therapeutically effective amount" is intended to include an amount of a compound of the present invention that is effective when administered alone or in combination to inhibit RIPK1.

The methods of treating RIPK1 kinase-associated conditions may comprise administering compounds of Formula (I)-(IX) alone or in combination with each other and/or other suitable therapeutic agents useful in treating such conditions. Accordingly, "therapeutically effective amount" is also intended to include an amount of the combination of compounds claimed that is effective to inhibit RIPK1 and/or treat diseases associated with RIPK1.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; anti-inflammatory anti-bodies such as vedolizumab and ustekinumab, anti-infammatory kinase inhibitors such as TYK2 inhibitors, antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK1 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I)-(IX) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I)-(IX) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK1 enzyme levels.

MLKL Phosphorylation High-Content Assay

HT29-L23 human colorectal adenocarcinoma cells were maintained in RPMI 1640 medium containing 10% heat-inactivated FBS, 1% Penicillin-Streptomycin and 10 mM HEPES. Cells were seeded at 2,000 cells/well in 384w tissue culture-treated microplates (Greiner #781090-3B) and incubated at 37° C. (5% $CO_2$/95% $O_2$) for two days. On the day of assay, the cells were treated with test compounds at final concentrations of 6.25 to 0.106 µM for 30 min at 37° C. (5% $CO_2$/95% 02). Necroptopsis was induced using a mixture of human TNFα (35 ng/mL) (Peprotech #300-01A), SMAC mimetic (from US 2015/0322111 A1) (700 nM) and Z-VAD (140 nM) (BD pharmingen #51-6936). Following six hours incubation at 37° C. (5% $CO_2$/95% 02), the cells were fixed with 4% formaldehyde (ACROS 11969-0010) for 15 min at room temperature and then permeabilized with phosphate buffered saline (PBS) containing 0.2% Triton-X-100 for 10 min. MLKL phosphorylation was detected using anti-MLKL (phospho S358) antibody (Abcam #ab187091) (1:1000 dilution in Blocking Buffer [PBS supplemented with 0.1% BSA]) with overnight incubation at 4° C. After washing three times in PBS, goat anti-rabbit Alexa-488 (1:1000 dilution) (Life Technologies, A11008) and Hoechst 33342 (Life Technologies, H3570) (1:2000 dilution) in Blocking Buffer were added for 1 h at room temperature. Following another three cycles of washes in PBS, the microplates were sealed, and cellular images were acquired in the Cellomics ArrayScan VTI high-content imager equipped with an X1 camera. Fluorescent images were taken using a 10× objective and the 386-23 BGRFRN_BGRFRN and 485-20 BGRFRN_BGRFRN filter sets, for nuclei and MLKL phosphorylation, respectively. The image sets were analyzed using the Compartmental Analysis Bioapplication software (Cellomics). The level of MLKL phosphorylation was quantified as MEAN_CircRingAvgIntenRatio. The maximal inhibitory response was defined by the activity induced by Nec1s (CAS #: 852391-15-2, 6.25 µM). The IC50 value was defined as the concentration of compound that produces 50% of the maximal inhibition. The data were fitted using the 4-parameter logistic equation to calculate the IC50 and Ymax values.

RIPK1 HTRF Binding Assay

A solution was prepared containing 0.2 nM Anti GST-Tb (Cisbio, 61GSTTLB), 90.6 nM probe and 1 nM His-GST-TVMV-hRIPK1(1-324) in FRET Buffer (20 mM HEPES, 10 mM $MgCl2$, 0.015% Brij-35, 4 mM DTT, 0.05 mg/mL BSA). Using Formulatrix Tempest, the detection antibody/enzyme/probe solution (2 µL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Cloning and Baculovirus Expression of RIPK1 Construct

The coding region of human RIPK1(1-324) flanked by NdeI site at 5' end and stop codon TGA and XhoI site at 3' end was codon optimized and gene synthesized at GenScript USA Inc. (Piscataway, N.J.) and subcloned into a modified pFastBac1 vector (Invitrogen, Carlsbad, Calif.) with N-terminal His-GST-TVMV tag, to generate His-GST-TVMV-hRIPK1(1-324)-pFB. The fidelity of the synthetic fragment was confirmed by sequencing.

Baculovirus was generated for the construct using the Bac-to-Bac baculovirus expression system (Invitrogen) according to the manufacturer's protocol. Briefly, recombinant bacmid was isolated from transformed DH10Bac *E. coli* competent cells (Invitrogen) and used to transfect *Spodoptera frugiperda* (Sf9) insect cells (Invitrogen). Baculovirus was harvested 72 hours post transfection and a virus stock was prepared by infecting fresh Sf9 cells at a ¹⁄₁₀₀₀ (v/v) ratio for 66 hours.

For large scale protein production, Sf9 cells (Expression System, Davis, Calif.) grown in ESF921 insect medium (Expression System) at 2×106 cells/ml were infected with virus stock at a ¹⁄₁₀₀ (v/v) ratio for 66 hours. The production was carried out either at a 10 L scale in a 22 L cellbag (GE Healthcare Bioscience, Pittsburgh, Pa.) or at a 20 L scale in a 50 L cellbag using WAVE-Bioreactor System 20/50 (GE Healthcare Bioscience). The infected cells were harvested by centrifugation at 2000 rpm for 20 min at 4° C. in a SORVALL® RC12BP centrifuge. The cell pellets was stored at −70° C. before protein was purified.

Purification of His-GST-TVMV-hRIPK1(1-324)

RIPK1 containing cell paste was resuspended in 50 mM Tris pH 7.5, 150 mM NaCl, 10 mM imidazole, 5% glycerol, 5 mM $MgSO_4$, 1 mM TCEP, 25 U/ml Benzonase, and Complete Protease Inhibitor tablets (¹⁄₅₀ ml, Roche Diagnostics, Indianapolis, Ind.). The cells were lysed by nitrogen cavitation using an unstirred pressure vessel @ 525 PSI (Parr Instrument Company, Moline, Ill.). The suspension was clarified by centrifugation at 136,000×g for 40 min, at 4° C. The lysate was decanted from the pellet and passed through a 5 ml NiNTA Superflow cartridge (Qiagen, Valencia, Calif.) using an AKTA Pure (GE Healthcare). Column was eluted with 10 CV linear gradient into 50 mM Tris 7.5, 150 mM NaCl, 500 mM imidazole, 5% glycerol, 1 mM TCEP. Peak fractions were pooled and loaded directly onto 5 ml GSTrap 4B column (GE Healthcare). Column was washed with 50 mM Tris 7.0, 150 mM NaCl, 5% glycerol, 1 mM DTT and eluted in 10 CV linear gradient into 50 mM Tris 8.0, 150 mM NaCl, 20 mM reduced glutathione, 5% glycerol, 1 mM DTT. Fractions identified by SDS-PAGE as containing RIPK1 were pooled and concentrated using 30 kDa MWCO spin concentrators (Amicon Ultra-15, Millipore, Billerica, Mass.) and loaded onto a HiLoad 26/600 Superdex 200 column (GE Healthcare) equilibrated in 25 mM Tris 7.5, 150 mM NaCl, 2 mM TCEP, 5% glycerol. The RPK1 protein eluted as dimer off the SEC column.

The yield was ~8 mg/L with a purity>95% as determined by Coomassie stained SDS-PAGE gel analysis. LCMS analysis of the protein showed that the protein had lost the N-terminal methionine, had one phosphorylated site, and was partially acetylated. Protein was aliquoted and stored at −80° C.

Using these assays, the $IC_{50}$ values of the following compounds were determined. See Table A.

TABLE A

| Patent Ex | RIPK1 HTRF binding | | | pMLKL cell activity | | |
|---|---|---|---|---|---|---|
| | <20 nM | 20-200 nM | >200 nM | <20 nM | 20-200 nM | >200 nM |
| 1 | | | x | | | x |
| 2 | | x | | | x | |
| 3 | | x | | | x | |
| 4 | x | | | | x | |
| 5 | x | | | | x | |
| 6 | x | | | x | | |
| 7 | x | | | | x | |
| 8 | x | | | | x | |
| 9 | x | | | x | | |
| 10 | | x | | | | x |
| 11 | x | | | | | x |
| 12 | x | | | | x | |
| 13 | | x | | | | x |
| 14 | x | | | | x | |
| 15 | x | | | x | | |
| 16 | x | | | | x | |
| 17 | x | | | | x | |
| 18 | | x | | | | x |
| 19 | | x | | | x | |
| 20 | x | | | | x | |
| 21 | x | | | | x | |
| 22 | x | | | x | | |
| 23 | x | | | x | | |
| 24 | | x | | | | x |
| 25 | x | | | | x | |
| 26 | x | | | | x | |
| 27 | x | | | x | | |
| 28 | x | | | | x | |
| 29 | x | | | | x | |
| 30 | | x | | | x | |
| 31 | x | | | | x | |
| 32 | x | | | x | | |
| 33 | x | | | | x | |
| 34 | x | | | x | | |
| 35 | | x | | | x | |
| 36-1 | | x | | | x | |
| 36-2 | | | x | | | x |
| 37 | x | | | | x | |
| 38-1 | x | | | x | | |
| 38-2 | | | x | | | x |
| 39 | x | | | | x | |
| 40 | x | | | | x | |
| 41 | x | | | | x | |
| 42 | x | | | x | | |
| 43 | x | | | | x | |
| 44 | x | | | | x | |
| 45 | | x | | | | x |
| 46 | | x | | | | x |
| 47 | | x | | | | x |
| 48 | x | | | x | | |
| 49 | x | | | | x | |
| 50 | x | | | | x | |
| 51 | x | | | | x | |
| 52 | x | | | x | | |
| 53 | x | | | | x | |
| 54 | x | | | | x | |
| 55 | x | | | | x | |
| 56 | x | | | | x | |
| 57 | x | | | | x | |
| 58 | x | | | | x | |
| 59 | x | | | | x | |
| 60 | | x | | | | x |
| 61 | x | | | x | | |
| 62 | x | | | | x | |
| 63 | x | | | | x | |
| 64 | | x | | | x | |
| 65 | x | | | | x | |
| 66 | x | | | | x | |
| 67 | | x | | | x | |
| 68 | | x | | | x | |
| 69 | x | | | | | x |
| 70 | x | | | | x | |
| 71-1 | | x | | | x | |
| 71-2 | | x | | | | x |
| 72 | | x | | | | x |
| 73 | x | | | | | x |
| 74 | x | | | | x | |
| 75 | | x | | | x | |
| 76-1 | x | | | x | | |
| 76-2 | x | | | | x | |
| 77 | | x | | | x | |
| 78 | | x | | | x | |
| 79 | | x | | | | x |
| 80 | x | | | | x | |
| 81 | x | | | x | | |
| 82 | x | | | | x | |
| 83 | x | | | x | | |
| 84 | | x | | | x | |
| 85 | x | | | x | | |
| 86 | x | | | | x | |
| 87 | x | | | | x | |
| 88 | x | | | x | | |
| 89-1 | | x | | | x | |
| 89-2 | x | | | | x | |
| 90 | x | | | | x | |
| 91 | | x | | | x | |
| 92 | x | | | x | | |
| 93 | x | | | | x | |
| 94 | x | | | x | | |
| 95-1 | | x | | | | x |
| 95-2 | x | | | x | | |
| 96 | x | | | | x | |
| 97-1 | | x | | | x | |
| 97-2 | x | | | | x | |
| 98-1 | | x | | | | x |
| 98-2 | x | | | x | | |
| 99-1 | | x | | | x | |
| 99-2 | x | | | | x | |
| 100 | | x | | | | x |
| 101 | | x | | | x | |
| 102 | | x | | | x | |
| 103 | | x | | | | x |
| 104 | x | | | | | x |
| 105 | x | | | | | x |
| 106 | x | | | x | | |
| 107 | | x | | | | x |
| 108 | x | | | x | | |
| 109 | x | | | x | | |
| 110 | x | | | x | | |

TABLE A-continued

| Patent Ex | RIPK1 HTRF binding | | | pMLKL cell activity | | |
|---|---|---|---|---|---|---|
| | <20 nM | 20-200 nM | >200 nM | <20 nM | 20-200 nM | >200 nM |
| 111 | x | | | | | x |
| 112 | | | | | | x |
| 113 | | | | x | | |
| 114 | x | | | x | | |
| 115 | x | | | x | | |
| 116 | | x | | x | | |
| 117 | | x | | | | x |
| 118 | | x | | x | | |
| 119 | | x | | | | x |
| 120 | | x | | x | | |
| 121 | | x | | x | | |
| 122 | x | | | x | | |
| 123 | x | | | x | | |
| 124 | x | | | x | | |
| 125 | x | | | x | | |
| 126 | x | | | x | | |
| 127 | x | | | x | | |
| 128 | x | | | | x | |
| 129 | x | | | x | | |
| 130 | x | | | x | | |
| 131 | x | | | | x | |
| 132 | | x | | x | | |
| 133 | | x | | | | x |
| 134 | | x | | x | | |
| 135 | x | | | x | | |
| 136 | x | | | x | | |
| 137 | x | | | x | | |
| 138 | x | | | x | | |
| 139 | x | | | x | | |
| 140 | x | | | x | | |
| 141 | x | | | x | | |
| 142 | x | | | x | | |
| 143 | x | | | x | | |
| 144 | x | | | x | | |
| 145 | x | | | x | | |
| 146 | x | | | x | | |
| 147 | x | | | x | | |
| 148 | x | | | x | | |
| 149 | x | | | x | | |
| 150 | x | | | x | | |
| 151 | x | | | x | | |
| 152 | | x | | x | | |
| 153 | x | | | x | | |
| 154 | | | x | | x | |
| 155 | x | | | x | | |
| 156 | | x | | | | x |
| 157 | | x | | x | | |
| 158 | x | | | x | | |
| 159 | | | x | x | | |
| 160 | x | | | x | | |
| 161 | x | | | x | | |
| 162 | x | | | x | | |
| 163 | x | | | x | | |
| 164 | | x | | x | | |
| 165 | | x | | x | | |
| 166 | | x | | | | x |
| 167 | x | | | x | | |
| 168 | | x | | | | x |
| 169 | | x | | | | x |
| 170 | | | | x | | |
| 171 | | x | | x | | |
| 172 | x | | | x | | |
| 173 | | x | | | | x |
| 174 | | x | | | | x |
| 175 | x | | | x | | |
| 176 | | x | | | | x |
| 177 | x | | | x | | |
| 178 | | x | | x | | |
| 179 | x | | | x | | |
| 180 | x | | | x | | |
| 181 | x | | | | x | |
| 182 | x | | | x | | |
| 183 | | x | | x | | |
| 184 | x | | | x | | |
| 185 | x | | | x | | |
| 186 | x | | | x | | |
| 187 | | x | | x | | |
| 188 | x | | | x | | |
| 189 | | x | | x | | |
| 190 | x | | | x | | |
| 191 | x | | | x | | |
| 192 | x | | | x | | |
| 193 | | x | | x | | |
| 194 | | x | | | | x |
| 195 | x | | | x | | |
| 196 | | x | | | | x |
| 197 | x | | | x | | |
| 198 | | x | | | | x |
| 199 | | x | | | | x |
| 200 | | x | | x | | |
| 201 | x | | | x | | |
| 202 | x | | | x | | |
| 203 | x | | | x | | |
| 204 | | x | | | | x |
| 205 | x | | | x | | |
| 206 | x | | | x | | |
| 207 | x | | | x | | |
| 208 | x | | | x | | |
| 209 | x | | | x | | |
| 210 | x | | | x | | |
| 211 | x | | | x | | |
| 212 | x | | | x | | |
| 213 | x | | | x | | |
| 214 | x | | | x | | |
| 215 | x | | | x | | |
| 216 | x | | | x | | |
| 217 | x | | | x | | |
| 218 | x | | | x | | |
| 219 | x | | | x | | |
| 220 | x | | | x | | |
| 221 | x | | | x | | |
| 222 | x | | | x | | |
| 223 | x | | | x | | |
| 224 | x | | | x | | |
| 225 | | x | | x | | |
| 226 | | x | | | | |
| 227 | | x | | | | x |
| 228 | x | | | x | | |
| 229 | x | | | x | | |
| 230 | x | | | x | | |
| 231 | | x | | | | x |
| 232 | x | | | x | | |
| 233 | x | | | | | x |
| 234 | | x | | | | x |
| 235 | x | | | x | | |
| 236 | | x | | x | | |
| 237 | x | | | x | | |
| 238 | | x | | x | | |
| 239 | x | | | x | | |
| 240 | x | | | x | | |
| 241 | x | | | x | | |
| 242 | x | | | x | | |
| 243 | | x | | | | x |
| 244 | | x | | | | x |
| 245 | x | | | x | | |
| 246 | | x | | | | x |
| 247 | x | | | x | | |
| 248 | x | | | x | | |
| 249 | x | | | x | | |
| 250 | x | | | x | | |
| 251 | | x | | x | | |
| 252 | x | | | x | | |
| 253 | x | | | x | | |
| 254 | x | | | x | | |
| 255 | x | | | x | | |
| 256 | | x | | | | x |
| 257 | | x | | | | x |
| 258 | x | | | | | x |
| 259 | x | | | x | | |
| 260 | x | | | | x | |

TABLE A-continued

| Patent Ex | RIPK1 HTRF binding | | | pMLKL cell activity | | |
|---|---|---|---|---|---|---|
| | <20 nM | 20-200 nM | >200 nM | <20 nM | 20-200 nM | >200 nM |
| 261 | | x | | | | x |
| 262 | x | | | | x | |
| 263 | x | | | | x | |
| 264 | x | | | x | | |
| 265 | | x | | | | x |
| 266 | x | | | | x | |
| 267 | x | | | | x | |
| 268 | x | | | | x | |
| 269 | x | | | | x | |
| 270 | x | | | | x | |
| 271 | | x | | | x | |
| 272 | x | | | | x | |
| 273 | | | x | | x | |
| 274 | | | x | | x | |
| 275 | x | | | x | | |
| 276 | | | x | | | x |
| 277 | x | | | x | | |
| 278 | | x | | | | x |
| 279 | | x | | | x | |
| 280 | x | | | | x | |
| 281 | x | | | | x | |
| 282 | x | | | x | | |
| 283 | x | | | x | | |
| 284 | x | | | | x | |
| 285 | | x | | | x | |
| 286 | x | | | | x | |
| 287 | x | | | x | | |
| 288 | x | | | | x | |
| 289 | x | | | | x | |
| 290 | x | | | | x | |
| 291 | | x | | | x | |
| 292 | | x | | | x | |
| 293 | | x | | | x | |
| 294 | | x | | | | x |
| 295 | | | | | x | |
| 296 | | x | | | x | |
| 297 | | x | | | x | |
| 298 | | x | | | | x |
| 299 | x | | | x | | |
| 300 | x | | | x | | |
| 301 | x | | | | x | |
| 302 | x | | | | x | |
| 303 | x | | | | x | |
| 304 | x | | | | x | |
| 305 | | x | | | x | |
| 306 | | x | | | x | |
| 307 | x | | | | x | |
| 308 | | x | | | x | |
| 309 | x | | | | | x |
| 310 | | x | | | | x |
| 311 | | x | | | | x |
| 312 | | x | | | | x |
| 313 | | x | | | | x |
| 314 | | x | | | x | |
| 315 | | x | | | | x |
| 316 | | x | | | | x |
| 317 | | x | | | | x |
| 318 | | | x | | x | |
| 319 | | | | | x | |
| 320 | | x | | x | | |
| 321 | | x | | | x | |
| 322 | | x | | | x | |
| 323 | | x | | | x | |
| 324 | x | | | | x | |
| 325 | | x | | | x | |
| 326 | | x | | | | x |
| 327 | x | | | x | | |
| 328 | x | | | x | | |
| 329 | x | | | | x | |
| 330 | x | | | | x | |
| 331 | x | | | | x | |
| 332 | x | | | | x | |
| 333 | x | | | | x | |
| 334 | x | | | | x | |
| 335 | | x | | | x | |
| 336 | | x | | | x | |
| 337 | | x | | | | x |
| 338 | x | | | x | | |
| 339 | x | | | x | | |
| 340 | x | | | | x | |
| 341 | x | | | | x | |
| 342 | x | | | | x | |
| 343 | x | | | | x | |
| 344 | x | | | | x | |
| 345 | x | | | | x | |
| 346 | x | | | | x | |
| 347 | | x | | | x | |
| 348 | x | | | | x | |
| 349 | | x | | | x | |
| 350 | x | | | x | | |
| 351 | x | | | x | | |
| 352 | x | | | | x | |
| 353 | x | | | | x | |
| 354 | x | | | | x | |
| 355 | x | | | | x | |
| 356 | | x | | | | x |
| 356 | x | | | | | x |
| 358 | | x | | | | x |
| 359 | | x | | | | x |
| 360 | x | | | | x | |
| 361 | x | | | | x | |
| 362 | | x | | | x | |
| 363 | x | | | | x | |
| 364 | x | | | | x | |
| 365 | | x | | | | x |
| 366 | x | | | | | x |
| 367 | x | | | x | | |
| 368 | x | | | | x | |
| 369 | x | | | | x | |
| 370 | x | | | | x | |
| 371 | x | | | | x | |
| 372 | x | | | | | x |
| 373 | x | | | | | x |
| 374 | x | | | | x | |
| 375 | x | | | | x | |
| 376 | x | | | x | | |
| 377 | | x | | | x | |
| 378 | | | | | x | |
| 379 | x | | | | x | |
| 380 | x | | | x | | |
| 381 | x | | | x | | |
| 382 | | | | | x | |
| 383 | x | | | | | x |
| 384 | | x | | | | x |
| 385 | | x | | | | x |
| 386 | | x | | | | x |
| 387 | | x | | | | x |
| 388 | | x | | | x | |
| 389 | | x | | | | x |
| 390 | | x | | | | x |
| 391 | | | x | | | x |
| 392 | x | | | | x | |
| 393 | x | | | | x | |
| 394 | x | | | | x | |
| 395 | x | | | | x | |
| 396 | x | | | | x | |
| 397 | x | | | | x | |
| 398 | | x | | | x | |
| 399 | | x | | | x | |
| 400 | x | | | | x | |
| 401 | x | | | | x | |
| 402 | | x | | | x | |
| 403 | x | | | | x | |
| 404 | | x | | | x | |
| 405 | | x | | | | x |
| 406 | | x | | | | x |
| 407 | | x | | | x | |
| 408 | | x | | | x | |
| 409 | | x | | | x | |
| 410 | | x | | | x | |

TABLE A-continued

| Patent Ex | RIPK1 HTRF binding <20 nM | 20-200 nM | >200 nM | pMLKL cell activity <20 nM | 20-200 nM | >200 nM |
|---|---|---|---|---|---|---|
| 411 |  | x |  |  |  | x |
| 412 | x |  |  |  | x |  |
| 413 |  |  |  |  |  | x |
| 414 | x |  |  |  | x |  |
| 415 |  | x |  |  | x |  |
| 416 |  | x |  |  |  | x |
| 417 |  | x |  |  |  | x |
| 418 |  |  |  |  | x |  |
| 419 | x |  |  |  |  | x |
| 420 | x |  |  |  | x |  |
| 421 |  | x |  |  |  | x |
| 422 |  |  | x |  |  | x |
| 423 |  |  | x |  |  | x |
| 424 |  | x |  |  | x |  |
| 425 |  |  | x |  |  | x |
| 426 |  |  | x |  |  | x |
| 427 |  | x |  |  | x |  |
| 428 |  | x |  |  |  | x |

TNF-Induced Systemic Inflammatory Response Syndrome (SIRS)

RIPK1 inhibitors were evaluated for efficacy in vivo using a TNF-dependent model of systemic "shock", also known as systemic inflammatory response syndrome (STRS) (Duprez et al 0.2011, Immunity 35(6):908-918). Intravenous injection of murine TNF induces a systemic inflammatory response characterized by a decrease in body temperature and an increase in circulating cytokines (IL-6, KC) in the serum. The addition of zVAD-fmk strongly sensitizes mice to TNF-induced shock through the inhibition of caspases (Cauwels et al., 2003). The combination of pretreatment with zVAD-fmk prior to injection of mTNF forms the basis of the RPK1-dependent, TNF-induced, inflammatory response in this model.

Female C57/Bl6 mice (9 to 11 weeks old) were obtained from Jackson Labs (Bar Harbor, Me.). Mice were housed in BMS' animal facility with ad libitum access to food and water. Mice were and allowed to acclimate for at least 2 weeks and typically weighed at least 21 grams before being used in any studies. Group size was 6 mice per treatment. All experiments were conducted with the approval of BMS' Institutional Animal Care and Use Committee (IACUC)

Program compounds were dosed by oral gavage 2 h before IV challenge with 20 µg of murine TNF (#CRT192C, Cell Sciences, Canton Mass.). zVAD-fmk (16.7 mg/kg) was given IV, 15 min before mTNF injection. The RIPK1 kinase inhibitor, necrostatin-1s (Nec-1s) was used as a positive control and was dosed at 6 mg/kg, IV, 30 minutes before mTNF challenge. mTNF was diluted in endotoxin-free PBS and 20 µg/mouse was injected in a volume of 0.1 ml into the retro-orbital sinus. All IV injections were done via the retro-orbital sinus and injection sites were alternated (left and right sides).

Three (3) hours after mTNF injection, mice were assessed for hypothermia and mortality. Rectal body temperature was recorded with an electric thermometer (Acorn Series Model JKT with a Ret-3 probe, Oakton Instruments Vernon Hills Ill. 60061).

Blood samples for PK determination were collected into heparinized microtainer blood tubes (Part #365965, Becton Dickinson, Franklin Lakes N.J.) and mixed well. Dried blood spots (DBS) were prepared by pipetting 10 µl of whole blood, in duplicate, onto bioanalysis cards (#GR2261004, Perkin Elmer, Greenville, S.C.). A serum sample was obtained by collecting blood into a separator tube (#450472, Greiner Bio-One, Austria) and centrifuged (10 min at 10,000 RPM) to separate the serum. All blood samples were obtained from the retro-orbital sinus while under isoflurane anesthesia.

Serum cytokines were evaluated by ELISA assay. IL-6 was measured using OPTeia Kit (Becton Dickinson, Franklin Lakes N.J.) while KC was measured using an R&D Duoset kit (R&D Systems Inc. Minneapolis, Minn.)

Using these assays, the percent protection of body temperature and percent reduction in IL6 cytokine of the following compounds were determined. See Table B. % Protection is relative to a 6 mg/kg dose of Nec-1s (5-((7-Cl-1H-indol-3-yl)methyl)-3-methylimidazolidine-2,4-dione)).

TABLE B

| Example # | Dose (mg/kg) | % protection from body temp loss | % protection from IL6 increase | Exposure (nM) |
|---|---|---|---|---|
| 38-1 | 0.1 | 80 | 93 | 12 |
| 58 | 0.4 | 113 | 78 | 409 |
| 74 | 0.4 | 115 | 87 | 117 |
| 102 | 1.0 | 107 | 82 | 1287 |
| 131 | 0.4 | 15 | 8 | 50 |
| 136 | 0.4 | 106 | 80 | 364 |
| 160 | 1.0 | 107 | 60 | 693 |
| 251 | 1.0 | 86 | 97 | 1208 |

Methods of Preparation

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "ON" for overnight, "RT" for retention time, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "S" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
Boc (tert-butoxy)carbonyl
BOP benzotriazol-1-yloxytris(dimethylamino)phosphonium hexafluorophosphate
CBz carbobenzyloxy
$CH_2C_2$ dichloromethane
$CH_3CN$ or ACN acetonitrile
$CDCl_3$ deutero-chloroform
$CHCl_3$ chloroform
$Cs_2CO_3$ cesium carbonate
DCE 1,2 dichloroethane
DCM dichloromethane
DIEA/DIPEA/Hünig's Base diisopropylethylamine
DMAP 4-dimethylaminopyridine
DME 1,2-dimethoxyethane
DMF dimethyl formamide
DMSO dimethyl sulfoxide
EDC N-(3-dimethylaminopropyl)-N'-ethylcarbodiimide
EDCI N-(3-dimethylaminopropyl)-N'-ethylcarbodiimide hydrochloride
$Et_3N$ or TEA triethylamine
EtOAc ethyl acetate
$Et_2O$ diethyl ether
EtOH ethanol
HCl hydrochloric acid
HATU O-(7-azabenzotriazol-1-yl)-N,N,N',N'-tetramethyluronium
m hexafluorophosphate
Hex hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
MeI iodomethane
$MgSO_4$ magnesium sulfate
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
PG protecting group
$POCl_3$ phosphorus oxychloride
i-PrOH or IPA isopropanol
rt Room temperature
$SiO_2$ silica oxide
TBAI tetra-n-butylammonium iodide
TFA trifluoroacetic acid
THF tetrahydrofuran The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. The numbering of R groups within the scheme are for illustrative purposes and are not intended to limit the claims. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates an approach to the synthesis of compounds exemplified by 4. Functionalization of starting material 1 can be achieved through a Suzuki coupling reaction (Miyaura, N. and Suzuki, A. Chemical Reviews, 95:2457-2483, 1995) to provide compounds of the type exemplified by 2. Hydrolysis of the ester in 2 yields a carboxylic acid or carboxylate salt which can be functionalized by amidation (Tetrahedron, 61:10827-10852, 2005) to yield compounds such as 4. Appropriate functionalization of intermediates used in this invention to prepare compounds similar to 4 can be achieved through the Suzuki reaction or simple reactions known to those in the art.

Scheme 1

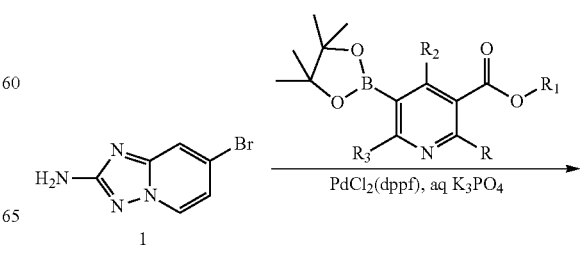

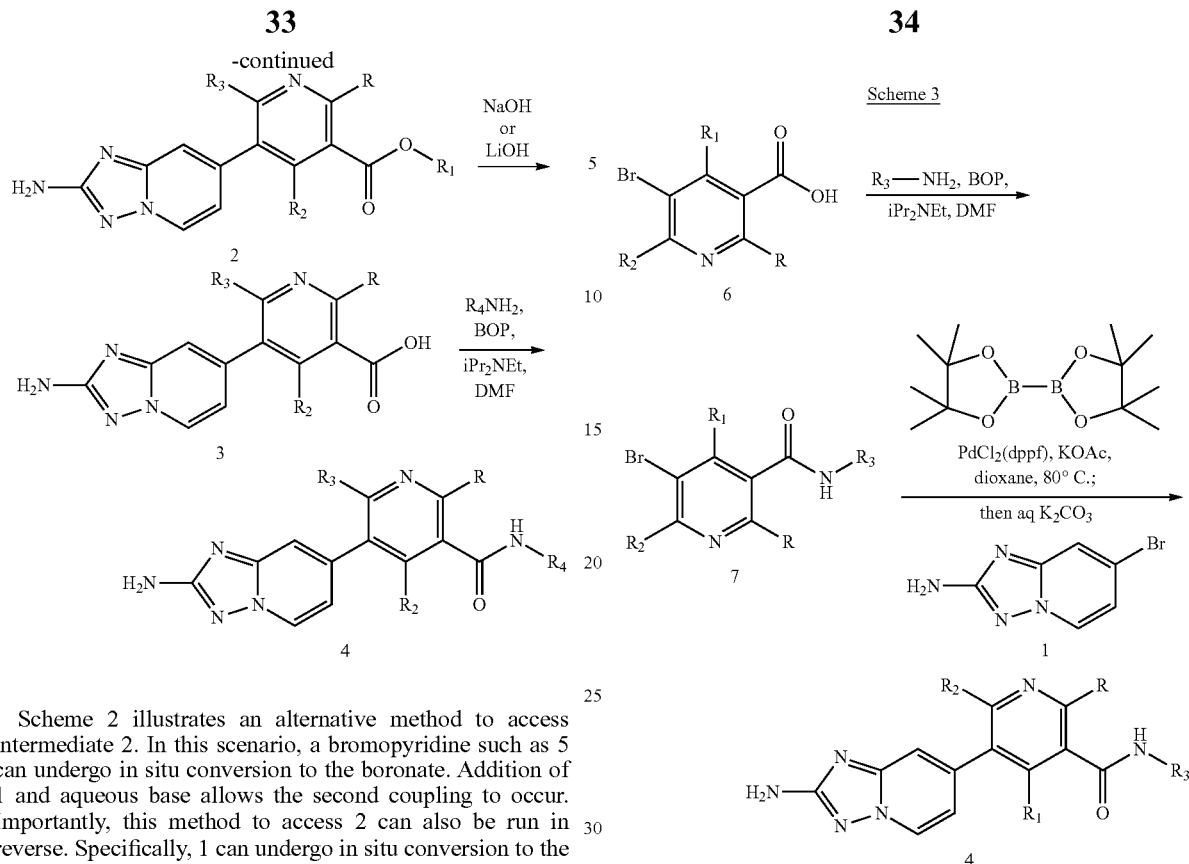

Scheme 2 illustrates an alternative method to access intermediate 2. In this scenario, a bromopyridine such as 5 can undergo in situ conversion to the boronate. Addition of 1 and aqueous base allows the second coupling to occur. Importantly, this method to access 2 can also be run in reverse. Specifically, 1 can undergo in situ conversion to the boronate and then undergo coupling with bromide 5 to produce intermediates exemplified by 2.

Scheme 3 details an alternative preparation of compounds characterized by 4. Carboxylic acid 6 can undergo amidation chemistry under various conditions known to those skilled in the art to yield intermediates like 7. Intermediates such as 7 can undergo in situ conversion to a boronate, followed by coupling with 1 to produce compounds similar to 4. Alternatively, compound 1 can undergo in situ conversion to the boronate, followed by coupling with 7 to produce compounds such as 4.

Scheme 4 details another alternative preparation for compounds similar to 4. Boronate esters such as 8 can be hydrolyzed to their acid counterparts. The carboxylic acids can undergo amidation under a variety of conditions known to those skilled in the art to yield compounds such as 10. Suzuki coupling with 1 produces compounds similar to 4.

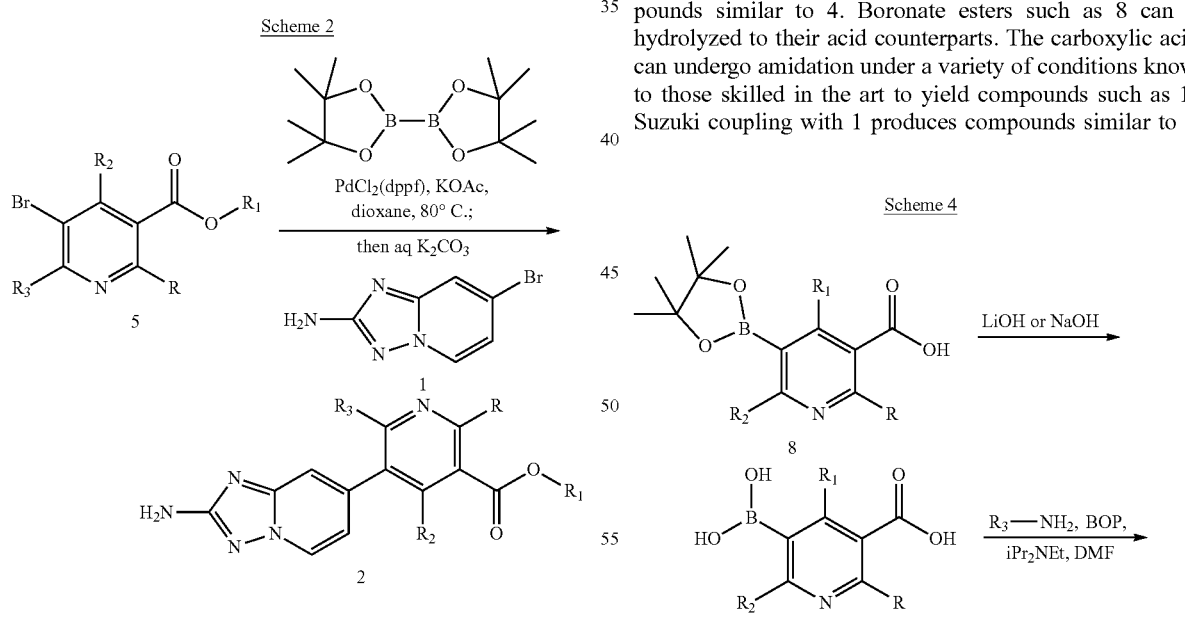

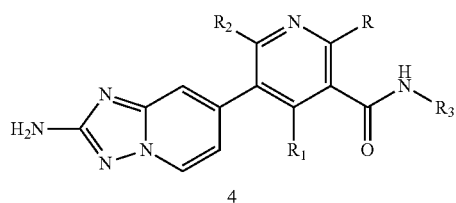

Purification of intermediates and final products was carried out via either normal or reverse phase chromatography. Normal phase chromatography using an Isco Rf or Isco Companion was carried out using prepacked SiO$_2$ cartridges eluting with either gradients of hexanes and ethyl acetate or dichloromethane and methanol unless otherwise indicated. Reverse phase preparative HPLC or LCMS was carried out using C18 columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analytical LCMS injections were used to determine final purity.

Method A: Column: Waters Acquity UPLC BEH C18, 2.1×50 mm, 1.7 µM particles; Mobile phase A: 5:95 acetonitrile:water with 10 mM ammonium acetate; Mobile phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 µm particles; Mobile phase A: 5:95 acetonitrile:water with 0.1% TFA; Mobile phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm.

In a minority of examples analytical HPLC injections were used to determine final purity.

Method A: Column: Sunfire C18, 3.0×150 mm, 3.5 µM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method B: Xbridge Phenyl, 3.0×150 mm, 3.5 µM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method C: Column: XBridge C18, 3.0×150 mm, 3.5 µM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

Method D: Column: XBridge Phenyl, 3.0×150 mm, 3.5 µM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS (ESI) m/z: [M+H]$^+$ BEH C18, 2.11×50 mm, 1.7 µm; Mobile phase A: 2:98 water:acetonitrile with 0.1% TFA; Mobile phase B: 98:2 acetonitrile:water with 0.1% TFA; Gradient: 0-100% B over 2 minutes; Flow: 0.8 mL/min; Detection: UV at 220 nm.

Proton NMRs were run with water suppression unless otherwise noted.

Example 1

5-(2-Amino-[1,2,4]triazolo[1,5-a]pyridin-7-yl)-2-chloro-N-([2-(cyclopropylmethoxy)-4-fluorophenyl]methyl)pyridine-3-carboxamide

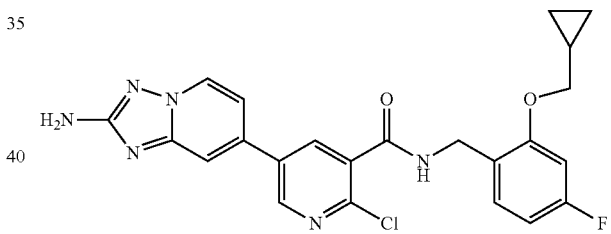

1A: 7-Bromo-[1,2,4]triazolo[1,5-a]pyridin-2-(di-t-butoxy carbonyl)amine: 4-Dimethylaminopyridine (0.406 g, 3.32 mmol) and di-t-butyl-dicarbonate (4.82 mL, 20.77 mmol) in DCM (30 mL) were added to a solution of 7-bromo-[1,2,4]triazolo[1,5-a]pyridin-2-amine (1.77 g, 8.31 mmol) in DCM (30 mL) at 0° C. The resulting mixture was allowed to warm to room temperature. After an hour, a second 600 mg of di-t-butyl-dicarbonate was added along with 10 mL DCM. After stirring ON at rt, the reaction mixture was concentrated to an oil and subjected to flash chromatography using a 40 g silica column eluting with 0-100% EtOAc in hexanes gradient. The pure fractions were concentrated to afford 7-bromo-[1,2,4]triazolo[1,5-a]pyridin-2-(di-t-butoxy carbonyl)amine (2.97 g, 7.19 mmol, 86% yield) as a crystalline off-white solid.

$^1$H NMR (400 MHz, CDCl$_3$) δ 8.40 (dd, J=7.2, 0.6 Hz, 1H), 7.90 (dd, J=2.0, 0.7 Hz, 1H), 7.16 (dd, J=7.2, 2.1 Hz, 1H), 1.47 (s, 18H).

1B: Ethyl 5-(2-amino-[1,2,4]triazolo[1,5-a]pyridin-7-yl)-2-chloronicotinate: A mixture of 7-bromo-[1,2,4]triazolo[1,5-a]pyridin-2-(di-t-butoxycarbonyl)amine (1.335 g, 3.23 mmol), 4,4,4',4',5,5,5',5'-octamethyl-2,2'-bi(1,3,2-dioxaborolane) (1.230 g, 4.85 mmol), PdCl$_2$(dppf)-CH$_2$Cl$_2$ adduct (0.264 g, 0.323 mmol) and potassium acetate (0.951 g, 9.69 mmol) in dioxane (15 mL) was heated to 100° C. for 2 h. After cooling to rt, ethyl 5-bromo-2-chloronicotinate (945 mg, 3.57 mmol) and PdCl$_2$(dppf)-CH$_2$Cl$_2$ adduct (133 mg, 0.162 mmol) were added and the mixture was degassed by bubbling nitrogen through the mixture for 5 minutes. Potassium carbonate (898 mg, 6.50 mmol) was quickly added and the reaction mixture heated at 100° C. for 1.5 h. The reaction mixture was partitioned between EtOAc (75 ml) and water (75 ml). The organic layer was washed with brine (50 ml), dried (Na$_2$SO$_4$) and concentrated to a residue that was chromatographed on a 80 g silica gel cartridge, eluting with a 0-100% EtOAc/Hex gradient. The pure fractions were concentrated to afford ethyl 5-(2-amino-[1,2,4]triazolo[1,5-a]pyridin-7-yl)-2-chloronicotinate (775 mg, 1.496 mmol, 46.1% yield) as a tan solid.

1C: 5-(2-Amino-[1,2,4]triazolo[1,5-a]pyridin-7-yl)-2-chloronicotinic acid, sodium salt: A mixture of 1B (125 mg, 0.241 mmol) and NaOH, 1N (0.724 ml, 0.724 mmol) in THF (1.5 mL) was stirred at rt for 5 h. At this time MeOH (1 mL) was added and the reaction mixture was allowed to stir ON. The volatiles were removed and the residue was diluted with water. The pH was adjusted to <2 with 1N HCl and the resulting suspension filtered. Drying of the filter cake afforded 5-(2-((tert-butoxycarbonyl)amino)-[1,2,4]triazolo[1,5-a]pyridin-7-yl)-2-chloronicotinic acid (54 mg, 0.139 mmol, 57.4% yield) as a tan solid.

$^1$H NMR (400 MHz, DMSO-d$_6$) δ 13.97 (br. s., 1H), 10.26 (s, 1H), 9.04 (d, J=2.1 Hz, 1H), 8.92 (d, J=7.1 Hz, 1H), 8.62 (d, J=2.1 Hz, 1H), 8.15 (s, 1H), 7.56 (d, J=6.8 Hz, 1H), 1.53-1.43 (m, 9H).

1D: tert-Butyl (7-(6-chloro-5-((2-(cyclopropylmethoxy)-4-fluorobenzyl)carbamoyl)pyridin-3-yl)-[1,2,4] triazolo[1,5-a]pyridin-2-yl)carbamate: A mixture of 5-(2-((tert-butoxycarbonyl)amino)-[1,2,4]triazolo[1,5-a]pyridin-7-yl)-2-chloronicotinic acid (12 mg, 0.031 mmol), (2-(cyclopropylmethoxy)-4-fluorophenyl)methanamine (106A, 6.01 mg, 0.031 mmol), BOP (14.98 mg, 0.034 mmol) and Et$_3$N (0.013 mL, 0.092 mmol) in THF (0.25 mL) was agitated at rt ON. The THF was removed and the residue was used as is in the next step.

1: A solution of tert-butyl (7-(6-chloro-5-((2-(cyclopropylmethoxy)-4-fluorobenzyl)carbamoyl)pyridin-3-yl)-[1,2,4] triazolo[1,5-a]pyridin-2-yl)carbamate (17.4 mg, 0.031 mmol) in TFA (70.9 µl, 0.921 mmol) was allowed to stand at rt for 18 h. The volatiles were removed, the residue dissolved in DMSO and submitted to purification.

The crude material was purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 19 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 27-52% B over 25 min, then a 2-minute hold at 52% B; Flow: 20 mL/min. Fractions containing the desired product were combined and dried via centrifugal evaporation to afford the product (1.2 mg, 2.1 µmol, 6.7%).

$^1$H NMR (500 MHz, DMSO-d6) δ 9.01 (br. s., 1H), 8.94 (d, J=2.4 Hz, 1H), 8.67 (d, J=7.0 Hz, 1H), 8.36 (d, J=1.7 Hz, 1H), 7.86 (s, 1H), 7.41-7.31 (m, 2H), 6.79-6.68 (m, 2H), 6.14 (br. s., 2H), 4.41 (d, J=5.6 Hz, 3H), 2.48-2.41 (m, 2H), 2.14-2.03 (m, 2H), 1.83-1.73 (m, 1H), 1.70-1.60 (m, 1H).

MS ESI m/z 467.3 (M+H)

Example 2

5-{2-Amino-[1,2,4]triazolo[1,5-a]pyridin-7-yl}-2-methoxy-N-{[2-(trifluoromethoxy)phenyl]($^2$H)methyl}pyridine-3-carboxamide

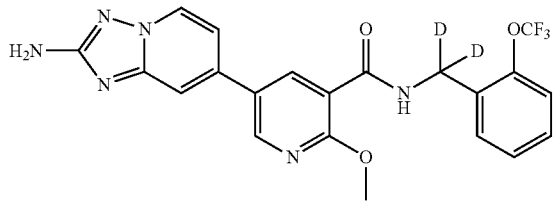 [SMILES: [2H]C([2H])(NC(=O)c1cc(-c2ccn3nc(N)nc3c2)cnc1OC)c1ccccc1OC(F)(F)F]

2A: 2-(Trifluoromethoxy)dideuterobenzylamine: To a mixture of 2-(trifluoromethoxy)benzonitrile (0.342 mL, 1.999 mmol) and sodium borodeuteride (192 mg, 4.60 mmol) in THF (10 mL) at 0° C. was added over 45 min, iodine (507 mg, 1.999 mmol) as a solution in THF (4 ml). The reaction mixture was refluxed for 2 h. At this time, it was cooled to 0° C. and 6 N HCl (2 ml) was carefully added. This mixture was refluxed for 30 min. After cooling to rt, the mixture was partitioned between EtOAc (40 ml) and 1N NaOH (40 ml). The organic layer was washed with water (20 ml) and brine (20 ml). After drying (Na$_2$SO$_4$) and filtration, the organic layer was concentrated to afford 2-(trifluoromethoxy)dideuterobenzylamine (385 mg, 1.993 mmol, 100% yield) as a light yellow oil. The material was impure and was used crude in the coupling step.

2: A mixture of 5-(2-amino-[1,2,4]triazolo[1,5-a]pyridin-7-yl)-2-methoxynicotinic acid (40 mg, 0.140 mmol), (2-(trifluoromethoxy)phenyl)methanamine-d2 (108 mg, 0.561 mmol), BOP (68.2 mg, 0.154 mmol) and Triethylamine (0.059 mL, 0.421 mmol) in THF (0.25 mL) was agitated at rt ON. The reaction mixture was partitioned between EtOAc (5 ml) and 10% LiCl solution (5 ml). The organic layer was washed with 10% LiCl solution (2×5 ml) and brine (5 ml). After drying over anhydrous sodium sulfate and filtration, the organic layer was concentrated to afford a residue that was chromatographed on a 4 g ISCO silica gel cartridge, eluting with a 0-5% MeOH/DCM gradient. The pure fractions were concentrated to a residue that was impure by NMR. The material was triturated with EtOAc, filtered and dried to afford 5-(2-amino-[1,2,4]triazolo[1,5-a]pyridin-7-yl)-2-methoxy-N-(2-(trifluoromethoxy)benzyl)nicotinamide-d2 (19 mg, 0.041 mmol, 29.1% yield) as a white solid.

$^1$H NMR (400 MHz, DMSO-d6) δ 8.90 (s, 1H), 8.79 (d, J=2.6 Hz, 1H), 8.60 (d, J=7.0 Hz, 1H), 8.46 (d, J=2.7 Hz, 1H), 7.72 (d, J=1.3 Hz, 1H), 7.56-7.50 (m, 1H), 7.46-7.34 (m, 3H), 7.24 (dd, J=7.0, 2.0 Hz, 1H), 6.05 (s, 2H), 4.05 (s, 3H).

MS ESI m/z (M+H)

Example 3

5-{2-Amino-[1,2,4]triazolo[1,5-a]pyridin-7-yl}-2-methoxy-6-methyl-N-({2-[(3-oxocyclobutyl)methoxy]phenyl}methyl)pyridine-3-carboxamide

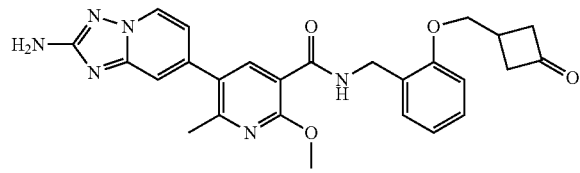 [SMILES: COc1nc(C)c(-c2ccn3nc(N)nc3c2)cc1C(=O)NCc1ccccc1OCC1CC(=O)C1]

3A: 2-(5,8-Dioxaspiro[3.4]octan-2-ylmethoxy)benzonitrile: 5,8-Dioxaspiro[3.4]octan-2-ylmethanol (339 mg, 2.351 mmol) was added to a solution of 2-hydroxybenzonitrile (200 mg, 1.679 mmol) and triphenylphosphine (617 mg, 2.351 mmol) in THF (10 mL) at 0° C. DIAD (0.457 mL, 2.351 mmol) was added dropwise. The yellow solution was stirred at RT 2 d. The reaction mixture was concentrated to an oil and purified by flash chromatography using a 40 g ISCO column eluting with 0-100% EtOAc in hexanes. A second column eluting with 0-5% MeOH in DCM was performed. Afforded 2-(5,8-dioxaspiro[3.4]octan-2-ylmethoxy)benzonitrile (222 mg, 0.887 mmol, 52.8%) as a colorless oil.

$^1$H NMR (400 MHz, DMSO-$d_6$) δ 7.71 (dd, J=7.6, 1.7 Hz, 1H), 7.65 (ddd, J=8.7, 7.4, 1.8 Hz, 1H), 7.25 (d, J=8.4 Hz, 1H), 7.09 (td, J=7.5, 0.8 Hz, 1H), 4.16 (d, J=6.7 Hz, 2H), 3.87-3.76 (m, 4H), 2.48-2.42 (m, 1H), 2.42-2.34 (m, 2H), 2.18-2.09 (m, 2H).

MS ESI m/z 246.1 (M+H)

3B: (2-(5,8-Dioxaspiro[3.4]octan-2-ylmethoxy)phenyl)methanamine: A solution of 2-(5,8-dioxaspiro[3.4]octan-2-ylmethoxy)benzonitrile (195 mg, 0.795 mmol) in diethyl ether (10 mL) was cooled to 0° C. LiAlH$_4$ (113 mg, 2.98 mmol) was added in portions and the resulting mixture was stirred ON, slowly warming to rt. The reaction mixture was diluted with ether (30 mL) and cooled to 0° C. Water (0.14 mL) was added, followed by the addition of 15% NaOH (0.14 mL) and water (0.42 mL). The mixture was stirred 15 min to insure complete quench and concentrated to afford (2-(5,8-dioxaspiro[3.4]octan-2-ylmethoxy)phenyl)methanamine (186 mg, 0.746 mmol, 94% yield), a colorless oil which was used as is in subsequent chemistry.

3C: Methyl 5-bromo-2-methoxy-6-methylnicotinate: To a rapidly stirring mixture of 5-bromo-2-hydroxy-6-methylnicotinic acid (0.54 g, 2.327 mmol) and iodomethane (0.873 mL, 13.96 mmol) in chloroform (50 mL) was added silver carbonate (3.21 g, 11.64 mmol). The resulting mixture was stirred in the dark (aluminum foil wrap) for 6 d. The reaction mixture was filtered through Celite. The filtrate was concentrated to an oil. The crude residue was loaded onto 24 g ISCO column and purified by flash chromatography eluting with 0-75% EtOAc in hexanes. Afforded methyl 5-bromo-2-methoxy-6-methylnicotinate (242 mg, 0.921 mmol, 39.6% yield) as a white solid.

$^1$H NMR (400 MHz, DMSO-$d_6$) δ 8.22 (s, 1H), 3.91 (s, 3H), 3.80 (s, 3H), 2.55 (s, 3H).

MS ESI m/z 261.9 (M+H)

3D: In a sealed 40 mL tube, a mixture of 1A (375 mg, 0.907 mmol), bis(pinacolato)diboron (288 mg, 1.134 mmol), potassium acetate (267 mg, 2.72 mmol), and [1,1'-bis(diphenylphosphino)ferrocene]dichloropalladium(II) (33.2 mg, 0.045 mmol) in 1,4-dioxane (6 mL) was stirred at 100° C. The reaction mixture was cooled to rt after 45 min. Methyl 5-bromo-2-methoxy-6-methylnicotinate (230 mg, 0.884 mmol) and 1,1'-bis(di-tert-butylphosphino)ferrocenepalladium dichloride (28.8 mg, 0.044 mmol) were added. The reaction mixture was degassed by nitrogen sparging for 5 min. 2M K$_3$PO$_4$ (aq) (1.326 mL, 2.65 mmol) was added and the reaction mixture heated at 100° C. for 25 min. The reaction mixture was concentrated onto Celite. And purified by column chromatography on the Isco system (40 g, 0-100% EtOAc/Hex. Afforded desired product (430 mg, 0.795 mmol, 90% yield) as a crystalline beige solid. Carried on to deprotection.

MS ESI m/z 514.2 (M+H)

3E: Methyl 5-(2-amino-[1,2,4]triazolo[1,5-a]pyridin-7-yl)-2-methoxy-6-methylnicotinate: A mixture of 3D (430 mg, 0.837 mmol) in TFA (5 mL) was stirred at rt for 45 min. The reaction mixture was concentrated to a solid which was slurried in saturated aqueous sodium bicarbonate. The slurry was extracted with EtOAc (3×100 mL). The combined organics were washed with brine, dried over anhydrous sodium sulfate, filtered and concentrated in vacuo. Afforded methyl 5-(2-amino-[1,2,4]triazolo[1,5-a]pyridin-7-yl)-2-methoxy-6-methylnicotinate (254 mg, 0.770 mmol, 92% yield) as a beige solid which was used as is in subsequent chemistry.

3F: 5-(2-Amino-[1,2,4]triazolo[1,5-a]pyridin-7-yl)-2-methoxy-6-methylnicotinic acid: To a mixture of methyl 5-(2-amino-[1,2,4]triazolo[1,5-a]pyridin-7-yl)-2-methoxy-6-methylnicotinate (254 mg, 0.811 mmol) in tetrahydrofuran (7.5 mL) was added a solution of lithium hydroxide monohydrate (40.8 mg, 0.973 mmol) in water (1.5 mL). The reaction mixture was stirred ON at rt and concentrated to a solid. Afforded 5-(2-amino-[1,2,4]triazolo[1,5-a]pyridin-7-yl)-2-methoxy-6-methylnicotinic acid (245 mg, 0.778 mmol, 96% yield) as a tan solid which was used as is in subsequent chemistry.

MS ESI m/z 299.9 (M+H)

3G: N-(2-(5,8-Dioxaspiro[3.4]octan-2-ylmethoxy)benzyl)-5-(2-amino-[1,2,4]triazolo[1,5-a]pyridin-7-yl)-2-methoxy-6-methylnicotinamide: A mixture of 5-(2-amino-[1,2,4]triazolo[1,5-a]pyridin-7-yl)-2-methoxy-6-methylnicotinic acid (48 mg, 0.160 mmol), BOP (106 mg, 0.241 mmol), (2-(5,8-dioxaspiro[3.4]octan-2-ylmethoxy)phenyl)methanamine (40.0 mg, 0.160 mmol) and Hünig's Base (0.140 mL, 0.802 mmol) in DMF (1.0 mL) was stirred at rt ON. The reaction mixture was diluted to 75 mL with EtOAc, then washed with 10% aq LiCl (1×) and brine (1×). The organics were dried over anhydrous sodium sulfate, filtered and concentrated. The crude residue was loaded onto a 4 g ISCO column and purified by flash chromatography eluting with 0-100% EtOAc in hexanes. Afforded N-(2-(5,8-dioxaspiro[3.4]octan-2-ylmethoxy)benzyl)-5-(2-amino-[1,2,4]triazolo[1,5-a]pyridin-7-yl)-2-methoxy-6-methylnicotinamide (71 mg, 0.131 mmol, 82% yield) as a white solid.

$^1$H NMR (500 MHz, DMSO-$d_6$) δ 8.56 (br d, J=6.4 Hz, 2H), 8.05 (s, 1H), 7.36 (s, 1H), 7.22 (br s, 2H), 6.99 (br d, J=8.2 Hz, 1H), 6.94-6.88 (m, 2H), 6.02 (s, 2H), 4.48 (br d, J=5.8 Hz, 2H), 4.06-4.00 (m, 5H), 3.79 (br dd, J=12.5, 4.9 Hz, 4H), 2.47 (s, 4H), 2.42-2.32 (m, 2H), 2.18 (br dd, J=12.1, 6.9 Hz, 2H).

MS ESI m/z 531.4 (M+H)

3: N-(2-(5,8-Dioxaspiro[3.4]octan-2-ylmethoxy)benzyl)-5-(2-amino-[1,2,4]triazolo[1,5-a]pyridin-7-yl)-2-methoxy-6-methylnicotinamide (61 mg, 0.115 mmol) was dissolved in methanol (1.0 mL) and 2M HCl (0.575 mL, 1.150 mmol) and stirred at rt ON. The reaction mixture was neutralized with 2N NaOH (6 mL). The aqueous layer was extracted with EtOAc (3×). The combined organics were washed with brine, dried over anhydrous sodium sulfate, filtered and concentrated in vacuo to afford 5-(2-amino-[1,2,4]triazolo[1,5-a]pyridin-7-yl)-2-methoxy-6-methyl-N-(2-((3-oxocyclobutyl)methoxy)benzyl)nicotinamide (56 mg, 0.109 mmol, 95% yield). A portion of the crude material (10 mg) was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-methoxy-6-methyl-N-(2-((3-oxocyclobutyl)methoxy)benzyl)nicotinamide (5.9 mg, 0.012 mmol, 56.6% yield).

$^1$H NMR (500 MHz, DMSO-d6) δ 8.55 (t, J=6.4 Hz, 2H), 8.04 (s, 1H), 7.35 (s, 1H), 7.27-7.17 (m, 2H), 7.02 (d, J=8.2 Hz, 1H), 6.91 (d, J=4.0 Hz, 2H), 6.01 (br. s., 1H), 4.47-4.41 (m, 2H), 4.19 (d, J=5.8 Hz, 2H), 4.02 (s, 3H), 3.26-3.15 (m, 2H), 3.01-2.93 (m, 3H), 2.87 (br. s., 1H), 2.46 (s, 3H).

MS ESI m/z 487.1 (M+H)

Example 4

5-{2-Amino-[1,2,4]triazolo[1,5-a]pyridin-7-yl}-N-({2-[(3,3-difluorocyclobutyl)methoxy]phenyl}methyl)-2-methoxy-6-methylpyridine-3-carboxamide

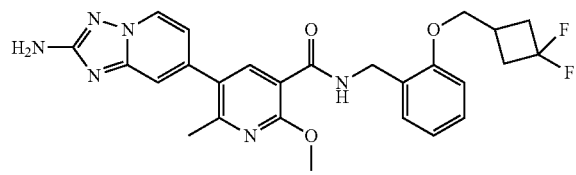 [SMILES: COc1nc(C)c(-c2ccn3nc(N)nc3c2)cc1C(=O)NCc1ccccc1OCC1CC(F)(F)C1]

To a solution of 3, 5-(2-amino-[1,2,4]triazolo[1,5-a]pyridin-7-yl)-2-methoxy-6-methyl-N-(2-((3-oxocyclobutyl)methoxy)benzyl)nicotinamide (40 mg, 0.082 mmol), in DCM (1.0 mL) at 0° C. was slowly added DAST (0.027 mL, 0.206 mmol). The reaction mixture was stirred vigorously as it slowly warmed up to rt ON. Cooled back to 0° C. and added additional DAST (100 μL). The reaction mixture was cooled to −5° C. in an ice/acetone bath. Saturated aqueous sodium bicarbonate (40 mL) was added dropwise using an addition funnel over 30 min. The aqueous layer was extracted with DCM (3×). The combined organics were dried over anhydrous sodium sulfate, filtered and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-((3,3-difluorocyclobutyl)methoxy)benzyl)-2-methoxy-6-methylnicotinamide (4.5 mg, 8.67 μmol, 10.55% yield).

$^1$H NMR (500 MHz, DMSO-d6) δ 8.61-8.51 (m, 2H), 8.04 (s, 1H), 7.22 (d, J=4.0 Hz, 2H), 6.99 (d, J=8.2 Hz, 1H), 6.95-6.84 (m, 2H), 6.01 (s, 2H), 4.48 (d, J=5.5 Hz, 2H), 4.07 (d, J=5.2 Hz, 2H), 4.02 (s, 3H), 2.88 (s, 2H), 2.72 (s, 4H), 2.46 (s, 3H).

MS ESI m/z 509 (M+H)

Example 5

5-{2-Amino-[1,2,4]triazolo[1,5-a]pyridin-7-yl}-2-methyl-N-{[2-(oxan-4-yloxy)phenyl]methyl}pyridine-3-carboxamide

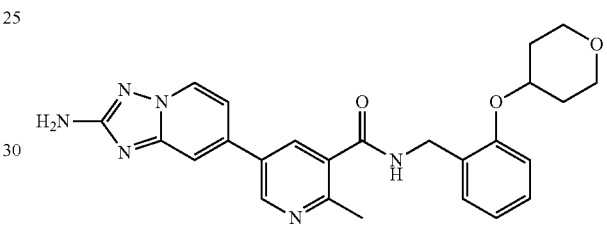

5A: (2-((Tetrahydro-2H-pyran-4-yl)oxy)phenyl)methanamine was prepared from 2-hydroxybenzonitrile and tetrahydro-2H-pyran-4-ol by the same method as intermediate 49B. Amine used as—is after filtration and evaporation.

5: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (2-((tetrahydro-2H-pyran-4-yl)oxy)phenyl)methanamine (7.70 mg, 0.037 mmol) and Hünig's Base (0.032 mL, 0.186 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-methyl-N-(2-((tetrahydro-2H-pyran-4-yl)oxy)benzyl)nicotinamide (6.5 mg, 0.014 mmol, 37.8% yield).

$^1$H NMR (500 MHz, DMSO-d6) δ 8.99-8.87 (m, 1H), 8.63 (d, J=6.6 Hz, 1H), 8.17 (br. s., 1H), 7.80 (br. s., 1H), 7.32 (d, J=4.6 Hz, 2H), 7.28-7.20 (m, 1H), 7.08 (d, J=8.2 Hz, 1H), 6.94 (t, J=7.4 Hz, 1H), 6.09 (br. s., 2H), 4.66 (br. s., 1H), 4.50 (d, J=5.3 Hz, 2H), 3.89-3.81 (m, 2H), 3.55-3.52 (m, 3H), 2.60 (s, 3H), 1.97 (d, J=11.0 Hz, 2H), 1.66 (d, J=8.5 Hz, 2H).

MS ESI m/z 459.3 (M+H)

Example 6

5-{2-Amino-[1,2,4]triazolo[1,5-a]pyridin-7-yl}-2-methoxy-6-methyl-N-{[2-(oxolan-3-yl oxy)phenyl]methyl}pyridine-3-carboxamide

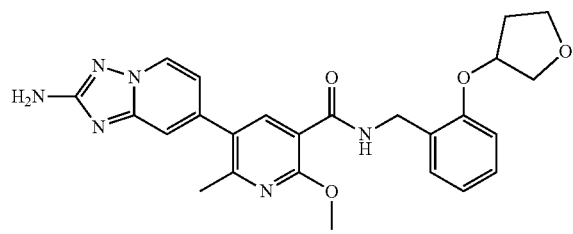 [SMILES: COc1nc(C)c(-c2ccn3nc(N)nc3c2)cc1C(=O)NCc1ccccc1OC1CCOC1]

6A: (2-((Tetrahydrofuran-3-yl)oxy)phenyl)methanamine was prepared from 2-hydroxybenzonitrile and 3-hydroxytetrahydrofuran (racemic) by the same method as intermediate 49B. Amine used as—is after filtration and evaporation.

6: A mixture of 5-(2-amino-[1,2,4]triazolo[1,5-a]pyridin-7-yl)-2-methoxy-6-methylnicotinic acid (27 mg, 0.090 mmol), BOP (59.9 mg, 0.135 mmol), (2-((tetrahydrofuran-3-yl)oxy)phenyl)methanamine (17.43 mg, 0.090 mmol) and Hünig's Base (0.079 mL, 0.451 mmol) in DMF (1.0 mL) was stirred at rt ON. The reaction mixture was diluted to 75 mL with EtOAc. The organic layer was washed 10% LiCl solution and brine. The organics were dried over anhydrous sodium sulfate, filtered and concentrated. The crude residue was loaded on a 4 g ISCO column, purified by flash chromatography eluting with 0-100% EtOAc/Hex, then 0-10% MeOH in DCM to afford the racemate (32 mg) which was further purified to separate the isomers. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-50% B over 20 min, then a 5-minute hold at 100% B; Flow: 20 mL/min. Fractions containing the desired product were combined and dried via centrifugal evaporation. Chiral separation afforded 5-(2-amino-[1,2,4]triazolo[1,5-a]pyridin-7-yl)-2-methoxy-6-methyl-N-(2-((tetrahydrofuran-3-yl)oxy)benzyl)nicotinamide (6.2 mg, 0.013 mmol, 14.34% yield, first eluting isomer) and 5-(2-amino-[1,2,4]triazolo[1,5-a]pyridin-7-yl)-2-methoxy-6-methyl-N-(2-((tetrahydrofuran-3-yl)oxy)benzyl)nicotinamide (6.0 mg, 0.013 mmol, 13.88% yield, second eluting isomer).

$^1$H NMR (500 MHz, DMSO-d6) δ 8.61 (br s, 1H), 8.55 (d, J=6.9 Hz, 1H), 8.04 (s, 1H), 7.35 (s, 1H), 7.25-7.21 (m, 2H), 6.98-6.90 (m, 4H), 6.03 (br s, 2H), 4.45 (br d, J=4.7 Hz, 2H), 4.02 (s, 3H), 3.92 (br dd, J=10.1, 4.5 Hz, 2H), 2.56-2.54 (m, 2H), 2.46 (s, 3H), 2.25-2.21 (m, 1H), 2.04-1.99 (m, 1H).

MS ESI m/z 475.3 (M+H)

Example 7

5-{2-Amino-[1,2,4]triazolo[1,5-a]pyridin-7-yl}-N-{[2-(cyclohexylmethoxy)phenyl]meth yl}-2-methoxy-6-methylpyridine-3-carboxamide 7A: (2-(Cyclohexylmethoxy)phenyl)methanamine was prepared from 2-hydroxybenzonitrile and cyclohexylmethanol by the same method as intermediate 49B. Amine used as—is after filtration and evaporation.

7: A mixture of 5-(2-amino-[1,2,4]triazolo[1,5-a]pyridin-7-yl)-2-methoxy-6-methylnicotinic acid (10 mg, 0.033 mmol), BOP (22.17 mg, 0.050 mmol), (2-(cyclohexylmethoxy)phenyl)methanamine (7.33 mg, 0.033 mmol) and Hünig's Base (0.029 mL, 0.167 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-90% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclohexylmethoxy)benzyl)-2-meth oxy-6-methylnicotinamide (7.7 mg, 0.015 mmol, 44.2% yield).

$^1$H NMR (500 MHz, DMSO-d6) δ 8.57-8.53 (m, 2H), 8.05 (s, 1H), 7.35 (s, 1H), 7.21 (br d, J=7.3 Hz, 2H), 6.96 (br d, J=8.2 Hz, 1H), 6.92-6.87 (m, 2H), 6.02 (s, 2H), 4.48 (br d, J=5.5 Hz, 2H), 4.02 (s, 3H), 3.82 (br d, J=6.1 Hz, 2H), 2.48-2.44 (m, 3H), 1.81 (br d, J=12.5 Hz, 2H), 1.76 (br s, 1H), 1.71-1.60 (m, 3H), 1.25-1.05 (m, 5H).

MS ESI m/z 501.2 (M+H)

Example 8

5-{2-Amino-[1,2,4]triazolo[1,5-a]pyridin-7-yl}-N-{[2-(cyclopentylmethoxy)pyridin-3-yl] methyl}-2-methoxy-6-methylpyridine-3-carboxamide 8A: (2-(Cyclopentylmethoxy)pyridin-3-yl)methanamine was prepared from 2-hydroxynicotinonitrile and cyclpentylmethanol by the same method as intermediate 37A. Amine used as—is after filtration and concentration.

8: A mixture of 5-(2-amino-[1,2,4]triazolo[1,5-a]pyridin-7-yl)-2-methoxy-6-methylnicotinic acid (10 mg, 0.033 mmol), BOP (22.17 mg, 0.050 mmol), (2-(cyclopentylmethoxy)pyridin-3-yl)methanamine (6.89 mg, 0.033 mmol) and Hünig's Base (0.029 mL, 0.167 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 44-74% B over 20 min, then a 2-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((2-(cyclopentylmethoxy)pyridin-3-yl)methyl)-2-methoxy-6-methylnicotinamide (8.7 mg, 0.018 mmol, 52.9% yield).

$^1$H NMR (500 MHz, DMSO-d6) δ 8.67 (br t, J=5.8 Hz, 1H), 8.58 (d, J=6.7 Hz, 1H), 8.06-8.05 (m, 1H), 8.03 (d, J=5.5 Hz, 1H), 7.57 (br d, J=7.0 Hz, 1H), 7.37 (s, 1H), 6.95 (t, J=6.5 Hz, 1H), 6.91 (d, J=7.1 Hz, 1H), 6.03 (s, 2H), 4.45 (br d, J=5.8 Hz, 2H), 4.21 (d, J=7.0 Hz, 2H), 4.04 (s, 3H), 2.49-2.46 (m, 3H), 2.34 (dt, J=14.9, 7.4 Hz, 1H), 1.82-1.74 (m, 2H), 1.63-1.50 (m, 4H), 1.39-1.32 (m, 2H).

MS ESI m/z 488 (M+H)

Example 9

5-{2-Amino-[1,2,4]triazolo[1,5-a]pyridin-7-yl}-N-{[2-(cyclopropylmethoxy)-3,5-difluoro phenyl]methyl}-2-methoxy-6-methylpyridine-3-carboxamide

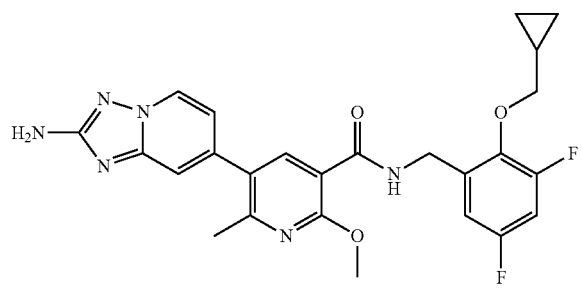 [SMILES: COc1nc(C)c(-c2ccn3nc(N)nc3c2)cc1C(=O)NCc1cc(F)cc(F)c1OCC1CC1]

9A: (2-(Cyclopropylmethoxy)-3,5-difluorophenyl)methanamine was prepared from 3,5-difluoro-2-hydroxybenzonitrile and cyclopropylmethanol by the same method as intermediate 49B. Amine used as—is after filtration and evaporation.

9: A mixture of 5-(2-amino-[1,2,4]triazolo[1,5-a]pyridin-7-yl)-2-methoxy-6-methylnicotinic acid (10 mg, 0.033 mmol), BOP (22.17 mg, 0.050 mmol), (2-(cyclopropylmethoxy)-3,5-difluorophenyl)methanamine (7.12 mg, 0.033 mmol) and Hünig's Base (0.029 mL, 0.167 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 28-68% B over 25 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)-3,5-difluorobenzyl)-2-methoxy-6-methylnicotinamide (7.6 mg, 0.015 mmol, 45.1% yield).

$^1$H NMR (500 MHz, DMSO-d6) δ 8.81 (br t, J=5.6 Hz, 1H), 8.58 (d, J=7.0 Hz, 1H), 8.04 (s, 1H), 7.38 (s, 1H), 7.20 (br t, J=8.7 Hz, 1H), 6.98-6.89 (m, 2H), 6.04 (s, 2H), 4.59 (br d, J=5.8 Hz, 2H), 4.05 (s, 3H), 3.91-3.85 (m, 2H), 2.47 (s, 3H), 1.25 (br s, 1H), 0.56 (br d, J=6.7 Hz, 2H), 0.30 (br d, J=4.6 Hz, 2H).

MS ESI m/z 495.3 (M+H)

Example 10

5-{2-Amino-[1,2,4]triazolo[1,5-a]pyridin-7-yl}-2-methoxy-N-({2-[(4-methylcyclohexyl) methoxy]phenyl}methyl)pyridine-3-carboxamide

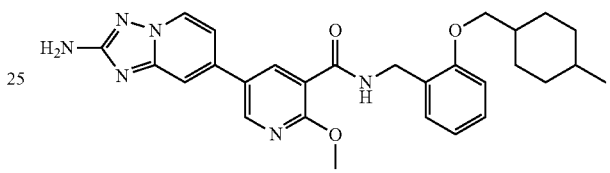

10A: (2-((4-Methylcyclohexyl)methoxy)phenyl)methanamine was prepared from 2-hydroxybenzonitrile and (4-methylcyclohexyl)methanol by the same method as intermediate 49B. Amine used as—is after filtration and evaporation.

10: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (2-((4-methylcyclohexyl)methoxy)phenyl)methanamine (8.18 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-methoxy-N-(2-((4-methylcyclohexyl)methoxy)benzyl)nicotinamide (9.7 mg, 0.019 mmol, 54.2% yield).

$^1$H NMR (500 MHz, DMSO-d6) δ 8.77 (d, J=2.1 Hz, 1H), 8.67-8.58 (m, 2H), 8.47 (d, J=2.1 Hz, 1H), 7.70 (s, 1H), 7.28-7.21 (m, 3H), 7.03-6.89 (m, 2H), 6.04 (s, 2H), 4.51 (br d, J=5.8 Hz, 2H), 4.04 (s, 3H), 3.94 (br d, J=6.7 Hz, 1H), 3.84 (br d, J=5.8 Hz, 1H), 1.84 (br d, J=12.2 Hz, 1H), 1.68 (br d, J=11.9 Hz, 2H), 1.59-1.53 (m, 2H), 1.53-1.45 (m, 1H), 1.32-1.25 (m, 2H), 1.14-1.07 (m, 1H), 0.96-0.88 (m, 3H), 0.85 (br d, J=6.7 Hz, 1H).

MS ESI m/z 501.4 (M+H)

Example 11

5-{2-Amino-[1,2,4]triazolo[1,5-a]pyridin-7-yl}-N-({2-[(4,4-difluorocyclohexyl)methoxy]phenyl}methyl)-2-methoxy-6-methylpyridine-3-carboxamide

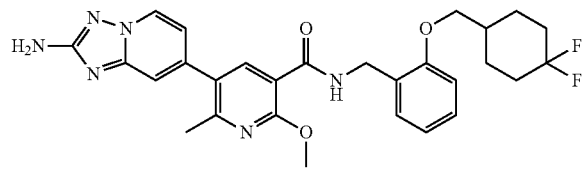 [SMILES: COc1nc(C)c(-c2ccn3nc(N)nc3c2)cc1C(=O)NCc1ccccc1OCC1CCC(F)(F)CC1]

11A: (2-((4,4-Difluorocyclohexyl)methoxy)phenyl)methanamine was prepared from 2-hydroxybenzonitrile and 4,4-difluorocyclohexylmethanol by the same method as intermediate 49B. Amine used as—is after filtration and evaporation.

11: A mixture of 5-(2-amino-[1,2,4]triazolo[1,5-a]pyridin-7-yl)-2-methoxy-6-methylnicotinic acid (10 mg, 0.033 mmol), BOP (22.17 mg, 0.050 mmol), (2-((4,4-difluorocyclohexyl)methoxy)phenyl)methanamine (8.53 mg, 0.033 mmol) and Hünig's Base (0.029 mL, 0.167 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-((4,4-difluorocyclohexyl)methoxy)benzyl)-2-methoxy-6-methylnicotinamide (13.0 mg, 0.024 mmol, 71.1% yield).

$^1$H NMR (500 MHz, DMSO-d6) δ 8.63-8.57 (m, 2H), 8.08 (s, 1H), 7.40 (br s, 1H), 7.23 (br d, J=5.8 Hz, 2H), 7.00 (br d, J=8.2 Hz, 1H), 6.96-6.90 (m, 2H), 4.51 (br d, J=5.8 Hz, 2H), 4.05 (s, 3H), 3.94-3.90 (m, 2H), 2.56-2.54 (m, 2H), 2.50-2.47 (m, 3H), 2.06 (br d, J=15.6 Hz, 2H), 1.98-1.79 (m, 5H), 1.40 (br d, J=11.9 Hz, 2H).

MS ESI m/z 536.9 (M+H)

Example 12

5-{2-amino-[1,2,4]triazolo[1,5-a]pyridin-7-yl}-N-{[3-(cyclopentylmethoxy)pyridin-2-yl] methyl}-2-methylpyridine-3-carboxamide

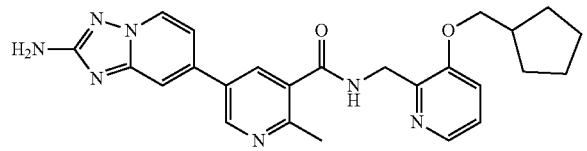 [SMILES: Cc1ncc(-c2ccn3nc(N)nc3c2)cc1C(=O)NCc1ncccc1OCC1CCCC1]

12A: (3-(Cyclopentylmethoxy)pyridin-2-yl)methanamine was prepared from 3-hydroxypicolinonitrile and cyclpentylmethanol by the same method as intermediate 37A. Amine used as—is after filtration and concentration.

12: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (3-(cyclopentylmethoxy)pyridin-2-yl)methanamine (7.66 mg, 0.037 mmol) and Hünig's Base (0.032 mL, 0.186 mmol) in DMF (1.0 mL) was stirred at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((3-(cyclopentylmethoxy)pyridin-2-yl)methyl)-2-methylnicotinamide (5.2 mg, 0.011 mmol, 29.7% yield).

$^1$H NMR (500 MHz, DMSO-d6) δ 8.94 (s, 1H), 8.80 (br t, J=5.3 Hz, 1H), 8.63 (d, J=6.7 Hz, 1H), 8.19 (s, 1H), 8.09 (d, J=4.3 Hz, 1H), 7.78 (s, 1H), 7.42 (d, J=8.2 Hz, 1H), 7.31-7.26 (m, 2H), 6.06 (s, 2H), 4.61 (br d, J=5.2 Hz, 2H), 3.95 (d, J=6.7 Hz, 2H), 2.62 (s, 3H), 2.35 (dt, J=14.8, 7.2 Hz, 1H), 1.80 (br d, J=7.6 Hz, 2H), 1.64-1.51 (m, 4H), 1.38 (br dd, J=12.2, 6.7 Hz, 2H).

MS ESI m/z 458.2 (M+H)

Example 13

5-{2-Amino-[1,2,4]triazolo[1,5-a]pyridin-7-yl}-N-{[2-(cyclopentylmethoxy)-4,6-difluoro phenyl]methyl}-2-ethoxypyridine-3-carboxamide

13A: (2-(Cyclopentylmethoxy)-4,6-difluorophenyl)methanamine was prepared from 2,4-difluoro-6-hydroxybenzonitrile and cyclopentylmethanol by the same method as intermediate 49B. Amine used as—is after filtration and evaporation.

13B: Ethyl 5-bromo-2-ethoxynicotinate: To a stirring mixture of methyl 5-bromo-2-chloronicotinate (350 mg, 1.397 mmol) in THF (10 mL) at 0° C. was added sodium ethoxide, 21% (1.565 mL, 4.19 mmol). The resulting solution was allowed to stir 1 h, before partitioning between EtOAc and saturated aqueous ammonium chloride. The organics were washed with water and brine, dried over anhydrous sodium sulfate, filtered and concentrated in vacuo. The crude residue was loaded onto a 24 g ISCO column for purification by flash chromatography, eluting with 0-100% EtOAc in hexanes. Afforded ethyl 5-bromo-2-ethoxynicotinate (102 mg, 0.372 mmol, 26.6% yield) as a white solid.

$^1$H NMR (400 MHz, DMSO-d$_6$) δ 8.48 (d, J=2.6 Hz, 1H), 8.23 (d, J=2.7 Hz, 1H), 4.37 (q, J=7.1 Hz, 2H), 4.27 (q, J=7.1 Hz, 2H), 1.31 (dt, J=8.2, 7.1 Hz, 7H).

MS ESI m/z 276.0 (M+H)

13C: In a sealed 20 mL tube, a mixture of 1A (80 mg, 0.194 mmol), bis(pinacolato)diboron (61.4 mg, 0.242 mmol), potassium acetate (57.0 mg, 0.581 mmol), and [1,1'-bis(diphenylphosphino)ferrocene]dichloropalladium (II) (7.08 mg, 9.68 µmol) in 1,4-dioxane (2 mL) was stirred at 100° C. 1 h. After cooling to rt, ethyl 5-bromo-2-ethoxynicotinate (51 mg, 0.186 mmol) and 1,1'-bis(di-tert-butylphosphino)ferrocenepalladium dichloride (5.77 mg, 8.86 µmol) was added. The crude mixture was degassed by sparging with nitrogen for 5 min. 2M $K_3PO_4$ (aq) (0.266 mL, 0.532 mmol) was quickly added and the reaction mixture heated at 100° C. for 15 min.

The reaction mixture was cooled to rt, diluted to 50 mL with EtOAc and transferred to a separatory funnel. The organics were washed with brine, dried over anhydrous sodium sulfate, filtered and concentrated. The crude residue was loaded onto a 12 g ISCO column and purified by flash chromatography eluting with 0-100% EtOAc in hexanes to afford product (90 mg, 0.162 mmol, 91% yield) as a beige solid.

MS ESI m/z 279.1 (M+H)

13D: 5-(2-((tert-Butoxycarbonyl)amino)-[1,2,4]triazolo[1,5-a]pyridin-7-yl)-2-ethoxynicotinic acid: To a stirring solution of 13C (90 mg, 0.171 mmol) in THF (3 mL) was added 1 N sodium hydroxide (0.853 mL, 0.853 mmol) and a few drops of methanol. The reaction mixture was stirred at rt ON. Excess solvent was removed in vacuo. The crude residue was acidified to pH ~3 with 1 N HCl (5 mL) and transferred to a separatory funnel. The aqueous layer was extracted with EtOAc (2×). The combine organics were washed with brine, dried over anhydrous sodium sulfate, filtered and concentrated in vacuo to afford 5-(2-((tert-butoxycarbonyl)amino)-[1,2,4]triazolo[1,5-a]pyridin-7-yl)-2-ethoxynicotinic acid (61 mg, 0.145 mmol, 85% yield) as an off-white solid.

MS ESI m/z 400.2 (M+H)

13: A mixture of 5-(2-amino-[1,2,4]triazolo[1,5-a]pyridin-7-yl)-2-ethoxynicotinic acid (10 mg, 0.033 mmol), BOP (22.17 mg, 0.050 mmol), (2-(cyclopentylmethoxy)-4,6-difluorophenyl)methanamine (8.06 mg, 0.033 mmol) and Hünig's Base (0.029 mL, 0.167 mmol) in DMF (1.0 mL) was stirred at rt for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)-4,6-difluorobenzyl)-2-ethoxynicotinamide (6.1 mg, 0.011 mmol, 34.2% yield).

$^1$H NMR (500 MHz, DMSO-d6) δ 8.76-8.72 (m, 1H), 8.59 (d, J=7.1 Hz, 1H), 8.45 (s, 1H), 8.29 (br s, 1H), 7.71-7.67 (m, 1H), 7.25-7.20 (m, 1H), 6.88-6.79 (m, 2H), 6.04 (s, 2H), 4.54-4.43 (m, 4H), 3.97-3.91 (m, 2H), 2.37-2.27 (m, 1H), 1.77 (br d, J=7.0 Hz, 2H), 1.62-1.46 (m, 4H), 1.39-1.26 (m, 5H).

MS ESI m/z 523.2 (M+H)

Example 14

5-{2-Amino-[1,2,4]triazolo[1,5-a]pyridin-7-yl}-N-{[2-(cyclopentylmethoxy)-3,5-difluoro phenyl]methyl}-2-ethoxypyridine-3-carboxamide

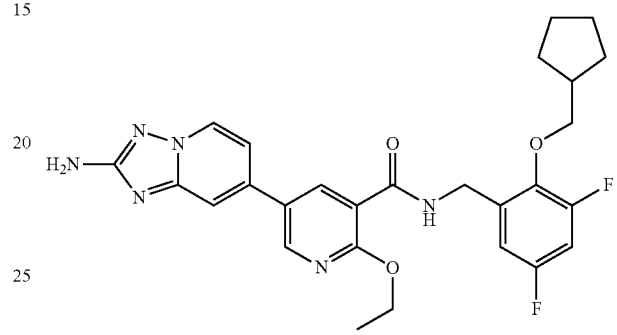

14A: (2-(Cyclopentylmethoxy)-3,5-difluorophenyl)methanamine was prepared from 3,5-difluoro-2-hydroxybenzonitrile and cyclopentylmethanol by the same method as intermediate 49B. Amine used as—is after filtration and evaporation.

14: A mixture of 5-(2-amino-[1,2,4]triazolo[1,5-a]pyridin-7-yl)-2-ethoxynicotinic acid (10 mg, 0.033 mmol), BOP (22.17 mg, 0.050 mmol), (2-(cyclopentylmethoxy)-3,5-difluorophenyl)methanamine (8.06 mg, 0.033 mmol) and Hünig's Base (0.029 mL, 0.167 mmol) in DMF (1.0 mL) was stirred at rt for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)-3,5-difluorobenzyl)-2-ethoxynicotinamide (7.8 mg, 0.014 mmol, 43.3% yield).

$^1$H NMR (500 MHz, DMSO-d6) δ 8.80 (br t, J=5.8 Hz, 1H), 8.75 (d, J=2.4 Hz, 1H), 8.59 (d, J=6.7 Hz, 1H), 8.42 (d, J=2.1 Hz, 1H), 7.71 (s, 1H), 7.26-7.19 (m, 2H), 7.06 (br d, J=8.2 Hz, 1H), 6.03 (s, 2H), 4.59-4.49 (m, 4H), 3.91 (br d, J=7.0 Hz, 2H), 2.33 (dt, J=14.8, 7.6 Hz, 1H), 1.79 (br d, J=7.3 Hz, 2H), 1.63-1.50 (m, 4H), 1.42-1.34 (m, 5H).

MS ESI m/z 523.2 (M+H)

Example 15

5-{2-Amino-[1,2,4]triazolo[1,5-a]pyridin-7-yl}-N-{[2-(cyclopentylmethoxy)-6-fluorophenyl]methyl}-2-methylpyridine-3-carboxamide

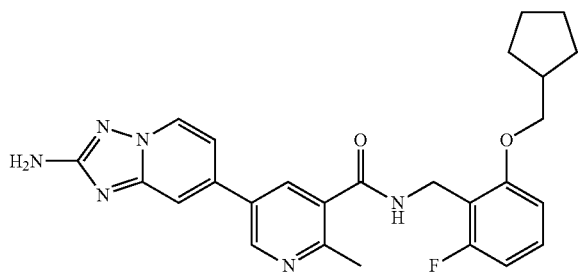 [SMILES: Cc1ncc(-c2ccn3nc(N)nc3c2)cc1C(=O)NCc1c(F)cccc1OCC1CCCC1]

15A: (2-(Cyclopentylmethoxy)-6-fluorophenyl)methanamine was prepared from 6-fluoro-2-hydroxybenzonitrile and cyclopentylmethanol by the same method as intermediate 49B. Amine used as—is after filtration and evaporation.

15: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (2-(cyclopentylmethoxy)-6-fluorophenyl)methanamine (8.29 mg, 0.037 mmol) and Hünig's Base (0.032 mL, 0.186 mmol) in DMF (1.0 mL) was stirred at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)-6-fluorobenzyl)-2-methylnicotinamide (3.2 mg, 6.61 µmol, 17.79% yield).

$^1$H NMR (500 MHz, DMSO-d6) δ 8.91 (s, 1H), 8.62 (s, 1H), 8.62 (d, J=11.9 Hz, 1H), 8.04-8.01 (m, 1H), 7.74 (s, 1H), 7.33-7.24 (m, 2H), 6.88 (br d, J=8.2 Hz, 1H), 6.81 (br t, J=8.9 Hz, 1H), 6.06 (s, 2H), 4.51 (br d, J=4.0 Hz, 2H), 3.92 (br d, J=6.4 Hz, 2H), 2.57 (s, 3H), 2.32 (dt, J=14.5, 7.1 Hz, 1H), 1.77 (br d, J=7.3 Hz, 2H), 1.60-1.44 (m, 4H), 1.36 (br dd, J=12.2, 6.7 Hz, 2H).

MS ESI m/z 475.1 (M+H)

Example 16

5-{2-Amino-[1,2,4]triazolo[1,5-a]pyridin-7-yl}-N-{[2-(1-cyclopentylethoxy)phenyl]methyl}-2,6-dimethylpyridine-3-carboxamide

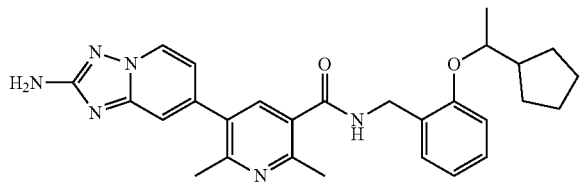 [SMILES: Cc1nc(C)c(-c2ccn3nc(N)nc3c2)cc1C(=O)NCc1ccccc1OC(C)C1CCCC1]

16A: (2-(1-Cyclopentylethoxy)phenyl)methanamine was prepared from 2-hydroxybenzonitrile and racemic 1-cyclopentylethanol by the same method as intermediate 49B. Amine used as—is after filtration and evaporation.

16B: (2Z,3E)-Ethyl 2-(1-aminoethylidene)-5-oxohex-3-enoate: To a solution of (Z)-ethyl 3-aminobut-2-enoate (400 mg, 3.10 mmol) in ethanol (40 mL) was added 4-(trimethylsilyl)but-3-yn-2-one (0.778 mL, 4.65 mmol) and the resulting solution was stirred at 50° C. for 18 h. The crude reaction mixture was cooled to rt and concentrated to an oil in a cold water bath. The crude oil was loaded onto a 40 g ISCO column and eluted with 0-100% EtOAc in hexanes. Afforded the (2Z,3E)-ethyl 2-(1-aminoethylidene)-5-oxohex-3-enoate (143 mg, 0.711 mmol, 22.94% yield) as a crystalline solid.

$^1$H NMR (400 MHz, DMSO-d$_6$) δ 9.75-9.00 (m, 1H), 8.89-7.91 (m, 1H), 7.47 (d, J=15.5 Hz, 1H), 6.37 (d, J=15.5 Hz, 1H), 4.16 (q, J=7.1 Hz, 2H), 2.27-2.22 (m, 3H), 2.12 (s, 3H), 1.26 (t, J=7.1 Hz, 3H).

16C: Ethyl 5-bromo-2,6-dimethylnicotinate: NBS (155 mg, 0.870 mmol) was added to a solution of (2Z,3E)-ethyl 2-(1-aminoethylidene)-5-oxohex-3-enoate (143 mg, 0.725 mmol) in ethanol (10 mL) at 0° C. After stirring 25 min, the crude reaction mixture was concentrated to an oil. The crude residue was loaded onto a 12 g ISCO column and eluted with 0-100% EtOAc in hexanes. Afforded ethyl 5-bromo-2,6-dimethylnicotinate (170 mg, 0.626 mmol, 86% yield), a crystalline white solid.

$^1$H NMR (400 MHz, DMSO-d$_6$) δ 8.27 (s, 1H), 4.31 (q, J=7.1 Hz, 2H), 2.64 (s, 3H), 2.59 (s, 3H), 1.32 (t, J=7.1 Hz, 3H).

MS ESI m/z 259.9 (M+H)

16D: In a sealed 40 mL tube, a mixture of 1A (0.25 g, 0.605 mmol), bis(pinacolato)diboron (0.192 g, 0.756 mmol), potassium acetate (0.178 g, 1.815 mmol), and [1,1'-bis(diphenylphosphino)ferrocene]dichloropalladium(II) (0.022 g, 0.030 mmol) in 1,4-dioxane (5 mL) was stirred at 100° C. 1 h. After cooling to rt, ethyl 5-bromo-2,6-dimethylnicotinate (165 mg, 0.639 mmol) and 1,1'-bis(di-tert-butylphosphino)ferrocenepalladium dichloride (19.84 mg, 0.030 mmol) was added and the mixture degassed with a nitrogen sparge for 5 min. 2M K$_3$PO$_4$ (aq) (0.913 mL, 1.826 mmol) was quickly added and the reaction mixture heated at 100° C. for 25 min. The reaction mixture was cooled to rt and concentrated onto Celite. The residue was loaded onto a 40 g ISCO column and purified by flash chromatography, eluting with 0-100% EtOAc in hexanes. Afforded product (255 mg, 0.474 mmol, 78% yield) as a crystalline beige solid.

MS ESI m/z 512.2 (M+H)

16E: Ethyl 5-(2-amino-[1,2,4]triazolo[1,5-a]pyridin-7-yl)-2,6-dimethylnicotinate: A mixture of 60D (205 mg, 0.401 mmol) in TFA (5 mL) was stirred at rt 45 min. The reaction mixture was concentrated to a solid. The crude solid was slurried in water and free-based utilizing SCX resin, washing with 7 N ammonia in methanol. Afforded ethyl 5-(2-amino-[1,2,4]triazolo[1,5-a]pyridin-7-yl)-2,6-dimethylnicotinate (105 mg, 0.331 mmol, 82% yield) as a white solid which was used as is in subsequent chemistry.

16F: 5-(2-Amino-[1,2,4]triazolo[1,5-a]pyridin-7-yl)-2,6-dimethylnicotinic acid, lithium salt: To a mixture of ethyl 5-(2-amino-[1,2,4]triazolo[1,5-a]pyridin-7-yl)-2,6-dimethylnicotinate (105 mg, 0.337 mmol) in tetrahydrofuran (3 mL) was added a solution of lithium hydroxide monohydrate (16.98 mg, 0.405 mmol) in water (1.5 mL). The reaction mixture was stirred ON at rt and concentrated in vacuo to a solid. Afforded 5-(2-amino-[1,2,4]triazolo[1,5-a]pyridin-7- yl)-2,6-dimethylnicotinic acid, lithium salt (99 mg, 0.322 mmol, 95% yield), a beige solid.

MS ESI m/z 284.1 (M+H)

16: A mixture of 5-(2-amino-[1,2,4]triazolo[1,5-a]pyridin-7-yl)-2,6-dimethylnicotinic acid, lithium salt (10 mg, 0.035 mmol), BOP (23.42 mg, 0.053 mmol), (2-(1-cyclopentylethoxy)phenyl)methanamine (7.74 mg, 0.035 mmol) and Hünig's Base (0.031 mL, 0.177 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(1-cyclopentylethoxy)benzyl)-2,6-dimethylnicotinamide (5.0 mg, 10.01 µmol, 28.4% yield).

$^1$H NMR (500 MHz, DMSO-d6) δ 8.72 (br t, J=5.5 Hz, 1H), 8.60 (d, J=6.7 Hz, 1H), 7.72 (s, 1H), 7.42 (s, 1H), 7.25-7.18 (m, 2H), 7.00-6.95 (m, 2H), 6.88 (br t, J=7.5 Hz, 1H), 6.04 (s, 2H), 4.42 (br d, J=5.5 Hz, 2H), 4.34 (br t, J=6.3 Hz, 1H), 2.58 (s, 3H), 2.48 (s, 3H), 2.12-2.08 (m, 1H), 1.78 (br s, 1H), 1.67 (br s, 1H), 1.56 (br s, 2H), 1.52-1.45 (m, 2H), 1.44-1.37 (m, 1H), 1.32-1.28 (m, 1H), 1.21 (br d, J=6.1 Hz, 3H).

MS ESI m/z 485 (M+H)

Example 17

5-{2-Amino-[1,2,4]triazolo[1,5-a]pyridin-7-yl}-N-{[3-(cyclopentyloxy)pyridin-2-yl]meth yl}-6-methylpyridine-3-carboxamide

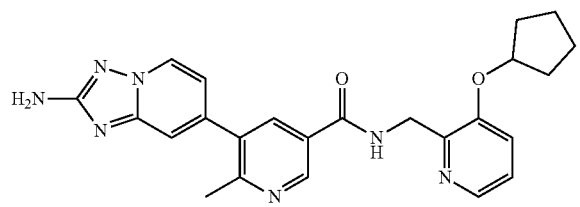 [SMILES: Cc1ncc(C(=O)NCc2ncccc2OC2CCCC2)cc1-c1ccn2nc(N)nc2c1]

17A: 3-(Cyclopentyloxy)picolinonitrile: Cyclopentanol (0.453 mL, 5.00 mmol) was added to a solution of 3-hydroxypicolinonitrile (300 mg, 2.498 mmol) and triphenylphosphine (1146 mg, 4.37 mmol) in THF (10 mL) at 0° C. DIAD (0.850 mL, 4.37 mmol) was added dropwise and the yellow solution was stirred at rt 3 d. The reaction mixture was concentrated to an oil and purified by flash chromatography eluting with 0-100% EtOAc/Hex. Afforded 3-(cyclopentyloxy)picolinonitrile (342 mg, 1.726 mmol, 69.1% yield) as a white solid.

$^1$H NMR (400 MHz, DMSO-d$_6$) δ 8.28 (dd, J=4.5, 1.2 Hz, 1H), 7.79 (dd, J=8.8, 1.1 Hz, 1H), 7.68 (dd, J=8.8, 4.5 Hz, 1H), 5.16-4.99 (m, 1H), 2.03-1.88 (m, 2H), 1.81-1.55 (m, 6H).

17B: (3-(Cyclopentyloxy)pyridin-2-yl)methanamine, HCl: To a solution of 3-(cyclopentyloxy)picolinonitrile (340 mg, 1.806 mmol) in THF (15 mL) at 65° C. was added borane-methyl sulfide complex, 2M in THF (2.71 mL, 5.42 mmol) dropwise over 10 min and the resulting mixture was refluxed for 2 h. After cooling to rt, HCl, 6N (1.174 mL, 7.04 mmol) was added dropwise to minimize rapid gas evolution. The mixture was brought back to reflux for 30 min. After cooling rt, the reaction mixture was concentrated and co-evaporated from THF/MeOH (3×) to afford a white solid that was triturated with THF. Filtration and drying afforded (3-(cyclopentyloxy)pyridin-2-yl)methanamine, HCl (399 mg, 1.483 mmol, 82% yield) as a white solid which was used as is in subsequent chemistry.

17C: A mixture of 1A (250 mg, 0.605 mmol), bis(pinacolato)diboron (192 mg, 0.756 mmol), potassium acetate (178 mg, 1.815 mmol) and PdCl2(dppf)-CH$_2$Cl$_2$ adduct (24.70 mg, 0.030 mmol) in dioxane (6 mL) was heated at 100° C. for 60 min. After cooling to rt, ethyl 5-bromo-6-methylnicotinate (150 mg, 0.615 mmol) and 1,1'-bis(di-tert-butylphosphino)ferrocenepalladium dichloride (20.03 mg, 0.031 mmol) were added. The reaction mixture was degassed by nitrogen sparge for 5 min. 2M K$_3$PO$_4$ (aq) (0.922 mL, 1.844 mmol) was quickly added and the reaction mixture heated at 100° C. for 15 min. After cooling to rt, volatiles were removed in vacuo. The crude residue was purified with column chromatography on the Isco system (40 g, 0-100% EtOAc/Hex to afford 17C (300 mg, 0.573 mmol, 93% yield) as a crystalline beige solid.

MS ESI m/z 498.0 (M+H)

17D: Ethyl 5-(2-amino-[1,2,4]triazolo[1,5-a]pyridin-7-yl)-6-methylnicotinate: A mixture of 87C (300 mg, 0.603 mmol) in TFA (5 mL) was stirred at rt 45 min. The reaction mixture was concentrated to a solid, then slurried in water. The slurry mixture was free-based utilizing SCX resin, washing with 10% ammonium hydroxide in methanol. Afforded ethyl 5-(2-amino-[1,2,4]triazolo[1,5-a]pyridin-7-yl)-6-methylnicotinate (111 mg, 0.373 mmol, 61.9% yield) as a white solid.

MS ESI m/z 298.1 (M+H)

17E: 5-(2-Amino-[1,2,4]triazolo[1,5-a]pyridin-7-yl)-6-methylnicotinic acid, lithium salt: To a mixture of ethyl 5-(2-amino-[1,2,4]triazolo[1,5-a]pyridin-7-yl)-6-methylnicotinate (111 mg, 0.373 mmol) in tetrahydrofuran (3 mL) was added a solution of lithium hydroxide monohydrate (18.80 mg, 0.448 mmol) in water (1.5 mL). After stirring ON at rt, the reaction mixture was concentrated to a solid. Afforded 5-(2-amino-[1,2,4]triazolo[1,5-a]pyridin-7-yl)-6-methylnicotinic acid, lithium salt (105 mg, 0.370 mmol, 99% yield) as a tan solid that was used as is in subsequent chemistry.

MS ESI m/z 298.1 (M+H)

17: A mixture of 5-(2-amino-[1,2,4]triazolo[1,5-a]pyridin-7-yl)-6-methylnicotinic acid, lithium salt (10 mg, 0.037 mmol), BOP (24.64 mg, 0.056 mmol), (3-(cyclopentyloxy)pyridin-2-yl)methanamine (7.14 mg, 0.037 mmol) and Hünig's Base (0.032 mL, 0.186 mmol) in DMF (1.0 mL) was stirred at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((3-(cyclopentyloxy)pyridin-2-yl)methyl)-6-methylnicotinamide (7.6 mg, 0.017 mmol, 45.2% yield).

$^1$H NMR (500 MHz, DMSO-d6) δ 9.00-8.87 (m, 2H), 8.63 (d, J=6.8 Hz, 1H), 8.16 (s, 1H), 8.04 (d, J=4.5 Hz, 1H), 7.45 (s, 1H), 7.39 (d, J=8.2 Hz, 1H), 7.25 (dd, J=8.2, 4.7 Hz, 1H), 6.98 (d, J=6.8 Hz, 1H), 6.09 (s, 2H), 4.90 (br. s., 1H), 4.57 (d, J=5.3 Hz, 2H), 2.54 (s, 3H), 1.96-1.82 (m, 2H), 1.77-1.61 (m, 4H), 1.56 (br. s., 2H).

MS ESI m/z 444.2 (M+H)

Example 18

5-{2-Amino-[1,2,4]triazolo[1,5-a]pyridin-7-yl}-N-{[2-(cyclopentylmethoxy)-4-fluorophenyl]methyl}-2-methylpyridine-3-carboxamide

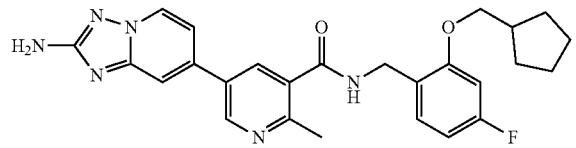 [SMILES: Cc1ncc(-c2ccn3nc(N)nc3c2)cc1C(=O)NCc1ccc(F)cc1OCC1CCCC1]

18A: (2-(Cyclopentylmethoxy)-4-fluorophenyl)methanamine was prepared from 4-fluoro-2-hydroxybenzonitrile and cyclopentylmethanol by the same method as intermediate 49B. Amine used as—is after filtration and evaporation.

18: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (2-(cyclopentylmethoxy)-4-fluorophenyl)methanamine (8.29 mg, 0.037 mmol) and Hünig's Base (0.032 mL, 0.186 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)-4-fluorobenzyl)-2-methylnicotinamide (8.5 mg, 0.017 mmol, 46.3% yield).

$^1$H NMR (500 MHz, DMSO-d6) δ 8.94 (s, 1H), 8.87 (t, J=5.3 Hz, 1H), 8.64 (d, J=7.0 Hz, 1H), 8.18 (s, 1H), 7.80 (s, 1H), 7.35-7.27 (m, 2H), 6.89 (d, J=11.2 Hz, 1H), 6.76-6.70 (m, 1H), 4.42 (d, J=5.2 Hz, 2H), 3.90 (d, J=6.6 Hz, 2H), 2.59 (s, 3H), 2.32 (dt, J=14.6, 7.4 Hz, 1H), 1.77 (d, J=6.9 Hz, 2H), 1.63-1.42 (m, 4H), 1.42-1.29 (m, 2H)[2 protons from on methylene group lost in water suppression].

MS ESI m/z 475.2 (M+H)

Example 19

5-{2-Amino-[1,2,4]triazolo[1,5-a]pyridin-7-yl}-2-cyclopropyl-N-{[3-(trifluoromethoxy)phenyl]methyl}pyridine-3-carboxamide

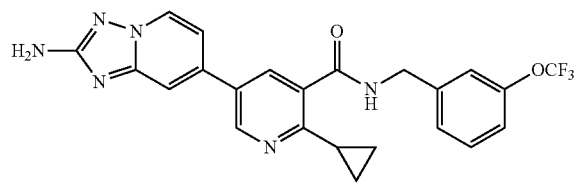 [SMILES: Nc1nc2cc(-c3cnc(C4CC4)c(C(=O)NCc4cccc(OC(F)(F)F)c4)c3)ccn2n1]

19A: Ethyl 5-(2-((tert-butoxycarbonyl)amino)-[1,2,4]triazolo[1,5-a]pyridin-7-yl)-2-cyclopropylnicotinate: To a solution of 7-bromo-[1,2,4]triazolo[1,5-a]pyridin-2-(di-t-butoxy carbonyl)amine (200 mg, 0.386 mmol), tri-tert-butylphosphonium tetrafluoroborate (13.44 mg, 0.046 mmol), palladium(II) acetate (8.67 mg, 0.039 mmol) and zinc bromide (26.1 mg, 0.116 mmol) in THF (1 mL) at rt was added cyclopropylmagnesium bromide, 0.5 M THF (1.236 mL, 0.618 mmol) dropwise over 5 min. The reaction mixture was allowed to stir at rt for 2 h. Additional cyclopropylmagnesium bromide, 0.5 M THF (1.236 mL, 0.618 mmol) was added and stirring was continued for 2 h. The reaction mixture was partitioned between EtOAc (30 ml) and water (30 ml). The organic layer was washed with brine (25 ml), dried over anhydrous sodium sulfate and concentrated to afford a residue that was chromatographed on a 12 g ISCO silica gel cartridge, eluting with a 0-100% EtOAc/Hex gradient. The pure fractions were concentrated to afford ethyl 5-(2-((tert-butoxycarbonyl)amino)-[1,2,4]triazolo[1,5-a]pyridin-7-yl)-2-cyclopropylnicotinate (57 mg, 0.135 mmol, 34.9% yield) as a white solid.

MS ESI m/z 424.0 (M+H).

19B: 5-(2-((tert-Butoxycarbonyl)amino)-[1,2,4]triazolo[1,5-a]pyridin-7-yl)-2-cyclopropylnicotinic acid: A mixture of ethyl 5-(2-((tert-butoxycarbonyl)amino)-[1,2,4]triazolo[1,5-a]pyridin-7-yl)-2-cyclopropylnicotinate (57 mg, 0.135 mmol) and NaOH, 1N (0.404 mL, 0.404 mmol) in methanol (0.4 mL) and THF (0.4 mL) was stirred at rt for 5 h. The methanol and THF were removed on the rotoevaporator and the residue was diluted with water (5 ml). The pH was adjusted to ~1 with 1 N HCl and the resulting suspension was filtered and dried to afford 5-(2-((tert-butoxycarbonyl)amino)-[1,2,4]triazolo[1,5-a]pyridin-7-yl)-2-cyclopropylnicotinic acid (47 mg, 0.119 mmol, 88% yield) as a white solid.

MS ESI m/z 396.2 (M+H).

19C: tert-Butyl (7-(6-cyclopropyl-5-((3-(trifluoromethoxy)benzyl)carbamoyl)pyridin-3-yl)-[1,2,4]triazolo[1,5-a]pyridin-2-yl)carbamate: A mixture of 5-(2-((tert-butoxycarbonyl)amino)-[1,2,4]triazolo[1,5-a]pyridin-7-yl)-2-cyclopropylnicotinic acid (12 mg, 0.030 mmol), (3-(trifluoromethoxy)phenyl)methanamine (8.70 mg, 0.046 mmol), BOP (14.76 mg, 0.033 mmol) and Et$_3$N (0.013 mL, 0.091 mmol) in THF (0.25 mL) was stirred at rt for 18 h. The volatiles were removed in vacuo and the residue was taken directly into the deprotection step.

MS ESI m/z 569.2 (M+H).

19: tert-Butyl (7-(6-cyclopropyl-5-((3-(trifluoromethoxy)benzyl)carbamoyl)pyridin-3-yl)-[1,2,4]triazolo [1,5-a]pyridin-2-yl)carbamate (17 mg, 0.030 mmol) was dissolved in TFA (69.1 µl, 0.897 mmol) and the solution allowed to stand at rt for 5 h. The volatiles were removed in vacuo. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 19 min, then a 5-minute hold at 100% B; Flow: 20 mL/min. Fractions containing the desired product were combined and dried via centrifugal evaporation.

$^1$H NMR (500 MHz, DMSO-d6) δ 9.25 (t, J=5.8 Hz, 1H), 8.91 (s, 1H), 8.62 (d, J=6.9 Hz, 1H), 8.13 (s, 1H), 7.77 (s, 1H), 7.54-7.46 (m, 1H), 7.43 (d, J=7.6 Hz, 1H), 7.36 (s, 1H), 7.28 (dd, J=12.2, 7.7 Hz, 2H), 6.08 (s, 2H), 4.57 (d, J=5.9 Hz, 2H), 2.47 (br. s., 1H), 1.04 (br. s., 2H), 0.99-0.90 (m, 2H).

MS ESI m/z 469.1 (M+H)

Example 20

5-{2-Amino-[1,2,4]triazolo[1,5-a]pyridin-7-yl}-N-{[2-(cyclopentylmethoxy)-5-fluorophenyl]methyl}-2-methylpyridine-3-carboxamide

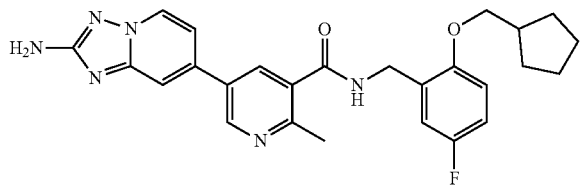 [SMILES: Cc1ncc(-c2ccn3nc(N)nc3c2)cc1C(=O)NCc1cc(F)ccc1OCC1CCCC1]

20A: (2-(Cyclopentylmethoxy)-5-fluorophenyl)methanamine was prepared from 5-fluoro-2-hydroxybenzonitrile and cyclopentylmethanol by the same method as intermediate 49B. Amine used as—is after filtration and evaporation.

20: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (2-(cyclopentylmethoxy)-5-fluorophenyl)methanamine (8.29 mg, 0.037 mmol) and Hünig's Base (0.032 mL, 0.186 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)-5-fluorobenzyl)-2-methylnicotinamide (8.3 mg, 0.017 mmol, 44.7% yield).

$^1$H NMR (500 MHz, DMSO-d6) δ 8.98-8.87 (m, 1H), 8.63 (d, J=7.0 Hz, 1H), 8.21 (s, 1H), 7.80 (s, 1H), 7.32 (d, J=6.7 Hz, 1H), 7.11 (d, J=9.2 Hz, 1H), 7.08-6.96 (m, 2H), 6.06 (s, 2H), 4.47 (d, J=5.2 Hz, 2H), 3.88 (d, J=6.7 Hz, 2H), 2.60 (s, 3H), 2.33 (dt, J=14.6, 7.2 Hz, 1H), 1.78 (d, J=7.6 Hz, 2H), 1.63-1.46 (m, 4H), 1.37 (dd, J=12.1, 6.6 Hz, 2H).

MS ESI m/z 475 (M+H)

Example 21

5-{2-Amino-[1,2,4]triazolo[1,5-a]pyridin-7-yl}-N-{[4-(cyclopentyloxy)pyridin-3-yl]methyl}-2-methoxypyridine-3-carboxamide

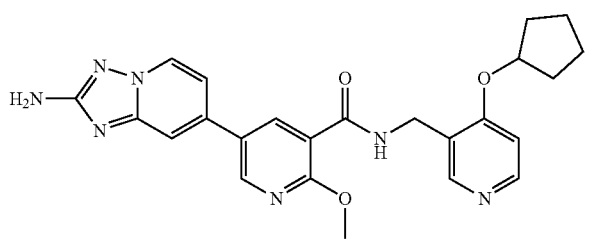 [SMILES: COc1ncc(-c2ccn3nc(N)nc3c2)cc1C(=O)NCc1cnccc1OC1CCCC1]

21A: 3-Bromo-4-(cyclopentyloxy)pyridine: DIAD (0.712 mL, 3.66 mmol) was added dropwise to a solution of 3-bromopyridin-4-ol (425 mg, 2.443 mmol), cyclopentanol (0.443 mL, 4.89 mmol) and triphenylphosphine (961 mg, 3.66 mmol) at 0° C. This solution was stirred at rt 3 d. The reaction mixture was concentrated to an oil and purified by flash chromatography eluting with 0-70% EtOAc in hexanes. A second column eluting with 0-5% MeOH in DCM was necessary to obtain pure product. Afforded 3-bromo-4-(cyclopentyloxy)pyridine (475 mg, 1.962 mmol, 80% yield) as a colorless oil.

21B: 4-(Cyclopentyloxy)nicotinonitrile: A mixture of 3-bromo-4-(cyclopentyloxy)pyridine (380 mg, 1.570 mmol), potassium ferrocyanide (127 mg, 0.345 mmol), sodium carbonate (166 mg, 1.570 mmol), and palladium acetate (17.62 mg, 0.078 mmol) was degassed by bubbling nitrogen through it for 5 min. After degassing was complete, the mixture was stirred and heated at 120° C. 45 h. The reaction mixture was concentrated to an oil which was purified by flash chromatography eluting with 0-70% EtOAc in hexanes. A second column eluting from 0-5% MeOH in DCM was necessary to obtain pure product. Afforded 4-(cyclopentyloxy)nicotinonitrile (110 mg, 0.573 mmol, 36.5% yield) as a colorless oil.

21C: (4-(Cyclopentyloxy)pyridin-3-yl)methanamine: To a solution of 4-(cyclopentyloxy)nicotinonitrile (92 mg, 0.489 mmol) in tetrahydrofuran (3 mL) and methanol (1.200 mL) and cooled to 0° C. was added a solution of cobalt(II) chloride hexahydrate (34.9 mg, 0.147 mmol) in water (1 mL). Sodium borohydride (114.7 mg, 3.032 mmol) was slowly added in portions. The reaction mixture was stirred at rt ON. The reaction mixture was concentrated onto Celite and purified by flash chromatography, eluting with 0-10% [1% ammonium hydroxide in methanol] in DCM. Afforded (4-(cyclopentyloxy)pyridin-3-yl)methanamine (55 mg, 0.272 mmol, 55.6% yield) as a colorless oil. Amine used as is after filtration and evaporation.

21: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (4-(cyclopentyloxy)pyridin-3-yl)methanamine (7.41 mg, 0.039 mmol) and Hünig's Base (0.031 mL, 0.175 mmol) in DMF (1.0 mL) was stirred at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((4-(cyclopentyloxy)pyridin-3-yl)methyl)-2-methoxynicotinamide (7.4 mg, 0.016 mmol, 45.0% yield).

$^1$H NMR (500 MHz, DMSO-d6) δ 8.78-8.68 (m, 2H), 8.57 (d, J=6.7 Hz, 1H), 8.43 (s, 1H), 8.34-8.27 (m, 2H), 7.67 (s, 1H), 7.25 (d, J=6.9 Hz, 1H), 7.04 (d, J=5.5 Hz, 1H), 6.04 (s, 2H), 4.98 (br. s., 1H), 4.44 (d, J=5.5 Hz, 2H), 4.02 (s, 3H), 1.94 (d, J=6.2 Hz, 2H), 1.80-1.63 (m, 4H), 1.59 (br. s., 2H).

MS ESI m/z 460.1 (M+H)

Example 22

5-{2-Amino-[1,2,4]triazolo[1,5-a]pyridin-7-yl}-N-{[3,5-difluoro-2-(propan-2-yloxy)phen yl]methyl}-2-methoxypyridine-3-carboxamide

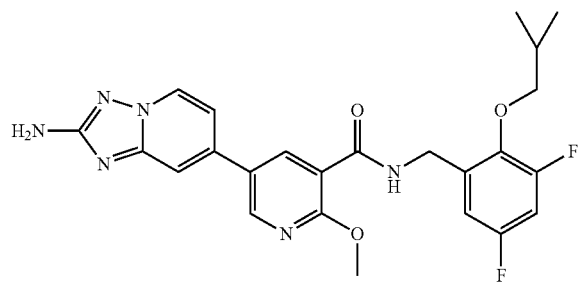 [SMILES: COc1ncc(-c2ccn3nc(N)nc3c2)cc1C(=O)NCc1cc(F)cc(F)c1OCC(C)C]

22A: (3,5-Difluoro-2-(isopropyloxy)phenyl)methanamine was prepared from 3,5-difluoro-2-hydroxybenzonitrile and isopropanol by the same method as intermediate 49B. Amine used as—is after filtration and evaporation.

22: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (3,5-difluoro-2-isopropoxyphenyl)methanamine (7.05 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3,5-difluoro-2-isopropoxybenzyl)-2-methoxynicotinamide (6.5 mg, 0.014 mmol, 38.8% yield).

$^1$H NMR (500 MHz, DMSO-d6) δ 8.92 (t, J=5.8 Hz, 1H), 8.78 (s, 1H), 8.60 (d, J=6.9 Hz, 1H), 8.45 (s, 1H), 7.72 (s, 1H), 7.29-7.13 (m, 2H), 7.00 (d, J=9.1 Hz, 1H), 6.06 (s, 2H), 4.59-4.51 (m, 2H), 4.44-4.32 (m, 1H), 4.05 (s, 3H), 1.30 (d, J=6.0 Hz, 6H).

MS ESI m/z 468.8 (M+H)

Example 23

5-{2-Amino-[1,2,4]triazolo[1,5-a]pyridin-7-yl}-N-({2-fluoro-6-[(3-methylcyclopentyl)oxy]phenyl}methyl)-2-methoxypyridine-3-carboxamide

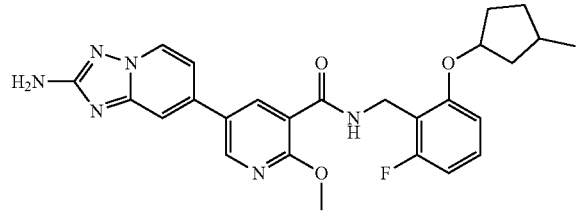 [SMILES: COc1ncc(-c2ccn3nc(N)nc3c2)cc1C(=O)NCc1c(F)cccc1OC1CCC(C)C1]

23A: (2-Fluoro-6-((3-methylcyclopentyl)oxy)phenyl)methanamine was prepared from 2-fluoro-6-hydroxybenzonitrile and racemic 3-methylcyclopentanol by the same method as intermediate 49B. Amine used as—is after filtration and evaporation.

23: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (2-fluoro-6-((3-methylcyclopentyl)oxy)phenyl)methanamine (7.83 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-85% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-fluoro-6-((3-methylcyclopentyl)oxy) benzyl)-2-methoxynicotinamide (8.3 mg, 0.017 mmol, 47.3% yield).

$^1$H NMR (500 MHz, DMSO-d6) δ 8.76 (br. s., 1H), 8.61 (d, J=6.8 Hz, 1H), 8.44 (br. s., 1H), 8.37 (d, J=4.9 Hz, 1H), 7.69 (s, 1H), 7.34-7.16 (m, 2H), 6.87-6.65 (m, 2H), 6.07 (s, 2H), 4.98-4.83 (m, 1H), 4.54 (d, J=5.3 Hz, 2H), 4.02 (s, 3H), 2.17 (br. s., 1H), 2.02-1.68 (m, 3H), 1.51-1.38 (m, 1H), 1.32 (d, J=9.4 Hz, 1H), 1.22-1.05 (m, 1H), 1.02-0.91 (m, 3H).

MS ESI m/z 491.2 (M+H)

Example 24

5-{2-Amino-[1,2,4]triazolo[1,5-a]pyridin-7-yl}-N-{[2-(cyclopropylmethoxy)-4-fluorophenyl]methyl}-2-methylpyridine-3-carboxamide

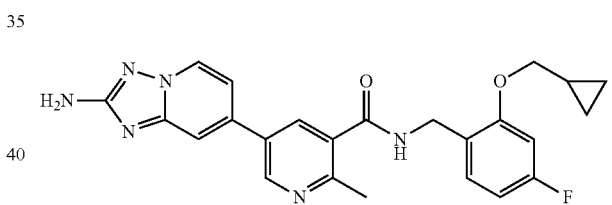

24A: (2-(Cyclopropylmethoxy)-4-fluorophenyl)methanamine was prepared from 4-fluoro-2-hydroxybenzonitrile and cyclopropylmethanol by the same method as intermediate 49B. Amine used crude after filtration and evaporation.

24: A mixture of 5-(2-amino-[1,2,4]triazolo[1,5-a]pyridin-7-yl)-2-methylnicotinic acid (10 mg, 0.037 mmol), BOP (24.64 mg, 0.056 mmol), (2-(cyclopropylmethoxy)-4-fluorophenyl)methanamine (7.25 mg, 0.037 mmol) and Hünig's Base (0.032 mL, 0.186 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)-4-fluorobenzyl)-2-methylnicotinamide (7.6 mg, 0.016 mmol, 43.5% yield).

$^1$H NMR (500 MHz, DMSO-d6) δ 8.95 (s, 1H), 8.89 (br. s., 1H), 8.64 (d, J=6.8 Hz, 1H), 8.19 (s, 1H), 7.81 (s, 1H), 7.37-7.28 (m, 2H), 6.88 (d, J=11.0 Hz, 1H), 6.75 (t, J=8.3 Hz, 1H), 4.45 (d, J=5.1 Hz, 2H), 3.89 (d, J=6.3 Hz, 2H), 3.47-3.10 (m, 2H), 2.59 (s, 3H), 1.25 (br. s., 1H), 0.56 (d, J=7.4 Hz, 2H), 0.35 (d, J=4.1 Hz, 2H).

MS ESI m/z 446.8 (M+H)

Example 25

5-{2-Amino-[1,2,4]triazolo[1,5-a]pyridin-7-yl}-N-{[2-(cyclobutylmethoxy)-6-fluorophenyl]methyl}-6-methoxypyridine-3-carboxamide

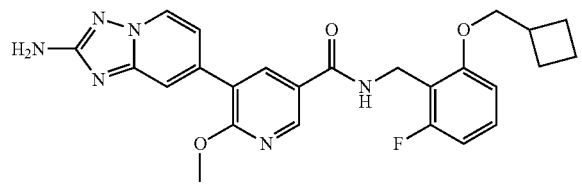 [SMILES: COc1ncc(C(=O)NCc2c(F)cccc2OCC2CCC2)cc1-c1ccn2nc(N)nc2c1]

A mixture of 5-(2-amino-[1,2,4]triazolo[1,5-a]pyridin-7-yl)-6-methoxynicotinic acid (10 mg, 0.035 mmol), BOP (23.26 mg, 0.053 mmol), (2-(cyclobutylmethoxy)-6-fluorophenyl)methanamine (7.34 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclobutylmethoxy)-6-fluorobenzyl)-6-methoxynicotinamide (5.5 mg, 10.97 μmol, 31.3% yield).

$^1$H NMR (500 MHz, DMSO-d$_6$) δ 8.68 (s, 1H), 8.63-8.54 (m, 2H), 8.30 (s, 1H), 7.57 (s, 1H), 7.30 (q, J=8.1 Hz, 1H), 7.11 (br d, J=6.9 Hz, 1H), 6.86 (br d, J=8.4 Hz, 1H), 6.80 (br t, J=8.8 Hz, 1H), 6.05 (s, 2H), 4.52 (br d, J=4.0 Hz, 2H), 3.97 (s, 5H), 2.76-2.62 (m, 1H), 1.97 (br d, J=8.2 Hz, 2H), 1.90-1.73 (m, 4H).

MS ESI m/z 477 (M+H)

Example 26

5-{2-Amino-[1,2,4]triazolo[1,5-a]pyridin-7-yl}-N-{[2-(cyclopropylmethoxy)-6-fluorophenyl]methyl}-6-methoxypyridine-3-carboxamide

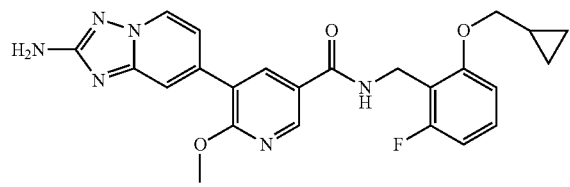

26A: (2-(Cyclopropylmethoxy)-6-fluorophenyl)methanamine was prepared from 2-fluoro-6-hydroxybenzonitrile and cyclopropylmethanol by the same method as intermediate 49B.

$^1$H NMR (400 MHz, DMSO-d$_6$) δ 7.18 (td, J=8.3, 7.1 Hz, 1H), 6.79 (d, J=8.4 Hz, 1H), 6.73 (t, J=8.9 Hz, 1H), 3.88 (d, J=6.8 Hz, 2H), 3.68 (d, J=1.5 Hz, 2H), 1.60 (br. s., 2H), 1.32-1.19 (m, 1H), 0.61-0.53 (m, 2H), 0.37-0.31 (m, 2H).

26B: A mixture of 1A (378 mg, 0.915 mmol), bis(pinacolato)diboron (290 mg, 1.143 mmol), potassium acetate (269 mg, 2.74 mmol) and PdCl2(dppf)-CH$_2$Cl$_2$ adduct (37.3 mg, 0.046 mmol) in dioxane (4 mL) was heated at 100° C. for 60 min. After cooling to rt, methyl 5-bromo-6-methoxynicotinate (154 mg, 0.625 mmol) and 1,1'-bis(di-tert-butylphosphino)ferrocenepalladium dichloride (19.39 mg, 0.030 mmol) were added and the mixture degassed by nitrogen sparge for 5 min. 2M K$_3$PO$_4$ (aq) (0.892 mL, 1.785 mmol) was quickly added and the reaction mixture heated at 100° C. for 15 min. The reaction mixture was cooled to rt and volatiles removed in vacuo. The crude residue was loaded onto a 40 g ISCO column and purified by flash chromatography, eluting with 0-100% EtOAc in hexanes. Afforded product (301 mg, 0.572 mmol, 96% yield) as a crystalline beige solid.

MS ESI m/z 499.9 (M+H)

26C: Methyl 5-(2-amino-[1,2,4]triazolo[1,5-a]pyridin-7-yl)-6-methoxynicotinate: A mixture of 26B (300 mg, 0.601 mmol) in TFA (5 mL) was stirred at rt for 45 min. The reaction mixture was concentrated to a solid and slurried in water. The slurry was free-based using SCX resin, washing with 10% ammonium hydroxide in methanol.

Afforded methyl 5-(2-amino-[1,2,4]triazolo[1,5-a]pyridin-7-yl)-6-methoxynicotinate (175 mg, 0.526 mmol, 88% yield) as a white solid.

MS ESI m/z 300.1 (M+H)

26D: Lithium 5-(2-amino-[1,2,4]triazolo[1,5-a]pyridin-7-yl)-6-methoxynicotinate: To a mixture of methyl 5-(2-amino-[1,2,4]triazolo[1,5-a]pyridin-7-yl)-6-methoxynicotinate (175 mg, 0.585 mmol) in tetrahydrofuran (5 mL) was added a solution of lithium hydroxide monohydrate (29.4 mg, 0.702 mmol) in water (1.5 mL). After stirring at rt 1 h, the reaction mixture was concentrated to a solid to afford lithium 5-(2-amino-[1,2,4]triazolo[1,5-a]pyridin-7-yl)-6-methoxynicotinate (166 mg, 0.513 mmol, 88% yield), an off-white solid.

MS ESI m/z 285.8 (M+H)

26: A mixture of 5-(2-amino-[1,2,4]triazolo[1,5-a]pyridin-7-yl)-6-methoxynicotinic acid, lithium salt (10 mg, 0.035 mmol), BOP (23.26 mg, 0.053 mmol), (2-(cyclopropylmethoxy)-6-fluorophenyl)methanamine (6.84 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)-6-fluorobenzyl)-6-methoxynicotinamide (4.5 mg, 9.54 μmol, 27.2% yield).

$^1$H NMR (500 MHz, DMSO-d6) δ 8.69 (s, 1H), 8.65-8.53 (m, 2H), 8.31 (s, 1H), 7.59 (s, 1H), 7.28 (q, J=7.9 Hz, 1H), 7.12 (d, J=6.9 Hz, 1H), 6.88-6.75 (m, 2H), 6.05 (s, 2H), 4.52 (d, J=4.2 Hz, 2H), 3.97 (s, 3H), 3.88 (d, J=6.7 Hz, 2H), 1.26-1.14 (m, 1H), 0.51-0.40 (m, 2H), 0.29 (d, J=4.7 Hz, 2H).

MS ESI m/z 463 (M+H)

Example 27

5-{2-Amino-[1,2,4]triazolo[1,5-a]pyridin-7-yl}-N-{[2-(cyclopentyloxy)-5-fluorophenyl] methyl}-6-methoxypyridine-3-carboxamide

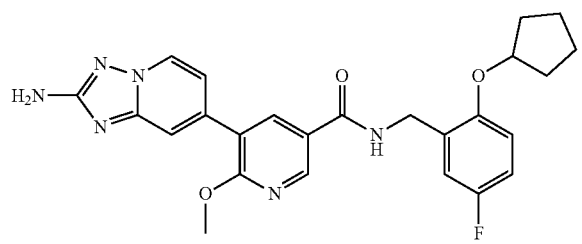 [SMILES: COc1ncc(C(=O)NCc2cc(F)ccc2OC2CCCC2)cc1-c1ccn2nc(N)nc2c1]

27A: (2-(Cyclopentyloxy)-5-fluorophenyl)methanamine was prepared from 2-fluoro-5-hydroxybenzonitrile and cyclopentanol by the same method as intermediate 49B. Amine used crude after filtration and evaporation.

27: A mixture of 5-(2-amino-[1,2,4]triazolo[1,5-a]pyridin-7-yl)-6-methoxynicotinic acid (10 mg, 0.035 mmol), BOP (23.26 mg, 0.053 mmol), (2-(cyclopentyloxy)-5-fluorophenyl)methanamine (7.34 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-5-fluorobenzyl)-6-methoxynicotinamide (6.5 mg, 0.013 mmol, 38.1% yield).

$^1$H NMR (500 MHz, DMSO-d6) δ 8.99-8.89 (m, 1H), 8.73 (s, 1H), 8.58 (d, J=7.0 Hz, 1H), 8.36 (s, 1H), 7.62 (s, 1H), 7.15 (d, J=6.7 Hz, 1H), 7.06-6.92 (m, 3H), 6.03 (s, 2H), 4.83 (br. s., 1H), 4.42 (d, J=5.5 Hz, 2H), 3.99 (s, 3H), 1.86 (br. s., 2H), 1.80-1.63 (m, 4H), 1.56 (br. s., 2H).

MS ESI m/z 476.9 (M+H)

Example 28

5-{2-Amino-[1,2,4]triazolo[1,5-a]pyridin-7-yl}-N-{[2-(cyclopropylmethoxy)phenyl]methyl}-6-methoxypyridine-3-carboxamide

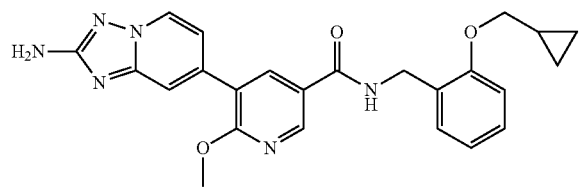 [SMILES: COc1ncc(C(=O)NCc2ccccc2OCC2CC2)cc1-c1ccn2nc(N)nc2c1]

A mixture of lithium 5-(2-amino-[1,2,4]triazolo[1,5-a]pyridin-7-yl)-6-methoxynicotinate (11 mg, 0.038 mmol), BOP (25.06 mg, 0.057 mmol), (2-(cyclopropylmethoxy)phenyl)methanamine (8.70 mg, 0.049 mmol) and Hünig's Base (0.033 mL, 0.189 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)benzyl)-6-methoxynicotinamide (5.8 mg, 0.013 mmol, 33.2% yield).

$^1$H NMR (500 MHz, DMSO-d6) δ 8.95 (t, J=5.5 Hz, 1H), 8.74 (d, J=2.1 Hz, 1H), 8.57 (d, J=7.0 Hz, 1H), 8.36 (d, J=1.8 Hz, 1H), 7.61 (s, 1H), 7.23-7.18 (m, 2H), 7.16 (d, J=5.5 Hz, 1H), 6.95 (d, J=8.5 Hz, 1H), 6.89 (t, J=7.3 Hz, 1H), 6.02 (s, 2H), 4.50 (d, J=5.5 Hz, 2H), 3.98 (s, 3H), 3.87 (d, J=6.7 Hz, 2H), 1.23 (br. s., 1H), 0.53 (d, J=7.0 Hz, 2H), 0.32 (d, J=4.6 Hz, 2H).

MS ESI m/z 444.9 (M+H)

Example 29

5-{2-Amino-[1,2,4]triazolo[1,5-a]pyridin-7-yl}-N-{[2-fluoro-6-(propan-2-yloxy)phenyl] methyl}-2-methoxypyridine-3-carboxamide

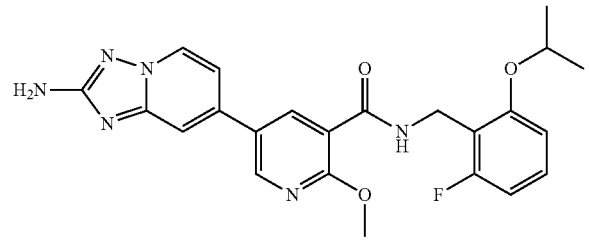 [SMILES: COc1ncc(-c2ccn3nc(N)nc3c2)cc1C(=O)NCc1c(F)cccc1OC(C)C]

29A: (2-Fluoro-6-(isopropyloxy)phenyl)methanamine was prepared from 2-fluoro-6-hydroxybenzonitrile and isopropanol by the same method as intermediate 49B. Amine used as—is after filtration and evaporation.

29: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (2-fluoro-6-isopropoxyphenyl)methanamine (6.42 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-fluoro-6-isopropoxybenzyl)-2-methoxynicotinamide (4.4 mg, 9.57 μmol, 27.3% yield).

$^1$H NMR (500 MHz, DMSO-d6) δ8.75 (d, J=2.4 Hz, 1H), 8.59 (d, J=7.0 Hz, 1H), 8.47 (d, J=2.1 Hz, 1H), 8.41 (t, J=5.3 Hz, 1H), 7.68 (s, 1H), 7.32-7.25 (m, 1H), 7.21 (d, J=7.0 Hz, 1H), 6.90 (d, J=8.5 Hz, 1H), 6.77 (t, J=8.7 Hz, 1H), 6.04 (s, 2H), 4.71 (dt, J=11.9, 6.0 Hz, 1H), 4.55 (d, J=5.5 Hz, 2H), 4.03 (s, 3H), 1.32 (d, J=6.1 Hz, 6H).

MS ESI m/z 451.2 (M+H)

Example 30

5-{2-Amino-[1,2,4]triazolo[1,5-a]pyridin-7-yl}-N-({2-[(1R,2R,4S)-bicyclo[2.2.1]heptan-2-yloxy]phenyl}methyl)-2-methoxypyridine-3-carboxamide

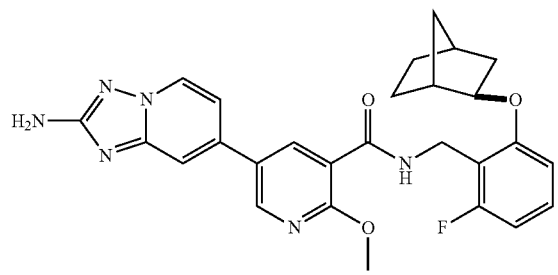

30A: (2-((1R,2S,4S)-Bicyclo[2.2.1]heptan-2-yloxy)phenyl)methanamine was prepared from 2-hydroxybenzonitrile and endo-norborneol by the same method as intermediate 49B. Amine used as—is after filtration and evaporation.

30: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (2-((1R,2S,4S)-bicyclo[2.2.1]heptan-2-yloxy)phenyl)methanamine (7.62 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-((1R,2S,4S)-bicyclo[2.2.1]heptan-2-yloxy)benzyl)-2-methoxynicotinamide (9.5 mg, 0.019 mmol, 54.8% yield).

$^1$H NMR (500 MHz, DMSO-d6) δ 8.76 (d, J=2.1 Hz, 1H), 8.65-8.55 (m, 2H), 8.47 (d, J=2.1 Hz, 1H), 7.70 (s, 1H), 7.29-7.19 (m, 3H), 6.94 (d, J=8.2 Hz, 1H), 6.89 (t, J=7.3 Hz, 1H), 6.04 (s, 2H), 4.46 (d, J=5.8 Hz, 2H), 4.33 (d, J=6.1 Hz, 1H), 4.04 (s, 3H), 2.39 (br. s., 1H), 2.29 (br. s., 1H), 1.81 (dd, J=12.7, 6.0 Hz, 1H), 1.61 (d, J=9.5 Hz, 1H), 1.57-1.39 (m, 3H), 1.25-1.08 (m, 3H).

MS ESI m/z 485 (M+H)

Example 31

5-{2-Amino-[1,2,4]triazolo[1,5-a]pyridin-7-yl}-N-{[5-fluoro-2-(propan-2-yloxy)phenyl]methyl}-2-methoxypyridine-3-carboxamide

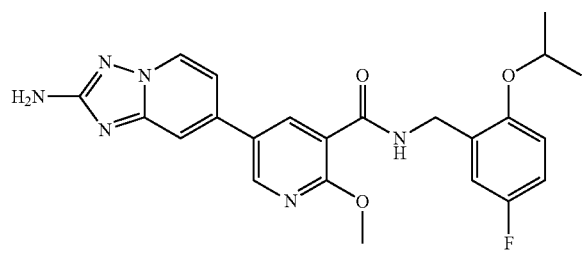 [SMILES: COc1ncc(-c2ccn3nc(N)nc3c2)cc1C(=O)NCc1cc(F)ccc1OC(C)C]

31A: (5-Fluoro-2-(isopropyloxy)phenyl)methanamine was prepared from 5-fluoro-2-hydroxybenzonitrile and isopropanol by the same method as intermediate 49B. Amine used as—is after filtration and evaporation.

31: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (5-fluoro-2-isopropoxyphenyl)methanamine (6.42 mg, 0.035 mmol) and Hünig's Base (0.031 mL, 0.175 mmol) in DMF (1.0 mL) was stirred at rt for 1 h. Hz, 2H), 4.06 (s, 3H), 1.30 (d, J=6.0 Hz, 6H) The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(5-fluoro-2-isopropoxybenzyl)-2-methoxynicotinamide (7.6 mg, 0.017 mmol, 47.2% yield).

$^1$H NMR (500 MHz, DMSO-d6) δ 8.84-8.73 (m, 2H), 8.61 (d, J=7.0 Hz, 1H), 8.47 (d, J=2.3 Hz, 1H), 7.73 (s, 1H), 7.26 (d, J=7.1 Hz, 1H), 7.09 (d, J=9.0 Hz, 1H), 7.04 (d, J=5.9 Hz, 2H), 6.07 (s, 2H), 4.61 (dt, J=12.0, 6.0 Hz, 1H), 4.46 (d, J=5.9 Hz, 2H), 4.06 (s, 3H), 1.30 (d, J=6.0 Hz, 6H).

MS ESI m/z 451 (M+H)

Example 32

5-{2-Amino-[1,2,4]triazolo[1,5-a]pyridin-7-yl}-2-methoxy-N-({2-[(3-methylcyclopentyl) oxy]phenyl}methyl)pyridine-3-carboxamide

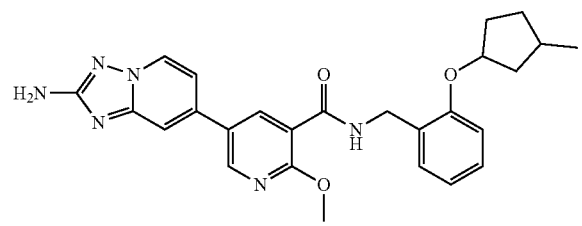 [SMILES: COc1ncc(-c2ccn3nc(N)nc3c2)cc1C(=O)NCc1ccccc1OC1CCC(C)C1]

32A: (2-((3-Methylcyclopentyl)oxy)phenyl)methanamine was prepared from 2-hydroxybenzonitrile and racemic 3-methylcyclopentanol by the same method as intermediate 49B. Amine used as—is after filtration and evaporation.

32: A mixture of lithium 5-(2-amino-[1,2,4]triazolo[1,5-a]pyridin-7-yl)-2-methoxynicotinate (10 mg, 0.034 mmol), BOP (22.78 mg, 0.052 mmol), (2-((3-methylcyclopentyl)oxy)phenyl)methanamine (8.46 mg, 0.041 mmol) and Hünig's Base (0.030 mL, 0.172 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-methoxy-N-(2-((3-methylcyclopentyl)oxy)benzyl)nicotinamide (7.8 mg, 0.016 mmol, 47.1% yield).

$^1$H NMR (500 MHz, DMSO-d6) δ 8.76 (s, 1H), 8.66-8.54 (m, 2H), 8.47 (br. s., 1H), 7.69 (s, 1H), 7.31-7.15 (m, 3H), 6.94 (d, J=7.9 Hz, 1H), 6.88 (t, J=7.3 Hz, 1H), 6.03 (s, 1H), 4.98-4.78 (m, 1H), 4.52-4.40 (m, 2H), 4.04 (s, 3H), 3.47-3.41 (m, 2H), 2.16 (d, J=5.8 Hz, 1H), 2.04-1.62 (m, 3H), 1.51-1.08 (m, 2H), 1.06-0.93 (m, 3H).

MS ESI m/z 473.2 (M+H)

Example 33

5-{2-Amino-[1,2,4]triazolo[1,5-a]pyridin-7-yl}-N-{[3-(cyclopropylmethoxy)pyridin-2-yl]methyl}-2-methoxy-6-methylpyridine-3-carboxamide

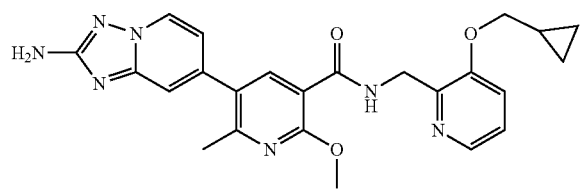 [SMILES: COc1nc(C)c(-c2ccn3nc(N)nc3c2)cc1C(=O)NCc1ncccc1OCC1CC1]

33A: (3-(Cyclopropylmethoxy)pyridin-2-yl)methanamine was prepared from 3-hydroxypicolinonitrile and cyclpropylmethanol by the same method as intermediate 37A. Amine used as—is after filtration and concentration.

33: A mixture of lithium 5-(2-amino-[1,2,4]triazolo[1,5-a]pyridin-7-yl)-2-methoxy-6-methylnicotinate (10 mg, 0.033 mmol), BOP (21.74 mg, 0.049 mmol), (3-(cyclopropylmethoxy)pyridin-2-yl)methanamine (5.84 mg, 0.033 mmol) and Hünig's Base (0.029 mL, 0.164 mmol) in DMF (1.0 mL) was stirred at rt for 90 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((3-(cyclopropylmethoxy)pyridin-2-yl) methyl)-2-methoxy-6-methylnicotinamide (7.7 mg, 0.016 mmol, 50.1% yield).

$^1$H NMR (500 MHz, DMSO-d6) δ 9.33 (br. s., 1H), 8.59 (d, J=6.8 Hz, 1H), 8.27-8.13 (m, 2H), 7.47-7.36 (m, 2H), 7.31 (dd, J=7.8, 4.9 Hz, 1H), 6.92 (d, J=6.7 Hz, 1H), 6.06 (s, 2H), 4.62 (d, J=4.1 Hz, 2H), 4.13 (s, 3H), 3.95 (d, J=6.8 Hz, 2H), 2.54 (s, 3H), 1.36-1.22 (m, 1H), 0.60 (d, J=7.7 Hz, 2H), 0.37 (d, J=4.5 Hz, 2H).

MS ESI m/z 460.2 (M+H)

Example 34

5-{2-Amino-[1,2,4]triazolo[1,5-a]pyridin-7-yl}-N-{[2-(cyclopentyloxy)pyridin-3-yl]methyl}-2-methoxy-6-methylpyridine-3-carboxamide

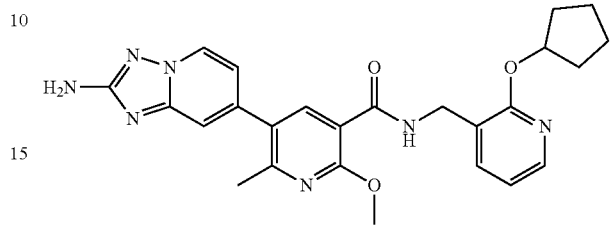

34A: Cyclopentanol (0.453 mL, 5.00 mmol) was added to a solution of 2-hydroxynicotinonitrile (300 mg, 2.498 mmol) and triphenylphosphine (1146 mg, 4.37 mmol) in THF (10 mL) at 0° C. DIAD (0.850 mL, 4.37 mmol) was added dropwise and the yellow solution was stirred at rt 3 d. The reaction mixture was concentrated to an oil and purified by flash chromatography eluting with 0-100% EtOAc in hexanes. Afforded 2-(cyclopentyloxy)nicotinonitrile (347 mg, 1.751 mmol, 70.1% yield) as a colorless oil.

34B: (2-(Cyclopentyloxy)pyridin-3-yl)methanamine: To a solution of 2-(cyclopentyloxy)nicotinonitrile (347 mg, 1.844 mmol) in ethanol (10 mL) under nitrogen was added 10% palladium on carbon (392 mg, 0.369 mmol). The mixture was degassed by vacuum thoroughly before being flooded with hydrogen from a balloon.

After stirring ON, the reaction mixture was filtered through Celite and concentrated to a colorless oil, (2-(cyclopentyloxy)pyridin-3-yl)methanamine (267 mg, 1.389 mmol, 75% yield). This material was used as is.

34: A mixture of 5-(2-amino-[1,2,4]triazolo[1,5-a]pyridin-7-yl)-2-methoxy-6-methylnicotinic acid (10 mg, 0.033 mmol), BOP (22.17 mg, 0.050 mmol), (2-(cyclopentyloxy)pyridin-3-yl)methanamine (6.42 mg, 0.033 mmol) and Hünig's Base (0.029 mL, 0.167 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((2-(cyclopentyloxy)pyridin-3-yl) methyl)-2-methoxy-6-methylnicotinamide (8.4 mg, 0.017 mmol, 52.0% yield).

$^1$H NMR (500 MHz, DMSO-d6) δ 8.66 (t, J=5.8 Hz, 1H), 8.59 (d, J=6.8 Hz, 1H), 8.10-7.99 (m, 2H), 7.55 (d, J=6.9 Hz, 1H), 7.38 (s, 1H), 6.98-6.87 (m, 2H), 6.07 (s, 2H), 5.45 (br. s., 1H), 4.40 (d, J=5.9 Hz, 2H), 4.04 (s, 3H), 2.48 (s, 3H), 2.00-1.86 (m, 2H), 1.74 (d, J=4.6 Hz, 4H), 1.60 (br. s., 2H).

MS ESI m/z 474.2 (M+H)

Example 35

5-{2-Amino-[1,2,4]triazolo[1,5-a]pyridin-7-yl}-2-methyl-N-{[2-(propan-2-yloxy)phenyl]methyl}pyridine-3-carboxamide

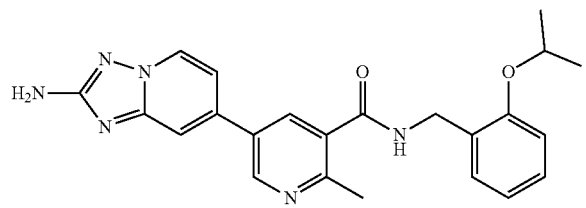 [SMILES: Cc1ncc(-c2ccn3nc(N)nc3c2)cc1C(=O)NCc1ccccc1OC(C)C]

35A: (2-(Isopropyloxy)phenyl)methanamine was prepared from 2-hydroxybenzonitrile and isopropanol by the same method as intermediate 49B.

$^1$H NMR (400 MHz, DMSO-d$_6$) δ 7.32-7.26 (m, 1H), 7.15 (td, J=7.8, 1.7 Hz, 1H), 6.94 (d, J=7.9 Hz, 1H), 6.86 (td, J=7.4, 1.0 Hz, 1H), 4.66-4.54 (m, 1H), 3.63 (s, 2H), 1.96-1.52 (m, 2H), 1.30-1.25 (m, 6H).

35: A mixture of lithium 5-(2-amino-[1,2,4]triazolo[1,5-a]pyridin-7-yl)-2-methylnicotinate (10 mg, 0.036 mmol), BOP (24.11 mg, 0.055 mmol), (2-isopropoxyphenyl)methanamine (6.00 mg, 0.036 mmol) and Hünig's Base (0.032 mL, 0.182 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-isopropoxybenzyl)-2-methylnicotinamide (8.2 mg, 0.019 mmol, 53.1% yield).

$^1$H NMR (500 MHz, DMSO-d6) δ 8.93 (d, J=1.8 Hz, 1H), 8.86 (t, J=5.5 Hz, 1H), 8.62 (d, J=6.7 Hz, 1H), 8.15 (d, J=1.8 Hz, 1H), 7.78 (s, 1H), 7.30 (t, J=5.2 Hz, 2H), 7.25-7.18 (m, 1H), 7.01 (d, J=8.2 Hz, 1H), 6.91 (t, J=7.3 Hz, 1H), 6.05 (s, 1H), 4.63 (dt, J=11.9, 6.0 Hz, 1H), 4.45 (d, J=5.5 Hz, 2H), 3.52 (s, 1H), 2.59 (s, 3H), 1.29 (d, J=6.1 Hz, 6H).

MS ESI m/z 416.9 (M+H)

Example 36

5-{2-Amino-[1,2,4]triazolo[1,5-a]pyridin-7-yl}-2-methoxy-N-{1-[3-(trifluoromethoxy)phenyl]ethyl}pyridine-3-carboxamide

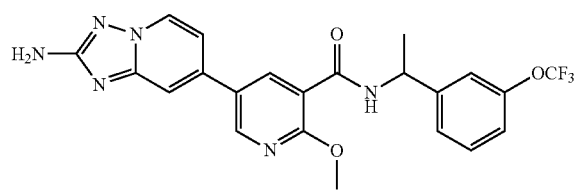 [SMILES: COc1ncc(-c2ccn3nc(N)nc3c2)cc1C(=O)NC(C)c1cccc(OC(F)(F)F)c1]

36A: 1-(3-(Trifluoromethoxy)phenyl)ethanamine, HCl: A solution of 1-(3-(trifluoromethoxy)phenyl)ethanone (1 g, 4.90 mmol), ammonium acetate (2.266 g, 29.4 mmol) and sodium cyanoborohydride (0.770 g, 12.25 mmol) in ethanol (10 mL) was heated to 80° C. for 16 h. The reaction mixture was filtered to remove the solid and concentrated. The residue was diluted with EtOAc (80 mL) and washed with water (10 mL×2) and brine (10 mL). The organics were dried over anhydrous sodium sulfate, filtered and concentrated. The crude product was dissolved ether (10 mL) and HCl, 2.0 M in Et$_2$O (2.449 mL, 4.90 mmol) was added. After stirring for 30 min, the white solid was collected as 1-(3-(trifluoromethoxy)phenyl)ethanamine, HCl (0.413 g, 1.709 mmol, 34.9% yield).

$^1$H NMR (400 MHz, CD$_3$OD) δ 7.63-7.57 (m, 1H), 7.49 (d, J=7.8 Hz, 1H), 7.44 (s, 1H), 7.38 (dt, J=8.3, 1.1 Hz, 1H), 4.54 (q, J=6.8 Hz, 1H), 1.65 (d, J=7.0 Hz, 3H).

MS ESI m/z 206.1 (M+H)

36: A mixture of 5-(2-amino-[1,2,4]triazolo[1,5-a]pyridin-7-yl)-2-methoxynicotinic acid (30 mg, 0.105 mmol), 1-(3-(trifluoromethoxy)phenyl)ethanamine, HCl (30.5 mg, 0.126 mmol), BOP (51.2 mg, 0.116 mmol) and triethylamine (0.044 mL, 0.316 mmol) in DMF (0.8 mL) was agitated at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 min, then a 5-minute hold at 100% B; Flow: 20 mL/min. Fractions containing the desired product were combined and dried via centrifugal evaporation to provide the product (6.6 mg, 14 µmol, 41.1%). The racemate was separated using chiral SFC to yield first eluting enantiomer, 36-1, and second eluting isomer, 36-2.

Racemic: $^1$H NMR (500 MHz, DMSO-d6) δ 8.81 (d, J=5.6 Hz, 1H), 8.75 (d, J=2.4 Hz, 1H), 8.59 (d, J=6.9 Hz, 1H), 8.30 (d, J=2.5 Hz, 1H), 7.71 (s, 1H), 7.53-7.44 (m, 2H), 7.43 (s, 1H), 7.29-7.21 (m, 2H), 6.06 (br. s., 2H), 5.19 (t, J=7.2 Hz, 1H), 4.01 (s, 3H), 1.47 (d, J=7.0 Hz, 3H).

36-1, Enantiomer 1: $^1$H NMR (500 MHz, DMSO-d6) δ 8.81 (d, J=5.8 Hz, 1H), 8.75 (d, J=2.5 Hz, 1H), 8.59 (d, J=7.1 Hz, 1H), 8.30 (t, J=2.1 Hz, 1H), 7.71 (br. s., 1H), 7.53-7.44 (m, 2H), 7.42 (br. s., 1H), 7.29-7.18 (m, 2H), 6.05 (br. s., 2H), 5.18 (t, J=7.2 Hz, 1H), 4.01 (s, 3H), 1.47 (d, J=6.9 Hz, 3H).

36-2, Enantiomer 2: $^1$H NMR (500 MHz, DMSO-d6) δ 8.82 (d, J=6.5 Hz, 1H), 8.75 (d, J=2.5 Hz, 1H), 8.59 (d, J=6.9 Hz, 1H), 8.30 (d, J=2.5 Hz, 1H), 7.71 (s, 1H), 7.53-7.44 (m, 2H), 7.42 (br. s., 1H), 7.27-7.22 (m, 2H), 6.05 (br. s., 2H), 5.18 (t, J=6.8 Hz, 1H), 4.01 (s, 3H), 1.47 (d, J=6.9 Hz, 3H).

MS ESI m/z 473 (M+H)

Example 37

5-{2-Amino-[1,2,4]triazolo[1,5-a]pyridin-7-yl}-N-{[3-(cyclobutylmethoxy)pyridin-2-yl] methyl}-2-methoxypyridine-3-carboxamide

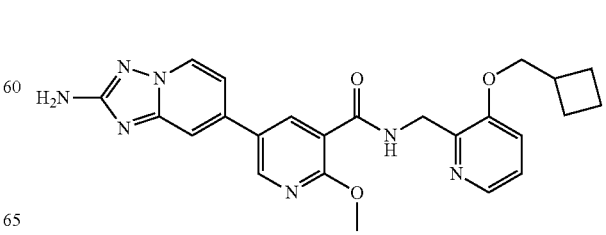

37A: 3-(Cyclobutylmethoxy)picolinomtrile: Cyclobutylmethanol 636 mg, 7.39 mmol) was added to a solution of 3-hydroxypicolinonitrile (355 mg, 2.96 mmol) and triphenylphosphine (1357 mg, 5.17 mmol) in THF (10 mL) at 0° C. DIAD (1.006 mL, 5.17 mmol) was added dropwise and the yellow solution was stirred at rt 3 d. The reaction mixture was concentrated to an oil and purified by flash chromatography eluting with 0-100% EtOAc in hexanes. A second column eluting with 0-5% MeOH in DCM was necessary. Afforded 3-(cyclobutylmethoxy)picolinonitrile (210 mg, 1.116 mmol, 37.7% yield) as a colorless oil.

$^1$H NMR (400 MHz, DMSO-d$_6$) δ 8.30 (dd, J=4.5, 1.2 Hz, 1H), 7.82-7.78 (m, 1H), 7.73-7.68 (m, 1H), 4.19 (d, J=6.5 Hz, 2H), 2.83-2.71 (m, 1H), 2.16-2.03 (m, 2H), 2.00-1.79 (m, 4H).

37B: (3-(Cyclobutylmethoxy)pyridin-2-yl)methanamine: To a solution of 3-(cyclobutylmethoxy)picolinonitrile (210 mg, 1.116 mmol) in ethanol (10 mL) under nitrogen was added 10% palladium on carbon (416 mg, 0.390 mmol). The mixture was degassed by vacuum thoroughly before being flooded with hydrogen from a balloon.

After stirring 5 h at rt, the reaction mixture was filtered through Celite and concentrated to a colorless oil, (3-(cyclobutylmethoxy)pyridin-2-yl)methanamine (204 mg, 1.061 mmol, 95% yield) which was used as is.

37: A mixture of lithium 5-(2-amino-[1,2,4]triazolo[1,5-a]pyridin-7-yl)-2-methoxynicotinate (10 mg, 0.034 mmol), BOP (22.78 mg, 0.052 mmol), (3-(cyclobutylmethoxy)pyridin-2-yl)methanamine (7.92 mg, 0.041 mmol) and Hünig's Base (0.030 mL, 0.172 mmol) in DMF (1.0 mL) was stirred at rt for 90 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((3-(cyclobutylmethoxy)pyridin-2-yl)methyl)-2-methoxynicotinamide (2.1 mg, 4.43 µmol, 12.91% yield).

$^1$H NMR (500 MHz, DMSO-d6) δ 9.27 (br. s., 1H), 8.82 (d, J=2.4 Hz, 1H), 8.66-8.56 (m, 2H), 8.18 (d, J=4.6 Hz, 1H), 7.71 (s, 1H), 7.47 (d, J=8.2 Hz, 1H), 7.34 (dd, J=8.1, 4.7 Hz, 1H), 7.25 (d, J=7.0 Hz, 1H), 6.06 (s, 2H), 4.65 (d, J=4.6 Hz, 2H), 4.14 (s, 2H), 4.08 (d, J=6.4 Hz, 2H), 2.87-2.73 (m, 1H), 2.16-2.04 (m, 2H), 1.98-1.83 (m, 4H).

MS ESI m/z 460 (M+H)

Example 38

5-{2-Amino-[1,2,4]triazolo[1,5-a]pyridin-7-yl}-2-methoxy-N-{1-[2-(trifluoromethoxy)phenyl]ethyl}pyridine-3-carboxamide

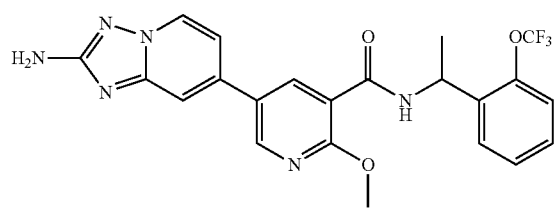 [SMILES: COc1ncc(-c2ccn3nc(N)nc3c2)cc1C(=O)NC(C)c1ccccc1OC(F)(F)F]

38A: 1-(2-(Trifluoromethoxy)phenyl)ethanamine, HCl: A solution of 1-(2-(trifluoromethoxy)phenyl)ethanone (300 mg, 1.470 mmol), ammonium acetate (1133 mg, 14.70 mmol) and sodium cyanoborohydride (111 mg, 1.763 mmol) in ethanol (3 mL) was heated to 80° C. for 24 h. The reaction mixture was filtered to remove the solid. The filterate was concentrated. EtOAc (5 mL) was added and the slurry filtered again. The filtrate was concentrated. Ether (5 mL) was added, followed by the addition of HCl, 2M in ether (0.735 mL, 1.470 mmol). After stirring 20 min, the solid was collected by filtration to yield 1-(2-(trifluoromethoxy)phenyl)ethanamine, HCl (75.4 mg, 0.30 mmol, 20.4% yield).

$^1$H NMR (400 MHz, CD$_3$OD) δ 7.66 (dd, J=7.6, 2.0 Hz, 1H), 7.60-7.50 (m, 2H), 7.49-7.44 (m, 1H), 4.84-4.79 (m, 1H merge with water), 1.65 (d, J=6.8 Hz, 3H).

MS ESI m/z 206.1 (M+H)

38: A mixture of 5-(2-amino-[1,2,4]triazolo[1,5-a]pyridin-7-yl)-2-methoxynicotinic acid (30 mg, 0.105 mmol), 1-(2-(trifluoromethoxy)phenyl)ethanamine (86 mg, 0.421 mmol), BOP (51.2 mg, 0.116 mmol) and triethylamine (0.044 mL, 0.316 mmol) in THF (1 mL) was agitated at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield the desired product (18.6 mg, 0.039 mmol, 37.1% yield). The enantiomers were separated using chiral SFC conditions to yield the first eluting isomer, 38-1 (6.8 mg, 0.014 mmol, 13.6%) and the second eluting enantiomer, 38-2 (6.4 mg, 0.013 mmol 12.8%).

Racemic: $^1$H NMR (500 MHz, DMSO-d6) δ 8.81 (d, J=7.7 Hz, 1H), 8.75 (d, J=2.5 Hz, 1H), 8.59 (d, J=6.9 Hz, 1H), 8.32 (d, J=2.5 Hz, 1H), 7.71 (s, 1H), 7.67-7.63 (m, 1H), 7.41 (dd, J=6.8, 3.1 Hz, 2H), 7.37-7.31 (m, 1H), 7.24 (dd, J=7.0, 1.5 Hz, 1H), 6.06 (br. s., 2H), 5.40 (t, J=7.2 Hz, 1H), 4.02 (s, 3H), 1.45 (d, J=7.0 Hz, 3H).

38-1, Enantiomer 1: $^1$H NMR (500 MHz, DMSO-d6) δ 8.82 (d, J=7.2 Hz, 1H), 8.75 (d, J=2.7 Hz, 1H), 8.58 (d, J=6.8 Hz, 1H), 8.35-8.28 (m, 1H), 7.70 (br. s., 1H), 7.64 (br. s., 1H), 7.44-7.37 (m, 2H), 7.35 (br. s., 1H), 7.24 (dd, J=7.1, 1.9 Hz, 1H), 6.05 (br. s., 2H), 5.40 (t, J=6.8 Hz, 1H), 4.02 (s, 3H), 1.44 (d, J=7.0 Hz, 3H).

38-2, Enantiomer 2: $^1$H NMR (500 MHz, DMSO-d6) δ 8.82 (d, J=7.7 Hz, 1H), 8.72 (d, J=2.3 Hz, 1H), 8.56 (d, J=6.9 Hz, 1H), 8.30 (d, J=2.4 Hz, 1H), 7.67 (s, 1H), 7.65-7.59 (m, 1H), 7.43-7.36 (m, 2H), 7.34 (d, J=4.8 Hz, 1H), 7.24 (dd, J=7.1, 1.9 Hz, 1H), 6.03 (br. s., 2H), 5.56-5.27 (m, 1H), 4.01 (s, 3H), 1.44 (d, J=7.0 Hz, 3H).

MS ESI m/z 472.8 (M+H)

Example 39

5-{2-Amino-[1,2,4]triazolo[1,5-a]pyridin-7-yl}-N-{[2-(cyclopentylmethoxy)phenyl]methyl}-2-methylpyridine-3-carboxamide

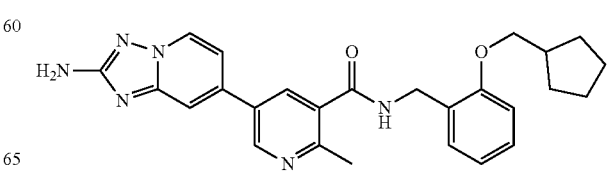

39A: (2-(Cyclopentylmethoxyoxy)phenyl)methanamine was prepared from 2-hydroxybenzonitrile and cyclopentylmethanol by the same method as intermediate 49B. Amine used as—is after filtration and evaporation.

39: A mixture of lithium 5-(2-amino-[1,2,4]triazolo[1,5-a]pyridin-7-yl)-2-methylnicotinate (12 mg, 0.044 mmol), BOP (28.9 mg, 0.065 mmol), (2-(cyclopentylmethoxy)phenyl)methanamine (10.74 mg, 0.052 mmol) and Hünig's Base (0.038 mL, 0.218 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentylmethoxy)benzyl)-2-methylnicotinamide (9.6 mg, 0.021 mmol, 47.3% yield).

$^1$H NMR (500 MHz, DMSO-d6) δ 8.97 (s, 1H), 8.89 (br. s., 1H), 8.66 (d, J=6.9 Hz, 1H), 8.22 (s, 1H), 7.83 (s, 1H), 7.32 (dd, J=16.1, 7.1 Hz, 2H), 7.28-7.17 (m, 1H), 7.00 (d, J=8.1 Hz, 1H), 6.94 (t, J=7.4 Hz, 1H), 4.49 (d, J=5.2 Hz, 2H), 3.91 (d, J=4.5 Hz, 3H), 3.17 (s, 1H), 2.62 (s, 3H), 2.41-2.28 (m, 1H), 1.80 (d, J=7.3 Hz, 2H), 1.67-1.46 (m, 4H), 1.45-1.30 (m, 2H).

MS ESI m/z 457 (M+H)

Example 40

5-{2-Amino-[1,2,4]triazolo[1,5-a]pyridin-7-yl}-N-{[2-(cyclopentyloxy)-6-fluorophenyl]methyl}pyridine-3-carboxamide

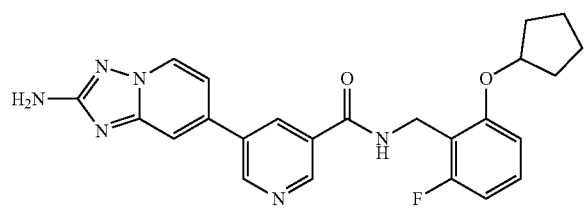 [SMILES: Nc1nc2cc(-c3cncc(C(=O)NCc4c(F)cccc4OC4CCCC4)c3)ccn2n1]

A mixture of 5-(2-amino-[1,2,4]triazolo[1,5-a]pyridin-7-yl)nicotinic acid (10 mg, 0.039 mmol), BOP (26.0 mg, 0.059 mmol), (2-(cyclopentyloxy)-6-fluorophenyl)methanamine (10.25 mg, 0.049 mmol) and Hünig's Base (0.034 mL, 0.196 mmol) in DMF (1.0 mL) was stirred at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-6-fluorobenzyl)nicotinamide (9.0 mg, 0.020 mmol, 50.4% yield).

$^1$H NMR (500 MHz, DMSO-d6) δ 9.30-8.93 (m, 2H), 8.78 (br. s., 1H), 8.68 (d, J=5.8 Hz, 1H), 8.54 (br. s., 1H), 7.83 (br. s., 1H), 7.41-7.25 (m, 2H), 6.86 (d, J=8.2 Hz, 1H), 6.78 (t, J=8.8 Hz, 1H), 6.12 (br. s., 2H), 4.88 (br. s., 1H), 4.57-4.43 (m, 2H), 1.90-1.78 (m, 2H), 1.74 (br. s., 2H), 1.66-1.55 (m, 2H), 1.49 (br. s., 2H).

MS ESI m/z 447.1 (M+H)

Example 41

5-{2-Amino-[1,2,4]triazolo[1,5-a]pyridin-7-yl}-N-{[2-(cyclopentyloxy)-5-fluorophenyl]methyl}pyridine-3-carboxamide

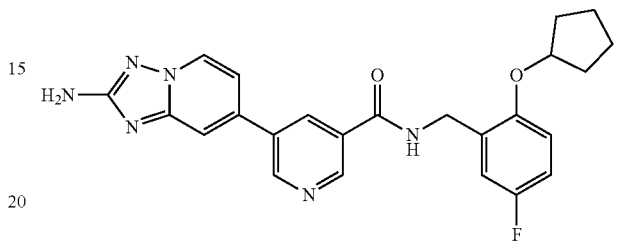

A mixture of 5-(2-amino-[1,2,4]triazolo[1,5-a]pyridin-7-yl)nicotinic acid (10 mg, 0.039 mmol), BOP (26.0 mg, 0.059 mmol), (2-(cyclopentyloxy)-5-fluorophenyl)methanamine (10.25 mg, 0.049 mmol) and Hünig's Base (0.034 mL, 0.196 mmol) in DMF (1.0 mL) was stirred at rt for 3 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-100% B over 20 min, then a 2-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-5-fluorobenzyl)nicotinamide (6.8 mg, 0.015 mmol, 38.1% yield).

$^1$H NMR (500 MHz, DMSO-d6) δ 9.21-9.02 (m, 3H), 8.67 (d, J=7.0 Hz, 1H), 8.64 (s, 1H), 7.86 (s, 1H), 7.36 (d, J=6.7 Hz, 1H), 7.29-7.12 (m, 3H), 7.10-7.02 (m, 2H), 4.85 (br. s., 1H), 4.47 (d, J=5.5 Hz, 2H), 1.93-1.81 (m, 2H), 1.80-1.46 (m, 6H).

MS ESI m/z 447.1 (M+H)

Example 42

5-{2-Amino-[1,2,4]triazolo[1,5-a]pyridin-7-yl}-N-{[2-(cyclopropylmethoxy)phenyl]methyl}pyridine-3-carboxamide

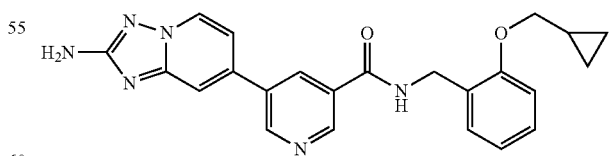

A mixture of 5-(2-amino-[1,2,4]triazolo[1,5-a]pyridin-7-yl)nicotinic acid (10 mg, 0.039 mmol), BOP (26.0 mg, 0.059 mmol), 2-(cyclopropylmethoxy)phenyl)methanamine (8.68 mg, 0.049 mmol) and Hünig's Base (0.034 mL, 0.196 mmol) in DMF (1.0 mL) was stirred at rt for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)benzyl)nicotinamide (1.2 mg, 2.84 µmol, 7.24% yield).

$^1$H NMR (500 MHz, DMSO-d6) δ 9.18 (br. s., 2H), 9.09 (s, 1H), 8.73-8.62 (m, 2H), 7.88 (s, 1H), 7.37 (d, J=6.8 Hz, 1H), 7.30-7.16 (m, 2H), 6.97 (d, J=8.2 Hz, 1H), 6.91 (t, J=7.4 Hz, 1H), 6.14 (s, 2H), 4.55 (d, J=5.2 Hz, 2H), 3.88 (d, J=6.6 Hz, 2H), 1.24 (d, J=4.7 Hz, 1H), 0.54 (d, J=7.6 Hz, 2H), 0.33 (d, J=4.5 Hz, 2H).

MS ESI m/z 415.4 (M+H)

Example 43

5-{2-Amino-[1,2,4]triazolo[1,5-a]pyridin-7-yl}-N-{[2-(cyclopentyloxy)phenyl]methyl}pyridine-3-carboxamide

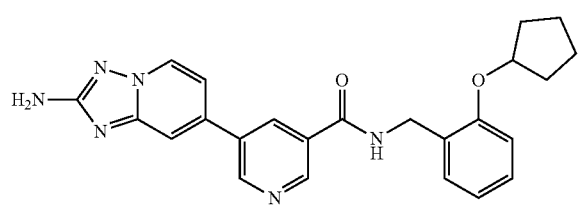 [SMILES: Nc1nc2cc(-c3cncc(C(=O)NCc4ccccc4OC4CCCC4)c3)ccn2n1]

43A: (2-(Cyclopentyloxy)phenyl)methanamine was prepared from 2-hydroxybenzonitrile and cyclopentanol by the same method as intermediate 49B.

$^1$H NMR (400 MHz, DMSO-d$_6$) δ 7.31-7.25 (m, 1H), 7.15 (td, J=7.8, 1.8 Hz, 1H), 6.91 (d, J=7.9 Hz, 1H), 6.85 (td, J=7.4, 0.9 Hz, 1H), 4.87-4.80 (m, 1H), 3.61 (s, 2H), 3.43-3.16 (m, 2H), 1.96-1.81 (m, 3H), 1.70-1.53 (m, 5H).

43B: A mixture of methyl 5-(4,4,5,5-tetramethyl-1,3,2-dioxaborolan-2-yl)nicotinate (319 mg, 1.212 mmol), 1A (501 mg, 1.212 mmol) and 1,1'-bis(di-tert-butylphosphino)ferrocenepalladium dichloride (39.5 mg, 0.061 mmol) in dioxane (7.5 mL) was degassed by bubbling nitrogen through it for 5 min. 2M K$_3$PO$_4$ (aq) (1.819 mL, 3.64 mmol) was quickly added and the reaction mixture heated at 100° C. for 15 min. After cooling to rt and removal of the volatiles in vacuo, the crude residue was loaded onto a 40 g ISCO column and purified by flash chromatography, eluting with 0-100% EtOAc in hexanes. Afforded 43B (331 mg, 0.691 mmol, 57.0%) as a crystalline, beige solid.

MS ESI m/z 470.0 (M+H)

43C: Methyl 5-(2-amino-[1,2,4]triazolo[1,5-a]pyridin-7-yl)nicotinate: A mixture of 145B (331 mg, 0.705 mmol) in TFA (5 mL) was stirred at rt 45 min. The reaction mixture was concentrated to a solid. The crude solid was slurried in water and free-based utilizing SCX resin, washing with 10% ammonium hydroxide in methanol. Afforded methyl 5-(2-amino-[1,2,4]triazolo[1,5-a]pyridin-7-yl)nicotinate (94 mg, 0.346 mmol, 49.0% yield) as a white solid.

MS ESI m/z 269.8 (M+H)

43D: 5-(2-Amino-[1,2,4]triazolo[1,5-a]pyridin-7-yl)nicotinic acid, lithium salt: To a mixture of methyl 5-(2-amino-[1,2,4]triazolo[1,5-a]pyridin-7-yl)nicotinate (94 mg, 0.349 mmol) in tetrahydrofuran (2.5 mL) was added a solution of lithium hydroxide monohydrate (17.58 mg, 0.419 mmol) in water (1.5 mL). After stirring 1 h, the reaction mixture was concentrated to a solid to afford 5-(2-amino-[1,2,4]triazolo[1,5-a]pyridin-7-yl)nicotinic acid, lithium salt (91 mg, 0.339 mmol, 97% yield) as a tan solid which was used as is in subsequent chemistry.

43: A mixture of 5-(2-amino-[1,2,4]triazolo[1,5-a]pyridin-7-yl)nicotinic acid, lithium salt (10 mg, 0.039 mmol), BOP (26.0 mg, 0.059 mmol), (2-(cyclopentyloxy)phenyl)methanamine (9.37 mg, 0.049 mmol) and Hünig's Base (0.034 mL, 0.196 mmol) in DMF (1.0 mL) was stirred at rt for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)benzyl)nicotinamide (7.7 mg, 0.018 mmol, 44.9% yield).

$^1$H NMR (500 MHz, DMSO-d6) δ 9.18 (br. s., 1H), 9.13-9.01 (m, 2H), 8.68 (d, J=6.9 Hz, 1H), 8.64 (br. s., 1H), 7.86 (s, 1H), 7.36 (d, J=6.8 Hz, 1H), 7.30-7.15 (m, 2H), 6.99 (d, J=8.1 Hz, 1H), 6.89 (t, J=7.4 Hz, 1H), 6.13 (br. s., 2H), 4.88 (br. s., 1H), 4.49 (d, J=5.4 Hz, 2H), 1.96-1.83 (m, 2H), 1.81-1.64 (m, 4H), 1.57 (br. s., 2H).

MS ESI m/z 428.9 (M+H)

Example 44

5-{2-Amino-[1,2,4]triazolo[1,5-a]pyridin-7-yl}-N-{[2-(cyclohexyloxy)phenyl]methyl}-2-methoxypyridine-3-carboxamide

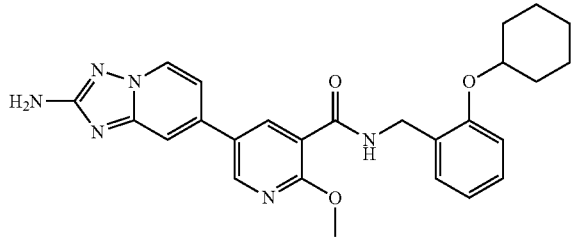 [SMILES: COc1ncc(-c2ccn3nc(N)nc3c2)cc1C(=O)NCc1ccccc1OC1CCCCC1]

44A: (2-(Cyclohexyloxy)phenyl)methanamine was prepared from 2-hydroxybenzonitrile and cyclohexanol by the same method as intermediate 49B. Amine used as—is after filtration and evaporation.

44: A mixture of 5-(2-amino-[1,2,4]triazolo[1,5-a]pyridin-7-yl)-2-methoxynicotinic acid (30 mg, 0.105 mmol), BOP (69.8 mg, 0.158 mmol), (2-(cyclohexyloxy)phenyl)methanamine (64.8 mg, 0.316 mmol) and Hünig's Base (0.092 mL, 0.526 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]

pyridin-7-yl)-N-(2-(cyclohexyloxy)benzyl)-2-methoxynicotinamide (9.5 mg, 0.020 mmol, 18.73% yield).

$^1$H NMR (500 MHz, DMSO-d6) δ 8.73 (d, J=2.4 Hz, 1H), 8.66 (t, J=5.8 Hz, 1H), 8.56 (d, J=7.0 Hz, 1H), 8.46 (d, J=2.1 Hz, 1H), 7.67 (s, 1H), 7.29-7.16 (m, 3H), 7.00 (d, J=8.2 Hz, 1H), 6.88 (t, J=7.3 Hz, 1H), 6.01 (s, 2H), 4.49 (d, J=5.8 Hz, 2H), 4.42 (br. s., 1H), 4.03 (s, 3H), 1.87 (br. s., 2H), 1.68 (br. s., 2H), 1.63-1.43 (m, 3H), 1.43-1.22 (m, 3H).

MS ESI m/z 473.2 (M+H)

Example 45

5-{2-Amino-[1,2,4]triazolo[1,5-a]pyridin-7-yl}-N-{[3-(cyclopentyloxy)phenyl]methyl}-2-methoxypyridine-3-carboxamide

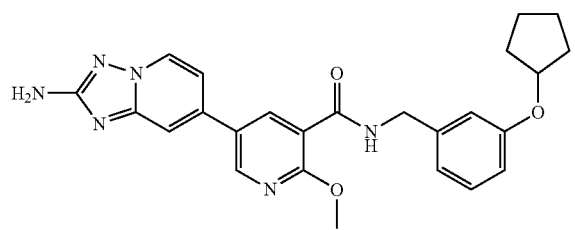 [SMILES: COc1ncc(-c2ccn3nc(N)nc3c2)cc1C(=O)NCc1cccc(OC2CCCC2)c1]

45A: (3-(Cyclopentyloxy)phenyl)methanamine was prepared from 3-hydroxybenzonitrile and cyclopentanol by the same method as intermediate 49B. Amine used crude after filtration and evaporation.

45: A mixture of 5-(2-amino-[1,2,4]triazolo[1,5-a]pyridin-7-yl)-2-methoxynicotinic acid (11 mg, 0.039 mmol), BOP (25.6 mg, 0.058 mmol), (3-(cyclopentyloxy)phenyl)methanamine (7.38 mg, 0.039 mmol) and Hünig's Base (0.034 mL, 0.193 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3-(cyclopentyloxy)benzyl)-2-methoxynicotinamide (10.6 mg, 0.023 mmol, 58.8% yield).

$^1$H NMR (500 MHz, DMSO-d6) δ 8.89 (t, J=5.8 Hz, 1H), 8.75 (s, 1H), 8.59 (d, J=6.8 Hz, 1H), 8.42 (s, 1H), 7.70 (s, 1H), 7.27-7.17 (m, 2H), 6.92-6.83 (m, 2H), 6.77 (d, J=8.0 Hz, 1H), 6.06 (s, 2H), 4.77 (br. s., 1H), 4.48 (d, J=5.9 Hz, 2H), 4.02 (s, 3H), 1.89 (d, J=5.9 Hz, 2H), 1.67 (br. s., 4H), 1.55 (br. s., 2H).

MS ESI m/z 459.2 (M+H)

Example 46

5-{2-Amino-[1,2,4]triazolo[1,5-a]pyridin-7-yl}-N-{[3-(cyclobutylmethoxy)phenyl]methyl}-2-methoxypyridine-3-carboxamide

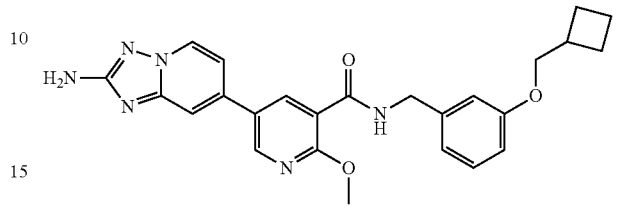

46A: (3-(Cyclobutylmethoxy)phenyl)methanamine was prepared from 3-hydroxybenzonitrile and cyclobutylmethanol by the same method as intermediate 49B. Amine used crude after filtration and evaporation.

46: A mixture of 5-(2-amino-[1,2,4]triazolo[1,5-a]pyridin-7-yl)-2-methoxynicotinic acid (11 mg, 0.039 mmol), BOP (25.6 mg, 0.058 mmol), (3-(cyclobutylmethoxy)phenyl)methanamine (9.22 mg, 0.048 mmol) and Hünig's Base (0.034 mL, 0.193 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-75% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3-(cyclobutylmethoxy)benzyl)-2-methoxynicotinamide (8.3 mg, 0.018 mmol, 46.0% yield).

$^1$H NMR (500 MHz, DMSO-d6) δ 8.89 (t, J=5.8 Hz, 1H), 8.77 (br. s., 1H), 8.71 (br. s., 1H), 8.44 (br. s., 1H), 7.73 (br. s., 1H), 7.32-7.19 (m, 2H), 6.97-6.88 (m, 2H), 6.81 (d, J=6.9 Hz, 1H), 6.07 (br. s., 1H), 4.50 (d, J=5.9 Hz, 2H), 4.04 (s, 3H), 3.96-3.86 (m, 2H), 3.39 (br. s., 1H), 2.70 (dt, J=14.5, 7.2 Hz, 1H), 2.06 (d, J=4.1 Hz, 2H), 1.96-1.74 (m, 4H).

MS ESI m/z 459.3 (M+H)

Example 47

5-{2-Amino-[1,2,4]triazolo[1,5-a]pyridin-7-yl}-N-{[3-(cyclopropylmethoxy)phenyl]methyl}-2-methoxypyridine-3-carboxamide

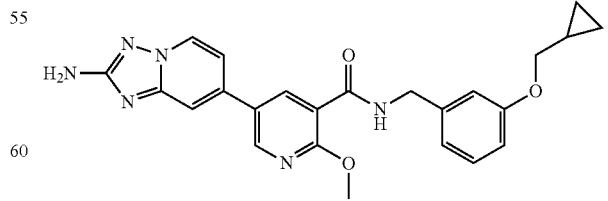

47A: (3-(Cyclopropylmethoxy)phenyl)methanamine was prepared from 3-hydroxybenzonitrile and cyclopropylmethanol by the same method as intermediate 49B. Amine used crude after filtration and evaporation.

47: A mixture of 5-(2-amino-[1,2,4]triazolo[1,5-a]pyridin-7-yl)-2-methoxynicotinic acid (12 mg, 0.042 mmol), BOP (27.9 mg, 0.063 mmol), (3-(cyclopropylmethoxy)phenyl)methanamine (9.32 mg, 0.053 mmol) and Hünig's Base (0.037 mL, 0.210 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 18 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3-(cyclopropylmethoxy)benzyl)-2-methoxynicotinamide (11.0 mg, 0.024 mmol, 57.7% yield).

$^1$H NMR (500 MHz, DMSO-d6) δ 8.86 (t, J=6.0 Hz, 1H), 8.76 (d, J=2.4 Hz, 1H), 8.59 (d, J=7.0 Hz, 1H), 8.43 (d, J=2.1 Hz, 1H), 7.71 (s, 1H), 7.29-7.19 (m, 2H), 6.96-6.87 (m, 2H), 6.79 (d, J=7.3 Hz, 1H), 6.03 (s, 2H), 4.49 (d, J=5.8 Hz, 2H), 4.03 (s, 3H), 3.79 (d, J=6.7 Hz, 2H), 1.21 (d, J=7.0 Hz, 1H), 0.61-0.48 (m, 2H), 0.36-0.24 (m, 2H).

MS ESI m/z 445 (M+H)

Example 48

2-Amino-5-{2-amino-[1,2,4]triazolo[1,5-a]pyridin-7-yl}-N-{[2-(cyclopentyloxy)-6-fluorophenyl]methyl}pyridine-3-carboxamide

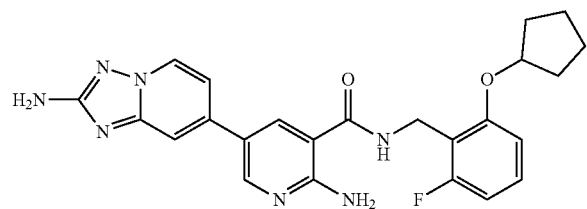

A mixture of 2-amino-5-(2-amino-[1,2,4]triazolo[1,5-a]pyridin-7-yl)nicotinic acid (10 mg, 0.037 mmol), BOP (24.55 mg, 0.056 mmol), (2-(cyclopentyloxy)-6-fluorophenyl)methanamine (7.74 mg, 0.037 mmol) and Hünig's Base (0.032 mL, 0.185 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 19 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-45% B over 25 min, then a 2-minute hold at 45% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 3-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-(cyclopentyloxy)-6-fluorobenzyl)nicotinamide (7.7 mg, 0.016 mmol, 43.3% yield).

$^1$H NMR (500 MHz, DMSO-d6) δ 8.70-8.51 (m, 3H), 8.27 (s, 1H), 7.68 (br. s., 1H), 7.38 (br. s., 2H), 7.33-7.25 (m, 1H), 7.23 (d, J=6.7 Hz, 1H), 6.86 (d, J=8.2 Hz, 1H), 6.78 (t, J=8.9 Hz, 1H), 5.97 (br. s., 2H), 4.88 (br. s., 1H), 4.47 (d, J=4.3 Hz, 2H), 1.91-1.79 (m, 2H), 1.75 (br. s., 2H), 1.63 (d, J=4.6 Hz, 2H), 1.49 (br. s., 2H).

MS ESI m/z 462.1 (M+H)

Example 49

2-Amino-5-{2-amino-[1,2,4]triazolo[1,5-a]pyridin-7-yl}-N-{[2-(cyclobutylmethoxy)phenyl]methyl}pyridine-3-carboxamide

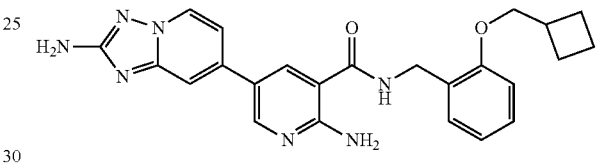

49A: 2-(Cyclobutylmethoxy)benzonitrile: DIAD (0.737 mL, 3.79 mmol) was added dropwise to a solution of 2-hydroxybenzonitrile (301 mg, 2.53 mmol) and triphenylphosphine (994 mg, 3.79 mmol) in THF (12 mL). Lastly, cyclobutylmethanol (218 mg, 2.53 mmol) was added and the yellow solution stirred at rt for 3 d. The reaction mixture was then concentrated to an oil and purified by flash chromatography using a 40 g silica column eluting with 0-100% EtOAc in hexanes. Afforded 2-(cyclobutylmethoxy)benzonitrile (214 mg, 1.143 mmol, 45.2% yield) as a colorless oil. (400 MHz, DMSO-d$_6$) δ 7.71 (dd, J=7.6, 1.5 Hz, 1H), 7.68-7.62 (m, 1H), 7.25 (d, J=8.3 Hz, 1H), 7.12-7.05 (m, 1H), 4.12 (d, J=6.4 Hz, 2H), 2.83-2.69 (m, 1H), 2.13-2.03 (m, 2H), 1.97-1.83 (m, 4H).

49B: (2-(Cyclobutylmethoxy)phenyl)methanamine: A solution of 2-(cyclobutylmethoxy)benzonitrile (212 mg, 1.132 mmol) in diethyl ether (10 mL) was cooled to 0° C. Lithium aluminum hydride (161 mg, 4.25 mmol) was added in portions, and the resulting mixture was stirred ON, slowly warming to rt. The reaction mixture was diluted with diethyl ether (30 mL), and was cooled back to 0° C. Water (161 μL) was added followed by 15% NaOH (161 μL) and water (483 μL) again. The mixture was stirred 15 min at rt to insure a complete quench. Magnesium sulfate was added to absorb excess water. The resulting mixture was stirred 15 min, filtered and concentrated to afford (2-(cyclobutylmethoxy)phenyl)methanamine (189 mg, 0.939 mmol, 83% yield) as a colorless oil. $^1$H NMR (400 MHz, DMSO-d$_6$) δ 7.33-7.26 (m, 1H), 7.17 (td, J=7.8, 1.7 Hz, 1H), 6.95-6.84 (m, 2H), 3.95 (d, J=6.4 Hz, 2H), 3.72-3.64 (m, 2H), 3.39-3.24 (m, 1H), 2.83-2.66 (m, 2H), 2.18-2.00 (m, 2H), 2.00-1.80 (m, 4H).

49C: In a sealed 40 mL tube, a mixture of 1A (500 mg, 1.210 mmol), bis(pinacolato)diboron (384 mg, 1.512 mmol), potassium acetate (356 mg, 3.63 mmol) and [1,1'-bis(diphenylphosphino)ferrocene]dichloropalladium(II) (44.3 mg, 0.060 mmol) in dioxane (7.5 mL) was stirred at 100° C. 1 h. After cooling to rt, methyl 2-amino-5-bromonicotinate (290 mg, 1.255 mmol) and 1,1'-bis(di-tert-butylphosphino)ferrocenepalladium dichloride (39.0 mg, 0.060 mmol) were added. The crude mixture was degassed by nitrogen sparging for 5 minutes. 2M $K_3PO_4$ (aq) (1.793 mL, 3.59 mmol) was quickly added and the reaction mixture heated at 100° C. for 15 min. The reaction mixture was diluted to 50 mL EtOAc and transferred to a separatory funnel. The organics were washed with brine, dried over anhydrous sodium sulfate, filtered and concentrated in vacuo. The crude residue was loaded onto a 12 g ISCO column and purified by flash chromatography, eluting with 0-100% EtOAc in hexanes. Afforded 49C (582 mg, 1.141 mmol, 95% yield) as a tan solid.

MS ESI m/z 485.3 (M+H)

49D: Methyl 2-amino-5-(2-amino-[1,2,4]triazolo[1,5-a]pyridin-7-yl)nicotinate, HCl: To a mixture of 49C (582 mg, 1.201 mmol) in DCE (5 mL) was added 4N HCl in dioxane (9.01 mL, 36.0 mmol). After stirring ON at rt, the reaction mixture was concentrated to a solid to afford methyl 2-amino-5-(2-amino-[1,2,4]triazolo[1,5-a]pyridin-7-yl) nicotinate, HCl (350 mg, 1.037 mmol, 86%).

MS ESI m/z 285.0 (M+H)

49E: 2-Amino-5-(2-amino-[1,2,4]triazolo[1,5-a]pyridin-7-yl)nicotinic acid: To a mixture of methyl 2-amino-5-(2-amino-[1,2,4]triazolo[1,5-a]pyridin-7-yl)nicotinate, HCl (350 mg, 1.091 mmol) in tetrahydrofuran (8 mL) was added a solution of lithium hydroxide monohydrate (101 mg, 2.401 mmol) in water (1.5 mL). A few drops of methanol were added, and the mixture was stirred ON at rt. 1 N NaOH (1.7 mL) was added and stirring continued ON. The reaction mixture was concentrated to a solid to afford 2-amino-5-(2-amino-[1,2,4]triazolo[1,5-a]pyridin-7-yl)nicotinic acid (290 mg, 0.966 mmol, 89% yield) which was used as is in subsequent chemistry.

MS ESI m/z 271.0 (M+H)

49: A mixture of 2-amino-5-(2-amino-[1,2,4]triazolo[1,5-a]pyridin-7-yl)nicotinic acid (10 mg, 0.037 mmol), BOP (24.55 mg, 0.056 mmol), (2-(cyclobutylmethoxy)phenyl)methanamine (8.85 mg, 0.046 mmol) and Hünig's Base (0.032 mL, 0.185 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 12-52% B over 25 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-(cyclobutylmethoxy)benzyl) nicotinamide, TFA (17.8 mg, 0.031 mmol, 85% yield).

$^1$H NMR (500 MHz, DMSO-d6) δ 9.11 (br. s., 1H), 8.68-8.60 (m, 2H), 8.56 (s, 1H), 7.79 (s, 1H), 7.38 (d, J=6.0 Hz, 1H), 7.28-7.16 (m, 2H), 7.15-6.97 (m, 2H), 6.91 (t, J=7.4 Hz, 1H), 4.50 (d, J=5.2 Hz, 2H), 3.98 (d, J=6.1 Hz, 2H), 3.16 (s, 1H), 2.74 (br. s., 1H), 2.05 (d, J=6.3 Hz, 2H), 1.88 (br. s., 4H) [2 protons lost in water suppression].

MS ESI m/z 444 (M+H)

Example 50

5-{2-Amino-[1,2,4]triazolo[1,5-a]pyridin-7-yl}-N-{[2-(cyclopentyloxy)-3-fluorophenyl] methyl}-2-methoxypyridine-3-carboxamide

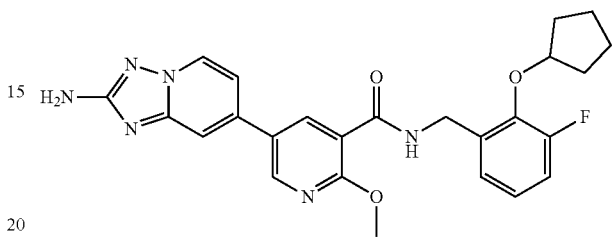

50A: (2-(Cyclopentyloxy)-3-fluorophenyl)methanamine was prepared from 3-fluoro-2-hydroxybenzonitrile and cyclopentanol by the same method as intermediate 49B. Amine used crude after filtration and evaporation.

50: A mixture of 5-(2-amino-[1,2,4]triazolo[1,5-a]pyridin-7-yl)-2-methoxynicotinic acid (11 mg, 0.039 mmol), BOP (25.6 mg, 0.058 mmol), (2-(cyclopentyloxy)-3-fluorophenyl)methanamine (8.07 mg, 0.039 mmol) and Hünig's Base (0.034 mL, 0.193 mmol) in DMF (1.0 mL) was stirred at rt for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 15 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-3-fluorobenzyl)-2-methoxynicotinamide (9.2 mg, 0.019 mmol, 49.1% yield).

$^1$H NMR (500 MHz, DMSO-d6) δ 8.84 (t, J=5.8 Hz, 1H), 8.78 (s, 1H), 8.60 (d, J=6.9 Hz, 1H), 8.46 (d, J=1.8 Hz, 1H), 7.72 (s, 1H), 7.25 (d, J=6.4 Hz, 1H), 7.20-7.10 (m, 2H), 7.09-7.00 (m, 1H), 6.07 (s, 2H), 4.88 (br. s., 1H), 4.53 (d, J=5.8 Hz, 2H), 4.05 (s, 3H), 1.92-1.70 (m, 6H), 1.62 (br. s., 2H).

MS ESI m/z 477.1 (M+H)

Example 51

5-{2-Amino-[1,2,4]triazolo[1,5-a]pyridin-7-yl}-N-{[2-(cyclopentyloxy)-4-fluorophenyl] methyl}-2-methoxypyridine-3-carboxamide

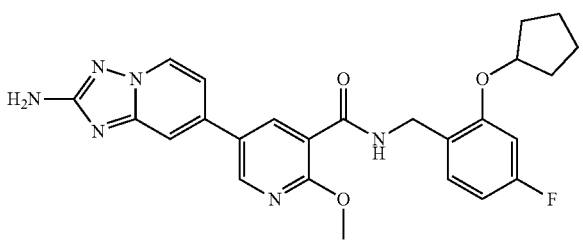 [SMILES: COc1ncc(-c2ccn3nc(N)nc3c2)cc1C(=O)NCc1ccc(F)cc1OC1CCCC1]

51A: (2-(Cyclopentyloxy)-4-fluorophenyl)methanamine was prepared from 4-fluoro-2-hydroxybenzonitrile and cyclopentanol by the same method as intermediate 49B. Amine used crude after filtration and evaporation.

51: A mixture of 5-(2-amino-[1,2,4]triazolo[1,5-a]pyridin-7-yl)-2-methoxynicotinic acid (11 mg, 0.039 mmol), BOP (25.6 mg, 0.058 mmol), (2-(cyclopentyloxy)-4-fluorophenyl)methanamine (8.07 mg, 0.039 mmol) and Hünig's Base (0.034 mL, 0.193 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-4-fluorobenzyl)-2-methoxynicotinamide (11.4 mg, 0.023 mmol, 60.8% yield).

$^1$H NMR (500 MHz, DMSO-d6) δ 8.77 (s, 1H), 8.62 (dd, J=11.3, 6.4 Hz, 2H), 8.45 (br. s., 1H), 7.71 (br. s., 1H), 7.30-7.19 (m, 2H), 6.89 (d, J=10.2 Hz, 1H), 6.72 (t, J=7.7 Hz, 1H), 6.07 (br. s., 2H), 4.91 (br. s., 1H), 4.40 (d, J=5.6 Hz, 2H), 4.03 (s, 3H), 1.92 (br. s., 2H), 1.82-1.67 (m, 4H), 1.60 (br. s., 2H).

MS ESI m/z 477.2 (M+H)

Example 52

5-{2-Amino-[1,2,4]triazolo[1,5-a]pyridin-7-yl}-N-{[2-(cyclopentyloxy)-6-fluorophenyl] methyl}-2-methoxypyridine-3-carboxamide

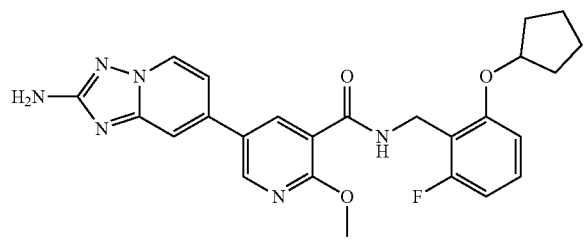 [SMILES: COc1ncc(-c2ccn3nc(N)nc3c2)cc1C(=O)NCc1c(F)cccc1OC1CCCC1]

52A: (2-(Cyclopentyloxy)-6-fluorophenyl)methanamine was prepared from 2-fluoro-6-hydroxybenzonitrile and cyclopentanol by the same method as intermediate 49B. Amine used crude after filtration and evaporation.

52: A mixture of 5-(2-amino-[1,2,4]triazolo[1,5-a]pyridin-7-yl)-2-methoxynicotinic acid (10 mg, 0.035 mmol), BOP (23.26 mg, 0.053 mmol), (2-(cyclopentyloxy)-6-fluorophenyl)methanamine (7.34 mg, 0.035 mmol) and Hünig's Base (0.031 mL, 0.175 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopentyloxy)-6-fluorobenzyl)-2-methoxynicotinamide (12.4 mg, 0.026 mmol, 72.7% yield).

$^1$H NMR (500 MHz, DMSO-d6) δ 8.73 (d, J=2.0 Hz, 1H), 8.58 (d, J=6.9 Hz, 1H), 8.43 (d, J=2.1 Hz, 1H), 8.38 (t, J=5.2 Hz, 1H), 7.67 (s, 1H), 7.28 (q, J=8.0 Hz, 1H), 7.22 (d, J=6.0 Hz, 1H), 6.86 (d, J=8.3 Hz, 1H), 6.76 (t, J=8.8 Hz, 1H), 6.05 (s, 2H), 4.91 (br. s., 1H), 4.52 (d, J=5.2 Hz, 2H), 4.00 (s, 3H), 1.97-1.85 (m, 2H), 1.81-1.63 (m, 4H), 1.57 (br. s., 2H).

MS ESI m/z 477 (M+H)

Example 53

2-Amino-5-{2-amino-[1,2,4]triazolo[1,5-a]pyridin-7-yl}-N-{[2-(cyclopropylmethoxy)-6-fluorophenyl]methyl}pyridine-3-carboxamide

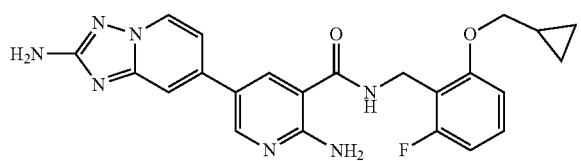 [SMILES: Nc1nc2cc(-c3cnc(N)c(C(=O)NCc4c(F)cccc4OCC4CC4)c3)ccn2n1]

A mixture of 2-amino-5-(2-amino-[1,2,4]triazolo[1,5-a]pyridin-7-yl)nicotinic acid (10 mg, 0.037 mmol), BOP (24.55 mg, 0.056 mmol), (2-(cyclopropylmethoxy)-6-fluorophenyl)methanamine (9.03 mg, 0.046 mmol) and Hünig's Base (0.032 mL, 0.185 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 19 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-(cyclopropylmethoxy)-6-fluorobenzyl)nicotinamide (12.6 mg, 0.027 mmol, 73.1% yield).

$^1$H NMR (500 MHz, DMSO-d6) δ 8.68 (br. s., 1H), 8.50 (d, J=1.7 Hz, 1H), 8.47 (d, J=7.0 Hz, 1H), 8.24 (s, 1H), 7.61 (s, 1H), 7.32 (br. s., 2H), 7.28-7.14 (m, 2H), 6.84-6.71 (m, 2H), 5.92 (s, 2H), 4.47 (d, J=4.1 Hz, 2H), 3.84 (d, J=6.5 Hz, 2H), 1.16 (br. s., 1H), 0.46-0.38 (m, 2H), 0.23 (d, J=4.7 Hz, 2H).

MS ESI m/z 448.2 (M+H)

Example 54

2-Amino-5-{2-amino-[1,2,4]triazolo[1,5-a]pyridin-7-yl}-N-{[2-(cyclopentyloxy)phenyl]methyl}pyridine-3-carboxamide

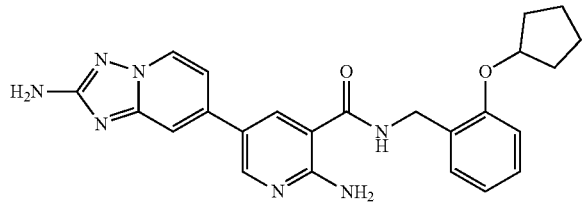

A mixture of 2-amino-5-(2-amino-[1,2,4]triazolo[1,5-a]pyridin-7-yl)nicotinic acid (10 mg, 0.037 mmol), BOP (24.55 mg, 0.056 mmol), (2-(cyclopentyloxy)phenyl)methanamine (7.08 mg, 0.037 mmol) and Hünig's Base (0.032 mL, 0.185 mmol) in DMF (1.0 mL) was stirred at rt for 2 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-(cyclopentyloxy)benzyl)nicotinamide (10.6 mg, 0.023 mmol, 63.3% yield).

<sup>1</sup>H NMR (500 MHz, DMSO-d6) δ 8.96 (br. s., 1H), 8.58 (s, 1H), 8.53 (d, J=7.0 Hz, 1H), 8.40 (s, 1H), 7.69 (s, 1H), 7.37 (br. s., 2H), 7.26 (d, J=7.0 Hz, 1H), 7.24-7.17 (m, 2H), 6.97 (d, J=8.2 Hz, 1H), 6.88 (t, J=7.4 Hz, 1H), 5.97 (s, 2H), 4.86 (br. s., 1H), 4.42 (d, J=5.2 Hz, 2H), 1.94-1.81 (m, 2H), 1.79-1.62 (m, 4H), 1.55 (br. s., 2H).

MS ESI m/z 444.2 (M+H)

Example 55

2-Amino-5-{2-amino-[1,2,4]triazolo[1,5-a]pyridin-7-yl}-N-{[2-(propan-2-yloxy)phenyl]methyl}pyridine-3-carboxamide

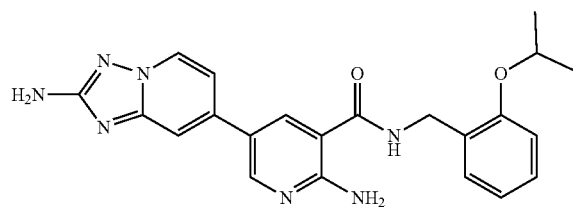 [SMILES: CC(C)Oc1ccccc1CNC(=O)c1cc(-c2ccn3nc(N)nc3c2)cnc1N]

A mixture of 2-amino-5-(2-amino-[1,2,4]triazolo[1,5-a]pyridin-7-yl)nicotinic acid (15 mg, 0.056 mmol), BOP (36.8 mg, 0.083 mmol), (2-isopropoxyphenyl)methanamine (11.46 mg, 0.069 mmol) and Hünig's Base (0.048 mL, 0.278 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 3-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-isopropoxybenzyl)nicotinamide (19.1 mg, 0.045 mmol, 81% yield).

<sup>1</sup>H NMR (500 MHz, DMSO-d6) δ 8.99 (t, J=5.5 Hz, 1H), 8.57 (d, J=1.8 Hz, 1H), 8.52 (d, J=7.1 Hz, 1H), 8.40 (d, J=1.8 Hz, 1H), 7.68 (s, 1H), 7.34 (br. s., 2H), 7.26 (d, J=5.6 Hz, 1H), 7.23-7.18 (m, 2H), 6.99 (d, J=8.4 Hz, 1H), 6.88 (t, J=7.4 Hz, 1H), 5.96 (br. s., 1H), 4.62 (dt, J=12.0, 6.0 Hz, 1H), 4.44 (d, J=5.4 Hz, 2H), 1.26 (d, J=6.0 Hz, 6H).

MS ESI m/z 418 (M+H)

Example 56

2-Amino-5-{2-amino-[1,2,4]triazolo[1,5-a]pyridin-7-yl}-N-{[2-(cyclopropylmethoxy)phenyl]methyl}pyridine-3-carboxamide

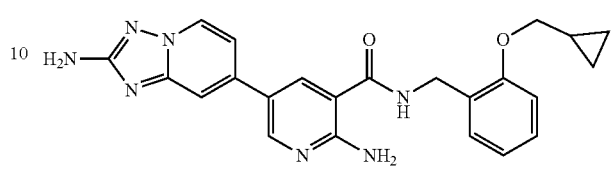

A mixture of 2-amino-5-(2-amino-[1,2,4]triazolo[1,5-a]pyridin-7-yl)nicotinic acid (15 mg, 0.056 mmol), BOP (36.8 mg, 0.083 mmol), (2-(cyclopropylmethoxy)phenyl)methanamine (12.30 mg, 0.069 mmol) and Hünig's Base (0.048 mL, 0.278 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-(cyclopropylmethoxy)benzyl)nicotinamide (18.4 mg, 0.042 mmol, 76% yield).

<sup>1</sup>H NMR (500 MHz, DMSO-d6) δ 9.03 (t, J=5.4 Hz, 1H), 8.65-8.49 (m, 2H), 8.43 (s, 1H), 7.70 (br. s., 1H), 7.35 (br. s., 2H), 7.27 (d, J=7.0 Hz, 1H), 7.23-7.14 (m, 2H), 6.95 (d, J=8.5 Hz, 1H), 6.90 (t, J=7.4 Hz, 1H), 5.97 (br. s., 2H), 4.48 (d, J=5.4 Hz, 2H), 3.90-3.84 (m, 2H), 1.23 (br. s., 1H), 0.57-0.48 (m, 2H), 0.37-0.28 (m, 2H).

MS ESI m/z 430.3 (M+H)

Example 57

5-{2-Amino-[1,2,4]triazolo[1,5-a]pyridin-7-yl}-N-[(2-{[2-(hydroxymethyl)phenyl]sulfanyl}phenyl)methyl]-2-(methylamino)pyridine-3-carboxamide

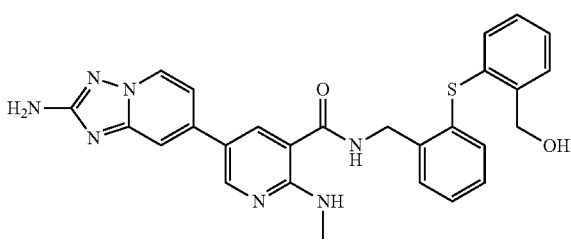

57A: Methyl 5-(2-bis-Boc-amino-[1,2,4]triazolo[1,5-a]pyridin-7-yl)-2-chloronicotinate: Ina sealed 40 mL tube, a mixture of bis-Boc-7-bromo-[1,2,4]triazolo[1,5-a]pyridin-2-amine (1.023 g, 2.475 mmol), bis(pinacolato)diboron (0.786 g, 3.09 mmol), potassium acetate (0.729 g, 7.43 mmol) and [1,1'-bis(diphenylphosphino)ferrocene]dichloropalladium(II) (0.091 g, 0.124 mmol) in 1,4-dioxane (8 mL) was stirred at 100° C. 1 h. To the cooled, crude mixture was added methyl 5-bromo-2-chloronicotinate (678 mg, 2.71 mmol) and PdCl$_2$(dppf)-CH$_2$Cl$_2$ adduct (100 mg, 0.123 mmol). The mixture was degassed by bubbling nitrogen through the mixture for 5 min. Potassium carbonate (680 mg, 4.92 mmol) was added and the reaction mixture heated at 100° C. for 45 min. After cooling to rt, the reaction mixture was diluted to a volume of 100 mL with ethyl acetate. The organics were washed with water and brine, dried over anhydrous sodium sulfate, filtered and concentrated. The crude residue was purified by flash chromatography eluting with 0-60% EtOAc in hexanes. Afforded methyl 5-(2-bis-Boc-amino-[1,2,4]triazolo[1,5-a]pyridin-7-yl)-2-chloronicotinate (605 mg, 1.177 mmol, 48% yield) as an off-white solid.

MS ESI m/z 504.1 (M+H)

57B: Methyl 5-(2-((tert-butoxycarbonyl)amino)-[1,2,4]triazolo[1,5-a]pyridin-7-yl)-2-(methylamino)nicotinate: To a solution of methyl 5-(2-bis-Boc-amino-[1,2,4]triazolo[1,5-a]pyridin-7-yl)-2-chloronicotinate (77 mg, 0.153 mmol) in THF (2 mL) was added 1 M methylamine in THF (0.191 mL, 0.382 mmol). The reaction mixture was stirred at 40° C. ON. Volatiles were removed in vacuo to afford off-white solid which was purified by flash chromatography, eluting with 0-10% MeOH in DCM. Afforded methyl 5-(2-((tert-butoxycarbonyl)amino)-[1,2,4]triazolo[1,5-a]pyridin-7-yl)-2-(methylamino)nicotinate (55 mg, 0.131 mmol, 86% yield).

MS ESI m/z 399.0 (M+H)

57C: 5-(2-Amino-[1,2,4]triazolo[1,5-a]pyridin-7-yl)-2-(methylamino)nicotinic acid, lithium salt: A stirred mixture of methyl 5-(2-((tert-butoxycarbonyl)amino)-[1,2,4]triazolo[1,5-a]pyridin-7-yl)-2-(methylamino)nicotinate (55 mg, 0.138 mmol) and 4N HCl in dioxane (0.863 mL, 3.45 mmol) in DCE (1 mL) was stirred ON at rt. Volatiles were removed in vacuo to yield a solid. To a mixture of this solid in tetrahydrofuran (2 mL) was added a solution of lithium hydroxide monohydrate (12.69 mg, 0.302 mmol) in water (1.5 mL). A few drops of methanol were added and the mixture stirred ON at rt. The reaction mixture was concentrated to a solid to afford 5-(2-amino-[1,2,4]triazolo[1,5-a]pyridin-7-yl)-2-(methylamino)nicotinic acid, lithium salt (40 mg, 0.130 mmol, 95% yield). Material was used as is in subsequent chemistry.

MS ESI m/z 285.0 (M+H)

57: A mixture of 5-(2-amino-[1,2,4]triazolo[1,5-a]pyridin-7-yl)-2-(methylamino)nicotinic acid (12 mg, 0.042 mmol), BOP (28.0 mg, 0.063 mmol), (2-((2-(aminomethyl)phenyl)thio)phenyl)methanol (12.43 mg, 0.051 mmol) and Hünig's Base (0.037 mL, 0.211 mmol) in DMF (1.0 mL) was stirred at rt for 7 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 27 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-((2-(hydroxymethyl)phenyl)thio)benzyl)-2-(methylamino)nicotinamide (13.1 mg, 0.024 mmol, 57.6% yield).

$^1$H NMR (500 MHz, DMSO-d6) δ 9.20 (t, J=5.6 Hz, 1H), 8.70 (d, J=1.9 Hz, 1H), 8.56 (d, J=7.0 Hz, 1H), 8.43 (br. s., 2H), 7.71 (s, 1H), 7.54 (d, J=7.4 Hz, 1H), 7.45-7.38 (m, 1H), 7.37-7.17 (m, 5H), 7.14 (d, J=7.7 Hz, 1H), 7.04 (d, J=7.7 Hz, 1H), 5.99 (br. s., 1H), 4.59 (d, J=4.8 Hz, 2H), 4.54 (d, J=5.4 Hz, 2H), 2.95 (d, J=4.7 Hz, 3H), 1.22 (s, 2H).

MS ESI m/z 512.1 (M+H)

Example 58

5-{2-Amino-[1,2,4]triazolo[1,5-a]pyridin-7-yl}-2-methoxy-N-{[3-(trifluoromethoxy)phenyl]methyl}pyridine-3-carboxamide

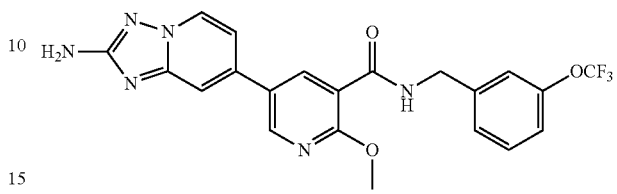

A mixture 5-(2-amino-[1,2,4]triazolo[1,5-a]pyridin-7-yl)-2-methoxynicotinic acid, lithium salt (30 mg, 0.103 mmol), (3-(trifluoromethoxy)phenyl)methanamine (21.59 mg, 0.113 mmol), BOP (49.9 mg, 0.113 mmol) and triethylamine (0.043 mL, 0.308 mmol) in DMF (0.6 mL) was stirred at rt for 16 h. The reaction mixture was partitioned between EtOAc (25 ml) and 10% LiCl solution (25 ml). The organic layer was washed with 10% LiCl solution (2×20 ml) and brine (20 ml). After drying over anhydrous sodium sulfate and filtration, the organic layer was concentrated to a residue that was chromatographed on a 4 gm ISCO silica gel cartridge, eluting with a 0-10% MeOH/DCM gradient. The pure fractions were concentrated to afford 5-(2-amino-[1,2,4]triazolo[1,5-a]pyridin-7-yl)-2-methoxy-N-(3-(trifluoromethoxy)benzyl)nicotinamide (29 mg, 0.062 mmol, 60.4% yield) as a white solid.

1H NMR (400 MHz, DMSO-d6) δ8.98 (t, J=5.8 Hz, 1H), 8.78 (d, J=2.4 Hz, 1H), 8.60 (d, J=7.0 Hz, 1H), 8.44 (d, J=2.3 Hz, 1H), 7.72 (s, 1H), 7.55-7.45 (m, 1H), 7.44-7.32 (m, 2H), 7.25 (d, J=7.0 Hz, 2H), 6.05 (s, 2H), 4.58 (d, J=5.9 Hz, 2H), 4.04 (s, 3H).

MS ESI m/z 459.3 (M+H)

Example 59

5-{2-Amino-[1,2,4]triazolo[1,5-a]pyridin-7-yl}-N-[(2-{[2-(hydroxymethyl)phenyl]sulfanyl}phenyl)methyl]pyridine-3-carboxamide

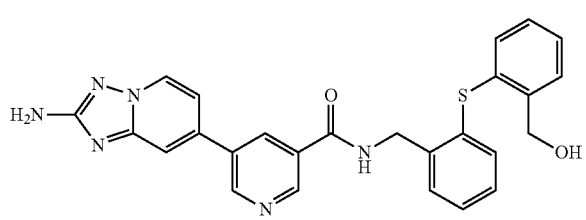 [SMILES: Nc1nc2cc(-c3cncc(C(=O)NCc4ccccc4Sc4ccccc4CO)c3)ccn2n1]

A mixture of 5-(2-((tert-butoxycarbonyl)amino)-[1,2,4]triazolo[1,5-a]pyridin-7-yl)nicotinic acid (12 mg, 0.034 mmol), BOP (22.40 mg, 0.051 mmol), (2-((2-(aminomethyl)phenyl)thio)phenyl)methanol (9.94 mg, 0.041 mmol) and Hünig's Base (0.029 mL, 0.169 mmol) in DMF (1.0 mL) was stirred at rt ON. The reaction mixture was concentrated to a solid. The crude residue was dissolved in dichloromethane (1 mL) and TFA (0.5 mL) was added. The reaction mixture was stirred 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 20 min, then a 5-minute hold at 100% B; Flow: 20 mL/min. Fractions containing the desired product were combined and dried via centrifugal evaporation. Afforded 5-(2-amino-[1, 2,4]triazolo[1,5-a]pyridin-7-yl)-N-(2-((2-(hydroxymethyl) phenyl)thio)benz yl)nicotinamide (7.8 mg, 0.016 mmol, 46.9% yield).

$^1$H NMR (500 MHz, DMSO-d6) δ 9.28 (t, J=5.5 Hz, 1H), 9.18 (br. s., 1H), 9.05 (br. s., 1H), 8.68 (d, J=6.9 Hz, 1H), 8.61 (s, 1H), 7.86 (s, 1H), 7.53 (d, J=7.5 Hz, 1H), 7.46 (d, J=7.6 Hz, 1H), 7.38-7.32 (m, 2H), 7.32-7.24 (m, 2H), 7.23-7.18 (m, 1H), 7.16-7.11 (m, 1H), 7.06-7.00 (m, 1H), 4.64-4.54 (m, 3H) [4 protons lost in water suppression].

MS ESI m/z 483.1 (M+H)

Example 60

2-{2-Amino-[1,2,4]triazolo[1,5-a]pyridin-7-yl}-6-fluoro-N-[(2-{[2-(hydroxymethyl)phen yl]sulfanyl}phenyl)methyl]quinoline-4-carboxamide

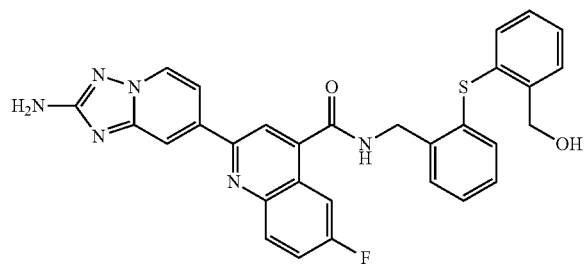 [SMILES: Nc1nc2cc(-c3cc(C(=O)NCc4ccccc4Sc4ccccc4CO)c4cc(F)ccc4n3)ccn2n1]

60A: Methyl 2-((bis-Boc-amino)-[1,2,4]triazolo[1,5-a] pyridin-7-yl)-6-fluoroquinoline-4-carboxylate: In a sealed 40 mL tube, a mixture of bis-Boc-7-bromo-[1,2,4]triazolo [1,5-a]pyridin-2-amine (320 mg, 0.774 mmol), bis(pinacolato)diboron (246 mg, 0.968 mmol), potassium acetate (228 mg, 2.323 mmol), and [1,1'-bis(diphenylphosphino)ferrocene]dichloropalladium(II) (28.3 mg, 0.039 mmol) in 1,4-dioxane (5 mL) was stirred at 100° C. 1 h. To the cooled reaction mixture was added methyl 2-chloro-6-fluoroquinoline-4-carboxylate (220 mg, 0.918 mmol) and 1,1'-bis(di-tert-butylphosphino)ferrocene palladium dichloride (24.93 mg, 0.038 mmol). The mixture was degassed by bubbling nitrogen through it for 5 min. 2M aqueous K$_3$PO$_4$ (1.148 mL, 2.295 mmol) was added and the reaction mixture heated at 100° C. for 15 min. The reaction mixture was diluted to 75 mL with ethyl acetate. The organics were washed with brine, dried over anhydrous sodium sulfate, filtered and concentrated. The crude residue was purified by flash chromatography, eluting with 0-100% ethyl acetate in hexanes. Afforded methyl 2-((bis-Boc-amino)-[1,2,4]triazolo[1,5-a] pyridin-7-yl)-6-fluoroquinoline-4-carboxylate (231 mg, 0.425 mmol, 55.6% yield) as a tan solid.

MS ESI m/z 538.0 (M+H)

60B: 2-(2-Amino-[1,2,4]triazolo[1,5-a]pyridin-7-yl)-6-fluoroquinoline-4-carboxylic acid: A solution of methyl 2-((bis-Boc-amino)-[1,2,4]triazolo[1,5-a]pyridin-7-yl)-6-fluoroquinoline-4-carboxylate (231 mg, 0.430 mmol) in 4 N HCl in dioxane (1.306 mL, 43.0 mmol) was stirred at rt ON. The volatiles were removed in vacuo to afford an off-white solid. To a solution of this material in tetrahydrofuran (3.5 mL) was added 1 N NaOH (2.372 mL, 2.372 mmol). A few drops of methanol were added, and the resulting solution was stirred ON at rt. The volatiles were removed in vacuo and the residue acidified with 1 N HCl (8.5 mL). The solid product was isolated by filtration and dried to afford 2-(2-amino-[1,2,4]triazolo[1,5-a]pyridin-7-yl)-6-fluoroquinoline-4-carboxylic acid (119 mg, 0.368 mmol, 78% yield) as a brown solid.

MS ESI m/z 338.0 (M+H)

60: A mixture of 2-(2-amino-[1,2,4]triazolo[1,5-a]pyridin-7-yl)-6-fluoroquinoline-4-carboxylic acid (20 mg, 0.062 mmol), BOP (41.0 mg, 0.093 mmol), (2-((2-(aminomethyl) phenyl)thio)phenyl)methanol (18.21 mg, 0.074 mmol) and Hünig's Base (0.054 mL, 0.309 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-100% B over 20 min, then a 2-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 43-66% B over 25 min, then a 2-minute hold at 66% B; Flow: 20 mL/min. Fractions containing the desired product were combined and dried via centrifugal evaporation. Afforded 2-(2-amino-[1, 2,4]triazolo[1,5-a]pyridin-7-yl)-6-fluoro-N-(2-((2-(hydroxymethyl)phenyl) thio)benzyl)quinoline-4-carboxamide (4.4 mg, 7.19 μmol, 11.63% yield).

$^1$H NMR (500 MHz, DMSO-d6) δ 9.44 (t, J=5.5 Hz, 1H), 8.71 (d, J=7.0 Hz, 1H), 8.47 (s, 1H), 8.30 (s, 1H), 8.26 (dd, J=9.2, 5.7 Hz, 1H), 8.04 (dd, J=10.3, 2.7 Hz, 1H), 7.85 (dd, J=7.0, 1.6 Hz, 1H), 7.80 (td, J=8.7, 2.8 Hz, 1H), 7.57 (dd, J=7.1, 3.9 Hz, 2H), 7.39 (t, J=7.4 Hz, 1H), 7.36-7.27 (m, 2H), 7.24 (t, J=7.3 Hz, 1H), 7.14 (d, J=7.6 Hz, 1H), 7.09 (d, J=7.7 Hz, 1H), 6.19 (s, 2H), 5.39 (t, J=5.5 Hz, 1H), 4.68 (d, J=5.4 Hz, 2H), 4.62 (d, J=5.4 Hz, 2H).

MS ESI m/z 551.2 (M+H)

Example 61

5-{2-Amino-[1,2,4]triazolo[1,5-a]pyridin-7-yl}-2-ethyl-N-[(2-{[2-(hydroxymethyl)phenyl] sulfanyl}phenyl)methyl]pyridine-3-carboxamide

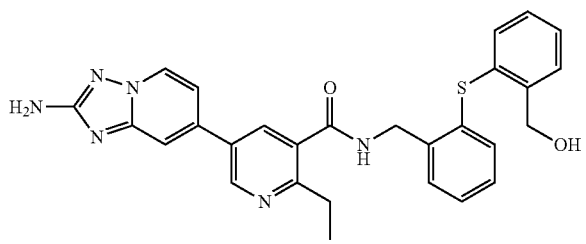 [SMILES: CCc1ncc(-c2ccn3nc(N)nc3c2)cc1C(=O)NCc1ccccc1Sc1ccccc1CO]

61A: Methyl 5-(2-((bis-Boc)amino)-[1,2,4]triazolo[1,5-a] pyridin-7-yl)-2-vinylnicotinate: A solution of 57A (175 mg, 0.347 mmol), dicyclohexyl(2',6'-dimethoxy-[1,1'-biphenyl]-

2-yl)phosphine (15.68 mg, 0.038 mmol), palladium(II) acetate (3.90 mg, 0.017 mmol) and 6-methyl-2-vinyl-1,3,6,2-dioxazaborocane-4,8-dione (159 mg, 0.868 mmol) in dioxane (3 mL) was purged with nitrogen for 1 min. K$_3$PO$_4$, 2M (0.955 mL, 1.910 mmol) was added and the reaction mixture heated to 100° C. for 5 h. After cooling to rt, the reaction mixture was diluted with EtOAc (35 mL). The organics were washed with saturated aqueous ammonium chloride and brine, dried over anhydrous sodium sulfate, filtered and concentrated. The crude residue was purified by flash chromatography, eluting with 0-100% ethyl acetate in hexanes. Afforded methyl 5-(2-((bis-Boc)amino)-[1,2,4]triazolo[1,5-a]pyridin-7-yl)-2-vinylnicotinate (101 mg), as a mixture of mono- and bis-Boc protected species.

MS ESI m/z 496.1 (M+H) and 396.1 (M+H)

61B: Methyl 5-(2-amino-[1,2,4]triazolo[1,5-a]pyridin-7-yl)-2-ethylnicotinate: A stirred mixture of methyl 5-(2-((bis-Boc)amino)-[1,2,4]triazolo[1,5-a]pyridin-7-yl)-2-vinylnicotinate (101 mg, 0.219 mmol, 50% mono-Boc) and 10% Pd on carbon (55.4 mg, 0.052 mmol) in ethanol (3 mL) was degassed by vacuum before being flooded with hydrogen gas. The mixture was stirred at rt for 90 min. The reaction mixture was filtered and concentrated to afford the protected product. The intermediate was dissolved in dichloromethane (1 mL) and 4 N HCl in dioxane (1.085 mL, 4.34 mmol) was added. After stirring at rt ON, the the mixture was concentrated to a solid, methyl 5-(2-amino-[1,2,4]triazolo[1,5-a]pyridin-7-yl)-2-ethylnicotinate (65 mg, 0.219 mmol) and carried forward into subsequent chemistry as is.

MS ESI m/z 298.1 (M+H)

61C: 5-(2-Amino-[1,2,4]triazolo[1,5-a]pyridin-7-yl)-2-ethylnicotinic acid: To a mixture of methyl 5-(2-amino-[1,2,4]triazolo[1,5-a]pyridin-7-yl)-2-ethylnicotinate (65 mg, 0.219 mmol) in tetrahydrofuran (2 ml) was added a solution of lithium hydroxide monohydrate (20.18 mg, 0.481 mmol) in water (1.5 mL). A few drops of methanol were added and the mixture stirred 2 h at rt. The reaction mixture was concentrated to a solid product, 5-(2-amino-[1,2,4]triazolo[1,5-a]pyridin-7-yl)-2-ethylnicotinic acid, lithium salt, (63 mg, 0.202 mmol, 92% yield).

MS ESI m/z 284.0 (M+H)

61: A mixture of 5-(2-amino-[1,2,4]triazolo[1,5-a]pyridin-7-yl)-2-ethylnicotinic acid (22 mg, 0.078 mmol), BOP (51.5 mg, 0.116 mmol), (2-((2-(aminomethyl)phenyl)thio)phenyl)methanol (22.86 mg, 0.093 mmol) and Hünig's Base (0.068 mL, 0.388 mmol) in DMF (1.0 mL) was stirred at rt for 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 4-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-ethyl-N-(2-((2-(hydroxymethyl)phenyl)thio)benzyl)nicotinamide (9.9 mg, 0.019 mmol, 24.47% yield).

$^1$H NMR (500 MHz, DMSO-d6) δ 9.07 (t, J=5.5 Hz, 1H), 8.99 (d, J=2.1 Hz, 1H), 8.64 (d, J=7.0 Hz, 1H), 8.18 (d, J=2.0 Hz, 1H), 7.81 (s, 1H), 7.57 (d, J=7.6 Hz, 1H), 7.49 (d, J=7.5 Hz, 1H), 7.38-7.29 (m, 4H), 7.25 (dt, J=19.0, 7.6 Hz, 2H), 7.08 (dd, J=19.7, 7.7 Hz, 2H), 6.09 (s, 2H), 4.73-4.46 (m, 4H), 2.93 (q, J=7.5 Hz, 2H), 1.23 (t, J=7.5 Hz, 3H).

MS ESI m/z 511.1 (M+H)

Example 62

2-Amino-5-{2-amino-[1,2,4]triazolo[1,5-a]pyridin-7-yl}-N-[(2-{[2-(hydroxymethyl)phenyl]sulfanyl}phenyl)methyl]pyridine-3-carboxamide

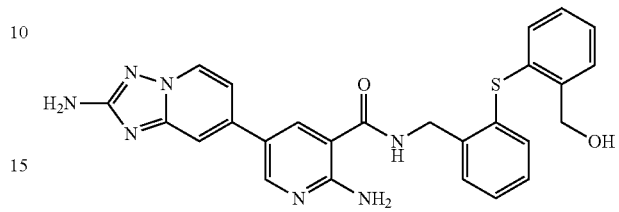

A mixture of 2-amino-5-(2-amino-[1,2,4]triazolo[1,5-a]pyridin-7-yl)nicotinic acid (17 mg, 0.063 mmol), BOP (41.7 mg, 0.094 mmol), (2-((2-(aminomethyl)phenyl)thio)phenyl)methanol (18.52 mg, 0.075 mmol) and Hünig's Base (0.055 mL, 0.315 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(2-((2-(hydroxymethyl)phenyl) thio)benzyl)nicotinamide (13.7 mg, 0.026 mmol, 42.0% yield).

$^1$H NMR (500 MHz, DMSO-d6) δ 9.17 (t, J=5.5 Hz, 1H), 8.62 (d, J=2.0 Hz, 1H), 8.57 (d, J=7.0 Hz, 1H), 8.44 (d, J=1.9 Hz, 1H), 7.72 (s, 1H), 7.56 (d, J=7.5 Hz, 1H), 7.45-7.19 (m, 8H), 7.14 (d, J=7.6 Hz, 1H), 7.06 (d, J=7.6 Hz, 1H), 6.01 (s, 2H), 5.37 (t, J=5.5 Hz, 1H), 4.61 (d, J=5.4 Hz, 2H), 4.55 (d, J=5.4 Hz, 2H).

MS ESI m/z 498 (M+H)

Example 63

5-{2-Amino-[1,2,4]triazolo[1,5-a]pyridin-7-yl}-N-[(2-{[2-(hydroxymethyl)phenyl]sulfanyl}phenyl)methyl]-2-propoxypyridine-3-carboxamide

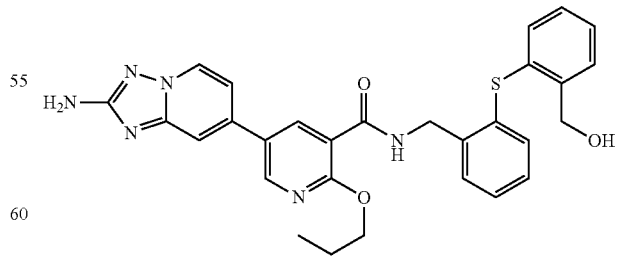

63A: Propyl 5-bromo-2-propoxynicotinate: To a solution of methyl 5-bromo-2-chloronicotinate (0.56 g, 2.236 mmol) in THF (8 mL) at 0° C. was slowly added 20% sodium n-propoxide in n-propanol (2.331 mL, 4.92 mmol). The reaction mixture was stirred at 0° C. for 1 h. Ethanol (10 mL) was added and volatiles removed in vacuo. The reaction mixture was poured into water (50 mL) water and extracted with ethyl acetate (3×75 mL). The combined organics were washed with brine, dried over anhydrous sodium sulfate, filtered and concentrated in vacuo. The crude residue was loaded onto a 24 g ISCO column and purified by flash chromatography, eluting with 0-25% EtOAc in hexanes. Afforded propyl 5-bromo-2-propoxynicotinate (173 mg, 0.567 mmol, 25.4% yield).

MS ESI m/z 304.0 (M+H)

63B: Propyl 5-(2-((bis-tert-butoxycarbonyl)amino)-[1,2,4]triazolo[1,5-a]pyridin-7-yl)-2-propoxynicotinate: In a sealed 40 mL tube, a mixture of bis-Boc-7-bromo-[1,2,4]triazolo[1,5-a]pyridin-2-amine (220 mg, 0.532 mmol), bis(pinacolato)diboron (169 mg, 0.665 mmol), potassium acetate (157 mg, 1.597 mmol) and [1,1'-bis(diphenylphosphino)ferrocene]dichloropalladium(II) (19.48 mg, 0.027 mmol) in 1,4-dioxane (4 mL) was stirred at 100° C. 1 h. After cooling to rt, propyl 5-bromo-2-propoxynicotinate (173 mg, 0.573 mmol) and 1,1'-bis(di-tert-butylphosphino)ferrocene palladium dichloride (16.96 mg, 0.026 mmol) were added and the mixture degassed by bubbling nitrogen through it for 5 min. 2 M K$_3$PO$_4$ (aq) (0.781 mL, 1.561 mmol) was added and the reaction mixture heated at 100° C. for 15 min. After cooling to rt, the reaction mixture was concentrated onto Celite.

Using a 40 g ISCO column, the crude material was purified by flash chromatography, eluting with 0-100% EtOAc in hexanes. Concentration of the fractions containing product afforded propyl 5-(2-((bis-tert-butoxycarbonyl)amino)-[1,2,4]triazolo[1,5-a]pyridin-7-yl)-2-propoxynicotinate (232 mg, 0.409 mmol, 79% yield) as a off-white solid.

MS ESI m/z 556.3 (M+H)

63C: Propyl 5-(2-amino-[1,2,4]triazolo[1,5-a]pyridin-7-yl)-2-propoxynicotinate, HCl: A solution of propyl 5-(2-((bis-tert-butoxycarbonyl)amino)-[1,2,4]triazolo[1,5-a]pyridin-7-yl)-2-propoxynicotinate (230 mg, 0.414 mmol) in 4 N HCl in dioxane (1258 µl, 41.4 mmol) was stirred at rt ON. The reaction mixture was concentrated to afford an off-white solid, propyl 5-(2-amino-[1,2,4]triazolo[1,5-a]pyridin-7-yl)-2-propoxynicotinate, HCl (171 mg, 0.415 mmol, 100% yield).

MS ESI m/z 356.3 (M+H)

63D: 5-(2-Amino-[1,2,4]triazolo[1,5-a]pyridin-7-yl)-2-propoxynicotinic acid, lithium salt: To a solution of propyl 5-(2-amino-[1,2,4]triazolo[1,5-a]pyridin-7-yl)-2-propoxynicotinate, HCl (171 mg, 0.436 mmol) in tetrahydrofuran (3 mL) was added a solution of lithium hydroxide monohydrate (40.3 mg, 0.960 mmol) in water (1 mL). A few drops of methanol were added, and the resulting solution was stirred ON at rt. The reaction mixture was concentrated to a solid to afford 5-(2-amino-[1,2,4]triazolo[1,5-a]pyridin-7-yl)-2-propoxynicotinic acid, lithium salt (135 mg, 0.409 mmol, 94% yield).

MS ESI m/z 314.1 (M+H)

63: A mixture of 5-(2-amino-[1,2,4]triazolo[1,5-a]pyridin-7-yl)-2-propoxynicotinic acid, lithium salt (19 mg, 0.061 mmol), BOP (40.2 mg, 0.091 mmol), (2-((2-(aminomethyl)phenyl)thio)phenyl)methanol (17.85 mg, 0.073 mmol) and Hünig's Base (0.053 mL, 0.303 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-((2-(hydroxymethyl)phenyl)thio)benz yl)-2-propoxynicotinamide (12.3 mg, 0.023 mmol, 37.1% yield).

$^1$H NMR (500 MHz, DMSO-d6) δ 8.79-8.67 (m, 2H), 8.60 (d, J=7.0 Hz, 1H), 8.43 (d, J=2.5 Hz, 1H), 7.72 (s, 1H), 7.54 (t, J=8.2 Hz, 2H), 7.39-7.17 (m, 5H), 7.13 (d, J=7.6 Hz, 1H), 7.03 (d, J=7.7 Hz, 1H), 6.07 (s, 2H), 5.36 (t, J=5.4 Hz, 1H), 4.59 (t, J=5.5 Hz, 4H), 4.40 (t, J=6.6 Hz, 2H), 1.79 (sxt, J=7.1 Hz, 2H), 0.94 (t, J=7.4 Hz, 3H).

MS ESI m/z 541.2 (M+H)

Example 64

5-{2-Amino-[1,2,4]triazolo[1,5-a]pyridin-7-yl}-2-(dimethylamino)-N-(3-phenylbutyl)pyridine-3-carboxamide

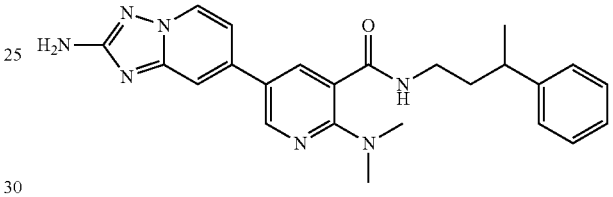

64A: Ethyl 5-bromo-2-fluoronicotinate: To a mixture of 5-bromo-2-fluoronicotinic acid (600 mg, 2.73 mmol) in DMF (15 mL) was added potassium carbonate (754 mg, 5.45 mmol) and iodoethane (0.264 mL, 3.27 mmol). The reaction mixture was stirred at rt ON. The reaction mixture was diluted to a volume of 125 mL with EtOAc. The organics were washed with water, 10% LiCl solution, saturated aqueous ammonium chloride and brine. The organics were dried over anhydrous sodium sulfate, filtered and concentrated in vacuo. The crude residue was loaded onto a 24 g ISCO column and purified by flash chromatography, eluting with 0-25% EtOAc in hexanes. Afforded ethyl 5-bromo-2-fluoronicotinate (511 mg, 2.019 mmol, 74.0% yield) as a crystalline white solid.

$^1$H NMR (400 MHz, DMSO-d$_6$) δ 8.65 (dd, J=2.6, 1.3 Hz, 1H), 8.56 (dd, J=8.2, 2.6 Hz, 1H), 4.38-4.31 (m, 2H), 1.35-1.30 (m, 3H).

MS ESI m/z 249.9 (M+H)

64B: Ethyl 5-bromo-2-(dimethylamino)nicotinate: To a solution of ethyl 5-bromo-2-fluoronicotinate (105 mg, 0.423 mmol) in THF (2 mL) was added dimethylamine (0.529 mL, 1.058 mmol). The reaction mixture was stirred at rt 20 min. The reaction mixture was concentrated to a solid and dried under vacuum. Isolated ethyl 5-bromo-2-(dimethylamino)nicotinate (115 mg, 0.413 mmol, 97%).

MS ESI m/z 275.0 (M+H)

64C: Ethyl 5-(2-((bis-tert-butoxycarbonyl)amino)-[1,2,4]triazolo[1,5-a]pyridin-7-yl)-2-(dimethylamino)nicotinate: A mixture of bis-Boc-7-bromo-[1,2,4]triazolo[1,5-a]pyridin-2-amine (200 mg, 0.484 mmol), 4,4,4',4',5,5,5',5'-octamethyl-2,2'-bi(1,3,2-dioxaborolane) (141 mg, 0.557 mmol), potassium acetate (142 mg, 1.452 mmol), and PdCl2(dppf)-CH$_2$Cl$_2$ adduct (19.76 mg, 0.024 mmol) in 1,4-dioxane (5 mL) was stirred 1 h at 100° C. After cooling to rt, ethyl 5-bromo-2-(dimethylamino)nicotinate (115 mg, 0.421 mmol) and 1,1'-bis(di-tert-butylphosphino)ferrocene palladium dichloride (13.59 mg, 0.021 mmol) were added. The mixture was degassed by bubbling nitrogen through it for 5 min. 2M K₃PO₄ (aq) (0.625 mL, 1.251 mmol) was added and the reaction mixture heated at 100° C. for 15 min. The reaction mixture was diluted to a total volume of 50 mL with EtOAc. The organics were washed with brine, dried over anhydrous sodium sulfate, filtered and concentrated. The crude residue was loaded onto a 12 g ISCO column and purified by flash chromatography, eluting with 0-100% EtOAc in hexanes to afford the desired product (209 mg, 0.377 mmol, 90% yield) as a beige solid.

MS ESI m/z 527.1 (M+H)

64D: Ethyl 5-(2-amino-[1,2,4]triazolo[1,5-a]pyridin-7-yl)-2-(dimethylamino)nicotinate, HCl: To a solution of ethyl 5-(2-((bis-tert-butoxycarbonyl)amino)-[1,2,4]triazolo[1,5-a]pyridin-7-yl)-2-(dimethylamino)nicotinate (209 mg, 0.397 mmol) in DCE (0.4 mL) was added 4 N HCl in dioxane (1.488 mL, 5.95 mmol) and the resulting solution was stirred at rt ON. The reaction mixture was concentrated to afford an off-white solid, ethyl 5-(2-amino-[1,2,4]triazolo[1,5-a]pyridin-7-yl)-2-(dimethylamino)nicotinate, HCl (144 mg, 0.377 mmol, 95% yield).

MS ESI m/z 327.1 (M+H)

64E: 5-(2-Amino-[1,2,4]triazolo[1,5-a]pyridin-7-yl)-2-(dimethylamino)nicotinic acid: To a solution of ethyl 5-(2-amino-[1,2,4]triazolo[1,5-a]pyridin-7-yl)-2-(dimethylamino)nicotinate, HCl (144 mg, 0.397 mmol) in tetrahydrofuran (2 mL) was added a solution of lithium hydroxide monohydrate (36.6 mg, 0.873 mmol) in water (1 mL). A few drops of methanol were added, and the reaction mixture was stirred 3 d at rt. Additional lithium hydroxide monohydrate (20 mg) as a solution in water (0.75 mL) was added and stirring continued ON. Extraction of the compound was attempted, however it remained in the aqueous layer. The aqueous layer was concentrated to a powder. The desired product was triturated away from salts with isopropanol. The organics were concentrated to a solid to afford 5-(2-amino-[1,2,4]triazolo[1,5-a]pyridin-7-yl)-2-(dimethylamino)nicotinic acid (91 mg, 0.290 mmol, 73.0% yield).

MS ESI m/z 299.1 (M+H)

64: A mixture of 5-(2-amino-[1,2,4]triazolo[1,5-a]pyridin-7-yl)-2-(dimethylamino)nicotinic acid (19 mg, 0.064 mmol) BOP (42.3 mg, 0.096 mmol), 3-phenylbutan-1-amine, HCl (14.19 mg, 0.076 mmol) and Hünig's Base (0.056 mL, 0.318 mmol) in DMF (1.0 mL) was stirred 6 h at rt. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-(dimethylamino)-N-(3-phenylbutyl)nicotinamide (6.9 mg, 0.016 mmol, 24.97% yield).

¹H NMR (500 MHz, DMSO-d6) δ 8.73-8.30 (m, 5H), 7.89 (d, J=2.3 Hz, 1H), 7.62 (s, 1H), 7.37-7.08 (m, 6H), 3.21-3.06 (m, 2H), 2.99 (s, 6H), 2.80 (q, J=7.0 Hz, 1H), 1.81 (q, J=7.3 Hz, 2H), 1.23 (d, J=6.9 Hz, 3H).

MS ESI m/z 430 (M+H)

Example 65

2-Amino-5-{2-amino-[1,2,4]triazolo[1,5-a]pyridin-7-yl}-N-(3-phenylbutyl)pyridine-3-carboxamide

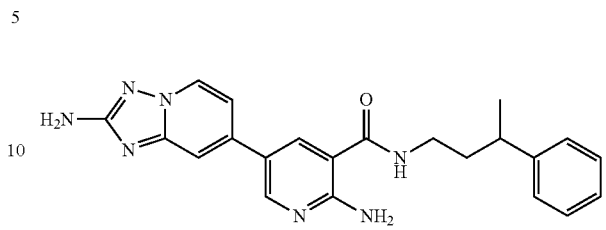

A mixture of 2-amino-5-(2-amino-[1,2,4]triazolo[1,5-a]pyridin-7-yl)nicotinic acid (17 mg, 0.063 mmol) BOP (41.7 mg, 0.094 mmol), 3-phenylbutan-1-amine, HCl (14.02 mg, 0.075 mmol) and Hünig's Base (0.055 mL, 0.315 mmol) in DMF (1.0 mL) was stirred 6 h at rt. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 min, then a 5-minute hold at 100% B; Flow: 20 mL/min. Fractions containing the desired product were combined and dried via centrifugal evaporation. Afforded 2-amino-5-(2-amino-[1,2,4]triazolo[1,5-a]pyridin-7-yl)-N-(3-phenylbutyl)nicotinamide (12.5 mg, 0.031 mmol, 49.0% yield).

¹H NMR (500 MHz, DMSO-d6) δ 8.62-8.52 (m, 3H), 8.27 (d, J=2.0 Hz, 1H), 7.69 (s, 1H), 7.33-7.22 (m, 5H), 7.20-7.14 (m, 1H), 3.38-3.03 (m, 2H), 2.84-2.74 (m, 1H), 1.84 (q, J=7.3 Hz, 2H), 1.24 (d, J=6.9 Hz, 3H) 4 protons missing due to water suppression.

MS ESI m/z 402.2 (M+H)

Example 66

5-{2-Amino-[1,2,4]triazolo[1,5-a]pyridin-7-yl}-2-ethyl-N-(3-phenylbutyl)pyridine-3-carb oxamide

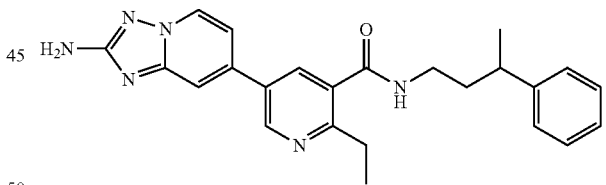

A mixture of lithium 5-(2-amino-[1,2,4]triazolo[1,5-a]pyridin-7-yl)-2-ethylnicotinate (12 mg, 0.041 mmol), BOP (27.5 mg, 0.062 mmol), 3-phenylbutan-1-amine, HCl (9.25 mg, 0.050 mmol) and Hünig's Base (0.036 mL, 0.207 mmol) in DMF (1.0 mL) was stirred 6 h at rt. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-ethyl-N-(3-phenylbutyl)nicotinamide (6.4 mg, 0.015 mmol, 36.1% yield).

MS ESI m/z 414.9 (M+H)

Example 67

2-{2-Amino-[1,2,4]triazolo[1,5-a]pyridin-7-yl}-6-fluoro-N-(3-phenylbutyl)quinoline-4-carboxamide

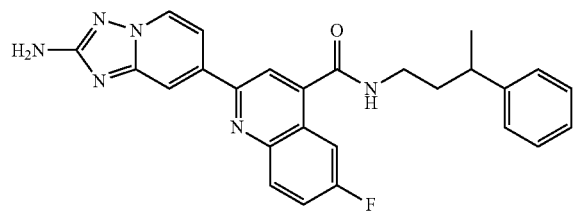 [SMILES: CC(CCNC(=O)c1cc(-c2ccn3nc(N)nc3c2)nc2ccc(F)cc12)c1ccccc1]

A mixture of 2-(2-amino-[1,2,4]triazolo[1,5-a]pyridin-7-yl)-6-fluoroquinoline-4-carboxylic acid (18 mg, 0.056 mmol), BOP (36.9 mg, 0.084 mmol), 3-phenylbutan-1-amine, HCl (12.41 mg, 0.067 mmol) and Hünig's Base (0.049 mL, 0.278 mmol) in DMF (1.0 mL) was stirred ON at rt. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 2-(2-amino-[1,2,4]triazolo[1,5-a]pyridin-7-yl)-6-fluoro-N-(3-phenylbutyl)quinoline-4-carboxamide (12.6 mg, 0.027 mmol, 48.3% yield).

$^1$H NMR (500 MHz, DMSO-d6) δ 8.89 (br. s., 1H), 8.70 (d, J=6.9 Hz, 1H), 8.34 (s, 1H), 8.29 (s, 1H), 8.24 (dd, J=9.0, 5.6 Hz, 1H), 7.94 (d, J=8.2 Hz, 1H), 7.85 (d, J=6.9 Hz, 1H), 7.79 (t, J=8.6 Hz, 1H), 7.35-7.16 (m, 5H), 3.34-3.19 (m, 1H), 2.90-2.81 (m, 1H), 1.91 (q, J=7.2 Hz, 2H), 1.27 (d, J=6.8 Hz, 3H). 3 protons not observed due to water suppression.

MS ESI m/z 455.1 (M+H)

Example 68

2-{2-Amino-[1,2,4]triazolo[1,5-a]pyridin-7-yl}-N-(1-benzyl-1H-pyrazol-4-yl)-6-fluoroquinoline-4-carboxamide

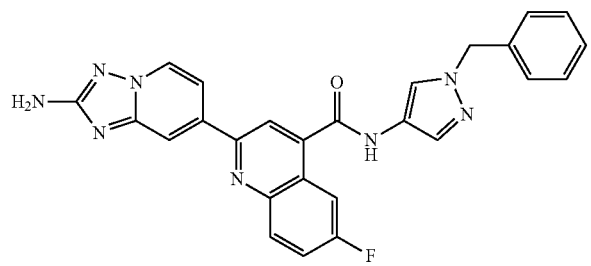 [SMILES: Nc1nc2cc(-c3cc(C(=O)Nc4cnn(Cc5ccccc5)c4)c4cc(F)ccc4n3)ccn2n1]

A mixture of 2-(2-amino-[1,2,4]triazolo[1,5-a]pyridin-7-yl)-6-fluoroquinoline-4-carboxylic acid (18 mg, 0.056 mmol), BOP (36.9 mg, 0.084 mmol), 1-benzyl-1H-pyrazol-4-amine, HCl (14.01 mg, 0.067 mmol) and Hünig's Base (0.039 mL, 0.223 mmol) in DMF (1 mL) was stirred ON at rt. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 2-(2-amino-[1,2,4]triazolo[1,5-a]pyridin-7-yl)-N-(1-benzyl-1H-pyrazol-4-yl)-6-fluoroquinoline-4-carboxamide (13.0 mg, 0.027 mmol, 47.8% yield).

$^1$H NMR (500 MHz, DMSO-d6) δ 11.05 (s, 1H), 8.71 (d, J=7.0 Hz, 1H), 8.57 (s, 1H), 8.33 (s, 1H), 8.31-8.25 (m, 2H), 8.03-7.98 (m, 1H), 7.89 (d, J=6.9 Hz, 1H), 7.84-7.77 (m, 1H), 7.67 (s, 1H), 7.41-7.35 (m, 2H), 7.34-7.26 (m, 3H), 6.18 (s, 2H), 5.37 (s, 2H).

MS ESI m/z 478.9 (M+H)

Example 69

5-{2-Amino-[1,2,4]triazolo[1,5-a]pyridin-7-yl}-N-(3-phenylbutyl)-2-propoxypyridine-3-carboxamide

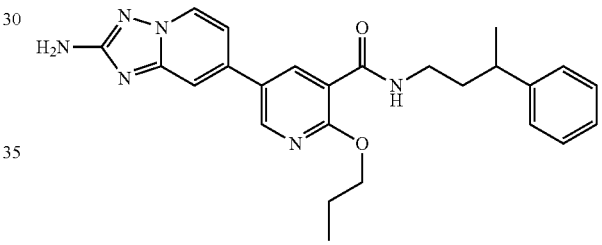

A mixture of lithium 5-(2-amino-[1,2,4]triazolo[1,5-a]pyridin-7-yl)-2-propoxynicotinate (16 mg, 0.050 mmol), BOP (33.2 mg, 0.075 mmol), 3-phenylbutan-1-amine, HCl (11.17 mg, 0.060 mmol) and Hünig's Base (0.044 mL, 0.251 mmol) in DMF (1.0 mL) was stirred ON at rt. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 min, then a 3-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3-phenylbutyl)-2-propoxynicotinamide (10.3 mg, 0.023 mmol, 45.3% yield).

$^1$H NMR (500 MHz, DMSO-d6) δ 8.72 (d, J=2.4 Hz, 1H), 8.59 (d, J=7.0 Hz, 1H), 8.36 (d, J=2.4 Hz, 1H), 8.22 (t, J=5.3 Hz, 1H), 7.69 (s, 1H), 7.34-7.16 (m, 6H), 6.04 (s, 2H), 4.40 (t, J=6.6 Hz, 2H), 3.21 (d, J=7.3 Hz, 2H), 2.87-2.79 (m, 1H), 1.89-1.74 (m, 4H), 1.24 (d, J=6.7 Hz, 3H), 0.99 (t, J=7.5 Hz, 3H).

MS ESI m/z 445.3 (M+H)

Example 70

5-{2-Amino-[1,2,4]triazolo[1,5-a]pyridin-7-yl}-2-(methylamino)-N-(3-phenylbutyl)pyridine-3-carboxamide

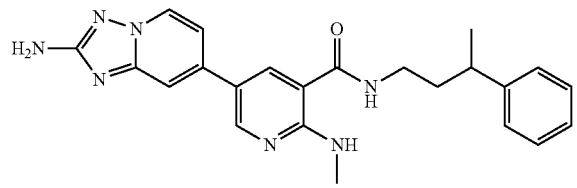

70A: Ethyl 5-bromo-2-(methylamino)nicotinate: To a solution of 64A (130 mg, 0.524 mmol) in THF (5 mL) was added 1 M methylamine in THF (0.655 mL, 1.310 mmol), and the resulting solution was stirred at rt 20 min. The reaction mixture was concentrated to a solid and partitioned between EtOAc (50 mL) and saturated aqueous ammonium chloride (15 mL). The organics were washed with brine, dried over anhydrous sodium sulfate, filtered and concentrated to afford ethyl 5-bromo-2-(methylamino)nicotinate (125 mg, 0.458 mmol, 87% yield) as a white solid.

MS ESI m/z 260.9 (M+H)

70B: Ethyl 5-(2-((bis-tert-butoxycarbonyl)amino)-[1,2,4]triazolo[1,5-a]pyridin-7-yl)-2-(methylamino)nicotinate: In a sealed 20 mL tube, a mixture of bis-Boc-7-bromo-[1,2,4]triazolo[1,5-a]pyridin-2-amine (195 mg, 0.472 mmol), bis(pinacolato)diboron (150 mg, 0.590 mmol), potassium acetate (139 mg, 1.416 mmol) and [1,1'-bis(diphenylphosphino)ferrocene]dichloropalladium(II) (17.26 mg, 0.024 mmol) in 1,4-dioxane (2 mL) was stirred at 100° C. 1 h. To the cooled reaction mixture was added ethyl 5-bromo-2-(methylamino)nicotinate (125 mg, 0.482 mmol) and 1,1'-bis(di-tert-butylphosphino)ferrocene palladium dichloride (14.97 mg, 0.023 mmol). The crude mixture was degassed by sparging the mixture for 5 min. 2 M $K_3PO_4$ (aq) (0.689 mL, 1.378 mmol) was added and the reaction mixture heated at 100° C. for 15 min. After cooling to rt, the reaction mixture was diluted to a volume of 50 mL with EtOAc. The organics were washed with brine, dried over anhydrous sodium sulfate, filtered and concentrated. The crude residue was loaded onto a 12 g ISCO column and purified by flash chromatography, eluting with 0-100% EtOAc in hexanes, to afford the desired product (189 mg, 0.361 mmol, 79% yield) as a beige solid.

MS ESI m/z 513.4 (M+H)

70C: 5-(2-((tert-Butoxycarbonyl)amino)-[1,2,4]triazolo[1,5-a]pyridin-7-yl)-2-(methylamino)nicotinic acid: To a solution of Ethyl 5-(2-((bis-tert-butoxycarbonyl)amino)-[1,2,4]triazolo[1,5-a]pyridin-7-yl)-2-(methylamino)nicotinate (189 mg, 0.369 mmol) in THF (3 mL) was added 1 N sodium hydroxide (1.844 mL, 1.844 mmol) and a few drops of methanol. The reaction mixture was stirred at rt ON. Volatiles were removed in vacuo. The crude residue was acidified to pH ~3 with 1 N HCl (~5 mL). The aqueous layer was extracted with EtOAc (2×). The combined organics were washed with brine, dried over anhydrous sodium sulfate, filtered and concentrated to afford 5-(2-((tert-butoxycarbonyl)amino)-[1,2,4]triazolo[1,5-a]pyridin-7-yl)-2-(methylamino)nicotinic acid (107 mg, 0.273 mmol, 74.0% yield) as an off-white solid.

MS ESI m/z 385.2 (M+H)

70: A mixture of 5-(2-((tert-butoxycarbonyl)amino)-[1,2,4]triazolo[1,5-a]pyridin-7-yl)-2-(methylamino)nicotinic acid (20 mg, 0.052 mmol), BOP (34.5 mg, 0.078 mmol), 3-phenylbutan-1-amine, HCl (14.49 mg, 0.078 mmol) and Hünig's Base (0.045 mL, 0.260 mmol) in DMF (1.0 mL) was stirred ON at rt. The reaction mixture was diluted to 50 mL with EtOAc, then washed with 10% LiCl solution and brine (2×). The organics were dried over anhydrous sodium sulfate, filtered and concentrated. The crude residue was dissolved in TFA (0.200 mL, 2.60 mmol), stirred 15 min and concentrated in vacuo. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-(methylamino)-N-(3-phenylbutyl)nicotinamide (15 mg, 0.035 mmol, 67.3% yield).

$^1$H NMR (500 MHz, DMSO-d6) δ 8.67 (d, J=1.8 Hz, 1H), 8.63 (br. s., 1H), 8.56 (d, J=7.0 Hz, 1H), 8.40 (d, J=4.9 Hz, 1H), 8.26 (d, J=1.8 Hz, 1H), 7.69 (s, 1H), 7.35-7.22 (m, 5H), 7.21-7.13 (m, 1H), 5.97 (s, 2H), 3.12 (td, J=13.2, 7.2 Hz, 2H), 2.95 (d, J=4.6 Hz, 3H), 2.85-2.75 (m, 1H), 1.85 (q, J=7.1 Hz, 2H), 1.25 (d, J=7.0 Hz, 3H).

MS ESI m/z 416.2 (M+H)

Example 71

5-{2-Amino-[1,2,4]triazolo[1,5-a]pyridin-7-yl}-N-[(3R)-3-(4-fluorophenyl)-3-hydroxypropyl]-2-methoxypyridine-3-carboxamide

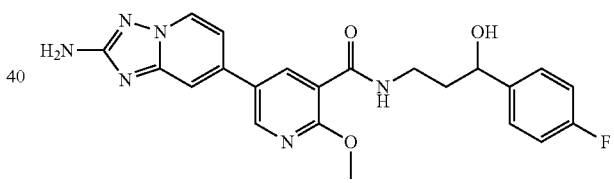

71A: 3-Amino-1-(4-fluorophenyl)propan-1-ol: To a solution of 3-(4-fluorophenyl)-3-oxopropanenitrile (1.73 g, 10.60 mmol) in THF (35.3 ml) was added $BH_3$-dimethyl sulfide (2 M in THF, 10.60 ml, 21.21 mmol). The reaction mixture was heated to 60° C. for 16 h. The reaction mixture was quenched with MeOH and heated to reflux for 1 h. The reaction mixture was concentrated in vacuo and purified by column chromatography on the Isco system (24 g, 0-10% [20% (2 N $NH_3$/MeOH)/DCM]/DCM) to yield 3-amino-1-(4-fluorophenyl)propan-1-ol (0.75 g, 4.43 mmol, 41.8% yield) as a viscous yellow oil.

$^1$H NMR (400 MHz, $CD_3OD$) δ 7.40-7.35 (m, 2H), 7.09-7.02 (m, 2H), 4.75 (dd, J=8.0, 5.1 Hz, 1H), 2.86-2.73 (m, 2H), 1.95-1.79 (m, 2H).

MS ESI m/z 170.1 (M+H)

71: 5-(2-Amino-[1,2,4]triazolo[1,5-a]pyridin-7-yl)-N-(3-(4-fluorophenyl)-3-hydroxypropyl)-2-methoxynicotinamide: To a solution of 5-(2-amino-[1,2,4]triazolo[1,5-a]pyridin-7-yl)-2-methoxynicotinic acid (100 mg, 0.351 mmol), 3-amino-1-(4-fluorophenyl)propan-1-ol (104 mg, 0.613 mmol) and DIPEA (0.184 mL, 1.052 mmol) in DMF (1.5 mL) was added BOP (233 mg, 0.526 mmol) and the reaction mixture was stirred at rt 16 h. The reaction mixture was concentrated to yield a crude product which was purified on silica gel column with $CH_2Cl_2$/MeOH (10/1) to yield 5-(2-amino-[1,2,4]triazolo[1,5-a]pyridin-7-yl)-N-(3-(4-fluorophenyl)-3-hydroxypropyl)-2-methoxynicotinamide as the racemate. This was further purified and enantiomers separated using two step preparative SFC with the following conditions: Waters Thar 350 Column: Princeton CN (3×25 cm, 5 micron); Column Temp: 40° C.; Pressure: 100 bar; Mobile Phase: A=$CO_2$; B=MeOH w/0.1% $NH_4OH$; Isocratic: A/B=70:30; Flow rate: 180 mL/min; UV at 220 nm. Column: Princeton CN (5×25 cm, 5 micron); Column Temp: 30° C.; Pressure: 100 bar; Mobile Phase: A=$CO_2$, B=MeOH w/0.1% $NH_4OH$; Isocratic: A/B=55/45; Flow rate: 270 mL/min; UV at 220 nm.

The fractions from peak 1 was concentrated to yield 71-1, enantiomer 1 (18.4 mg, 0.041 mmol, 12% yield). The fractions from peak 2 was concentrated to yield 71-2, enantiomer 2 (17.4 mg, 0.041 mmol, 11.4% yield).

71-1, Enantiomer 1: $^1$H NMR (400 MHz, $CD_3OD$) δ 8.71 (d, J=2.7 Hz, 1H), 8.63 (d, J=2.7 Hz, 1H), 8.53-8.50 (m, 1H), 7.65 (d, J=1.2 Hz, 1H), 7.44 (dd, J=8.6, 5.4 Hz, 2H), 7.30 (dd, J=7.1, 2.0 Hz, 1H), 7.11-7.04 (m, 2H), 4.83-4.81 (m, 1H), 4.17 (s, 3H), 3.65-3.52 (m, 2H), 2.10-1.99 (m, 2H).

MS ESI m/z 437.0 (M+H).

71-2, Enantiomer 2: $^1$H NMR (400 MHz, $CD_3OD$) δ 8.71 (d, J=2.7 Hz, 1H), 8.63 (d, J=2.6 Hz, 1H), 8.51 (dd, J=7.0, 0.7 Hz, 1H), 7.65 (dd, J=1.9, 0.8 Hz, 1H), 7.46-7.41 (m, 2H), 7.30 (dd, J=7.0, 2.0 Hz, 1H), 7.11-7.04 (m, 2H), 4.81-4.74 (m, 1H), 4.17 (s, 3H), 3.66-3.48 (m, 2H), 2.14-1.94 (m, 2H).

MS ESI m/z 437.0 (M+H).

Example 72

2-{2-Amino-[1,2,4]triazolo[1,5-a]pyridin-7-yl}-N-(3-phenylbutyl)pyridine-4-carboxamide

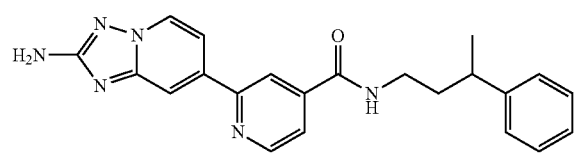 [SMILES: CC(CCNC(=O)c1ccnc(-c2ccn3nc(N)nc3c2)c1)c1ccccc1]

72A: Methyl 2-(2-((bis-tert-butoxycarbonyl)amino)-[1,2,4]triazolo[1,5-a]pyridin-7-yl)isonicotinate: In a sealed 40 mL tube, a mixture of bis-Boc-7-bromo-[1,2,4]triazolo[1,5-a]pyridin-2-amine (375 mg, 0.907 mmol), bis(pinacolato)diboron (288 mg, 1.134 mmol), potassium acetate (267 mg, 2.72 mmol) and [1,1'-bis(diphenylphosphino)ferrocene]dichloropalladium(II) (33.2 mg, 0.045 mmol) in 1,4-dioxane (5 mL) was stirred at 100° C. 1 h. The reaction mixture was cooled to rt and concentrated to a solid. To the crude solid was added methyl 2-chloroisonicotinate (175 mg, 1.020 mmol), 1,1'-bis(di-tert-butylphosphino)ferrocene palladium dichloride (27.7 mg, 0.042 mmol) and dioxane (8 mL). The mixture was degassed by sparging with nitrogen for 5 min. 2 M $K_3PO_4$ (aq) (1.275 mL, 2.55 mmol) was added and the reaction mixture heated at 100° C. for 25 min. After cooling to rt, the reaction mixture was concentrated onto Celite.

Using a 24 g ISCO column, the crude material was purified by flash chromatography, eluting with 0-100% EtOAc in hexanes. Afforded methyl 2-(2-((bis-tert-butoxycarbonyl)amino)-[1,2,4]triazolo[1,5-a]pyridin-7-yl)isonicotinate (367 mg, 0.743 mmol, 87% yield) as a tan solid. Material carried forward into subsequent chemistry as is.

72B: 2-(2-((tert-Butoxycarbonyl)amino)-[1,2,4]triazolo[1,5-a]pyridin-7-yl)isonicotinic acid: To a solution of methyl 2-(2-((bis-tert-butoxycarbonyl)amino)-[1,2,4]triazolo[1,5-a]pyridin-7-yl)isonicotinate (367 mg, 0.782 mmol) in THF (8 mL) was added 1 N sodium hydroxide (3.91 mL, 3.91 mmol) and a few drops of methanol. The reaction mixture was stirred at rt ON. Volatiles were removed in vacuo and the residue was acidified to pH ~3 with 1 N HCl (~5 mL). The aqueous layer was extracted with EtOAc (2×). The combined organics were washed with brine, dried over anhydrous sodium sulfate, filtered and concentrated to afford 2-(2-((tert-butoxycarbonyl)amino)-[1,2,4]triazolo[1,5-a]pyridin-7-yl)isonicotinic acid (192 mg, 0.513 mmol, 65.7% yield) as an off-white solid.

MS ESI m/z 356.1 (M+H)

72C: tert-Butyl (7-(4-((3-phenylbutyl)carbamoyl)pyridin-2-yl)-[1,2,4]triazolo[1,5-a]pyridin-2-yl)carbamate: A mixture of 2-(2-((tert-butoxycarbonyl)amino)-[1,2,4]triazolo[1,5-a]pyridin-7-yl)isonicotinic acid (20 mg, 0.056 mmol) and BOP (37.3 mg, 0.084 mmol) in DMF (1.0 mL) was stirred 10 min at rt. 3-Phenylbutan-1-amine, HCl (12.54 mg, 0.068 mmol) and Hünig's Base (0.049 mL, 0.281 mmol) were added. The reaction mixture was stirred 45 min at rt. The reaction mixture was diluted to a total volume of 50 mL with EtOAc. The organics were washed with 10% lithium chloride solution (1×) and brine (2×). After drying over anhydrous sodium sulfate, the organics were filtered and concentrated to afford tert-butyl (7-(4-((3-phenylbutyl)carbamoyl)pyridin-2-yl)-[1,2,4]triazolo[1,5-a]pyridin-2-yl)carbamate (26 mg, 0.051 mmol, 90%).

MS ESI m/z 487.1 (M+H)

72: To a solution of tert-butyl (7-(4-((3-phenylbutyl)carbamoyl)pyridin-2-yl)-[1,2,4]triazolo[1,5-a]pyridin-2-yl)carbamate (27 mg, 0.055 mmol) in DCM (1 mL) was added 4N HCl in dioxane (0.169 mL, 5.55 mmol) and the resulting solution was stirred at rt over the weekend. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 min, then a 2-minute hold at 100% B; Flow: 20 mL/min. Fractions containing the desired product were combined and dried via centrifugal evaporation. Afforded 2-(2-amino-[1,2,4]triazolo[1,5-a]pyridin-7-yl)-N-(3-phenylbutyl)isonicotinamide (4.6 mg, 0.012 mmol, 21.24% yield).

$^1$H NMR (500 MHz, DMSO-d6) δ 8.82 (d, J=4.9 Hz, 2H), 8.64 (d, J=7.0 Hz, 1H), 8.36 (s, 1H), 8.08 (s, 1H), 7.73 (d, J=4.6 Hz, 1H), 7.65 (d, J=5.5 Hz, 1H), 7.35-7.22 (m, 4H), 7.20-7.12 (m, 1H), 6.09 (s, 2H), 3.32-3.12 (m, 2H), 2.84-2.76 (m, 1H), 1.86 (q, J=7.3 Hz, 2H), 1.24 (d, J=7.0 Hz, 3H).

MS ESI m/z 387 (M+H)

Example 73

5-{2-Amino-[1,2,4]triazolo[1,5-a]pyridin-7-yl}-N-(3-phenylbutyl)pyridine-3-carboxamide

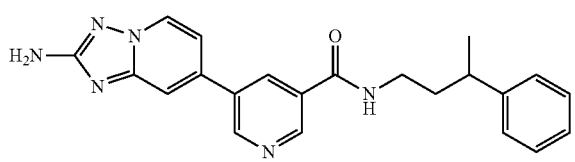 [SMILES: CC(CCNC(=O)c1cncc(-c2ccn3nc(N)nc3c2)c1)c1ccccc1]

To a solution of tert-butyl (7-(5-((3-phenylbutyl)carbamoyl)pyridin-3-yl)-[1,2,4]triazolo[1,5-a]pyridin-2-yl)carbamate (40 mg, 0.082 mmol) in DCM (1 mL) was added 4N HCl in dioxane (0.250 mL, 8.22 mmol) and the resulting solution was stirred at rt over the weekend. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 min, then a 2-minute hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(3-phenylbutyl)nicotinamide (16.9 mg, 0.043 mmol, 52.7% yield).

$^1$H NMR (500 MHz, DMSO-d6) δ 9.16 (br. s., 1H), 9.00 (br. s., 1H), 8.72 (d, J=7.0 Hz, 2H), 8.52 (s, 1H), 7.87 (s, 1H), 7.41 (d, J=7.0 Hz, 1H), 7.33-7.15 (m, 5H), 7.14-7.00 (m, 1H), 3.47 (br. s., 1H), 3.32-3.12 (m, 2H), 2.86-2.76 (m, 1H), 1.86 (q, J=7.3 Hz, 2H), 1.25 (d, J=7.0 Hz, 3H).

MS ESI m/z 387 (M+H)

Example 74

5-{2-Amino-[1,2,4]triazolo[1,5-a]pyridin-7-yl}-2-methoxy-N-{[2-(trifluoromethoxy)phenyl]methyl}pyridine-3-carboxamide

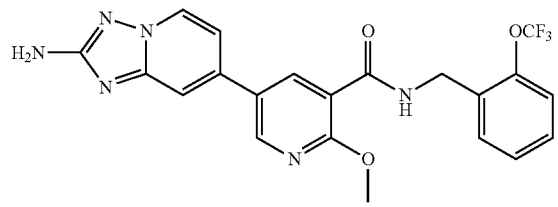

74A: Methyl 5-(2-amino-[1,2,4]triazolo[1,5-a]pyridin-7-yl)-2-methoxynicotinate: A mixture of 7-bromo-[1,2,4]triazolo[1,5-a]pyridin-2-amine (0.939 g, 4.41 mmol), methyl 2-methoxy-5-(4,4,5,5-tetramethyl-1,3,2-dioxaborolan-2-yl)nicotinate (1.55 g, 5.29 mmol), tripotassium phosphate (2 M in water) (6.61 mL, 13.22 mmol), and dioxane (25 mL) was degassed with vacuum and nitrogen (3×). 1,1'-Bis(diphenylphosphino)ferrocene palladium dichloride-CH$_2$Cl$_2$ adduct (0.360 g, 0.441 mmol) was added, and the reaction mixture was degassed (2×). The reaction mixture was immersed in an oil bath at 70° C. and stirred ON. A white precipitate was caked on the bottom and sides of the flask. The heterogeneous reaction mixture was diluted with ethyl acetate and water. The solid was collected by vacuum filtration and washed well with ethyl acetate, water, and ethyl acetate. The compound was dried to give methyl 5-(2-amino-[1,2,4]triazolo[1,5-a]pyridin-7-yl)-2-methoxynicotinate (0.630 g, 2.105 mmol, 47.8% yield) as a white solid. The filtrate was transferred to a separatory flask, and the organic layer was collected and washed with brine. The aqueous layers were sequentially extracted with ethyl acetate (2×). The combined organic layers were dried over anhydrous sodium sulfate and concentrated. The residue was diluted with dichloromethane and sonicated. The resulting solid was collected by vacuum filtration and dried well to give methyl 5-(2-amino-[1,2,4]triazolo[1,5-a]pyridin-7-yl)-2-methoxynicotinate (0.280 g, 0.936 mmol, 21.23% yield) as a white solid.

MS ESI m/z 300.1 (M+H)

74B: 5-(2-Amino-[1,2,4]triazolo[1,5-a]pyridin-7-yl)-2-methoxynicotinic acid, lithium salt: A mixture of methyl 5-(2-amino-[1,2,4]triazolo[1,5-a]pyridin-7-yl)-2-methoxynicotinate (0.728 g, 2.432 mmol) and lithium hydroxide monohydrate (0.102 g, 2.432 mmol) in a mixture of methanol (10 mL), tetrahydrofuran (10.00 mL), and water (5.00 mL) was stirred at rt until the reaction became homogeneous (~4-5 h). The reaction was concentrated, dried under reduced pressure over the weekend to give 5-(2-amino-[1,2,4]triazolo[1,5-a]pyridin-7-yl)-2-methoxynicotinic acid, lithium salt (0.711 g, 2.433 mmol, 100% yield) as an off-white solid.

MS ESI m/z 286.1 (M+H)

74: To a solution of 5-(2-amino-[1,2,4]triazolo[1,5-a]pyridin-7-yl)-2-methoxynicotinic acid, lithium salt (35 mg, 0.123 mmol), (2-(trifluoromethoxy)phenyl)methanamine (24.69 mg, 0.123 mmol) and Hünig's Base (0.107 mL, 0.613 mmol) in DMF (1 mL) was added BOP (65.1 mg, 0.147 mmol) and the reaction mixture was stirred at rt 16 h. The reaction mixture was purified on Combiflash RF200 with the following conditions: Column: 43 g C18 RediSep Reverse Phase Column, Solvent A: 0.1% TFA in water/MeOH (90/10) Solvent B: 0.1% TFA in water/MeOH (10/90) Flow rate: 40 mL/min. Start % B: 10% Final % B: 100% Wavelength 1: 254 Wavelength 1: 214. The isolated product was taken up in ethyl acetate (100 mL). The organic phase was washed with saturated aqueous sodium bicarbonate (20 mL), water (20 mL) and brine (20 mL). The organics were dried over anhydrous sodium sulfate, filtered and concentrated in vacuo to yield 5-{2-amino-[1,2,4]triazolo[1,5-a]pyridin-7-yl}-2-methoxy-N-{[2-(trifluoromethoxy)phenyl]methyl}pyridine-3-carboxamide (41 mg).

$^1$H NMR (400 MHz, DMSO-d6) δ 8.92 (br t, J=6.0 Hz, 1H), 8.80 (d, J=2.4 Hz, 1H), 8.61 (d, J=7.0 Hz, 1H), 8.47 (d, J=2.4 Hz, 1H), 7.73 (d, J=1.1 Hz, 1H), 7.57-7.50 (m, 1H), 7.46-7.35 (m, 3H), 7.25 (dd, J=7.0, 1.8 Hz, 1H), 6.05 (s, 2H), 4.61 (d, J=6.0 Hz, 2H), 4.06 (s, 3H).

MS ESI m/z 459.3 (M+H)

Example 75

5-{2-Amino-[1,2,4]triazolo[1,5-a]pyridin-7-yl}-N-[3-(5-chloropyridin-2-yl)-3-hydroxypropyl]-2-methoxypyridine-3-carboxamide

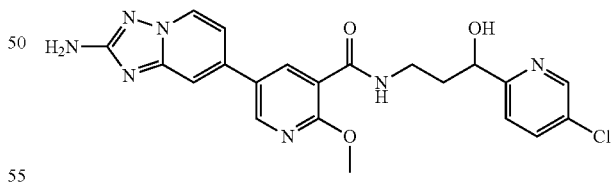

75A: 3-Amino-1-(5-chloropyridin-2-yl)propan-1-ol, 2 HCl was prepared from 3-(5-chloropyridin-2-yl)-3-oxopropanenitrile by the same method as intermediate 71A.

75: To a solution of 5-(2-amino-[1,2,4]triazolo[1,5-a]pyridin-7-yl)-2-methoxynicotinic acid (15 mg, 0.037 mmol), 3-amino-1-(5-chloropyridin-2-yl)propan-1-ol, 2 HCl (7.17 mg, 0.028 mmol) and Hünig's Base (0.032 mL, 0.184 mmol) in DMF (1 mL) was added BOP (19.54 mg, 0.044 mmol). The reaction mixture was stirred at rt 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 min, then a 5-minute hold at 100% B; Flow: 20 mL/min. Fractions containing the desired product were combined and dried via centrifugal evaporation to provide the product (3.8 mg, 8.4 μmol, 22.6%).

$^1$H NMR (500 MHz, DMSO-d6) δ 8.73 (d, J=1.9 Hz, 1H), 8.61-8.48 (m, 3H), 8.42 (d, J=2.0 Hz, 1H), 7.94-7.86 (m, 1H), 7.68 (s, 1H), 7.56 (d, J=8.4 Hz, 1H), 7.24 (br d, J=5.9 Hz, 1H), 6.05 (s, 2H), 5.85 (br d, J=4.6 Hz, 1H), 4.77-4.68 (m, 1H), 4.02 (s, 3H), 3.48-3.34 (m, 2H), 2.12-2.01 (m, 1H), 1.86 (br dd, J=13.8, 7.2 Hz, 1H).

MS ESI m/z 454.1 (M+H)

Example 76

5-{2-Amino-[1,2,4]triazolo[1,5-a]pyridin-7-yl}-N-{1-[(1S)-1-(4-fluorophenyl)ethyl]-1H-pyrazol-4-yl}-2-methoxypyridine-3-carboxamide

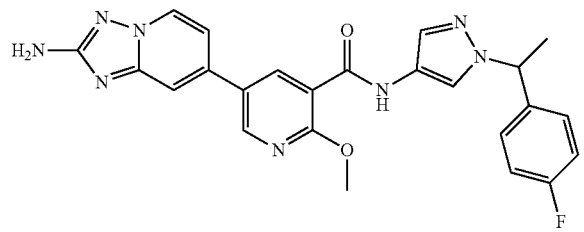 [SMILES: COc1ncc(-c2ccn3nc(N)nc3c2)cc1C(=O)Nc1cnn(C(C)c2ccc(F)cc2)c1]

76A: 1-(1-Bromoethyl)-4-fluorobenzene: A solution of 1-(4-fluorophenyl)ethanol (0.455 mL, 3.57 mmol) and phosphorus tribromide (0.673 mL, 7.13 mmol) in CHCl$_3$ (10 mL) was heated at 70° C. for 3 d. The reaction mixture was quenched in ice water and diluted in ethyl acetate. The organic layer was separated and washed with water followed by brine, dried over anhydrous sodium sulfate and concentrated in vacuo to get the crude material. The crude product was purified on a silica gel column with Hexanes/CH$_2$Cl (2/1) to afford 1-(1-bromoethyl)-4-fluorobenzene (154 mg, 0.758 mol, 21.3%) as a colourless oil. $^1$H NMR (400 MHz, CHLOROFORM-d) δ 7.49-7.40 (m, 2H), 7.09-7.00 (m, 2H), 5.23 (q, J=7.0 Hz, 1H), 2.06 (d, J=6.8 Hz, 3H).

76B: 1-(1-(4-Fluorophenyl)ethyl)-4-nitro-1H-pyrazole: To a solution of 4-nitro-1H-pyrazole (25 mg, 0.221 mmol) and potassium carbonate (36.7 mg, 0.265 mmol) in DMF (1 mL) was added 1-(1-bromoethyl)-4-fluorobenzene (44.9 mg, 0.221 mmol) at 23° C. and stirred for 2 h. The reaction mixture was purified by column chromatography on the Isco system (12 g, 0-50% EtOAc/Hex) to yield 1-(1-(4-fluorophenyl)ethyl)-4-nitro-1H-pyrazole as the racemate. (42 mg, 0.179 mol, 81%).

$^1$H NMR (400 MHz, CD$_3$OD) δ 8.66 (s, 1H), 8.14 (s, 1H), 7.44-7.37 (m, 2H), 7.15-7.07 (m, 2H), 5.67 (q, J=7.0 Hz, 1H), 1.92 (d, J=7.1 Hz, 3H).

MS ESI m/z 236.1 (M+H).

The racemic material underwent chiral purification using the following preparative SFC conditions: Preparative Column: AD-H (3×25 cm, 5 μm, #122090); BPR pressure: 100 bars; Temperature: 35° C.; Flow rate: 150 mL/min; Mobile Phase: CO$_2$/MeOH w 0.1% NH$_4$OH (90/10); Detector Wavelength: 220 nm; Separation Program: stack injection; injection: 0.5 mL with cycle time: 1.5 mins; Sample preparation: 42 mg/5 mL MeOH, 8.4 mg/mL; Throughput: 168 mg/hr. The fractions from peak 1 was concentrated to yield enantiomer 1 (76B-1, 11.7 mg, 0.050 mmol, 27.9% yield). MS ESI m/z 236.1 (M+H). The fractions from peak 2 was concentrated to yield enantiomer 2 (76B-2, 14.9 mg, 0.063 mmol, 35.5% yield).

76C: A suspension solution of 1-(1-(4-fluorophenyl)ethyl)-4-nitro-1H-pyrazole (enantiomer 1, 11.7 mg, 0.050 mmol), Pd/C (0.318 mg, 2.98 μmol) in MeOH (2 mL) under 1 atm hydrogen was stirred at 23° C. for 16 h. Filtration of the reaction mixture and concentration in vacuo provided (1-(1-(4-fluorophenyl)ethyl)-1H-pyrazol-4-amine (enantiomer 1) (7.8 mg, 0.038 mmol, 76%). MS ESI m/z 206.1 (M+H). (1-(1-(4-Fluorophenyl)ethyl)-1H-pyrazol-4-amine (enantiomer 2) was reacted under similar conditions to yield (1-(1-(4-fluorophenyl)ethyl)-1H-pyrazol-4-amine (enantiomer 2) (10.8 mg, 0.053 mmol, 83%).

MS ESI m/z 206.2 (M+H).

76: To separate solutions of 5-(2-amino-[1,2,4]triazolo[1,5-a]pyridin-7-yl)-2-methoxynicotinic acid (22 mg, 0.077 mmol), one enantiomer of 1-(1-(4-fluorophenyl)ethyl)-1H-pyrazol-4-amine (10.29 mg, 0.050 mmol) and Hünig's Base (0.040 mL, 0.231 mmol) in DMF (1 mL) was added BOP (40.9 mg, 0.093 mmol). The reaction mixture was stirred at rt 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 min, then a 5-minute hold at 100% B; Flow: 20 mL/min. Fractions containing the desired product were combined and dried via centrifugal evaporation to provide the product, 76-1 (10 mg, 0.021 mmol, 36.6%) and the product, 76-2 (13.4 mg, 0.028 mmol, 36.8%).

76-1 Enantiomer 1: $^1$H NMR (500 MHz, DMSO-d6) δ 10.34 (s, 1H), 8.77 (d, J=2.2 Hz, 1H), 8.60 (d, J=6.9 Hz, 1H), 8.41 (d, J=2.3 Hz, 1H), 8.13 (s, 1H), 7.73 (s, 1H), 7.64 (s, 1H), 7.33 (br dd, J=8.2, 5.6 Hz, 2H), 7.27 (br d, J=6.0 Hz, 1H), 7.17 (br t, J=8.8 Hz, 2H), 6.04 (s, 2H), 5.63 (q, J=6.8 Hz, 1H), 4.02 (s, 3H), 1.80 (br d, J=7.0 Hz, 3H).

MS ESI m/z 473.1 (M+H)

76-2 Enantiomer 2: $^1$H NMR (500 MHz, DMSO-d6) δ 10.35 (s, 1H), 8.76 (s, 1H), 8.59 (d, J=6.9 Hz, 1H), 8.40 (d, J=1.3 Hz, 1H), 8.12 (s, 1H), 7.72 (s, 1H), 7.65 (s, 1H), 7.36-7.29 (m, 2H), 7.27 (br d, J=6.8 Hz, 1H), 7.17 (br t, J=8.6 Hz, 2H), 6.03 (s, 2H), 5.62 (q, J=6.7 Hz, 1H), 4.02 (s, 3H), 1.79 (br d, J=6.9 Hz, 3H).

MS ESI m/z 473.3 (M+H)

Example 77

5-{2-Amino-[1,2,4]triazolo[1,5-a]pyridin-7-yl}-N-[3-(3,4-difluorophenyl)-3-hydroxypropyl]-2-methoxypyridine-3-carboxamide

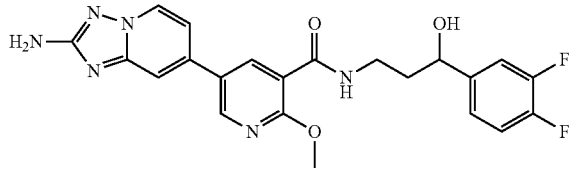 [SMILES: COc1ncc(-c2ccn3nc(N)nc3c2)cc1C(=O)NCCC(O)c1ccc(F)c(F)c1]

77A: 3-Amino-1-(5-chloropyridin-2-yl)propan-1-ol, 2 HCl was prepared from 3-(3,4-difluorophenyl)-3-oxopropanenitrile by the same method as intermediate 71A.

77: To a solution of 5-(2-amino-[1,2,4]triazolo[1,5-a]pyridin-7-yl)-2-methoxynicotinic acid (20 mg, 0.070 mmol), 3-amino-1-(3,4-difluorophenyl)propan-1-ol (8.53 mg, 0.046 mmol) and Hünig's Base (0.037 mL, 0.210 mmol) in DMF (1 mL) was added BOP (46.5 mg, 0.105 mmol). The reaction mixture was stirred at rt 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 20 min, then a 5-minute hold at 100% B; Flow: 20 mL/min. Fractions containing the desired product were combined and dried via centrifugal evaporation to provide the product (11.2 mg, 24.6 μmol, 35.2%).

¹H NMR (500 MHz, DMSO-d6) δ 8.72 (d, J=2.1 Hz, 1H), 8.57 (d, J=7.0 Hz, 1H), 8.53 (br t, J=5.0 Hz, 1H), 8.41 (d, J=2.2 Hz, 1H), 7.67 (s, 1H), 7.41-7.31 (m, 2H), 7.24 (br d, J=6.9 Hz, 1H), 7.20 (br s, 1H), 6.02 (s, 2H), 5.70 (br d, J=4.0 Hz, 1H), 4.70 (br d, J=4.0 Hz, 1H), 4.02 (s, 3H), 3.37 (br d, J=6.2 Hz, 2H), 1.94-1.79 (m, 2H), 0.20-0.12 (m, 1H).

MS ESI m/z 455.2 (M+H)

Example 78

5-{2-Amino-[1,2,4]triazolo[1,5-a]pyridin-7-yl}-N-[3-(4-fluorophenyl)-3-hydroxypropyl]-2-methoxypyridine-3-carboxamide To a solution of 5-(2-amino-[1,2,4]triazolo[1,5-a]pyridin-7-yl)-2-methoxynicotinic acid (20 mg, 0.070 mmol), 3-amino-1-(4-fluorophenyl)propan-1-ol (7.71 mg, 0.046 mmol) and Hünig's Base (0.037 mL, 0.210 mmol) in DMF (1 mL) was added BOP (46.5 mg, 0.105 mmol). The reaction mixture was stirred at rt 4 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 18 min, then a 5-minute hold at 100% B; Flow: 20 mL/min. Fractions containing the desired product were combined and dried via centrifugal evaporation to provide the product (11.1 mg, 25.4 μmol, 36.3%).

¹H NMR (500 MHz, DMSO-d6) δ 8.73 (d, J=1.9 Hz, 1H), 8.58 (br d, J=6.9 Hz, 1H), 8.54 (br s, 1H), 8.42 (d, J=1.6 Hz, 1H), 7.69 (s, 1H), 7.39 (br dd, J=7.5, 6.1 Hz, 2H), 7.24 (br d, J=6.8 Hz, 1H), 7.14 (br t, J=8.7 Hz, 2H), 6.03 (s, 2H), 5.53 (br d, J=3.5 Hz, 1H), 4.74-4.66 (m, 1H), 4.02 (s, 3H), 3.38 (br q, J=6.1 Hz, 2H), 1.86 (dt, J=12.9, 6.5 Hz, 2H).

MS ESI m/z 437.3 (M+H)

Example 79

5-{2-Amino-[1,2,4]triazolo[1,5-a]pyridin-7-yl}-N-{[4-fluoro-2-(oxolan-3-yloxy)phenyl]methyl}-2-methoxypyridine-3-carboxamide

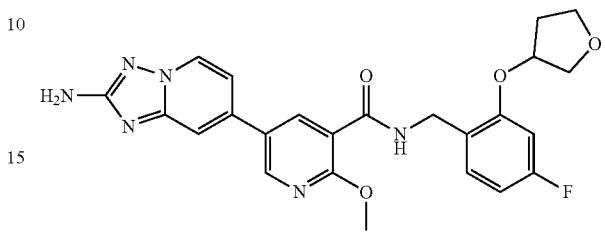

79A: 4-Fluoro-2-((tetrahydrofuran-3-yl)oxy)benzonitrile: To a solution of tetrahydrofuran-3-ol (0.33 mL, 4.03 mmol) in THF (7 mL) was added NaH (60% wt, 138 mg, 3.45 mmol). After stirring 15 min, 2,4-difluorobenzonitrile (0.4 g, 2.88 mmol) was added. After stirring at rt 1 h, the reaction mixture was poured into a separatory funnel containing saturated aqueous sodium bicarbonate and dichloromethane. The aqueous layer was extracted with dichloromethane (3×). The combined organics were dried over anhydrous sodium sulfate, filtered and concentrated in vacuo. The crude residue was purified by column chromatography on a Biotage system (10-30% EtOAc/Hex). The product (400 mg, 1.930 mmol, 67%) was isolated as a white solid.

¹H NMR (400 MHz, CDCl₃) δ ppm 7.52-7.62 (m, 1H), 6.70-6.82 (m, 1H), 6.55-6.65 (m, 1H), 4.91-5.01 (m, 1H), 3.90-4.17 (m, 4H), 2.12-2.35 (m, 2H).

79B: (4-Fluoro-2-((tetrahydrofuran-3-yl)oxy)phenyl)methanamine, HCl salt: To a solution of 4-fluoro-2-((tetrahydrofuran-3-yl)oxy)benzonitrile (400 mg, 1.930 mmol) in EtOH (50 mL) in a Parr shaker was added 10% Pd/C (2 spatula tips). The reaction mixture was stirred under 50 psi hydrogen ON. The reaction mixture was filtered through Celite and concentrated in vacuo. The crude residue was taken up in EtOAC and again filtered through Celite. The crude residue was taken up in ether and treated with HCl (2 M in ether, 4 mL). The product (395 mg, 83%) was isolated as a white solid.

¹H NMR (free base, 400 MHz, CDCl₃) δ ppm 7.17 (dd, J=8.31, 6.80 Hz, 1H), 6.61 (td, J=8.31, 2.52 Hz, 1H), 6.51 (dd, J=10.70, 2.39 Hz, 1H), 4.88-4.95 (m, 1H), 3.86-4.04 (m, 4H), 3.77 (d, J=14.40 Hz, 1H), 3.73 (d, J=14.40 Hz, 1H), 2.12-2.29 (m, 2H).

79: To a vial charged with 5-(2-amino-[1,2,4]triazolo[1,5-a]pyridin-7-yl)-2-methoxynicotinic acid, Na⁺ (25 mg, 0.081 mmol) in DMF (406 μl) was added (4-fluoro-2-((tetrahydrofuran-3-yl)oxy)phenyl)methanamine, HCl (20.09 mg, 0.081 mmol), Hünig's Base (42.5 μl, 0.243 mmol) and BOP (35.9 mg, 0.081 mmol). The reaction mixture was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-minute hold at 100% B; Flow: 20 mL/min.

Fractions containing the desired product were combined and dried via centrifugal evaporation. The yield of the product was 5.5 mg.

¹H NMR (500 MHz, DMSO-d6) δ 8.75 (s, 1H), 8.65 (br t, J=5.7 Hz, 1H), 8.59 (d, J=7.0 Hz, 1H), 8.44 (d, J=1.9 Hz, 1H), 7.70 (s, 1H), 7.29 (br t, J=7.6 Hz, 1H), 7.24 (br d, J=6.6 Hz, 1H), 6.91 (br d, J=9.7 Hz, 1H), 6.76 (br t, J=9.3 Hz, 1H), 6.04 (s, 2H), 5.11 (br s, 1H), 4.42 (br d, J=5.3 Hz, 2H), 4.03 (s, 3H), 3.96-3.91 (m, 1H), 3.91-3.86 (m, 1H), 3.86-3.82 (m, 1H), 3.81-3.75 (m, 1H), 2.30-2.19 (m, 1H), 2.05-1.96 (m, 1H).

MS ESI m/z 479.1 (M+H)

Example 80

5-{2-Amino-[1,2,4]triazolo[1,5-a]pyridin-7-yl}-N-{[4-fluoro-2-(oxan-4-yloxy)phenyl]methyl}-2-methoxypyridine-3-carboxamide

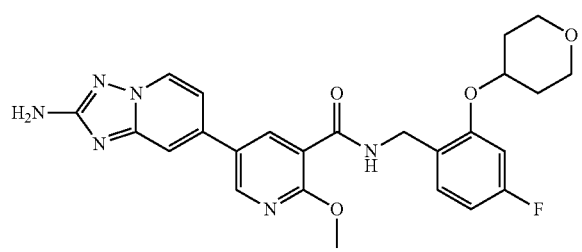 [SMILES: COc1ncc(-c2ccn3nc(N)nc3c2)cc1C(=O)NCc1ccc(F)cc1OC1CCOCC1]

80A: 4-Fluoro-2-((tetrahydro-2H-pyran-4-yl)oxy)benzonitrile: To a solution of tetrahydro-4H-pyran-4-ol (0.37 mL, 3.92 mmol) in THF (7 mL) was added NaH (60% wt, 138 mg, 3.45 mmol). After stirring 45 min, 2,4-difluorobenzonitrile (0.4 g, 2.88 mmol) was added. After stirring at rt 1 h, the reaction mixture was poured into a separatory funnel containing saturated aqueous sodium bicarbonate and dichloromethane. The aqueous layer was extracted with dichloromethane (3×). The combined organics were dried over anhydrous sodium sulfate, filtered and concentrated in vacuo. The crude residue was purified by column chromatography on a Biotage system (10-30% EtOAc/Hex). The product (280 mg, 1.266 mmol, 44%) was isolated as a white solid.

¹H NMR (400 MHz, CDCl₃) δ ppm 7.56 (dd, J=8.56, 6.30 Hz, 1H), 6.72 (ddd, J=8.31, 2.27 Hz, 1H), 6.67 (dd, J=10.58, 2.27 Hz, 1H), 4.55-4.64 (m, J=7.11, 7.11, 3.65, 3.53 Hz, 1H), 4.00 (ddd, J=11.46, 7.43, 3.78 Hz, 2H), 3.63 (ddd, J=11.46, 7.43, 3.53 Hz, 2H), 2.00-2.09 (m, 2H), 1.83-1.93 (m, 2H).

80B: (4-Fluoro-2-((tetrahydro-2H-pyran-4-yl)oxy)phenyl)methanamine, HCl salt: To a solution of 4-fluoro-2-((tetrahydro-2H-pyran-4-yl)oxy)benzonitrile (280 mg, 1.266 mmol) in EtOH (50 mL) in a Parr shaker was added 10% Pd/C (2 spatula tips). The reaction mixture was stirred under 50 psi hydrogen ON. The reaction mixture was filtered through Celite and concentrated in vacuo. The crude residue was taken up in EtOAC and again filtered through Celite. The crude residue was taken up in ether and treated with HCl (2 M in ether, 4 mL). The product (286 mg, 86%) was isolated as a white solid.

¹H NMR (free base, 400 MHz, CDCl₃) δ ppm 7.18 (t, J=7.10 Hz, 1H), 6.56-6.65 (m, 2H), 4.47-4.55 (m, 1H), 3.93-4.01 (m, 2H), 3.80 (s, 2H), 3.62 (ddd, J=11.46, 7.93, 3.27 Hz, 2H), 2.00-2.10 (m, 2H), 1.76-1.88 (m, 2H).

80: To a vial charged with 5-(2-amino-[1,2,4]triazolo[1,5-a]pyridin-7-yl)-2-methoxynicotinic acid, Na⁺ (25 mg, 0.081 mmol) in DMF (406 µl) was added (4-fluoro-2-((tetrahydro-2H-pyran-4-yl)oxy)phenyl)methanamine, HCl (21.23 mg, 0.081 mmol), Hünig's Base (42.5 µl, 0.243 mmol) and BOP (35.9 mg, 0.081 mmol). The reaction mixture was stirred at rt 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 min, then a 5-minute hold at 100% B; Flow: 20 mL/min. Fractions containing the desired product were combined and dried via centrifugal evaporation. The yield of the product was 9.4 mg.

¹H NMR (500 MHz, DMSO-d6) δ 8.76 (d, J=2.3 Hz, 1H), 8.68 (br t, J=5.8 Hz, 1H), 8.58 (d, J=7.0 Hz, 1H), 8.45 (d, J=2.2 Hz, 1H), 7.69 (s, 1H), 7.29 (br t, J=7.7 Hz, 1H), 7.23 (br d, J=6.9 Hz, 1H), 7.00 (br d, J=9.8 Hz, 1H), 6.73 (br t, J=8.5 Hz, 1H), 6.03 (s, 2H), 4.69 (br s, 1H), 4.46 (br d, J=5.7 Hz, 2H), 4.04 (s, 3H), 3.89-3.79 (m, 2H), 1.98 (br d, J=10.1 Hz, 2H), 1.71-1.60 (m, 2H) Note: CH2 from THP ring not showing up—hidden under water suppressed peak.

MS ESI m/z 493.1 (M+H)

Example 81

5-{2-Amino-[1,2,4]triazolo[1,5-a]pyridin-7-yl}-N-{[2-(cyclopropylmethoxy)phenyl]methyl}-2-methoxypyridine-3-carboxamide

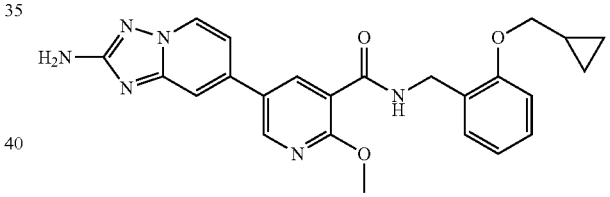

81A: Methyl 5-(2-amino-[1,2,4]triazolo[1,5-a]pyridin-7-yl)-2-methoxynicotinate: A mixture of 7-bromo-[1,2,4]triazolo[1,5-a]pyridin-2-amine (0.2 g, 0.939 mmol), methyl 2-methoxy-5-(4,4,5,5-tetramethyl-1,3,2-dioxaborolan-2-yl)nicotinate (0.330 g, 1.127 mmol), tripotassium phosphate (2 M, 1.408 ml, 2.82 mmol), 1,1'-bis(diphenylphosphino)ferrocene palladium dichloride-CH₂Cl₂ adduct (0.038 g, 0.047 mmol) and tetrahydrofuran (4.69 ml) was degassed by sparging with nitrogen (3 min). The reaction was heated at 80° C. ON. Additional catalyst (5%) was added and heating continued 2 h. After cooling to rt, water was added. After stirring for 20 min, the solid product was isolated. The solid product was rinsed with dichloromethane. Methyl 5-(2-amino-[1,2,4]triazolo[1,5-a]pyridin-7-yl)-2-methoxynicotinate (90 mg, 0.301 mmol, 32.0% yield) was isolated as a tan solid.

MS ESI m/z 300.1 (M+H)

81B: 5-(2-Amino-[1,2,4]triazolo[1,5-a]pyridin-7-yl)-2-methoxynicotinate, lithium salt: To a mixture of methyl 5-(2-amino-[1,2,4]triazolo[1,5-a]pyridin-7-yl)-2-methoxynicotinate (300 mg, 1.002 mmol) in tetrahydrofuran (7 mL) was added a solution of lithium hydroxide monohydrate (50.5 mg, 1.203 mmol) in water (0.5 mL). A few drops of methanol were added, and the resulting mixture was stirred ON at rt. The reaction mixture was concentrated to a solid to afford 5-(2-amino-[1,2,4]triazolo[1,5-a]pyridin-7-yl)-2-methoxynicotinate, lithium salt (232 mg, 0.770 mmol, 77% yield). Material used as is in subsequent chemistry.

MS ESI m/z 286.0 (M+H)

81: A mixture of lithium 5-(2-amino-[1,2,4]triazolo[1,5-a]pyridin-7-yl)-2-methoxynicotinate (65 mg, 0.223 mmol), BOP (148 mg, 0.335 mmol), (2-(cyclopropylmethoxy)phenyl)methanamine (49.5 mg, 0.279 mmol) and Hünig's Base (0.195 mL, 1.116 mmol) in DMF (3 mL) was stirred at rt ON. The reaction mixture was diluted with EtOAc (100 mL) and washed with water (1×), 10% LiCl solution (1×) and brine (1×). The organics were dried over anhydrous sodium sulfate, filtered and concentrated. The crude residue was purified by flash chromatography, eluting with 0-10% MeOH/DCM. The residue was further purified with a second column, eluting with 0-100% EtOAc/Hex. Afforded 5-(2-amino-[1,2,4]triazolo[1,5-a]pyridin-7-yl)-N-(2-(cyclopropylmethoxy)benzyl)-2-meth oxynicotinamide (25 mg, 0.054 mmol, 24.19% yield) as a white solid.

$^1$H NMR (400 MHz, DMSO-d6) δ 8.79 (d, J=2.7 Hz, 1H), 8.69 (t, J=6.0 Hz, 1H), 8.61 (d, J=7.0 Hz, 1H), 8.49 (d, J=2.6 Hz, 1H), 7.73 (d, J=1.3 Hz, 1H), 7.32-7.20 (m, 3H), 6.99 (d, J=7.6 Hz, 1H), 6.93 (t, J=7.4 Hz, 1H), 6.05 (s, 2H), 4.54 (d, J=6.0 Hz, 2H), 4.08-4.03 (m, 3H), 3.96-3.90 (m, 2H), 1.35-1.22 (m, 1H), 0.63-0.52 (m, 2H), 0.42-0.32 (m, 2H).

MS ESI m/z 445.1 (M+H)

Example 82

5-{2-Amino-[1,2,4]triazolo[1,5-a]pyridin-7-yl}-2-methyl-N-(3-phenylbutyl)pyridine-3-carboxamide

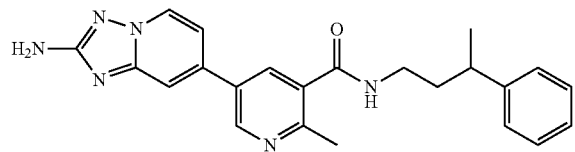 [SMILES: Cc1ncc(-c2ccn3nc(N)nc3c2)cc1C(=O)NCCC(C)c1ccccc1]

82A: Ethyl 5-(2-amino-[1,2,4]triazolo[1,5-a]pyridin-7-yl)-2-methylnicotinate: To a vial charged with ethyl 5-bromo-2-methylnicotinate (48.8 mg, 0.2 mmol), 4,4,4',4',5,5,5',5'-octamethyl-2,2'-bi(1,3,2-dioxaborolane) (60.9 mg, 0.240 mmol), potassium acetate (29.4 mg, 0.300 mmol) and PdCl$_2$(dppf)-CH$_2$Cl$_2$ adduct (16.33 mg, 0.020 mmol) was added 1,4-dioxane (1000 μl). The reaction mixture was sparged with nitrogen for 5 min. The vial was capped and heated at 80° C. 3 h and 90° C. 1 h. After cooling tort, 7-bromo-[1,2,4]triazolo[1,5-a]pyridin-2-amine (38.3 mg, 0.180 mmol) was added followed by potassium carbonate (2 M, 250 μl, 0.500 mmol). The mixture was sparged with nitrogen again for 3 min. The vial was capped and the reaction mixture heated at 90° C. 1 h. The reaction mixture was cooled to rt. Water was added and the solid product isolated by vacuum filtration, washing with water. Ethyl 5-(2-amino-[1,2,4]triazolo[1,5-a]pyridin-7-yl)-2-methylnicotinate (45.8 mg, 0.154 mmol, 77% yield) was isolated as a brown solid.

MS ESI m/z 298.1 (M+H)

82B: 5-(2-Amino-[1,2,4]triazolo[1,5-a]pyridin-7-yl)-2-methylnicotinate, sodium salt: To a round bottom flask charged with ethyl 5-(2-amino-[1,2,4]triazolo[1,5-a]pyridin-7-yl)-2-methylnicotinate (45.8 mg, 0.154 mmol) in ethanol (770 μl) was added sodium hydroxide (1 N, 308 μl, 0.308 mmol). The reaction mixture was stirred at rt 4 h. The reaction mixture was concentrated in vacuo and dried ON under vacuum. Material used as is is subsequent chemistry.

MS ESI m/z 270.1 (M+H)

82: To a vial charged with 5-(2-amino-[1,2,4]triazolo[1,5-a]pyridin-7-yl)-2-methylnicotinic acid, Na+ (21.92 mg, 0.075 mmol) in DMF (375 μl) was added 3-phenylbutan-1-amine, HCl (13.93 mg, 0.075 mmol), Hünig's Base (39.3 μl, 0.225 mmol) and BOP (33.2 mg, 0.075 mmol). The reaction mixture was stirred at rt 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 min, then a 5-minute hold at 100% B; Flow: 20 mL/min. Fractions containing the desired product were combined and dried via centrifugal evaporation. The yield of the product was 10.7 mg.

$^1$H NMR (500 MHz, DMSO-d6) δ 8.89 (d, J=1.7 Hz, 1H), 8.60 (d, J=7.0 Hz, 1H), 8.54 (br t, J=5.3 Hz, 1H), 8.02 (d, J=1.7 Hz, 1H), 7.75 (s, 1H), 7.32-7.27 (m, 3H), 7.26-7.21 (m, 2H), 7.20-7.13 (m, 1H), 3.23-3.07 (m, 2H), 2.85-2.74 (m, 1H), 2.54 (s, 3H), 1.81 (q, J=7.3 Hz, 2H), 1.22 (d, J=6.9 Hz, 3H) Note: Unknown peak at 3.54 ppm MS ESI m/z 401.1 (M+H)

Example 83

5-{2-Amino-[1,2,4]triazolo[1,5-a]pyridin-7-yl}-N-(1-benzyl-1H-pyrazol-4-yl)-2-chloropyridine-3-carboxamide

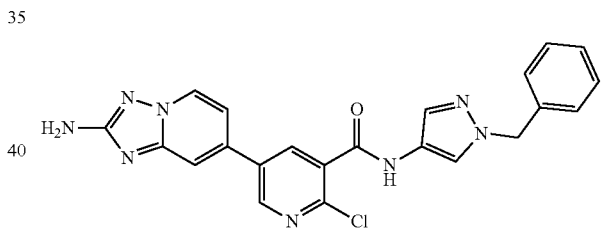

83A: Methyl 5-(2-amino-[1,2,4]triazolo[1,5-a]pyridin-7-yl)-2-chloronicotinate: To a vial charged with methyl 5-bromo-2-chloronicotinate (50 mg, 0.200 mmol), 4,4,4',4',5,5,5',5'-octamethyl-2,2'-bi(1,3,2-dioxaborolane) (60.8 mg, 0.240 mmol), potassium acetate (29.4 mg, 0.299 mmol) and PdCl$_2$(dppf)-CH$_2$Cl$_2$ adduct (16.30 mg, 0.020 mmol) was added 1,4-dioxane (998 μl). The reaction mixture was sparged with nitrogen for 5 min. The vial was capped and heated at 80° C. 3 h and 90° C. 1 h. After cooling tort, 7-bromo-[1,2,4]triazolo[1,5-a]pyridin-2-amine (38.3 mg, 0.180 mmol) was added followed by potassium carbonate (2 M, 250 μl, 0.499 mmol). The mixture was sparged with nitrogen for 3 min. The vial was capped and the reaction mixture heated at 90° C. 1 h and cooled to rt ON. Water was added and the solid product isolated by vacuum filtration, washing with water. Methyl 5-(2-amino-[1,2,4]triazolo[1,5-a]pyridin-7-yl)-2-chloronicotinate (53 mg, 0.175 mmol, 87% yield) was isolated as a yellow solid.

MS ESI m/z 304.0 (M+H)

83B: 5-(2-Amino-[1,2,4]triazolo[1,5-a]pyridin-7-yl)-2-chloronicotinate, sodium salt: To a round bottom flask charged with methyl 5-(2-amino-[1,2,4]triazolo[1,5-a]pyridin-7-yl)-2-chloronicotinate (53 mg, 0.175 mmol) in methanol (873 µl) was added sodium hydroxide (1 N, 349 µl, 0.349 mmol). The reaction mixture was stirred at rt ON. The reaction mixture was concentrated in vacuo and dried ON under vacuum. Used as is in subsequent chemistry.

MS ESI m/z 290.0 (M+H)

83: To a vial charged with 5-(2-amino-[1,2,4]triazolo[1,5-a]pyridin-7-yl)-2-chloronicotinic acid, Na+(27.5 mg, 0.088 mmol) in DMF (440 µl) was added 1-benzyl-1H-pyrazol-4-amine (15.24 mg, 0.088 mmol), Hünig's Base (46.1 Âµl, 0.264 mmol) and BOP (38.9 mg, 0.088 mmol). The reaction mixture was stirred at rt 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 20 mL/min. Fractions containing the desired product were combined and dried via centrifugal evaporation. The yield of the product was 4.6 mg (10.3 µmol, 11.3%).

$^1$H NMR (500 MHz, DMSO-d6) δ 10.88 (s, 1H), 8.94 (d, J=2.0 Hz, 1H), 8.62 (d, J=7.0 Hz, 1H), 8.46 (d, J=1.9 Hz, 1H), 8.14 (s, 1H), 7.84 (s, 1H), 7.56 (s, 1H), 7.40-7.21 (m, 6H), 6.10 (s, 1H), 5.31 (s, 2H).

MS ESI m/z 445.2 (M+H)

Example 84

5-{2-Amino-[1,2,4]triazolo[1,5-a]pyridin-7-yl}-N-(1-benzyl-1H-pyrazol-4-yl)-2-methoxy pyridine-3-carboxamide

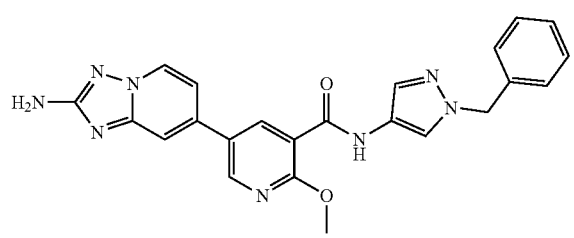 [SMILES: COc1ncc(-c2ccn3nc(N)nc3c2)cc1C(=O)Nc1cnn(Cc2ccccc2)c1]

84A: Methyl 5-(2-amino-[1,2,4]triazolo[1,5-a]pyridin-7-yl)-2-methoxynicotinate: To a vial charged with methyl 5-bromo-2-methoxynicotinate (0.13 g, 0.528 mmol), 4,4,4',4',5,5,5',5'-octamethyl-2,2'-bi(1,3,2-dioxaborolane) (0.161 g, 0.634 mmol), potassium acetate (0.078 g, 0.792 mmol) and PdCl$_2$(dppf)-CH$_2$Cl$_2$ adduct (0.043 g, 0.053 mmol) was added 1,4-dioxane (2.64 ml). The reaction mixture was sparged with nitrogen for 5 min. The vial was capped and heated at 80° C. ON. The reaction mixture was cooled to rt. 7-Bromo-[1,2,4]triazolo[1,5-a]pyridin-2-amine (0.050 g, 0.235 mmol) was added followed by potassium carbonate (2 M, 0.660 ml, 1.321 mmol). The mixture was sparged with nitrogen again for 3 min. The vial was capped and the reaction mixture heated at 100° C. 45 min. The reaction mixture was cooled to rt and diluted with water. The precipitated solid was isolated by vacuum filtration, washing with water. The product methyl 5-(2-amino-[1,2,4]triazolo[1,5-a]pyridin-7-yl)-2-methoxynicotinate (68 mg, 0.227 mmol, 43.0% yield) was isolated as a pale gray solid.

MS ESI m/z 300.0 (M+H)

84B: 5-(2-Amino-[1,2,4]triazolo[1,5-a]pyridin-7-yl)-2-methoxynicotinate, sodium salt: To a round bottom flask charged with methyl 5-(2-amino-[1,2,4]triazolo[1,5-a]pyridin-7-yl)-2-methoxynicotinate (68.3 mg, 0.228 mmol) in methanol (1141 µl) was added sodium hydroxide (1 N, 685 µl, 0.685 mmol). The reaction mixture was stirred at rt 3 h. Solvent was removed in vacuo and the material dried under vacuum ON. Material used as is in subsequent chemistry.

MS ESI m/z 286.0 (M+H)

84: To a round bottom flask charged with 5-(2-amino-[1,2,4]triazolo[1,5-a]pyridin-7-yl)-2-methoxynicotinic acid, Na$^+$ (0.2 g, 0.649 mmol) in DMF (3.24 ml) was added 1-benzyl-1H-pyrazol-4-amine, HCl (0.136 g, 0.649 mmol), Hünig's Base (0.340 ml, 1.946 mmol) and BOP (0.287 g, 0.649 mmol). The reaction mixture was stirred at rt ON. Additional BOP and amine were added and stirring continued 60 min. The reaction mixture was diluted with water and the solid product was isolated by vacuum filtration, washing with water. The solid product was triturated with ether and DCM. 5-(2-Amino-[1,2,4]triazolo[1,5-a]pyridin-7-yl)-N-(1-benzyl-1H-pyrazol-4-yl)-2-methoxy nicotinamide (45.3 mg, 0.101 mmol, 15.53% yield) was isolated as an off-white solid.

$^1$H NMR (500 MHz, DMSO-d6) δ 10.37 (s, 1H), 8.77 (d, J=1.9 Hz, 1H), 8.59 (d, J=7.0 Hz, 1H), 8.41 (d, J=2.0 Hz, 1H), 8.15 (s, 1H), 7.73 (s, 1H), 7.62 (s, 1H), 7.39-7.22 (m, 6H), 6.06 (s, 2H), 5.31 (s, 2H), 4.01 (s, 3H).

MS ESI m/z 441.2 (M+H)

Example 85

5-{2-Amino-[1,2,4]triazolo[1,5-a]pyridin-7-yl}-2-methoxy-N-(3-phenylbutyl)pyridine-3-carboxamide

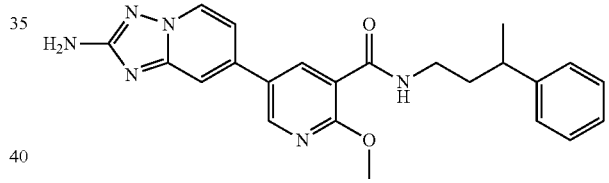

85A: 5-Borono-2-methoxynicotinic acid, lithium salt: To a round bottom flask charged with methyl 2-methoxy-5-(4,4,5,5-tetramethyl-1,3,2-dioxaborolan-2-yl)nicotinate (0.5 g, 1.706 mmol) in tetrahydrofuran (6.40 ml) and water (2.132 ml) was added lithium hydroxide monohydrate (0.215 g, 5.12 mmol). The reaction mixture was stirred at rt 4 h. The reaction mixture was concentrated in vacuo and dried ON under vacuum. Material used crude in next step MS ESI m/z 198.0 (M+H)

85B: (6-Methoxy-5-((3-phenylbutyl)carbamoyl)pyridin-3-yl)boronic acid: To a solution of 5-borono-2-methoxynicotinic acid, lithium salt (0.348 g, 1.706 mmol), 3-phenylbutan-1-amine, HCl (0.317 g, 1.706 mmol) and Hünig's base (0.626 ml, 3.58 mmol) in DMF (5.69 ml) was added BOP (0.755 g, 1.706 mmol). The reaction mixture was stirred at rt 6 h. The reaction mixture was diluted with EtOAc which was washed with 10% LiCl solution (2×), water and brine. The organics were dried over anhydrous sodium sulfate and concentrated in vacuo. The material was dried under vacuum ON. Isolated (6-ethoxy-5-((3-phenylbutyl)carbamoyl)pyridin-3-yl)boronic acid (0.54 g, 1.65 mmol, 96%).

MS ESI m/z 319.0 (M+H)

85: To a vial containing 7-bromo-[1,2,4]triazolo[1,5-a]pyridin-2-amine (17 mg, 0.080 mmol) was added (6-methoxy-5-((3-phenylbutyl)carbamoyl)pyridin-3-yl)boronic acid (13 mg, 0.040 mmol), tripotassium phosphate (25 mg, 0.120 mmol) in water (60 µL), 1,1'-bis(diphenylphosphino)ferrocene-palladium(ii)dichloride dichloromethane complex (3.27 mg, 4.00 µmol) and dioxane (0.4 mL). The reaction mixture was sparged with nitrogen and heated to 100° C. for 2.5 h. After cooling to rt, the crude reaction mixture was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation to afford 5-{2-amino-[1,2,4]triazolo[1,5-a]pyridin-7-yl}-2-methoxy-N-(3-phenylbutyl)pyridine-3-carboxamide (5 mg, 0.012 mmol, 29%).

$^1$H NMR (500 MHz, DMSO-d6) δ 8.74 (s, 1H), 8.59 (d, J=7.0 Hz, 1H), 8.36 (s, 1H), 8.29 (br t, J=5.7 Hz, 1H), 7.70 (s, 1H), 7.34-7.28 (m, 2H), 7.28-7.21 (m, 3H), 7.21-7.16 (m, 1H), 6.05 (s, 2H), 4.01 (s, 3H), 3.22-3.15 (m, 2H), 2.85-2.76 (m, 1H), 1.83 (q, J=7.3 Hz, 2H).

MS ESI m/z 417.1 (M+H)

Example 86

5-{2-amino-[1,2,4]triazolo[1,5-a]pyridin-7-yl}-2-ethyl-N-{[2-fluoro-5-(trifluoromethoxy) phenyl] methyl}pyridine-3-carboxamide

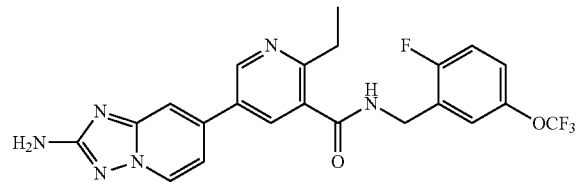 [SMILES: CCc1ncc(-c2ccn3nc(N)nc3c2)cc1C(=O)NCc1cc(OC(F)(F)F)ccc1F]

A mixture of 5-(2-amino-[1,2,4]triazolo[1,5-a]pyridin-7-yl)-2-ethylnicotinic acid (15 mg, 0.053 mmol) and BOP (35.1 mg, 0.079 mmol), (2-fluoro-5-(trifluoromethoxy)phenyl)methanamine (14.40 mg, 0.069 mmol) and Hünig's Base (0.046 mL, 0.265 mmol) in DMF (1.0 mL) was stirred at rt ON. The reaction mixture containing the product was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 19-59% B over 20 min, then a 4-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-2-ethyl-N-(2-fluoro-5-(trifluoromethoxy)benzyl)nicotinamide (6.5 mg, 0.013 mmol, 25.4% yield)

$^1$H NMR (500 MHz, DMSO-d6) δ 9.22 (br s, 1H), 8.99 (s, 1H), 8.63 (br d, J=6.7 Hz, 1H), 8.15 (s, 1H), 7.78 (s, 1H), 7.45-7.34 (m, 3H), 7.31 (br d, J=6.5 Hz, 1H), 6.09 (br s, 2H), 4.55 (br d, J=5.4 Hz, 2H), 2.87 (q, J=7.3 Hz, 2H), 1.17 (br t, J=7.4 Hz, 3H).

MS ESI m/z 475.3 (M+H)

Example 87

5-{2-amino-[1,2,4]triazolo[1,5-a]pyridin-7-yl}-N-{[2-fluoro-5-(trifluoromethoxy)phenyl] (deutero) methyl}-2-methoxypyridine-3-carboxamide

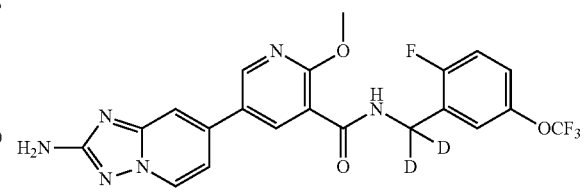

87A: 2-fluoro-5-(trifluoromethoxy)benzylamine-d2: To a mixture of 2-fluoro-5-(trifluoromethoxy)benzonitrile (374 mg, 1.823 mmol) and sodium borodeuteride (176 mg, 4.19 mmol) in THF (10 mL) at 0° C. was added over 45 min, iodine (463 mg, 1.823 mmol) as a solution in 4 ml THF. The reaction mixture was heated at reflux for 2 h. After cooling to 0° C., 6 N HCl (2 ml) was carefully added. This mixture was heated at reflux for 30 min. After cooling to rt, the mixture was partitioned between EtOAc (40 mL) and 1 N NaOH (40 mL). The organic layer was washed with water (20 mL) and brine (20 mL). After drying over anhydrous sodium sulfate, the organic layer was filtered and concentrated to afford 2-fluoro-5-(trifluoromethoxy)benzylamine-d2 (385 mg, 1.823 mmol, 100% yield). The material contains a number of side products and was used as is.

87: A mixture of 5-(2-amino-[1,2,4]triazolo[1,5-a]pyridin-7-yl)-2-methoxynicotinic acid (25 mg, 0.088 mmol), (2-fluoro-5-(trifluoromethoxy)phenyl)methanamine-d2, HCl (26.0 mg, 0.105 mmol), BOP (42.6 mg, 0.096 mmol) and Et$_3$N (0.037 mL, 0.263 mmol) in DMF (0.8 mL) was agitated at rt for 4 h. The reaction mixture containing the product was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 min, then a 5-min hold at 100% B; Flow: 20 mL/min. Fractions containing the desired product were combined and dried via centrifugal evaporation.

$^1$H NMR (500 MHz, DMSO-d6) δ 8.99 (s, 1H), 8.76 (s, 1H), 8.69 (br. s., 1H), 8.41 (br. s., 1H), 7.40 (d, J=4.1 Hz, 1H), 7.36-7.30 (m, 2H), 7.25 (d, J=6.9 Hz, 1H), 4.03 (s, 3H) missing exchangeable protons.

MS ESI m/z 479.1 (M+H)

Example 88

5-{2-amino-[1,2,4]triazolo[1,5-a]pyridin-7-yl}-N-{[2-(cyclopropylmethoxy)-3,5-difluoro phenyl](deutero)methyl}-2-methoxypyridine-3-carboxamide

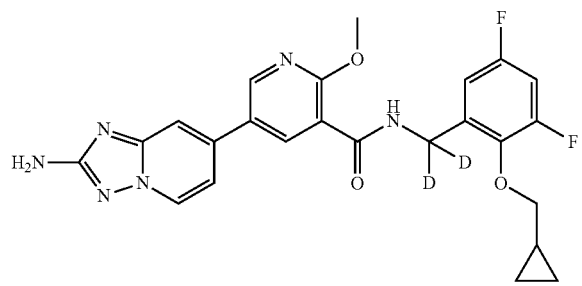 [SMILES: [2H]C([2H])(NC(=O)c1cc(-c2ccn3nc(N)nc3c2)cnc1OC)c1cc(F)cc(F)c1OCC1CC1]

88A: 2-(cyclopropylmethoxy)-3,5-difluorobenzonitrile: To a solution of 3,5-difluoro-2-hydroxybenzonitrile (413 mg, 2.66 mmol) in DMF (6 mL) was added potassium carbonate (552 mg, 3.99 mmol). After 10 min, (bromomethyl)cyclopropane (0.284 mL, 2.93 mmol) was added. The resulting solution was stirred at rt. The reaction mixture was diluted to a total volume of 100 mL with EtOAc and water (10 mL) was added. The aqueous layer was extracted with ethyl acetate (1×20 mL). The combined organics were washed with 10% lithium chloride solution (2×) and brine. The organics were dried over anhydrous sodium sulfate, filtered and concentrated to an oil. The crude oil was loaded onto a 40 g ISCO column and purified by flash chromatography, eluting with 0-100% EtOAc in hexanes. Afforded 2-(cyclopropylmethoxy)-3,5-difluorobenzonitrile (515 mg, 2.339 mmol, 88% yield) as a yellow oil.

$^1$H NMR (400 MHz, DMSO-$d_6$) δ 7.82 (ddd, J=11.7, 8.7, 3.1 Hz, 1H), 7.71 (ddd, J=8.1, 3.1, 1.8 Hz, 1H), 4.04 (dd, J=7.3, 0.9 Hz, 2H), 1.25-1.12 (m, 1H), 0.59-0.52 (m, 2H), 0.31-0.25 (m, 2H).

MS (ESI) m/z 210.1 (M+H)

88B: (2-(cyclopropylmethoxy)-3,5-difluorophenyl)methan-d2-amine: To a mixture of 2-(cyclopropylmethoxy)-3,5-difluorobenzonitrile (255 mg, 1.219 mmol) and sodium borodeuteride (117 mg, 2.80 mmol) in THF (7 mL) at 0° C. was added over 45 min, iodine (309 mg, 1.219 mmol) as a solution on 2.5 ml of THF. The reaction mixture was heated at reflux for 2 h. After cooling to 0° C., 6 N HCl (1.75 ml) was carefully added. This mixture was returned to reflux for 30 min. After cooling to rt, the mixture was diluted with water (20 mL) and extracted with ether. The aqueous layer was basified with 1 N NaOH (30 ml), then extracted with EtOAc (3×50 mL). The organic layer was washed with water (20 mL) and brine (20 mL). After drying over anhydrous sodium sulfate and filtration, the organic layer was concentrated to afford (2-(cyclopropylmethoxy)-3,5-difluorophenyl)methan-d2-amine (157 mg, 0.693 mmol, 56.8%) as a pale orange solid.

$^1$H NMR (400 MHz, DMSO-d6) δ 7.27-6.96 (m, 2H), 3.79 (d, J=6.1 Hz, 2H), 1.17 (br. s., 1H), 0.53 (d, J=5.9 Hz, 2H), 0.25 (br. s., 2H).

MS (ESI) m/z 216.1 (M+H)

88: A mixture of 5-(2-amino-[1,2,4]triazolo[1,5-a]pyridin-7-yl)-2-methoxynicotinic acid (15 mg, 0.053 mmol) and BOP (34.9 mg, 0.079 mmol), (2-(cyclopropylmethoxy)-3,5-difluorophenyl)methan-d2-amine (13.58 mg, 0.063 mmol) and Hünig's Base (0.046 mL, 0.263 mmol) in DMF (1.0 mL) was stirred at rt 3 d. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 min, then a 3-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-((2-(cyclopropylmethoxy)-3,5-difluorophenyl)methyl-d2)-2-methoxynicotinamide (8.8 mg, 0.018 mmol, 34.3% yield).

$^1$H NMR (500 MHz, DMSO-d6) δ 8.91 (s, 1H), 8.77 (d, J=2.1 Hz, 1H), 8.58 (d, J=7.0 Hz, 1H), 8.45 (d, J=2.4 Hz, 1H), 7.70 (s, 1H), 7.26 (br d, J=7.0 Hz, 1H), 7.19 (br t, J=8.5 Hz, 1H), 7.00 (br d, J=8.9 Hz, 1H), 6.03 (s, 2H), 4.05 (s, 3H), 3.88 (d, J=7.3 Hz, 2H), 1.24 (br d, J=4.6 Hz, 1H), 0.61-0.51 (m, 2H), 0.30 (br d, J=4.9 Hz, 2H).

MS ESI m/z 483.3 (M+H)

Example 89

5-{2-amino-[1,2,4]triazolo[1,5-a]pyridin-7-yl}-N-{1-[2-fluoro-5-(trifluoromethoxy)phen yl]ethyl}-2-methoxypyridine-3-carboxamide

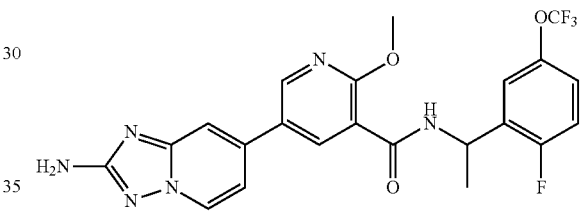

89A: 1-(2-fluoro-5-(trifluoromethoxy)phenyl)ethanone: To a solution of 2-fluoro-5-(trifluoromethoxy)benzonitrile (410 mg, 1.999 mmol) in ethyl ether (15 mL) at −78° C. was added methyllithium, 1.6 M (4.37 mL, 7.00 mmol) dropwise over 5 min. The reaction mixture was allowed to stir at −78° C. 2 h. The reaction mixture was quenched by the addition of saturated ammonium chloride solution (5 mL). The mixture was allowed to stir vigorously as it warmed to rt. The mixture was partitioned between ether (40 mL) and water (30 mL). The organic layer was washed with brine (20 mL), dried over anhydrous magnesium sulfate, filtered and concentrated to a yellow oil. The crude residue was purified by column chromatography on a 24 g ISCO silica gel cartridge, eluting with a 0-50% EtOAc/Hex gradient. The pure fractions were concentrated to afford 1-(2-fluoro-5-(trifluoromethoxy)phenyl)ethanone (114 mg, 0.513 mmol, 25.7% yield) as a light yellow liquid.

$^1$H NMR (400 MHz, CDCl$_3$) δ 7.75 (dd, J=5.1, 3.1 Hz, 1H), 7.41-7.34 (m, 1H), 7.23-7.15 (m, 1H), 2.66 (d, J=5.0 Hz, 3H).

89B: 1-(2-fluoro-5-(trifluoromethoxy)phenyl)ethanamine: A solution of 1-(2-fluoro-5-(trifluoromethoxy)phenyl)ethanone (110 mg, 0.495 mmol), ammonium acetate (382 mg, 4.95 mmol) and sodium cyanoborohydride (37.3 mg, 0.594 mmol) in EtOH (4 mL) was stirred at rt 4 d. The reaction mixture was concentrated to a thick oily residue. The residue was partitioned between EtOAc (50 mL) and saturated sodium bicarbonate solution (40 mL). The organic layer was washed with water (15 mL) and brine (15 mL). After drying over anhydrous sodium sulfate and filtration, the organic layer was concentrated to afford 1-(2-fluoro-5-(trifluoromethoxy)phenyl)ethanamine (110 mg, 0.493 mmol, 100%) as a yellow oil. The crude material was used as is in subsequent chemistry.

89: A mixture of 5-(2-amino-[1,2,4]triazolo[1,5-a]pyridin-7-yl)-2-methoxynicotinic acid, lithium salt (30 mg, 0.102 mmol), 1-(2-fluoro-5-(trifluoromethoxy)phenyl)ethanamine (45.6 mg, 0.204 mmol), BOP (49.7 mg, 0.112 mmol) and Et$_3$N (0.043 mL, 0.307 mmol) in DMF (0.8 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-min hold at 100% B; Flow: 20 mL/min. Fractions containing the desired product were combined and dried via centrifugal evaporation to afford 5-(2-amino-[1,2,4]triazolo[1,5-a]pyridin-7-yl)-N-(1-(2-fluoro-5-(trifluoromethoxy)phenyl)ethyl)-2-methoxynicotinamide (18.9 mg, 0.038 mmol, 37.3%). This material underwent chiral SFC to isolate the individual enantiomers 89-1 (7.2 mg, 0.015 mmol) and 89-2 (7.0 mg, 0.014 mmol).

Racemate: $^1$H NMR (500 MHz, DMSO-d6) δ 8.88 (d, J=7.4 Hz, 1H), 8.76 (d, J=2.2 Hz, 1H), 8.59 (d, J=6.9 Hz, 1H), 8.30 (d, J=2.5 Hz, 1H), 7.71 (s, 1H), 7.54 (br. s., 1H), 7.41-7.31 (m, 2H), 7.24 (d, J=5.8 Hz, 1H), 6.04 (s, 2H), 5.35 (t, J=7.0 Hz, 1H), 4.02 (s, 3H), 1.47 (d, J=7.2 Hz, 3H).

MS (ESI) m/z 491.2 (M+H)

89-1: $^1$H NMR (500 MHz, DMSO-d6) δ 8.93 (d, J=6.2 Hz, 1H), 8.73 (s, 1H), 8.57 (d, J=7.1 Hz, 1H), 8.28 (d, J=2.4 Hz, 1H), 7.69 (s, 1H), 7.51 (br. s., 1H), 7.39-7.30 (m, 2H), 7.27-7.21 (m, 1H), 6.04 (br. s., 2H), 5.33 (t, J=7.1 Hz, 1H), 4.00 (s, 3H), 1.45 (d, J=7.0 Hz, 3H).

89-2: $^1$H NMR (500 MHz, DMSO-d6) δ 8.93 (d, J=6.6 Hz, 1H), 8.73 (s, 1H), 8.56 (d, J=6.9 Hz, 1H), 8.27 (d, J=1.9 Hz, 1H), 7.68 (s, 1H), 7.50 (br. s., 1H), 7.38-7.29 (m, 2H), 7.27-7.21 (m, 1H), 6.04 (br. s., 2H), 5.32 (t, J=7.2 Hz, 1H), 4.00 (s, 3H), 1.45 (d, J=7.0 Hz, 3H).

Example 90

5-{2-amino-[1,2,4]triazolo[1,5-a]pyridin-7-yl}-2-(deutero)methoxy-N-{[2-(trifluoromethoxy)phenyl]methyl}pyridine-3-carboxamide

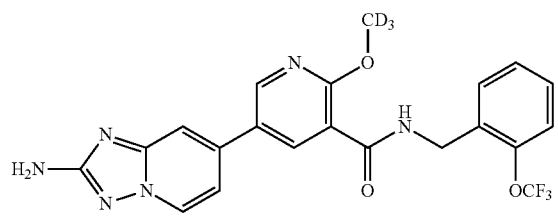 [SMILES: [2H]C([2H])([2H])Oc1ncc(-c2ccn3nc(N)nc3c2)cc1C(=O)NCc1ccccc1OC(F)(F)F]

90A: Methyl d$_3$ 5-bromo-2-methoxy d$_3$-nicotinate: Sodium (0.385 g, 16.77 mmol) was added to CD$_3$OD (10 mL) and stirred until the reaction was complete. Methyl 5-bromo-2-chloronicotinate (1.5 g, 5.99 mmol) was added and stirred for 16 h. The reaction mixture was diluted with EtOAc (100 mL) and washed with water (20 mL) and brine (20 mL). The organics were dried over anhydrous sodium sulfate. Filtration and concentration yielded a product which was identified as a mixture of methyl d$_3$ 5-bromo-2-methoxy d$_3$-nicotinate and ethyl 5-bromo-2-methoxy d3-nicotinate (1.012 g).

MS (ESI) m/z 252.1 (M+H) and 262.1 (M+H)

90B: Methyl-d$_3$ 5-(2-((bis-tert-butoxycarbonyl)amino)-[1,2,4]triazolo[1,5-a]pyridin-7-yl)-2-(methoxy-d3) nicotinate: A mixture of 1A (310 mg, 0.750 mmol), 4,4,4',4',5,5,5',5'-octamethyl-2,2'-bi(1,3,2-dioxaborolane) (286 mg, 1.125 mmol), PdCl$_2$(dppf)-CH$_2$Cl$_2$ adduct (61.3 mg, 0.075 mmol) and potassium acetate (221 mg, 2.250 mmol) in dioxane (6 mL) was heated to 100° C. for 2 h. After cooling to rt, 90A (284 mg, 0.751 mmol) and 1,1'-bis(diphenylphosphino)ferrocene-palladium(II)dichloride dichloromethane complex (30.7 mg, 0.038 mmol) in dioxane (5 mL) was degassed by bubbling nitrogen through the mixture for 5 min. 2 M K$_3$PO$_4$ (aq) (1.126 mL, 2.253 mmol) was added and the reaction mixture heated to 100° C. for 1.5 h. After cooling to rt, the reaction mixture was partitioned between EtOAc (40 mL) and brine (30 mL). After drying over anhydrous sodium sulfate and filtration, the organic layer was concentrated to afford a dark residue. The crude residue was purified by column chromatography on a 24 g ISCO silica gel cartridge, eluting with a 0-100% EtOAc/Hex gradient. The pure fractions were concentrated to afford the desired product, along with the ethyl ester (380 mg, 0.752 mmol, 100% yield) as a tan solid.

ME (ESI) m/z 506.4 (M+H)

90C: Methyl 5-(2-amino-[1,2,4]triazolo[1,5-a]pyridin-7-yl)-2-methoxynicotinate-d$_6$: A solution of 90B (380 mg, 0.752 mmol) in TFA (1737 μl, 22.55 mmol) was allowed to stand at rt for 1 h. The volatiles were removed in vacuo and the residue was co-evaporated from EtOAc/heptane (3×). The residue was partitioned between ether (25 mL) and water (20 mL). The ether layer was extracted with 1 N HCl (20 mL) and the combined aqueous layers were basified to pH 8 with 1.5 M dibasic potassium phosphate solution. After standing for 15 min, the suspension was filtered and the filter cake was rinsed with water and dried to afford methyl 5-(2-amino-[1,2,4]triazolo[1,5-a]pyridin-7-yl)-2-methoxynicotinate-d$_6$ (229 mg, 0.750 mmol, 100% yield) as a tan solid, mixed with the ethyl ester analog.

MS (ESI) m/z 306.2 (M+H)

90D: 5-(2-Amino-[1,2,4]triazolo[1,5-a]pyridin-7-yl)-2-methoxynicotinic acid-d-3, lithium salt: To a suspension of 90C (223 mg, 0.730 mmol) in THF (6 mL) at rt was added LiOH, hydrate (39.9 mg, 0.949 mmol) as a solution in water (1 mL). The reaction mixture was stirred at rt ON. The volatiles were removed in vacuo and the residue dried to afford 5-(2-amino-[1,2,4]triazolo[1,5-a]pyridin-7-yl)-2-methoxynicotinic acid-d$_3$, lithium salt (217 mg, 0.730 mmol, 100% yield) as a tan solid.

MS (ESI) m/z 289.2 (M+H)

90: A mixture of 5-(2-amino-[1,2,4]triazolo[1,5-a]pyridin-7-yl)-2-methoxynicotinic acid-d$_3$, lithium salt (15 mg, 0.050 mmol), (2-(trifluoromethoxy)phenyl)methanamine (11.57 mg, 0.061 mmol), BOP (24.55 mg, 0.055 mmol) and Et$_3$N (0.021 mL, 0.151 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-min hold at 100% B; Flow: 20 mL/min. Fractions containing the desired product were combined and dried via centrifugal evaporation. Afforded 5-(2-amino-[1,2,4]triazolo[1,5-a]

pyridin-7-yl)-2-methoxy-N-(2-(trifluoromethoxy)benzyl)
nicotinamide-d₃ (11.6 mg, 0.024 mmol, 47.8%).

¹H NMR (500 MHz, DMSO-d6) δ 8.92 (t, J=6.1 Hz, 1H), 8.77 (d, J=2.5 Hz, 1H), 8.59 (d, J=7.2 Hz, 1H), 8.45 (d, J=2.5 Hz, 1H), 7.70 (s, 1H), 7.57-7.48 (m, 1H), 7.45-7.33 (m, 3H), 7.24 (dd, J=7.0, 1.8 Hz, 1H), 6.03 (s, 2H), 4.59 (d, J=6.1 Hz, 2H).

MS ESI m/z 461.9 (M+H)

Example 91

5-{2-amino-[1,2,4]triazolo[1,5-a]pyridin-7-yl}-N-{[2-fluoro-5-(trifluoromethyl)phenyl]methyl}-2-(deutero)methoxypyridine-3-carboxamide

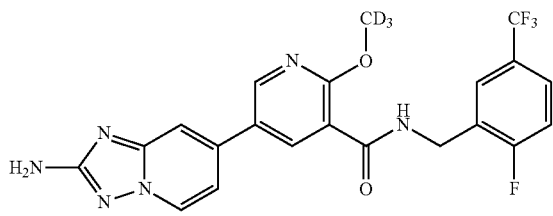 [SMILES: [2H]C([2H])([2H])Oc1ncc(-c2ccn3nc(N)nc3c2)cc1C(=O)NCc1cc(C(F)(F)F)ccc1F]

A mixture of 5-(2-amino-[1,2,4]triazolo[1,5-a]pyridin-7-yl)-2-methoxynicotinic acid-d₃, lithium salt (15 mg, 0.050 mmol), (2-fluoro-5-(trifluoromethyl)phenyl)methanamine (11.69 mg, 0.061 mmol), BOP (24.55 mg, 0.055 mmol) and Et₃N (0.021 mL, 0.151 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-fluoro-5-(trifluoromethyl)benzyl)-2-methoxynicotinamide-d₃ (11.5 mg, 0.024 mmol, 47.2%).

¹H NMR (500 MHz, DMSO-d6) δ 9.05 (br s, 1H), 8.71 (br s, 1H), 8.53 (br d, J=6.1 Hz, 1H), 8.37 (br s, 1H), 7.86-7.58 (m, 3H), 7.41 (br s, 1H), 7.25 (br s, 1H), 5.97 (br s, 2H), 4.60 (br s, 2H).

MS ESI m/z 464.3 (M+H)

Example 92

5-{2-amino-[1,2,4]triazolo[1,5-a]pyridin-7-yl}-N-{[2-fluoro-5-(trifluoromethoxy)phenyl] methyl}-2-(deutero)methoxypyridine-3-carboxamide

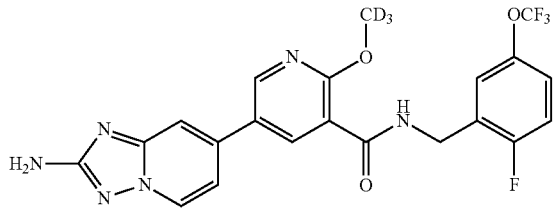 [SMILES: [2H]C([2H])([2H])Oc1ncc(-c2ccn3nc(N)nc3c2)cc1C(=O)NCc1cc(OC(F)(F)F)ccc1F]

A mixture of 5-(2-amino-[1,2,4]triazolo[1,5-a]pyridin-7-yl)-2-methoxynicotinic acid-d₃, lithium salt (15 mg, 0.050 mmol), (2-fluoro-5-(trifluoromethoxy)phenyl)methanamine (12.66 mg, 0.061 mmol), BOP (24.55 mg, 0.055 mmol) and Et₃N (0.021 mL, 0.151 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-fluoro-5-(trifluoromethoxy)benzyl)-2-methoxynicotinamide-d₃ (6.3 mg, 0.013 mmol, 25.8%).

1H NMR (500 MHz, DMSO-d6) δ 8.99 (t, J=5.9 Hz, 1H), 8.76 (d, J=2.5 Hz, 1H), 8.58 (d, J=7.2 Hz, 1H), 8.40 (d, J=2.5 Hz, 1H), 7.69 (s, 1H), 7.40 (br s, 1H), 7.38-7.29 (m, 2H), 7.24 (dd, J=7.0, 1.8 Hz, 1H), 6.02 (s, 2H), 4.57 (d, J=6.1 Hz, 2H).

MS ESI m/z 480 (M+H)

Example 93

5-{2-amino-[1,2,4]triazolo[1,5-a]pyridin-7-yl}-N-{[2-fluoro-5-(trifluoromethoxy)phenyl] (deutero)methyl}-2-(deutero)methoxypyridine-3-carboxamide

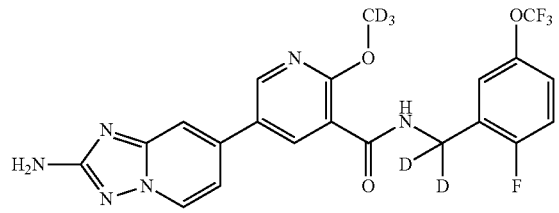 [SMILES: [2H]C([2H])([2H])Oc1ncc(-c2ccn3nc(N)nc3c2)cc1C(=O)NC([2H])([2H])c1cc(OC(F)(F)F)ccc1F]

A mixture of 5-(2-amino-[1,2,4]triazolo[1,5-a]pyridin-7-yl)-2-methoxynicotinic acid-d₃, lithium salt (15 mg, 0.050 mmol), (2-fluoro-5-(trifluoromethoxy)phenyl)methanamine-d2 (32.0 mg, 0.151 mmol), BOP (24.55 mg, 0.055 mmol) and Et₃N (0.021 mL, 0.151 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 min, then a 5-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-fluoro-5-(trifluoromethoxy)benzyl)-2-methoxynicotinamide-d₃ (11.2 mg, 0.023 mmol, 45.6%).

1H NMR (500 MHz, DMSO-d6) δ 9.02-8.95 (m, 1H), 8.77 (d, J=2.5 Hz, 1H), 8.62 (br d, J=6.9 Hz, 1H), 8.41 (d, J=2.5 Hz, 1H), 7.72 (br d, J=1.1 Hz, 1H), 7.41 (br d, J=4.7 Hz, 1H), 7.37-7.31 (m, 2H), 7.28 (d, J=6.9 Hz, 1H) Note: 2 exchangeable protons missing.

MS ESI m/z 482.1 (M+H)

Example 94

5-{2-amino-[1,2,4]triazolo[1,5-a]pyridin-7-yl}-N-{[2-(cyclopropylmethoxy)-3,5-difluoro phenyl]methyl}-2-(deutero)methoxypyridine-3-carboxamide

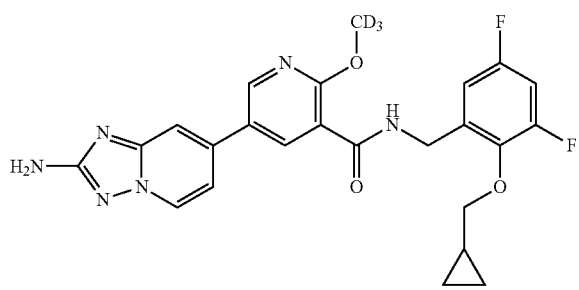 [SMILES: [2H]C([2H])([2H])Oc1ncc(-c2ccn3nc(N)nc3c2)cc1C(=O)NCc1cc(F)cc(F)c1OCC1CC1]

A mixture of 5-(2-amino-[1,2,4]triazolo[1,5-a]pyridin-7-yl)-2-methoxynicotinic acid-d₃, lithium salt (15 mg, 0.050 mmol), (2-(cyclopropylmethoxy)-3,5-difluorophenyl)methanamine (10.76 mg, 0.050 mmol), BOP (24.55 mg, 0.055 mmol) and Et₃N (0.021 mL, 0.151 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 min, then a 5-min hold at 100% B; Flow: 20 mL/min. Fractions containing the desired product were combined and dried via centrifugal evaporation. Afforded 5-(2-amino-[1,2,4]triazolo[1,5-a]pyridin-7-yl)-N-(2-(cyclopropylmethoxy)-3,5-difluorobenzyl)-2-methoxynicotinamide-d₃ (5.6 mg, 0.011 mmol, 22.7%).

¹H NMR (500 MHz, DMSO-d6) δ 8.91 (t, J=6.1 Hz, 1H), 8.76 (d, J=2.5 Hz, 1H), 8.58 (d, J=6.9 Hz, 1H), 8.44 (d, J=2.5 Hz, 1H), 7.70 (s, 1H), 7.25 (dd, J=7.0, 1.8 Hz, 1H), 7.22-7.12 (m, 1H), 6.99 (br d, J=9.4 Hz, 1H), 6.03 (s, 2H), 4.65-4.42 (m, 1H), 3.87 (d, J=7.4 Hz, 2H), 1.31-1.16 (m, 1H), 0.64-0.50 (m, 2H), 0.36-0.17 (m, 2H).

MS ESI m/z 483.9 (M+H)

Example 95

5-{2-amino-[1,2,4]triazolo[1,5-a]pyridin-7-yl}-2-(deutero)methoxy-N-{1-[2-(trifluoromethoxy)phenyl]ethyl}pyridine-3-carboxamide

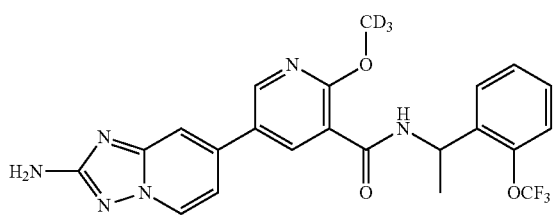 [SMILES: [2H]C([2H])([2H])Oc1ncc(-c2ccn3nc(N)nc3c2)cc1C(=O)NC(C)c1ccccc1OC(F)(F)F]

A mixture of 5-(2-amino-[1,2,4]triazolo[1,5-a]pyridin-7-yl)-2-methoxynicotinic acid-d₃, lithium salt (25 mg, 0.084 mmol), 1-(2-(trifluoromethoxy)phenyl)ethanamine (51.8 mg, 0.252 mmol), BOP (40.9 mg, 0.092 mmol) and Et₃N (0.035 mL, 0.252 mmol) in DMF (0.5 mL) was agitated at rt for 3 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-min hold at 100% B; Flow: 20 mL/min. Fractions containing the desired product were combined and dried via centrifugal evaporation to yield 5-(2-amino-[1,2,4]triazolo[1,5-a]pyridin-7-yl)-2-methoxy-N-(1-(2-(trifluoromethoxy)phenyl)ethyl)nicotinamide-d₃ (18.0 mg, 0.036 mmol, 42.8%). The racemate was separated using chiral SFC purification to afforded first eluting enantiomer, 95-1 (6.0 mg, 0.012 mmol, 14.26%) and second eluting enantiomer 95-2 (5.8 mg, 0.012 mmol, 13.9%).

Racemate: ¹H NMR (500 MHz, DMSO-d6) δ 8.79 (br d, J=7.7 Hz, 1H), 8.74 (d, J=2.5 Hz, 1H), 8.58 (d, J=7.2 Hz, 1H), 8.32 (d, J=2.5 Hz, 1H), 7.70 (s, 1H), 7.67-7.62 (m, 1H), 7.45-7.37 (m, 2H), 7.37-7.32 (m, 1H), 7.24 (dd, J=6.9, 1.7 Hz, 1H), 6.03 (s, 2H), 5.41 (t, J=7.2 Hz, 1H), 1.45 (d, J=6.9 Hz, 3H).

MS ESI m/z 476.4 (M+H)

First Eluting Isomer: ¹H NMR (500 MHz, DMSO-d6) δ 8.82 (br d, J=7.8 Hz, 1H), 8.74 (d, J=2.4 Hz, 1H), 8.58 (d, J=6.9 Hz, 1H), 8.32 (d, J=2.5 Hz, 1H), 7.70 (s, 1H), 7.67-7.60 (m, 1H), 7.45-7.37 (m, 2H), 7.37-7.29 (m, 1H), 7.24 (dd, J=7.1, 1.6 Hz, 1H), 6.05 (br s, 2H), 5.40 (t, J=7.2 Hz, 1H), 1.45 (d, J=7.0 Hz, 3H).

Second Eluting Isomer: ¹H NMR (500 MHz, DMSO-d6) δ 8.82 (br d, J=6.4 Hz, 1H), 8.73 (d, J=2.1 Hz, 1H), 8.57 (d, J=6.9 Hz, 1H), 8.31 (d, J=2.4 Hz, 1H), 7.69 (s, 1H), 7.67-7.60 (m, 1H), 7.46-7.37 (m, 2H), 7.35 (br s, 1H), 7.28-7.20 (m, 1H), 6.04 (br s, 2H), 5.39 (br t, J=7.2 Hz, 1H), 1.44 (d, J=7.0 Hz, 3H).

Example 96

5-{2-amino-[1,2,4]triazolo[1,5-a]pyridin-7-yl}-N-{[2-fluoro-5-(trifluoromethoxy)phenyl]methyl}-2-(deutero)methylpyridine-3-carboxamide

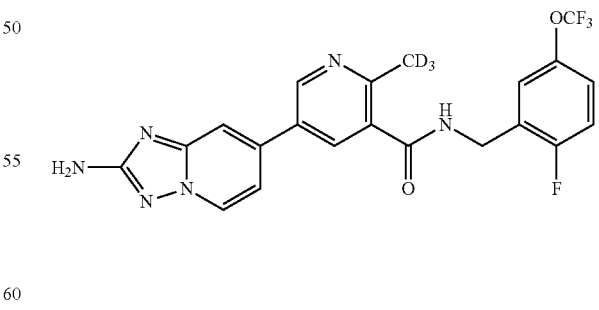

96A: To a solution of 1B (200 mg, 0.397 mmol), tri-tert-butylphosphonium tetrafluoroborate (13.82 mg, 0.048 mmol), palladium(II) acetate (8.91 mg, 0.040 mmol) and zinc bromide (26.8 mg, 0.119 mmol) in THF (1 mL) was added CD₃MgI (1.270 mL, 1.270 mmol) dropwise over 5 min. The reaction mixture was allowed to stir at rt for 2 h. The reaction mixture was partitioned between EtOAc (30 mL) and saturated ammonium chloride solution (30 mL). The organic layer was washed with brine (25 mL), dried over anhydrous sodium sulfate and concentrated to afford a residue that was ~3:1 starting material:product. The crude residue from the reaction was resubjected to the reaction conditions. The crude material from the second exposure to the reaction conditions was purified by column chromatography on a 12 g ISCO silica gel cartridge, eluting with a 0-100% EtOAc/Hex gradient. The pure fractions were concentrated to afford methyl 5-(2-((tert-butoxycarbonyl) amino)-[1,2,4]triazolo[1,5-a]pyridin-7-yl)-2-methylnicotinate-d₃ (22 mg, 0.057 mmol, 14.34% yield) as a tan solid.

MS (ESI) m/z 387.2 (M+H)

96B: Methyl 5-(2-((tert-butoxycarbonyl)amino)-[1,2,4] triazolo[1,5-a]pyridin-7-yl)-2-methylnicotinate-d₃: Methyl 5-(2-((tert-butoxycarbonyl)amino)-[1,2,4]triazolo[1,5-a] pyridin-7-yl)-2-methylnicotinate-d₃ (22 mg, 0.057 mmol) was dissolved in TFA and the solution was allowed to stand at rt for 1 h. The TFA was removed in vacuo and the residue co-evaporated from EtOAc/Heptane. The residue was taken up in water and the pH adjusted to 9 with 1.5 M dibasic potassium phosphate solution. Filtration and drying afforded methyl 5-(2-((tert-butoxycarbonyl)amino)-[1,2,4]triazolo[1, 5-a]pyridin-7-yl)-2-methylnicotinate-d3 as a tan solid. The material was carried forward as is into subsequent chemistry.

MS (ESI) m/z 287.2 (M+H)

96C: 5-(2-Amino-[1,2,4]triazolo[1,5-a]pyridin-7-yl)-2-trideuteromethylnicotinic acid, lithium salt: A mixture of methyl 5-(2-amino-[1,2,4]triazolo[1,5-a]pyridin-7-yl)-2-trideuteromethylnicotinate (16 mg, 0.056 mmol) in THF (1 mL) was treated with a solution of LiOH, hydrate (3.05 mg, 0.073 mmol) in water (0.2 mL) at rt. The reaction mixture was allowed to stir at rt for 4 h. The solvent was removed and the residue dried to afford 5-(2-amino-[1,2,4]triazolo[1, 5-a]pyridin-7-yl)-2-trideuteromethylnicotinic acid, lithium salt (15 mg, 0.053 mmol, 95% yield) as a tan solid.

MS (ESI) m/z 273.2 (M+H)

96: A mixture of 5-(2-amino-[1,2,4]triazolo[1,5-a]pyridin-7-yl)-2-trideuteromethylnicotinic acid, lithium salt (15 mg, 0.053 mmol), (2-fluoro-5-(trifluoromethoxy)phenyl) methanamine (13.38 mg, 0.064 mmol), BOP (25.9 mg, 0.059 mmol) and Et₃N (0.022 mL, 0.160 mmol) in DMF (0.5 mL) was agitated at rt for 3 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 22-47% B over 20 min, then a 2-min hold at 100% B; Flow: 20 mL/min. Fractions containing the desired product were combined and dried via centrifugal evaporation to afford 5-(2-amino-[1,2, 4]triazolo[1,5-a]pyridin-7-yl)-N-(2-fluoro-5-(trifluoromethoxy)benzyl)-2-trideuteromethylnicotinamide (11.7 mg, 0.023 mmol, 44.0%).

¹H NMR (500 MHz, DMSO-d6) δ 9.15 (t, J=5.8 Hz, 1H), 8.96 (d, J=2.2 Hz, 1H), 8.64 (d, J=6.9 Hz, 1H), 8.18 (d, J=2.2 Hz, 1H), 7.79 (d, J=1.4 Hz, 1H), 7.45 (br d, J=5.0 Hz, 1H), 7.41-7.34 (m, 2H), 7.30 (dd, J=7.0, 1.8 Hz, 1H), 6.07 (s, 2H), 4.56 (d, J=5.8 Hz, 2H).

MS ESI m/z 464.3 (M+H)

Example 97

5-{2-amino-[1,2,4]triazolo[1,5-a]pyridin-7-yl}-N-{1-[2-fluoro-5-(trifluoromethoxy)phen yl]ethyl}-2-(deutero)methoxy-6-methylpyridine-3-carboxamide

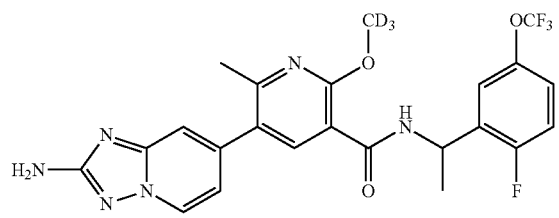 [SMILES: [2H]C([2H])([2H])Oc1nc(C)c(-c2ccn3nc(N)nc3c2)cc1C(=O)NC(C)c1cc(OC(F)(F)F)ccc1F]

97A: Methyl-d₃ 5-bromo-2-(methoxy-d₃)-6-methylnicotinate: To a rapidly stirring mixture of 5-bromo-2-hydroxy-6-methylnicotinic acid (1.20 g, 5.17 mmol) and iodomethane-d₃ (1.931 mL, 31.0 mmol) in chloroform (100 mL) was added silver carbonate (7.13 g, 25.9 mmol). The reaction mixture was stirred in the dark [aluminum foil wrap] for 4 d. The reaction mixture was filtered through Celite, then concentrated to an oil. This material was loaded onto a 40 g ISCO column and purified by flash chromatography, eluting with 0-75% EtOAc in hexanes. Afforded 97A (732 mg, 2.64 mmol, 51.1% yield) as a white solid.

MS (ESI) m/z 268.0 (M+H)

97B: Methyl-d₃ 5-(2-((tert-butoxycarbonyl)amino)-[1,2, 4]triazolo[1,5-a]pyridin-7-yl)-2-(methoxy-d₃)-6-methylnicotinate: In a sealed 40 mL tube, a mixture of 1A (475 mg, 1.149 mmol), bis(pinacolato)diboron (365 mg, 1.437 mmol), potassium acetate (338 mg, 3.45 mmol) and [1,1'-bis(diphenylphosphino)ferrocene]dichloropalladium(II) (42.1 mg, 0.057 mmol) in 1,4-dioxane (9 mL) was stirred at 100° C. After 45 minutes, the reaction was cooled to rt. 97A (299 mg, 1.124 mmol) and 1,1'-bis(di-tert-butylphosphino)ferrocene palladium dichloride (36.6 mg, 0.056 mmol) were added and the mixture degassed by nitrogen sparge for 5 min. 2 M K₃PO₄ (aq) (1.686 mL, 3.37 mmol) was added and the reaction mixture heated at 100° C. for 10 min. The reaction mixture was diluted to a total volume of 150 mL with EtOAc and washed with brine. After drying over anhydrous sodium sulfate, filtration and concentration in vacuo, the crude residue was loaded onto a 40 g ISCO column and purified by flash chromatography, eluting with 0-100% EtOAc in hexanes. Afforded ethyl-d₃ 5-(2-((tert-butoxycarbonyl)amino)-[1,2,4]triazolo[1,5-a]pyridin-7-yl)-2-(methoxy-d₃)-6-methylnicotinate (545 mg, 0.996 mmol, 89% yield) as a crystalline beige solid.

MS (ESI) m/z 520.5 (M+H)

97C: Methyl-d₃ 5-(2-amino-[1,2,4]triazolo[1,5-a]pyridin-7-yl)-2-(methoxy-d₃)-6-methylnicotinate: A mixture of 97B (545 mg, 1.049 mmol) in TFA (5 mL) was stirred at rt for 45 min. The reaction mixture was concentrated to a solid. The residue was slurried in aqueous saturated sodium bicarbonate, then extracted with EtOAc (4×). The combined organics were washed with brine and dried over anhydrous sodium sulfate. The slurry was filtered and concentrated to afford methyl-d₃ 5-(2-amino-[1,2,4]triazolo[1,5-a]pyridin-7-yl)-2-(methoxy-d₃)-6-methylnicotinate (359 mg, 1.012 mmol, 96% yield) as a free base.

MS (ESI) m/z 320.2 (M+H)

97D: 5-(2-Amino-[1,2,4]triazolo[1,5-a]pyridin-7-yl)-2-(methoxy-d₃)-6-methylnicotinic acid: To a mixture of methyl-d₃ 5-(2-amino-[1,2,4]triazolo[1,5-a]pyridin-7-yl)-2-(methoxy-d3)-6-methylnicotinate (359 mg, 1.124 mmol) in tetrahydrofuran (11 mL) was added a solution of lithium hydroxide monohydrate (56.6 mg, 1.349 mmol) in water (1.5 mL). The reaction mixture was stirred ON at rt. Additional lithium hydroxide monohydrate (18 mg) was added and stirring continued 4 h. The reaction mixture was concentrated to a solid and used as is in subsequent chemistry. Afforded 5-(2-amino-[1,2,4]triazolo[1,5-a]pyridin-7-yl)-2-(methoxy-d₃)-6-methylnicotinic acid, lithium salt (333 mg, 0.991 mmol, 88% yield) as a tan solid.

MS (ESI) m/z 303.1

97: A mixture of 5-(2-amino-[1,2,4]triazolo[1,5-a]pyridin-7-yl)-2-(methoxy-d₃)-6-methylnicotinic acid, lithium salt (35 mg, 0.116 mmol) and BOP (77 mg, 0.174 mmol), 1-(2-fluoro-5-(trifluoromethoxy)phenyl)ethanamine (25.8 mg, 0.116 mmol) and Hünig's Base (0.101 mL, 0.579 mmol) in DMF (1.0 mL) was stirred at rt ON. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 20 min, then a 4-min hold at 100% B; Flow: 20 mL/min. Fractions containing the desired product were combined and dried via centrifugal evaporation to afford the racemate 5-(2-amino-[1,2,4]triazolo[1,5-a]pyridin-7-yl)-N-(1-(2-fluoro-5-(trifluoromethoxy)phenyl)ethyl)-2-(methoxy-d₃)-6-methylnicotinamide (13.8 mg, 0.027 mmol, 23.25% yield).

Subsequent chiral separation afforded the first eluting enantiomer, 97-1 (5.6 mg, 10.93 µmol, 9.44% yield) and the second eluting enantiomer, 97-2 (5.4 mg, 10.53 µmol, 9.10% yield).

First eluting isomer: ¹H NMR (500 MHz, DMSO-d6) δ 8.76 (d, J=7.6 Hz, 1H), 8.55 (d, J=6.7 Hz, 1H), 7.86 (s, 1H), 7.49 (br d, J=4.0 Hz, 1H), 7.40-7.25 (m, 3H), 6.91 (dd, J=6.9, 1.7 Hz, 1H), 6.01 (s, 2H), 5.32 (quin, J=7.1 Hz, 1H), 2.48-2.43 (m, 3H), 1.46 (d, J=7.0 Hz, 3H).

Second eluting isomer: 1H NMR (500 MHz, DMSO-d6) 8.76 (d, J=7.6 Hz, 1H), 8.55 (d, J=6.7 Hz, 1H), 7.86 (s, 1H), 7.49 (br d, J=4.0 Hz, 1H), 7.40-7.25 (m, 3H), 6.91 (dd, J=6.9, 1.7 Hz, 1H), 6.01 (s, 2H), 5.32 (quin, J=7.1 Hz, 1H), 2.48-2.43 (m, 3H), 1.46 (d, J=7.0 Hz, 3H).

MS ESI m/z 508.1 (M+H)

Example 98

5-{2-amino-[1,2,4]triazolo[1,5-a]pyridin-7-yl}-2-(deutero)methoxy-6-methyl-N-{1-[2-(trifluoromethoxy)phenyl]ethyl}pyridine-3-carboxamide

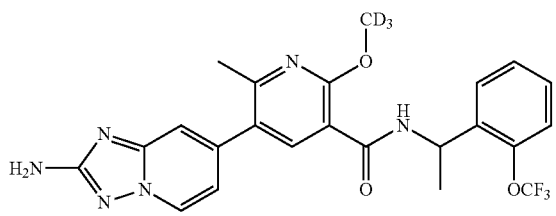 [SMILES: [2H]C([2H])([2H])Oc1nc(C)c(-c2ccn3nc(N)nc3c2)cc1C(=O)NC(C)c1ccccc1OC(F)(F)F]

A mixture of 5-(2-amino-[1,2,4]triazolo[1,5-a]pyridin-7-yl)-2-(methoxy-d3)-6-methylnicotinic acid (35 mg, 0.116 mmol) and BOP (77 mg, 0.174 mmol), 1-(2-(trifluoromethoxy)phenyl)ethanamine (30.9 mg, 0.151 mmol) and Hünig's Base (0.101 mL, 0.579 mmol) in DMF (1.0 mL) was stirred at rt ON. The crude material was purified via preparative LC/MS with the following conditions: Column: XBridge C18, 19×200 mm, 5-Âµm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford the racemate 5-(2-amino-[1,2,4]triazolo[1,5-a]pyridin-7-yl)-2-(methoxy-d3)-6-methyl-N-(1-(2-(trifluoromethoxy)phenyl)ethyl)nicotinamide (15.8 mg, 0.032 mmol, 27.6% yield).

Subsequent chiral separation afforded first eluting enantiomer, 98-1 (5.2 mg, 10.52 µmol, 9.08% yield) and second eluting enantiomer, 98-2 (5.3 mg, 10.61 µmol, 9.17% yield).

First Eluting Isomer: ¹H NMR (500 MHz, DMSO-d6) δ 8.64 (br d, J=7.6 Hz, 1H), 8.58 (d, J=6.7 Hz, 1H), 7.93 (s, 1H), 7.72-7.55 (m, 1H), 7.45-7.31 (m, 4H), 6.90 (dd, J=6.7, 1.5 Hz, 1H), 6.04 (s, 2H), 5.40 (quin, J=7.0 Hz, 1H), 2.47 (s, 3H), 1.46 (d, J=6.7 Hz, 3H).

Second Eluting Isomer: ¹H NMR (500 MHz, DMSO-d6) δ 8.64 (br d, J=7.6 Hz, 1H), 8.58 (d, J=6.7 Hz, 1H), 7.93 (s, 1H), 7.72-7.55 (m, 1H), 7.45-7.31 (m, 4H), 6.90 (dd, J=6.7, 1.5 Hz, 1H), 6.04 (s, 2H), 5.40 (quin, J=7.0 Hz, 1H), 2.47 (s, 3H), 1.46 (d, J=6.7 Hz, 3H).

MS ESI m/z 490.2 (M+H)

Example 99

5-{2-amino-[1,2,4]triazolo[1,5-a]pyridin-7-yl}-N-{1-[2-fluoro-5-(trifluoromethyl)phenyl] ethyl}-2-methylpyridine-3-carboxamide

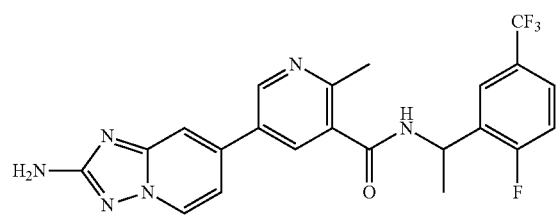 [SMILES: Cc1ncc(-c2ccn3nc(N)nc3c2)cc1C(=O)NC(C)c1cc(C(F)(F)F)ccc1F]

99A: 1-(2-Fluoro-5-(trifluoromethyl)phenyl)ethanamine: A solution of 1-(2-fluoro-5-(trifluoromethyl)phenyl)ethanone (805 mg, 3.91 mmol), ammonium acetate (3010 mg, 39.1 mmol) and sodium cyanoborohydride (294 mg, 4.69 mmol) in ethanol (18 mL) was stirred at rt for 3 d. 0 The reaction mixture was concentrated to a thick oily residue. The residue was partitioned between EtOAc (50 mL) and saturated sodium bicarbonate solution 40 (mL).

The organic layer was washed with water (15 mL) and brine (15 mL). After drying over anhydrous sodium sulfate and filtration, the organic layer was concentrated to afford 1-(2-fluoro-5-(trifluoromethyl)phenyl)ethanamine (777 mg, 3.19 mmol, 82% yield) as an amber oil. The crude product was used as is in subsequent chemistry.

99: A mixture of 82B (32 mg, 0.119 mmol), BOP (79 mg, 0.178 mmol), 1-(2-fluoro-5-(trifluoromethyl)phenyl) ethanamine (24.62 mg, 0.119 mmol) and Hünig's Base (0.104 mL, 0.594 mmol) in DMF (1.0 mL) was stirred at rt ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-min hold at 100% B; Flow: 20 mL/min. Fractions containing the desired product were combined and dried via centrifugal evaporation to afford the racemate 5-(2-amino-[1,2,4]triazolo[1,5-a]pyridin-7-yl)-N-(1-(2-fluoro-5-(trifluoromethyl)phenyl)ethyl)-2-methylnicotinamide (19.9 mg, 0.043 mmol, 36.2% yield). Subsequent chiral separation afforded first eluting enantiomer, 99-1 (7.7 mg, 0.017 mmol, 13.99% yield) and second eluting enantiomer, 99-2 (7.6 mg, 0.017 mmol, 13.95% yield).

$^1$H NMR (500 MHz, DMSO-d6) δ 9.16 (br d, J=7.3 Hz, 1H), 8.97 (d, J=1.8 Hz, 1H), 8.65 (d, J=7.0 Hz, 1H), 8.17 (s, 1H), 7.87 (br d, J=5.2 Hz, 1H), 7.81 (s, 1H), 7.74 (br s, 1H), 7.48 (t, J=9.2 Hz, 1H), 7.32 (br d, J=5.5 Hz, 1H), 6.08 (s, 2H), 5.41 (quin, J=7.0 Hz, 1H), 2.49 (s, 3H), 1.51 (d, J=7.0 Hz, 3H).

MS ESI m/z 459.1 (M+H)

TABLE 1

Compounds in Table 1 were prepared in a similar fashion to examples 81 and 84.

| Ex No | Name | R | M + H | 1H NNMR 9500 MHz, DMSO-d6) δ |
|---|---|---|---|---|
| 100 | 5-{2-amino-[1,2,4]triazolo[1,5-a]pyridin-7-yl}-2-methoxy-N-[(1S,2R)-2-phenylcyclopropyl]pyridine-3-carboxamide | (2-phenylcyclopropyl)amino | 401.3 | 8.74 (d, J = 2.4 Hz, 1H), 8.62 – 8.54 (m, 2H), 8.35 (d, J = 2.4 Hz, 1H), 7.71 (s, 1H), 7.32 – 7.22 (m, 3H), 7.21 – 7.13 (m, 3H), 6.05 (s, 2H), 4.00 (s, 3H), 3.05 (dq, J = 7.9, 4.1 Hz, 1H), 2.12 (ddd, J = 9.3, 6.1, 3.5 Hz, 1H), 1.38 – 1.31 (m, 1H), 1.28 – 1.22 (m, 1H). |
| 101 | 5-{2-amino-[1,2,4]triazolo[1,5-a]pyridin-7-yl}-2-methoxy-N-(4-phenylbutan-2-yl)pyridine-3-carboxamide | (4-phenylbutan-2-yl)amino | 417.2 | δ 8.72 (d, J = 2.2 Hz, 1H), 8.58 (d, J = 7.0 Hz, 1H), 8.31 (d, J = 2.3 Hz, 1H), 8.18 (br d, J = 8.2 Hz, 1H), 7.71 (s, 1H), 7.32 – 7.19 (m, 5H), 7.18 – 7.11 (m, 1H), 6.05 (s, 2H), 4.00 (s, 3H), 3.98 (br s, 1H), 2.74 – 2.57 (m, 2H), 1.89 – 1.71 (m, 2H), 1.18 (d, J = 6.6 Hz, 3H). |
| 102 | 5-{2-amino-[1,2,4]triazolo[1,5-a]pyridin-7-yl}-2-methoxy-N-(3-phenylpropyl)pyridine-3-carboxamide | (3-phenylpropyl)amino | 403.2 | 8.75 (d, J = 2.4 Hz, 1H), 8.62 (d, J = 7.0 Hz, 1H), 8.43 – 8.36 (m, 2H), 7.73 (s, 1H), 7.31 – 7.24 (m, 4H), 7.20 – 7.14 (m, 1H), 4.01 (s, 3H), 3.31 (q, J = 6.6 Hz, 1H), 2.65 (br t, J = 7.6 Hz, 2H), 1.84 (quin, J = 7.3 Hz, 2H) Note: ATP NH2 not visible in spectrum |
| 103 | 2-{[(5-{2-amino-[1,2,4]triazolo[1,5-a]pyridin-7-yl}-2-methoxypyridin-3-yl)formamido]methyl}-5-fluorophenyl N,N-dimethylcarbamate | 2-(N,N-dimethylcarbamoyloxy)-4-fluorobenzylamino | 480.0 | 8.74 (s, 2H), 8.57 (d, J = 7.0 Hz, 1H), 8.42 (d, J = 2.1 Hz, 1H), 7.68 (s, 1H), 7.43 (br t, J = 7.3 Hz, 1H), 7.24 (br d, J = 6.7 Hz, 1H), 7.12 – 7.03 (m, 2H), 6.02 (s, 2H), 4.44 (br d, J = 5.5 Hz, 2H), 4.01 (s, 3H), 3.06 (s, 3H), 2.88 (s, 3H) |

TABLE 1-continued

Compounds in Table 1 were prepared in a similar fashion to examples 81 and 84.

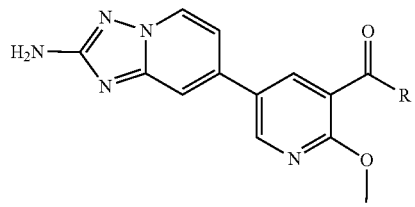

| Ex No | Name | R | M + H | 1H NNMR 9500 MHz, DMSO-d6) δ |
|---|---|---|---|---|
| 104 | 5-{2-amino-[1,2,4]triazolo[1,5-a]pyridin-7-yl}-2-methoxy-N-{[2-(propane-2-sulfonyl)phenyl]methyl}pyridine-3-carboxamide | | 481.0 | 9.12 (br t, J = 5.9 Hz, 1H), 8.77 (d, J = 2.1 Hz, 1H), 8.58 (d, J = 7.0 Hz, 1H), 8.49 (d, J = 2.2 Hz, 1H), 7.87 (br d, J = 7.8 Hz, 1H), 7.77 – 7.71 (m, 1H), 7.71 – 7.64 (m, 2H), 7.56 (br t, J = 7.5 Hz, 1H), 7.24 (br d, J = 6.0 Hz, 1H), 6.05 (s, 2H), 4.86 (brd, J = 5.9 Hz, 2H), 4.06 (s, 3H), 3.74 – 3.61 (m, 1H), 1.22 (br d, J = 6.7 Hz, 6H) |
| 105 | 5-{2-amino-[1,2,4]triazolo[1,5-a]pyridin-7-yl}-2-methoxy-N-({2-[(morpholin-4-yl)methyl]phenyl}methyl)pyridine-3-carboxamide | | 474.3 | 8.80 – 8.74 (m, 2H), 8.59 (d, J = 7.0 Hz, 1H), 8.41 (d, J =2.6 Hz, 1H), 7.71 (s, 1H), 7.40 (d, J = 7.3 Hz, 1H), 7.31 – 7.19 (m, 4H), 6.03 (s, 2H), 4.67 (d, J = 5.9 Hz, 2H), 4.02 (s, 3H), 3.55 (s, 2H), 3.50 (br s, 2H), 2.37 (br s, 4H) Note: One set of morpholine CH2 presumably lost in water suppression. |
| 106 | 5-{2-amino-[1,2,4]triazolo[1,5-a]pyridin-7-yl}-N-({[1,1'-biphenyl]-2-yl}methyl)-2-methoxypyridine-3-carboxamide | | 451.1 | 8.75 (d, J = 2.6 Hz, 1H), 8.68 (t, J = 5.9 Hz, 1H), 8.59 (d, J = 7.0 Hz, 1H), 8.36 (d, J = 2.6 Hz, 1H), 7.69 (d, J = 1.1 Hz, 1H), 7.53 – 7.46 (m, 3H), 7.45 – 7.32 (m, 5H), 7.24 (td, J = 7.3, 1.5 Hz, 2H), 6.03 (s, 2H), 4.48 (d, J = 5.9 Hz, 2H), 4.01 (s, 3H). |
| 107 | 5-{2-amino-[1,2,4]triazolo[1,5-a]pyridin-7-yl}-N-[1-(diphenylmethyl)-1H-pyrazol-4-yl]-2-methoxypyridine-3-carboxamide | | 517.1 | δ 10.36 (s, 1H), 8.77 (d, J = 2.6 Hz, 1H), 8.59 (d, J = 7.0 Hz, 1H), 8.42 (d, J = 2.6 Hz, 1H), 8.02 (s, 1H), 7.73 (d, J = 0.7 Hz, 1H), 7.70 (s, 1H), 7.42 – 7.36 (m, 4H), 7.36 – 7.30 (m, 2H), 7.26 (dd, J = 7.2, 2.0 Hz, 1H), 7.18 (d, J = 7.3 Hz, 4H), 6.92 (s, 1H), 6.02 (s, 2H), 4.02 (s, 3H). |

TABLE 1-continued

Compounds in Table 1 were prepared in a similar fashion to examples 81 and 84.

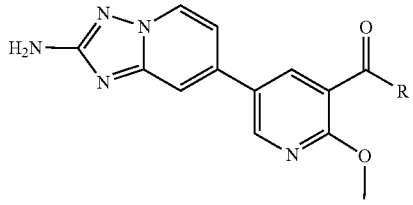

| Ex No | Name | R | M + H | 1H NNMR 9500 MHz, DMSO-d6) δ |
|---|---|---|---|---|
| 108 | 5-{2-amino-[1,2,4]triazolo[1,5-a]pyridin-7-yl}-2-methoxy-N-{[2-(4-methylpiperidin-1-yl)phenyl]methyl}pyridine-3-carboxamide | 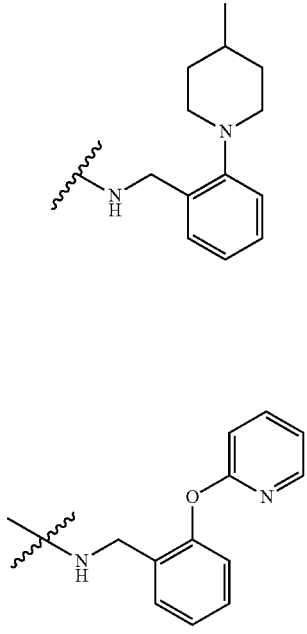 | 472.0 | 8.77 (d, J = 2.6 Hz, 1H), 8.73 (t, J = 5.7 Hz, 1H), 8.60 (d, J = 7.0 Hz, 1H), 8.45 (d, J = 2.6 Hz, 1H), 7.71 (d, J = 1.1 Hz, 1H), 7.33 (d, J = 7.7 Hz, 1H), 7.27 – 7.19 (m, 2H), 7.13 (d, J = 7.3 Hz, 1H), 7.09 – 7.02 (m, 1H), 6.03 (s, 2H), 4.59 (d, J = 5.9 Hz, 2H), 4.03 (s, 3H), 3.02 (br d, J = 11.7 Hz, 2H), 2.71 – 2.61 (m, 2H), 1.73 (br dd, J = 11.9, 2.0 Hz, 2H), 1.56 – 1.45 (m, 1H), 1.41 – 1.28 (m, 2H), 0.97 (d, J = 6.2 Hz, 3H). |
| 109 | 5-{2-amino-[1,2,4]triazolo[1,5-a]pyridin-7-yl}-2-methoxy-N-{[2-(pyridin-2-yloxy)phenyl]methyl{pyridine-3-carboxamide | 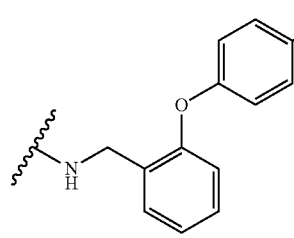 | 468.1 | 8.75 (d, J = 2.6 Hz, 1H), 8.69 (t, J = 5.9 Hz, 1H), 8.59 (d, J = 7.0 Hz, 1H), 8.38 (d, J = 2.6 Hz, 1H), 8.12 – 8.09 (m, 1H), 7.87 – 7.82 (m, 1H), 7.69 (s, 1H), 7.46 (d, J = 7.7 Hz, 1H), 7.36 – 7.30 (m, 1H), 7.27 – 7.20 (m, 2H), 7.11 – 7.04 (m, 3H), 6.03 (s, 2H), 4.45 (d, J = 5.9 Hz, 2H), 3.99 (s, 3H). |
| 110 | 5-{2-amino-[1,2,4]triazolo[1,5-a]pyridin-7-yl}-N-{[2-(4-fluorophenoxy)phenyl]methyl}-2-methoxypyridine-3-carboxamide | 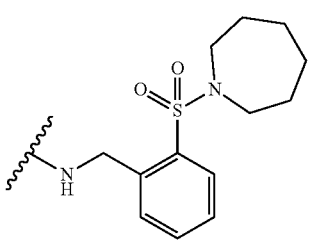 [SMILES: *NCc1ccccc1S(=O)(=O)N1CCCCCC1] | 485.1 | 8.78 (t, J = 6.1 Hz, 1H), 8.75 (d, J = 2.6 Hz, 1H), 8.59 (d, J = 7.0 Hz, 1H), 8.41 (d, J = 2.6 Hz, 1H), 7.69 (d, J = 0.7 Hz, 1H), 7.46 (d, J = 7.3 Hz, 1H), 7.31 – 7.25 (m, 1H), 7.24 – 7.13 (m, 4H), 7.07 – 7.01 (m, 2H), 6.86 (d, J = 8.1 Hz, 1H), 6.02 (s, 2H), 4.56 (d, J = 5.9 Hz, 2H), 3.99 (s, 3H). |
| 111 | 5-{2-amino-[1,2,4]triazolo[1,5-a]pyridin-7-yl}-N-{[2-(azepane-1-sulfonyl)phenyl]methyl}-2-methoxypyridine-3-carboxamide | | 536.1 | 9.01 (t, J = 6,1 Hz, 1H), 8.79 (d, J = 2.6 Hz, 1H), 8.59 (d, J = 7.0 Hz, 1H), 8.52 (d, J = 2.6 Hz, 1H), 7.76 (d, J = 8.1 Hz, 1H), 7.72 (s, 1H), 7.68 – 7.59 (m, 2H), 7.51 – 7.46 (m, 1H), 7.25 (dd, J = 6.8, 2.0 Hz, 1H), 6.03 (s, 2H), 4.87 (d, J = 6.2 Hz, 2H), 4.07 (s, 3H), 1.70 (br s, 4H), 1.60 (br d, J = 2.9 Hz, 4H) Note: 2 CH2s under water suppression and not included. |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 112 | 5-{2-amino-[1,2,4]triazolo[1,5-a]pyridin-7-yl}-N-{[(1S,2S)-2-(4-fluorophenyl)cyclopropyl]methyl}-2-methoxypyridine-3-carboxamide | | 433.3 | 8.75 (d, J = 2.4 Hz, 1H), 8.59 (d, J = 7.0 Hz, 1H), 8.54 (br t, J = 5.6 Hz, 1H), 8.41 (d, J = 2.4 Hz, 1H), 7.70 (s, 1H), 7.23 (dd, J = 7.0, 1.8 Hz, 1H), 7.16 – 7.09 (m, 2H), 7.09 – 7.01 (m, 2H), 6.06 (s, 2H), 4.00 (s, 3H), 3.42 (br d, J = 11.4 Hz, 1H), 3.36-3.24 (m, 1H), 1.98 – 1.90 (m, 1H), 1.37 – 1.28 (m, 1H), 1.01 – 0.94 (m, 1H), 0.94 – 0.88 (m, 1H). |
| 113 | 5-{2-amino-[1,2,4]triazolo[1,5-a]pyridin-7-yl}-2-methoxy-N-(2-methyl-3-phenylpropyl)pyridine-3-carboxamide | | 417.3 | 8.74 (d, J = 2.4 Hz, 1H), 8.59 (d, J = 7.0 Hz, 1H), 8.41 – 8.33 (m, 2H), 7.71 (s, 1H), 7.32 – 7.26 (m, 2H), 7.24 (dd, J = 7.0, 1.6 Hz, 1H), 7.22 – 7.16 (m, 3H), 6.06 (s, 2H), 4.01 (s, 3H), 3.32 – 3.23 (m, 1H), 3.17 (dt, J = 13.1, 6.6 Hz, 1H), 2.74 (dd, J = 13.3, 5.8 Hz, 1H), 2.39 (dd, J = 13.3, 8.5 Hz, 1H), 2.03 (dq, J = 13.6, 6.9 Hz, 1H), 0.86 (d, J = 6.7 Hz, 3H). |
| 114 | 7-{5-[(3S)-3-[(3-fluorophenyl)methyl]piperidine-1-carbonyl]-6-methoxypyridin-3-yl}-[1,2,4]triazolo[1,5-a]pyridin-2-amine | | 461.2 | 8.75 – 8.52 (m, 2H), 8.20 – 7.97 (m, 1H), 7.76 – 7.61 (m, 1H), 7.34 – 7.19 (m, 2H), 7.17 – 6.89 (m, 2H), 6.74 – 6.60 (m, 1H), 6.13 – 6.00 (m, 2H), 4.47 – 4.11 (m, 1H), 4.01 – 3.79 (m, 3H), 3.33 – 2.90 (m, 2H), 2.88 – 2.57 (m, 2H), 2.37 – 2.15 (m, 1H), 1.83 – 1.67 (m, 2H), 1.62 – 1.48 (m, 1H), 1.45 – 1.32 (m, 1H), and 1.30 – 1.17 (m, 1H). |
| 115 | 5-{2-amino-[1,2,4]triazolo[1,5-a]pyridin-7-yl}-2-methoxy-N-{[2-(oxan-4-yloxy)phenyl]methyl}pyridine-3-carboxamide | | 475.3 | 8.77 (s, 1H), 8.70 – 8.63 (m, 1H), 8.59 (d, J = 7.0 Hz, 1H), 8.47 (s, 1H), 7.71 (s, 1H), 7.30 (d, J = 7.0 Hz, 1H), 7.26 – 7.19 (m, 2H), 7.07 (d, J = 8.2 Hz, 1H), 6.92 (t, J = 7.3 Hz, 1H), 6.04 (s, 2H), 4.67 (br. s., 1H), 4.52 (d, J = 5.8 Hz, 2H), 4.05 (s, 3H), 3.93 – 3.80 (m, 2H), 3.53 (t, J = 8.7 Hz, 2H), 1.99 (d, J = 11.0 Hz, 2H), 1.71 – 1.61 (m, 2H). |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 116 | 5-{2-amino-[1,2,4]triazolo[1,5-a]pyridin-7-yl[2-fluoro-5-(trifluoromethyl)phenyl]methyl}-2-methoxy pyridine-3-carboxamide | 2-fluoro-5-(trifluoromethyl)benzyl amino | 461.2 | 9.01 (t, J = 6.0 Hz, 1H), 8.79 (d, J = 2.6 Hz, 1H), 8.60 (dd, J = 7.0, 0.6 Hz, 1H), 8.41 (d, J = 2.6 Hz, 1H), 7.83 (d, J = 6.6 Hz, 1H), 7.78 – 7.69 (m, 2H), 7.47 (t, J = 9.2 Hz, 1H), 7.25 (dd, J = 7.0, 2.0 Hz, 1H), 6.05 (s, 2H), 4.62 (d, J = 5.9 Hz, 2H), 4.04 (s, 3H). |
| 117 | 7-(5-{3-[(4-chlorophenyl)methyl]piperidine-1-carbonyl}-6-methoxypyridin-3-yl)-[1,2,4]triazolo[1,5-a]pyridin-2-amine | 3-[(4-chlorophenyl)methyl]piperidin-1-yl | 477.3 | 8.73 – 8.53 (m, 2H), 8.17 – 7.95 (m, 1H), 7.74 – 7.61 (m, 1H), 7.40 – 7.32 (m, 2H), 7.31 – 7.11 (m, 3H), 7.07 – 6.85 (m, 2H), 4.47 – 4.09 (m, 1H), 4.01 – 3.79 (m, 3H), 3.32 (s, 2H), 2.89 – 2.59 (m, 2H), 2.43 – 2.13 (m, 1H), 1.82 – 1.66 (m, 2H), 1.64 – 1.46 (m, 1H), 1.45 – 1.31 (m, 1H), and 1.29 – 1.16 (m, 1H). |
| 118 | 7-(5-{3-[(3-fluorophenyl)methyl]piperidine-1-carbonyl}-6-methoxypyridin-3-yl)-[1,2,4]triazolo[1,5-a]pyridin-2-amine | 3-[(3-fluorophenyl)methyl]piperidin-1-yl | 461.3 | 8.76 – 8.54 (m, 2H), 8.19 – 7.99 (m, 1H), 7.77 – 7.63 (m, 1H), 7.33 – 7.18 (m, 2H), 7.16 – 6.91 (m, 3H), 6.75 – 6.65 (m, 1H), 6.09 – 5.96 (m, 1H), 4.50 – 4.12 (m, 1H), 4.01 – 3.78 (m, 3H), 3.31 – 2.91 (m, 2H), 2.89 – 2.57 (m, 2H), 2.40 – 2.13 (m, 1H), 1.79 – 1.68 (m, 2H), 1.62 – 1.45 (m, 1H), 1.43 – 1.31 (m, 1H), and 1.29 – 1.16 (m, 1H). |
| 119 | 5-{2-amino-[1,2,4]triazolo[1,5-a]pyridin-7-yl}-2-methoxy-N-{[3-(trifluoromethyl)phenyl]methyl}pyridine-3-carboxamide | 3-(trifluoromethyl)benzyl amino | 443.2 | 9.05 (t, J = 6.6 Hz, 1H), 8.76 (s, 1H), 8.59 (br d, J = 7.0 Hz, 1H), 8.43 (s, 1H), 7.75 – 7.66 (m, 3H), 7.64 – 7.57 (m, 2H), 7.26 (br d, J = 6.7 Hz, 1H), 6.03 (s, 2H), 4.62 (br d, J = 5.8 Hz, 2H), 4.04 (s, 3H). |
| 120 | 7-(6-methoxy-5-{3-[(4-methoxyphenyl)methyl]piperidine-1-carbonyl}pyridin-3-yl)-[1,2,4]triazolo[1,5-a]pyridin-2-amine | 3-[(4-methoxyphenyl)methyl]piperidin-1-yl | 473.4 | 8.73 – 8.54 (m, 2H), 8.19 – 8.01 (m, 1H), 7.76 – 7.63 (m, 1H), 7.30 – 7.10 (m, 2H), 6.96 – 6.79 (m, 2H), 6.74 – 6.65 (m, 1H), 6.47 (br d, J = 6.7 Hz, |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| | | | | 1H), 5.98 (s, 2H), 4.50 – 4.16 (m, 1H), 4.01 – 3.81 (m, 3H), 3.43 (br d, J = 6.1 Hz, 3H), 3.30 – 3.06 (m, 1H), 3.05 – 2.78 (m, 1H), 2.77 – 2.60 (m, 1H), 2.46 – 2.35 (m, 1H), 2.30 – 2.11 (m, 1H), 1.79 – 1.68 (m, 2H), 1.63 – 1.47 (m, 1H), 1.45 – 1.31 (m, 1H), 1.29 – 1.14 (m, 1H). |
| 121 | 7-(6-methoxy-5-{3-[(4-methylphenyl)methyl] piperidine-1-carbonyl} pyridin-3-yl)-[1,2,4] triazolo[1,5-a]pyridin-2-amine | | 457.1 | 8.72 – 8.52 (m, 2H), 8.15 – 7.96 (m, 1H), 7.74 – 7.60 (m, 1H), 7.29 – 7.17 (m, 1H), 7.11 (br s, 2H), 6.96 – 6.82 (m, 1H), 6.80 – 6.58 (m, 1H), 6.11 – 5.95 (m, 2H), 4.47 – 4.15 (m, 1H), 4.00 – 3.79 (m, 3H), 3.30 – 3.10 (m, 1H), 3.08 – 2.79 (m, 1H), 2.78 – 2.56 (m, 1H), 2.33 – 2.10 (m, 3H), 1.73 (br d, J = 7.3 Hz, 2H), 1.62 – 1.46 (m, 1H), 1.44 – 1.30 (m, 1H), and 1.29 – 1.15 (m, 1H). |
| 122 | 5-{2-amino-[1,2,4] triazolo[1,5-a]pyridin-7-yl}-N-{[2-(cyclopentylmethoxy)-4,6-difluorophenyl]methyl}-2-methoxypyridine-3-carboxamide | | 509.3 | 8.76 – 8.73 (m, 1H), 8.58 (br d, J = 7.0 Hz, 1H), 8.45 (d, J = 2.1 Hz, 1H), 8.41 (d, J = 2.4 Hz, 1H), 8.38 – 8.35 (m, 1H), 7.70 – 7.66 (m, 1H), 7.29 – 7.21 (m, 1H), 6.85 – 6.76 (m, 2H), 6.03 (s, 2H), 4.51 (br d, J = 4.9 Hz, 1H), 4.45 (br d, J = 5.5 Hz, 1H), 4.04 – 3.98 (m, 3H), 2.37 – 2.31 (m, 1H), 1.78 (br d, J = 6.7 Hz, 2H), 1.58 (br d, J = 6.4 Hz, 3H), 1.52 (br d, J = 7.0 Hz, 2H), 1.36 (br dd, J = 12.8, 6.4 Hz, 2H). Rotomers are evident. |
| 123 | 5-{2-amino-[1,2,4] triazolo[1,5-a]pyridin-7-yl}-N-{[2-(cyclohexylmethoxy)phenyl] methyl}-2-methoxypyridine-3-carboxamide | | 487.0 | 8.76 (brs, 1H), 8.69 (br s, 1H), 8.59 (br d, J = 6.6 Hz, 1H), 8.47 (s, 1H), 7.70 (br s, 1H), 7.30 – 7.20 (m, 3H), 6.97 (d, J = 8.0 Hz, 1H), 6.91 (t, J = 7.6 Hz, 1H), 6.06 (br s, 2H), 4.50 (br d, J = 5.6 Hz, 2H), 4.04 (s, 3H), 3.90 – 3.74 (m, 2H), 1.83 (br d, J = 11.9 Hz, 2H), 1.77 (br s, |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| | | | | 1H), 1.74 – 1.61 (m, 3H), 1.29 – 1.19 (m, 2H), 1.19 – 1.05 (m, 3H). |
| 124 | 5-{2-amino-[1,2,4]triazolo[1,5-a]pyridin-7-yl}-N-{[3-(cyclopentylmethoxy)pyridin-2-yl]methyl}-2-methoxypyridine-3-carboxamide | 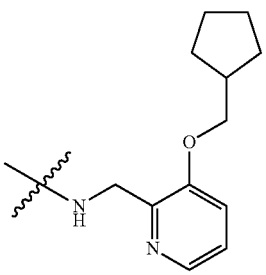 [SMILES: *NCc1ncccc1OCC1CCCC1] | 474.0 | 9.27 (brs, 1H), 8.80 (s, 1H), 8.61 (br s, 2H), 8.16 (br d, J = 4.5 Hz, 1H), 7.70 (s, 1H), 7.45 (br d, J = 8.2 Hz, 1H), 7.32 (dd, J = 8.2, 4.7 Hz, 1H), 7.25 (br d, J = 6.8 Hz, 1H), 6.07 (br s, 2H), 4.63 (br d, J = 4.5 Hz, 2H), 4.12 (s, 3H), 3.96 (br d, J = 6.7 Hz, 2H), 2.48 – 2.31 (m, 1H), 1.80 (br d, J = 7.3 Hz, 2H), 1.66 – 1.48 (m, 4H), 1.38 (br dd, J = 12.4, 6.3 Hz, 2H) |
| 125 | 5-{2-amino-[1,2,4]triazolo[1,5-a]pyridin-7-yl}-N-{[2-(1-cyclopentylethoxy)phenyl]methyl}-2-methoxypyridine-3-carboxamide | | 487.0 | 8.77 (s, 1H), 8.65 (brs, 1H), 8.60 (br d, J = 6.9 Hz, 1H), 8.48 (d, J = 2.0 Hz, 1H), 7.71 (s, 1H), 7.31 – 7.18 (m, 3H), 7.00 (d, J = 8.2 Hz, 1H), 6.89 (t, J = 7.4 Hz, 1H), 6.07 (br s, 2H), 4.56 – 4.41 (m, 2H), 4.37 (br t, J = 6.1 Hz, 1H), 4.04 (s, 3H), 2.29-2.10 (m, 1H), 1.80 (br s, 1H), 1.71 (br d, J = 7.1 Hz, 1H), 1.59 (br s, 2H), 1.56 – 1.48 (m, 2H), 1.48 – 1.36 (m, 1H), 1.31 (br d, J = 7.7 Hz, 1H), 1.28 – 1.19 (m, 3H). |
| 126 | 5-{2-amino-[1,2,4]triazolo[1,5-a]pyridin-7-yl}-N-{[2-(cyclopentylmethoxy)-6-fluorophenyl]methyl}-2-methoxypyridine-3-carboxamide | 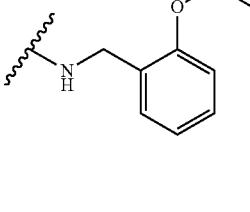 | 491.0 | 8.82 – 8.67 (m, 1H), 8.59 (br d, J = 6.9 Hz, 1H), 8.48 – 8.36 (m, 2H), 7.75 – 7.61 (m, 1H), 7.35 – 7.21 (m, 2H), 6.89 (d, J = 8.4 Hz, 1H), 6.80 (t, J = 8.8 Hz, 1H), 6.06 (br s, 2H), 4.57 (br d, J = 5.1 Hz, 2H), 4.00 (s, 2H), 3.98 – 3.88 (m, 2H), 3.17 (d, J = 5.2 Hz, 1H), 2.48 – 2.31 (m, 1H), 1.79 (br d, J = 6.6 Hz, 2H), 1.64 – 1.46 (m, 4H), 1.36 (br dd, J = 12.3, 6.4 Hz, 2H). |

TABLE 1-continued

Compounds in Table 1 were prepared in a similar fashion to examples 81 and 84.

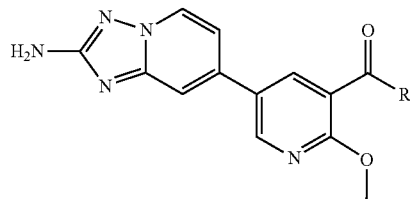

| Ex No | Name | R | M + H | 1H NNMR 9500 MHz, DMSO-d6) δ |
|---|---|---|---|---|
| 127 | 5-{2-amino-[1,2,4]triazolo[1,5-a]pyridin-7-yl}-N-{[2-(cyclopentylmethoxy)pyridin-3-yl]methyl}-2-methoxypyridine-3-carboxamide | | 474.1 | 8.81 – 8.73 (m, 2H), 8.60 (d, J = 7.0 Hz, 1H), 8.46 (d, J = 2.1 Hz, 1H), 8.04 (d, J = 3.7 Hz, 1H), 7.71 (s, 1H), 7.62 (d, J = 7.0 Hz, 1H), 7.24 (d, J = 7.0 Hz, 1H), 7.03 – 6.90 (m, 1H), 6.04 (s, 2H), 4.46 (d, J = 5.5 Hz, 2H), 4.21 (d, J = 7.0 Hz, 2H), 4.05 (s, 3H), 2.35 (dt, J = 14.6, 7.3 Hz, 1H), 1.78 (d, J = 7.3 Hz, 2H), 1.67 – 1.47 (m, 4H), 1.36 (dd, J = 12.4, 6.6 Hz, 2H). |
| 128 | 5-{2-amino-[1,2,4]triazolo[1,5-a]pyridin-7-yl}-N-{[2-(cyclopentylmethoxy)-3,5-difluorophenyl]methyl}-2-methoxypyridine-3-carboxamide | | 509.2 | 8.91 (t, J = 6.0 Hz, 1H), 8.78 (d, J = 2.3 Hz, 1H), 8.60 (d, J = 7.0 Hz, 1H), 8.45 (d, J = 2.3 Hz, 1H), 7.72 (s, 1H), 7.29 – 7.17 (m, 2H), 7.00 (d, J = 9.4 Hz, 1H), 6.06 (s, 2H), 4.56 (d, J = 5.8 Hz, 2H), 4.04 (s, 3H), 3.91 (d, J = 6.9 Hz, 2H), 2.34 (dt, J = 14.7, 7.4 Hz, 1H), 1.79 (d, J = 7.2 Hz, 2H), 1.67 – 1.48 (m, 4H), 1.37 (dd, J = 12.3, 6.6 Hz, 2H). |
| 129 | 5-{2-amino-[1,2,4]triazolo[1,5-a]pyridin-7-yl}-N-{[2-(cyclopentylmethoxy)-5-fluorophenyl]methyl}-2-methoxypyridine-3-carboxamide | | 491.1 | 8.81 – 8.72 (m, 2H), 8.59 (d, J = 7.0 Hz, 1H), 8.46 (d, J = 2.4 Hz, 1H), 7.71 (s, 1H), 7.25 (d, J = 5.5 Hz, 1H), 7.08 (d, J = 9.5 Hz, 1H), 7.05 – 6.96 (m, 2H), 6.04 (s, 2H), 4.48 (d, J = 5.8 Hz, 2H), 4.05 (s, 3H), 3.89 (d, J = 6.7 Hz, 2H), 2.34 (dt, J = 14.7, 7.1 Hz, 1H), 1.80 (d, J = 7.6 Hz, 2H), 1.67 – 1.48 (m, 4H), 1.43 – 1.31 (m, 2H). |
| 130 | 5-{2-amino-[1,2,4]triazolo[1,5-a]pyridin-7-yl}-N-{[2-(cyclopentylmethoxy)-4-fluorophenyl]methyl}-2-methoxypyridine-3-carboxamide | | 490.9 | 8.76 (s, 1H), 8.69 – 8.61 (m, 1H), 8.59 (d, J = 7.0 Hz, 1H), 8.45 (s, 1H), 7.70 (s, 1H), 7.32 – 7.19 (m, 2H), 6.89 (d, J = 11.3 Hz, 1H), 6.76 – 6.70 (m, 1H), 6.03 (s, 2H), 4.45 (d, J = 5.5 Hz, 2H), 4.03 (s, 3H), 3.92 (d, J = 6.7 Hz, 2H), 2.38 – 2.30 (m, 1H), 1.80 (d, J = 7.6 Hz, 2H), 1.67 – 1.48 (m, 4H), 1.43 – 1.32 (m, 2H). |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 131 | 5-{2-amino-[1,2,4]triazolo[1,5-a]pyridin-7-yl}-N-{[2-(cyclopropylmethoxy)-3,5-difluorophenyl]methyl}-2-methoxypyridine-3-carboxamide | | 481.1 | 8.90 (t, J = 6.1 Hz, 1H), 8.79 (d, J = 2.6 Hz, 1H), 8.62 – 8.58 (m, 1H), 8.49 – 8.43 (m, 1H), 7.73 (d, J = 1.2 Hz, 1H), 7.29 – 7.17 (m, 2H), 7.02 (d, J = 10.5 Hz, 1H), 6.05 (s, 2H), 4.61 (d, J = 6.0 Hz, 2H), 4.09 – 4.01 (m, 3H), 3.89 (d, J = 7.2 Hz, 2H), 1.27 – 1.22 (m, 1H), 0.63 – 0.52 (m, 2H), 0.34 – 0.24 (m, 2H). |
| 132 | 5-{2-amino-[1,2,4]triazolo[1,5-a]pyridin-7-yl}-N-{[3-(cyclopropylmethoxy)pyridin-2-yl]methyl}-2-methoxypyridine-3-carboxamide | | 446.0 | 9.33 (br. s., 1H), 8.83 (s, 1H), 8.65 (s, 1H), 8.19 (d, J = 4.6 Hz, 1H), 7.75 (s, 1H), 7.48 (d, J = 8.2 Hz, 1H), 7.35 (dd, J = 8.0, 4.8 Hz, 1H), 7.31 (d, J = 6.7 Hz, 1H), 7.26 (s, 1H), 7.15 (s, 1H), 7.05 (s, 1H), 4.67 (d, J = 4.4 Hz, 2H), 4.14 (s, 3H), 3.97 (d, J = 6.8 Hz, 2H), 1.29 (br. s., 1H), 0.61 (d, J = 7.6 Hz, 2H), 0.38 (d, J = 4.5 Hz, 2H). |
| 133 | 5-{2-amino-[1,2,4]triazolo[1,5-a]pyridin-7-yl}-N-[(2-ethylphenyl)methyl]-2-methoxypyridine-3-carboxamide | | 402.9 | 8.82 – 8.76 (m, 1H), 8.75 (d, J = 2.8 Hz, 1H), 8.58 (d, J = 6.9 Hz, 1H), 8.42 (d, J = 2.5 Hz, 1H), 7.70 (s, 1H), 7.32 (d, J = 6.9 Hz, 1H), 7.24 (d, J = 6.9 Hz, 1H), 7.22 – 7.07 (m, 3H), 6.03 (s, 2H), 4.54 (d, J = 5.5 Hz, 2H), 4.02 (s, 3H), 2.70 (q, J = 7.4 Hz, 2H), 1.19 (t, J = 7.6 Hz, 3H). |
| 134 | 7-{5-[(3R)-3-[(4-fluorophenyl)methyl]piperidine-1-carbonyl]-6-methoxypyridin-3-yl}-[1,2,4]triazolo[1,5-a]pyridin-2-amine | | 461.1 | 8.73 – 8.54 (m, 2H), 8.18 – 7.99 (m, 1H), 7.74 – 7.63 (m, 1H), 7.32 – 7.18 (m, 2H), 7.16 – 7.09 (m, 1H), 7.06 – 6.91 (m, 1H), 6.73 – 6.66 (m, 1H), 6.09 – 5.98 (m, 2H), 4.46 – 4.14 (m, 1H), 3.98 – 3.80 (m, 3H), 3.42 – 3.36 (m, 1H), 3.29 – 3.10 (m, 1H), 3.08 – 2.91 (m, 1H), 2.90 – 2.80 (m, 1H), 2.79 – 2.58 (m, 2H), 2.39 – 2.17 (m, 1H), 1.64 – 1.48 (m, 1H), 1.45 – 1.34 (m, 1H), and 1.25 (br s, 1H). |

TABLE 1-continued

Compounds in Table 1 were prepared in a similar fashion to examples 81 and 84.

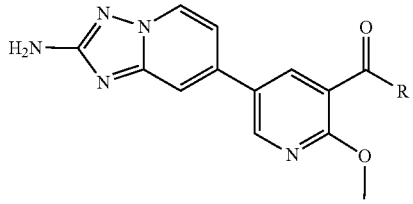

| Ex No | Name | R | M + H | 1H NNMR 9500 MHz, DMSO-d6) δ |
|---|---|---|---|---|
| 135 | 5-{2-amino-[1,2,4]triazolo[1,5-a]pyridin-7-yl}-N-{[2-(cyclopentyloxy)pyridin-3-yl]methyl}-2-methoxypyridine-3-carboxamide | 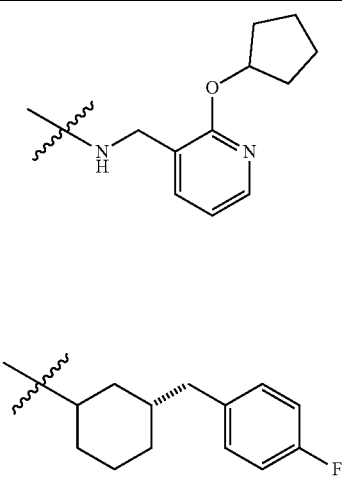 | 460.2 | 8.83 – 8.73 (m, 1H), 8.61 (d, J = 6.9 Hz, 1H), 8.47 (d, J = 2.2 Hz, 1H), 8.06 (d, J = 4.1 Hz, 1H), 7.72 (s, 1H), 7.61 (d, J = 6.8 Hz, 1H), 7.25 (d, J = 7.1 Hz, 1H), 6.99 – 6.89 (m, 1H), 6.07 (s, 2H), 5.46 (br. s., 1H), 4.42 (d, J = 5.7 Hz, 2H), 4.05 (s, 3H), 3.38 – 3.36 (m, 1H), 1.94 (d, J = 5.6 Hz, 2H), 1.76 (d, J = 4.0 Hz, 4H), 1.61 (br. s., 2H). |
| 136 | 7-{5-[(3S)-3-[(4-fluorophenyl)methyl]piperidine-1-carbonyl]-6-methoxypyridin-3-yl}-[1,2,4]triazolo[1,5-a]pyridin-2-amine | 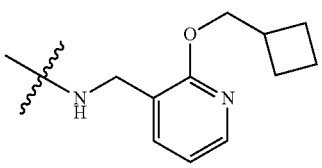 [SMILES: *NCc1cccnc1OCC1CCC1] | 461.0 | 8.73 – 8.54 (m, 2H) 8.18 – 7.99 (m, 1H) 7.74 – 7.63 (m, 1H) 7.32 – 7.18 (m, 2H) 7.16 – 7.09 (m, 1H) 7.06 – 6.91 (m, 1H) 6.73 – 6.66 (m, 1H) 6.09 – 5.98 (m, 2H) 4.46 – 4.14 (m, 1H) 3.98 – 3.80 (m, 3H) 3.42 – 3.36 (m, 1H) 3.29 – 3.10 (m, 1H) 3.08 – 2.91 (m, 1H) 2.90 – 2.80 (m, 1H) 2.79 – 2.58 (m, 2H) 2.39 – 2.17 (m, 1H) 1.64 – 1.48 (m, 1H) 1.45 – 1.34 (m, 1H) and 1.25 (br s, 1H). |
| 137 | 5-{2-amino-[1,2,4]triazolo[1,5-a]pyridin-7-yl}-N-{[2-(cyclobutylmethoxy)pyridin-3-yl]methyl}-2-methoxypyridine-3-carboxamide | 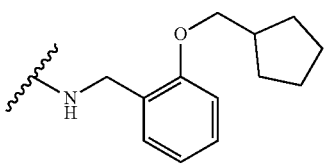 [SMILES: *NCc1ccccc1OCC1CCCC1] | 460.2 | 8.77 (br. s., 2H), 8.60 (d, J = 7.0 Hz, 1H), 8.47 (d, J = 2.1 Hz, 1H), 8.04 (d, J = 4.0 Hz, 1H), 7.71 (s, 1H), 7.62 (d, J = 6.7 Hz, 1H), 7.24 (d, J = 6.4 Hz, 1H), 7.01 – 6.92 (m, 1H), 6.04 (s, 2H), 4.46 (d, J = 5.5 Hz, 2H), 4.30 (d, J = 6.4 Hz, 2H), 4.05 (s, 3H), 2.82 – 2.70 (m, 1H), 2.07 (d, J = 5.8 Hz, 2H), 1.94 – 1.80 (m, 4H). |
| 138 | 5-{2-amino-[1,2,4]triazolo[1,5-a]pyridin-7-yl}-N-{[2-(cyclopentylmethoxy)phenyl]methyl}-2-methoxypyridine-3-carboxamide | | 473.3 | 8.77 (s, 1H), 8.67 (br. s., 1H), 8.60 (d, J = 7.0 Hz, 1H), 8.47 (s, 1H), 7.71 (s, 1H), 7.30 – 7.20 (m, 3H), 6.99 (d, J = 8.1 Hz, 1H), 6.91 (t, J = 7.3 Hz, 1H), 6.06 (s, 2H), 4.50 (d, J = 5.7 Hz, 2H), 4.04 (s, 3H), 3.91 (d, J = 6.6 Hz, 2H), 2.35 (t, J = 7.1 Hz, 1H), 1.80 (br. s., 2H), 1.68-1.49 (m, 4H), 1.43 – 1.31 (m, 2H). |

TABLE 1-continued

Compounds in Table 1 were prepared in a similar fashion to examples 81 and 84.

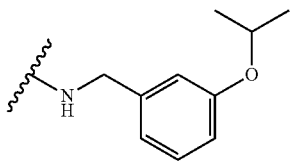 [SMILES: *NCc1cccc(OC(C)C)c1]

| Ex No | Name | R | M + H | 1H NNMR 9500 MHz, DMSO-d6) δ |
|---|---|---|---|---|
| 139 | 5-{2-amino-[1,2,4]triazolo[1,5-a]pyridin-7-yl}-2-methoxy-N-{[3-(propan-2-yloxy)phenyl]methyl}pyridine-3-carboxamide | 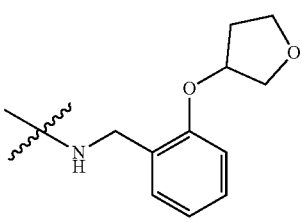 [SMILES: *NCc1ccccc1OC1CCOC1] | 433.2 | 8.87 (t, J = 6.0 Hz, 1H), 8.76 (d, J = 2.4 Hz, 1H), 8.59 (d, J = 7.0 Hz, 1H), 8.43 (d, J = 2.4 Hz, 1H), 7.71 (s, 1H), 7.28 – 7.19 (m, 2H), 6.93 – 6.87 (m, 2H), 6.79 (d, J = 7.3 Hz, 1H), 6.04 (s, 2H), 4.59 (dt, J = 12.1, 5.9 Hz, 1H), 4.49 (d, J = 5.8 Hz, 2H), 4.04 (s, 3H), 1.26 (d, J = 6.1 Hz, 6H). |
| 140 | 5-{2-amino-[1,2,4]triazolo[1,5-a]pyridin-7-yl}-2-methoxy-N-{[2-(oxolan-3-yloxy)phenyl]methyl{pyridine-3-carboxamide | 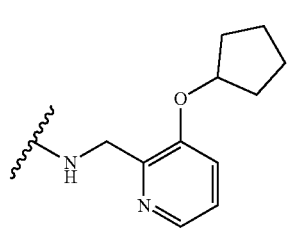 [SMILES: *NCc1ncccc1OC1CCCC1] | 461.1 | 8.77 (d, J = 2.4 Hz, 1H), 8.66 (t, J = 5.8 Hz, 1H), 8.60 (d, J =7.0 Hz, 1H), 8.47 (d, J = 2.4 Hz, 1H), 7.71 (s, 1H), 7.30 (d, J = 7.3 Hz, 1H), 7.28 – 7.21 (m, 2H), 6.99 (d, J = 8.2 Hz, 1H), 6.95 (t, J = 7.5 Hz, 1H), 6.05 (s, 2H), 5.10 (br. s., 1H), 4.49 (d, J = 5.2 Hz, 2H), 4.05 (s, 3H), 3.95 (dd, J = 10.1, 4.6 Hz, 1H), 3.91 – 3.74 (m, 3H), 2.30 – 2.18 (m, 1H), 2.10 – 1.97 (m, 1H). |
| 141 | 5-{2-amino-[1,2,4]triazolo[1,5-a]pyridin-7-yl}-N-{[3-(cyclopentyloxy)pyridin-2-yl]methyl}-2-methoxypyridine-3-carboxamide | 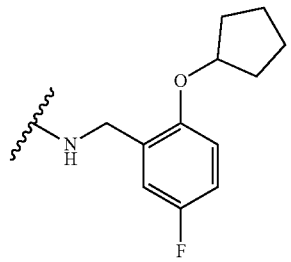 [SMILES: *NCc1cc(F)ccc1OC1CCCC1] | 460.0 | 9.25 (br. s, 1H), 8.80 (d, J = 2.0 Hz, 1H), 8.65 – 8.57 (m, 2H), 8.15 (d, J = 4.5 Hz, 1H), 7.70 (s, 1H), 7.45 (d, J = 8.2 Hz, 1H), 7.31 (dd, J = 8.2, 4.7 Hz, 1H), 7.24 (d, J = 6.9 Hz, 1H), 6.07 (s, 2H), 4.95 (br. s., 1H), 4.58 (d, J = 4.5 Hz, 2H), 4.12 (s, 3H), 1.93 (br. s., 2H), 1.75 (br. s., 4H), 1.61 (br. s., 2H). |
| 142 | 5-{2-amino-[1,2,4]triazolo[1,5-a]pyridin-7-yl}-N-{[2-(cyclopentyloxy)-5-fluorophenyl]methyl}-2-methoxypyridine-3-carboxamide | | 477.2 | 8.80 – 8.72 (m, 2H), 8.60 (d, J = 6.6 Hz, 1H), 8.45 (s, 1H), 7.72 (s, 1H), 7.25 (d, J = 6.8 Hz, 1H), 7.11 – 6.95 (m, 3H), 6.06 (s, 2H), 4.86 (br. s., 1H), 4.43 (d, J = 5.8 Hz, 2H), 4.04 (s, 3H), 1.89 (br. s., 2H), 1.80 – 1.68 (m, 4H), 1.60 (br. s., 2H). |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 143 | 5-{2-amino-[1,2,4]triazolo[1,5-a]pyridin-7-yl}-2-methoxy-N-{[2-(propan-2-ylsulfanyl)phenyl]methyl}pyridine-3-carboxamide | | 449.2 | 8.87 (t, J = 5.8 Hz, 1H), 8.77 (d, J = 2.2 Hz, 1H), 8.59 (d, J = 7.0 Hz, 1H), 8.46 (d, J = 2.2 Hz, 1H), 7.71 (s, 1H), 7.49 – 7.42 (m, 1H), 7.37 (d, J = 2.8 Hz, 1H), 7.30 – 7.22 (m, 3H), 6.06 (s, 2H), 4.60 (d, J = 5.9 Hz, 2H), 4.05 (s, 3H), 1.27 (d, J = 6.6 Hz, 6H). |
| 144 | 5-{2-amino-[1,2,4]triazolo[1,5-a]pyridin-7-yl}-2-methoxy-N-{[2-(propan-2-yloxy)phenyl]methyl}pyridine-3-carboxamide | | 433.1 | 8.74 (d, J = 2.3 Hz, 1H), 8.70 (t, J = 5.9 Hz, 1H), 8.57 (d, J = 7.0 Hz, 1H), 8.47 (d, J = 2.4 Hz, 1H), 7.68 (s, 1H), 7.28 – 7.18 (m, 3H), 7.00 (d, J = 8.2 Hz, 1H), 6.89 (t, J = 7.4 Hz, 1H), 6.04 (s, 2H), 4.65 (dt, J = 12.0, 6.0 Hz, 1H), 4.47 (d, J = 5.9 Hz, 2H), 4.04 (s, 3H), 1.30 (d, J = 6.0 Hz, 6H) |
| 145 | 5-{2-amino-[1,2,4]triazolo[1,5-a]pyridin-7-yl}-N-{[2-(cyclopropylmethoxy)-4-fluorophenyl]methyl}-2-methoxypyridine-3-carboxamide | | 463.0 | 8.78 (d, J = 2.7 Hz, 1H), 8.69 (t, J = 5.9 Hz, 1H), 8.61 (d, J = 7.0 Hz, 1H), 8.48 (d, J = 2.6 Hz, 1H), 7.72 (d, J = 1.3 Hz, 1H), 7.34 – 7.22 (m, 1H), 6.93 – 6.86 (m, 1H), 6.74 (td, J = 8.5, 2.4 Hz, 1H), 6.05 (s, 2H), 4.48 (d, J = 5.9 Hz, 2H), 4.10 – 4.03 (m, 3H), 3.97 – 3.90 (m, 2H), 1.28 – 1.22 (m, 1H), 0.63 – 0.56 (m, 2H), 0.41 – 0.34 (m, 2H). |
| 146 | 5-{2-amino-[1,2,4]triazolo[1,5-a]pyridin-7-yl}-N-{[2-(cyclobutylmethoxy)-6-fluorophenyl]methyl}-2-methoxypyridine-3-carboxamide | | 477.0 | 8.73 (d, J = 1.9 Hz, 1H), 8.58 (d, J = 6.8 Hz, 1H), 8.44 – 8.36 (m, 2H), 7.67 (s, 1H), 7.34 – 7.26 (m, 1H), 7.22 (d, J = 6.8 Hz, 1H), 6.88 (d, J = 8.3 Hz, 1H), 6.80 (t, J = 8.8 Hz, 1H), 6.06 (s, 2H), 4.57 (d, J = 5.0 Hz, 2H), 4.02 (d, J = 6.3 Hz, 2H), 3.99 (s, 3H), 2.76 (d, J = 6.3 Hz, 1H), 2.05 (d, J = 6.3 Hz, 2H), 1.88 (br. s., 4H). |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 147 | 5-{2-amino-[1,2,4]triazolo[1,5-a]pyridin-7-yl}-N-{[2-(cyclopropylmethoxy)-6-fluorophenyl]methyl}-2-methoxypyridine-3-carboxamide | | 463.2 | 8.75 (d, J = 2.0 Hz, 1H), 8.59 (d, J = 6.9 Hz, 1H), 8.52 – 8.43 (m, 2H), 7.68 (s, 1H), 7.35 – 7.19 (m, 2H), 6.90 – 6.83 (m, 1H), 6.80 (t, J = 8.8 Hz, 1H), 6.06 (s, 2H), 4.59 (d, J = 5.1 Hz, 2H), 4.02 (s, 3H), 3.94 (d, J = 6.7 Hz, 2H), 1.27 (br. s., 1H), 0.61 – 0.50 (m, 2H), 0.36 (d, J = 4.6 Hz, 2H). |
| 148 | 5-{2-amino-[1,2,4]triazolo[1,5-a]pyridin-7-yl}-N-{[2-(cyclopentyloxy)phenyl]methyl}-2-methoxypyridine-3-carboxamide | | 459.3 | 8.76 (d, J = 2.4 Hz, 1H), 8.65 (t, J = 5.8 Hz, 1H), 8.59 (d, J = 7.0 Hz, 1H), 8.46 (d, J = 2.4 Hz, 1H), 7.69 (s, 1H), 7.29 – 7.18 (m, 3H), 6.98 (d, J = 8.2 Hz, 1H), 6.88 (t, J = 7.4 Hz, 1H), 6.06 (s, 2H), 4.89 (br. s., 1H), 4.45 (d, J = 5.8 Hz, 2H), 4.03 (s, 3H), 1.96 – 1.85 (m, 2H), 1.81 – 1.66 (m, 4H), 1.59 (br. s., 2H). |
| 149 | 5-{2-amino-[1,2,4]triazolo[1,5-a]pyridin-7-yl}-N-{[2-(cyclobutylmethoxy)phenyl]methyl}-2-methoxypyridine-3-carboxamide | | 459.2 | 8.76 (d, J = 2.4 Hz, 1H), 8.69 (t, J = 5.8 Hz, 1H), 8.59 (d, J = 6.9 Hz, 1H), 8.47 (d, 7 = 2.3 Hz, 1H), 7.70 (s, 1H), 7.33 – 7.14 (m, 3H), 6.99 (d, J = 8.1 Hz, 1H), 6.92 (t, J = 7.4 Hz, 1H), 6.06 (s, 2H), 4.51 (d, J = 5.8 Hz, 2H), 4.04 (s, 3H), 3.99 (d, J = 6.2 Hz, 2H), 2.82 – 2.68 (m, 1H), 2.13 – 2.02 (m, 2H), 1.96 – 1.82 (m, 4H). |
| 150 | 5-{2-amino-[1,2,4]triazolo[1,5-a]pyridin-7-yl}-2-methoxy-N-{[2-(1,1,2,2-tetrafluoroethoxy)phenyl]methyl}pyridine-3-carboxamide | | 491.2 | (400 MHz, CDCl$_3$) δ 8.82 (d, J = 2.6 Hz, 1H), 8.56 (d, J = 2.6 Hz, 1H), 8.36 (d, J = 7.0 Hz, 2H), 7.59 (d, J = 1.1 Hz, 1H), 7.57 – 7.52 (m, 1H), 7.38 – 7.30 (m, 2H), 7.08 (dd, J = 7.0, 1.8 Hz, 1H), 6.25 – 5.89 (m, 1H), 4.73 (d, J = 6.1 Hz, 2H), 4.51 (s, 2H), 4.14 (s, 3H). |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| 151 | 5-{2-amino-[1,2,4]triazolo[1,5-a]pyridin-7-yl}-N-[(2-{[2-(hydroxymethyl)phenyl]sulfanyl}phenyl)methyl]-2-methoxypyridine-3-carboxamide | | 513.3 | 8.89 (t, J = 5.7 Hz, 1H), 8.76 (d, J = 1.9 Hz, 1H), 8.59 (d, J = 6.9 Hz, 1H), 8.44 (d, J = 1.9 Hz, 1H), 7.70 (s, 1H), 7.54 (d, J = 7.5 Hz, 1H), 7.46 (d, J = 7.6 Hz, 1H), 7.35 (t, J = 7.4 Hz, 1H), 7.31 (t, J = 7.4 Hz, 1H), 7.28 – 7.23 (m, 2H), 7.20 (t, J = 7.4 Hz, 1H), 7.16 – 7.10 (m, 1H), 7.07 – 6.99 (m, 1H), 4.60 (br. s., 2H), 4.57 (d, J = 5.6 Hz, 2H), 4.02 (s, 3H), 3.50 (br. s., 1H), 2.59 – 2.54 (m, 2H). |
| 152 | 5-{2-amino-[1,2,4]triazolo[1,5-a]pyridin-7-yl}-2-methoxy-N-[(3-phenyl-1H-pyrazol-4-yl)methyl]pyridine-3-carboxamide | | 441.2 | 8.73 (d, J = 2.2 Hz, 1H), 8.66 (br. s., 1H), 8.59 (d, J = 7.0 Hz, 1H), 8.30 (d, J = 1.9 Hz, 1H), 7.68 (br. s., 3H), 7.52 – 7.29 (m, 5H), 7.22 (d, J = 6.8 Hz, 1H), 6.06 (s, 2H), 4.53 (br. s., 2H), 3.94 (s, 3H). |
| 153 | 5-{2-amino-[1,2,4]triazolo[1,5-a]pyridin-7-yl}-N-[(2-ethoxyphenyl)methyl]-2-methoxypyridine-3-carboxamide | | 419.0 | 8.77 (d, J = 2.2 Hz, 1H), 8.71 (t, J = 5.8 Hz, 1H), 8.59 (d, J = 7.0 Hz, 1H), 8.47 (d, J = 2.2 Hz, 1H), 7.71 (s, 1H), 7.31 – 7.18 (m, 3H), 6.99 (d, J = 8.1 Hz, 1H), 6.91 (t, J = 7.4 Hz, 1H), 6.06 (s, 2H), 4.50 (d, J = 5.9 Hz, 2H), 4.10 (q, J = 6.9 Hz, 2H), 4.05 (s, 3H), 1.38 (t, J = 6.9 Hz, 3H). |
| 154 | 5-{2-amino-[1,2,4]triazolo[1,5-a]pyridin-7-yl}-2-methoxy-N-[(2-methoxyphenyl)methyl]pyridine-3-carboxamide | | 404.9 | 8.85 – 8.71 (m, 2H), 8.59 (d, J = 7.0 Hz, 1H), 8.51 – 8.42 (m, 1H), 7.71 (s, 1H), 7.26 (t, J = 8.2 Hz, 3H), 7.02 (d, J = 8.2 Hz, 1H), 6.93 (t, J = 7.4 Hz, 1H), 6.06 (s, 2H), 4.50 (d, J = 5.8 Hz, 2H), 4.06 (s, 2H), 3.86 (s, 2H). |
| 155 | 5-{2-amino-[1,2,4]triazolo[1,5-a]pyridin-7-yl}-N-[(2-chloro-6-phenoxyphenyl)methyl]-2-methoxypyridine-3-carboxamide | | 501.2 | 8.71 (d, J = 2.2 Hz, 1H), 8.59 (br d, J = 6.4 Hz, 2H), 8.30 (d, J = 2.3 Hz, 1H), 7.65 (s, 1H), 7.38 (br t, J = 7.8 Hz, 2H), 7.35 – 7.26 (m, 2H), 7.20 (br d, J = 6.8 Hz, 1H), 7.12 (br t, J = 7.3 Hz, 1H), 7.05 (br d, J = 8.0 Hz, 2H), 6.83 (br d, J = 7.8 Hz, 1H), 6.04 (s, 2H), 4.74 (br d, |

TABLE 1-continued

Compounds in Table 1 were prepared in a similar fashion to examples 81 and 84.

| Ex No | Name | R | M + H | 1H NNMR 9500 MHz, DMSO-d6) δ |
|---|---|---|---|---|
| | | | | J = 5.0 Hz, 2H), 3.89 (s, 3H). |
| 156 | 5-{2-amino-[1,2,4]triazolo[1,5-a]pyridin-7-yl}-2-methoxy-N-[(1R)-1-(2-methoxyphenyl)ethyl]pyridine-3-carboxamide | | 419.0 | 8.82 (br d, J = 8.4 Hz, 1H), 8.75 (s, 1H), 8.58 (br d, J = 6.8 Hz, 1H), 8.41 (s, 1H), 7.70 (s, 1H), 7.35 (br d, J = 7.3 Hz, 1H), 7.29 – 7.21 (m, 2H), 7.03 (br d, J = 8.2 Hz, 1H), 6.94 (br t, J = 7.4 Hz, 1H), 6.04 (s, 2H), 5.43 – 5.34 (m, 1H), 4.07 (s, 3H), 3.88 (s, 3H), 1.41 (br d, J = 6.8 Hz, 3H). |
| 157 | 5-{2-amino-[1,2,4]triazolo[1,5-a]pyridin-7-yl}-N-[(3S)-3-(4-chlorophenyl)-3-hydroxypropyl]-2-methoxypyridine-3-carboxamide | | 453.0 | 8.75 (d, J = 2.6 Hz, 1H), 8.60 (d, J = 7.0 Hz, 1H), 8.49 (t, J = 5.4 Hz, 1H), 8.42 (d, J = 2.6 Hz, 1H), 7.70 (d, J = 1.2 Hz, 1H), 7.39 (s, 4H), 7.23 (dd, J = 7.0, 2.0 Hz, 1H), 6.04 (s, 2H), 5.50 (d, J = 4.3 Hz, 1H), 4.75 – 4.67 (m, 1H), 4.02 (s, 3H), 3.38 (q, J = 6.6 Hz, 2H), 1.91 – 1.79 (m, 2H). |
| 158 | 5-{2-amino-[1,2,4]triazolo[1,5-a]pyridin-7-yl}-2-methoxy-N-[(2-phenoxyphenyl)methyl]pyridine-3-carboxamide | | 467.0 | 8.84 (d, J = 2.7 Hz, 1H), 8.60 (d, J = 2.7 Hz, 1H), 8.52 (t, J = 6.0 Hz, 1H), 8.45 (d, J = 7.1 Hz, 1H), 7.84 (d, J = 1.2 Hz, 1H), 7.53 (dd, J = 7.6, 1.6 Hz, 1H), 7.44 (dd, J = 7.0, 1.8 Hz, 1H), 7.40 – 7.32 (m, 2H), 7.30 (d, J = 1.6 Hz, 1H), 7.26 (d, J = 1.7 Hz, 1H), 7.19 – 7.10 (m, 2H), 7.07 – 7.00 (m, 2H), 6.92 (dd, J = 8.1, 1.0 Hz, 1H), 4.77 (d, J = 6.0 Hz, 3H), 4.00 (s, 3H). |
| 159 | 5-{2-amino-[1,2,4]triazolo[1,5-a]pyridin-7-yl}-N-[(3S)-1-benzylpyrrolidin-3-yl]-2-methoxypyridine-3-carboxamide | | 444.2 | 8.73 (d, J = 2.3 Hz, 1H), 8.59 (d, J = 7.0 Hz, 1H), 8.42 (d, J = 7.2 Hz, 1H), 8.34 (d, J = 2.3 Hz, 1H), 7.71 (s, 1H), 7.33 (d, J = 4.4 Hz, 4H), 7.27 – 7.19 (m, 2H), 6.06 (s, 2H), 4.39 (br. s., 1H), 4.00 (s, 3H), 3.68 – 3.54 (m, 2H), 2.76 – 2.65 (m, 2H), 2.48 – 2.36 (m, 2H), 2.27 – 2.12 (m, 1H), 1.72 (d, J = 6.5 Hz, 1H). |

TABLE 1-continued

Compounds in Table 1 were prepared in a similar fashion to examples 81 and 84.

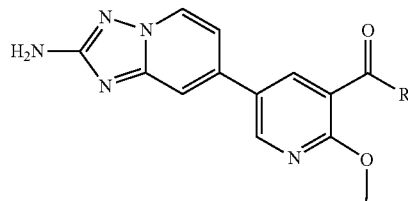

| Ex No | Name | R | M + H | 1H NNMR 9500 MHz, DMSO-d6) δ |
|---|---|---|---|---|
| 160 | 5-{2-amino-[1,2,4] triazolo[1,5-a]pyridin-7-yl}-N-{[2-fluoro-5-(trifluoromethoxy) phenyl]methyl}-2-methoxypyridine-3-carboxamide | *2-fluoro-5-(trifluoromethoxy)benzyl amine* | 477.1 | 9.00 (t, J = 5.8 Hz, 1H), 8.78 (d, J = 2.4 Hz, 1H), 8.60 (d, J = 7.0 Hz, 1H), 8.42 (d, J = 2.1 Hz, 1H), 7.71 (s, 1H), 7.42 (d, J = 4.6 Hz, 1H), 7.38 – 7.31 (m, 2H), 7.25 (d, J = 6.4 Hz, 1H), 6.04 (s, 2H), 4.58 (d, J = 6.1 Hz, 2H), 4.04 (s, 3H |
| 161 | 5-{2-amino-[1,2,4] triazolo[1,5-a]pyridin-7-yl}-N-{[2-chloro-5-(trifluoromethyl)phenyl] methyl}-2-methoxypyridine-3-carboxamide | *2-chloro-5-(trifluoromethyl)benzyl amine* | 477.3 | 9.06 (t, J = 5.9 Hz, 1H), 8.79 (d, J = 2.2 Hz, 1H), 8.60 (d, J = 6.9 Hz, 1H), 8.41 (d, J = 2.2 Hz, 1H), 7.81 (s, 1H), 7.78 – 7.66 (m, 3H), 7.25 (d, J = 6.9 Hz, 1H), 6.04 (s, 2H), 4.64 (d, J = 5.8 Hz, 2H), 4.05 (s, 3H) |
| 162 | 5-{2-amino-[1,2,4] triazolo[1,5-a]pyridin-7-yl}-2-methoxy-N-methyl-N-{[3-(trifluoromethoxy) phenyl]methyl}pyridine-3-carboxamide | *3-(trifluoromethoxy)benzyl N-methyl amine* | 473.3 | Mixture of rotomers: 8.74 – 8.63 (m, 1H), 8.61 – 8.51 (m, 1H), 8.22 – 8.11 (m, 1H), 7.76 – 7.59 (m, 1H), 7.58 – 7.45 (m, 1H), 7.44 – 7.11 (m, 4H), 6.01 (br s, 2H), 4.03 – 3.83 (m, 3H), 3.00 – 2.75 (m, 3H) Note: benzyl CH2 not visible |

TABLE 2

Compounds in Table 1 were prepared in a similar fashion to example 1.

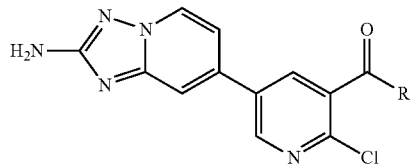

| Ex No | Name | R | M + H | 1H NMR (500 MHz, DMSO-d6) δ |
|---|---|---|---|---|
| 163 | 5-{2-amino-[1,2,4]triazolo[1,5-a]pyridin-7-yl}-2-chloro-N-{[3,5-difluoro-2-(propan-2-yloxy)phenyl]methyl}pyridine-3-carboxamide | *3,5-difluoro-2-isopropoxybenzyl amine* | 473.2 | 9.21 (br. s., 1H), 8.94 (br. s., 1H), 8.66 (d, J = 6.6 Hz, 1H), 8.42 (br. s., 1H), 7.86 (br. s., 1H), 7.34 (d, J = 6.9 Hz, 1H), 7.23 (d, J = 9.6 Hz, 1H), 7.08 (d, J = 7.8 Hz, 1H), 4.52 (d, J = 5.7 Hz, 2H), 4.41-4.19 (m, 1H), 1.28 (d, J = 6.0 Hz, 6H) 2-exchangeable protons are missing. |

TABLE 2-continued

Compounds in Table 1 were prepared in a similar fashion to example 1.

| Ex No | Name | R | M + H | 1H NMR (500 MHz, DMSO-d6) δ |
|---|---|---|---|---|
| 164 | 5-{2-amino-[1,2,4]triazolo[1,5-a]pyridin-7-yl}-2-chloro-N-{[3-(cyclopropylmethoxy)phenyl]methyl}pyridine-3-carboxamide | [3-(cyclopropylmethoxy)benzyl]amino | 448.9 | 9.19 (br. s., 1H), 8.94 (br. s., 1H), 8.66 (d, J = 6.7 Hz, 1H), 8.38 (br. s., 1H), 7.86 (br. s., 1H), 7.34 (d, J = 6.7 Hz, 1H), 7.24 (t, J = 7.9 Hz, 1H), 6.94 (d, J = 7.3 Hz, 1H), 6.86 (br. s., 1H), 6.73 (d, J = 8.0 Hz, 1H), 6.13 (br. s., 2H), 4.66 (t, J = 7.1 Hz, 1H), 4.46 (d, J = 5.6 Hz, 2H), 2.41 (d, J = 8.2 Hz, 2H), 2.08-1.92 (m, 2H), 1.76 (d, J = 10.6 Hz, 1H), 1.68-1.51 (m, 1H). |
| 165 | 5-{2-amino-[1,2,4]triazolo[1,5-a]pyridin-7-yl}-2-chloro-N-{[2-(oxolan-3-yloxy)phenyl]methyl}pyridine-3-carboxamide | [2-(oxolan-3-yloxy)benzyl]amino | 464.9 | 8.98 (br. s., 1H), 8.93 (s, 1H), 8.66 (d, J = 6.9 Hz, 1H), 8.36 (br. s., 1H), 7.86 (s, 1H), 7.37 (d, J = 7.5 Hz, 1H), 7.34 (d, J = 6.9 Hz, 1H), 7.25 (t, J = 7.1 Hz, 1H), 7.04-6.90 (m, 2H), 6.13 (br. s., 2H), 5.08 (br. s., 1H), 4.44 (d, J = 5.7 Hz, 2H), 3.94-3.89 (m, 1H), 3.88-3.81 (m, 2H), 3.76 (td, J = 8.3, 4.4 Hz, 1H), 2.27-2.15 (m, 1H), 2.10-1.95 (m, 1H). |
| 166 | 5-{2-amino-[1,2,4]triazolo[1,5-a]pyridin-7-yl}-2-chloro-N-{[2-fluoro-5-(trifluoromethoxy)phenyl]methyl}pyridine-3-carboxamide | [2-fluoro-5-(trifluoromethoxy)benzyl]amino | 481.2 | 9.29 (br. s., 1H), 8.95 (d, J = 2.5 Hz, 1H), 8.65 (d, J = 6.9 Hz, 1H), 8.38 (d, J = 2.5 Hz, 1H), 7.84 (s, 1H), 7.48 (br. s., 1H), 7.37 (d, J = 7.7 Hz, 2H), 7.33 (dd, J = 7.0, 1.8 Hz, 1H), 6.10 (s, 2H), 4.56 (d, J = 5.8 Hz, 2H). |
| 167 | 5-{2-amino-[1,2,4]triazolo[1,5-a]pyridin-7-yl}-2-chloro-N-{[3-(trifluoromethoxy)phenyl]methyl}pyridine-3-carboxamide | [3-(trifluoromethoxy)benzyl]amino | 463.0 | 9.30 (t, J = 6.1 Hz, 1H), 8.95 (s, 1H), 8.67 (d, J = 7.1 Hz, 1H), 8.42 (s, 1H), 7.87 (s, 1H), 7.54-7.47 (m, 1H), 7.45 (d, J = 7.5 Hz, 1H), 7.39 (br. s., 1H), 7.35 (d, J = 6.5 Hz, 1H), 7.27 (d, J = 7.6 Hz, 1H), 6.14 (s, 2H), 4.56 (d, J = 5.9 Hz, 2H). |
| 168 | 5-{2-amino-[1,2,4]triazolo[1,5-a]pyridin-7-yl}-2-chloro-N-{[2-(trifluoromethoxy)phenyl]methyl}pyridine-3-carboxamide | [2-(trifluoromethoxy)benzyl]amino | 463.1 | 9.25 (t, J = 5.8 Hz, 1H), 8.96 (s, 1H), 8.67 (d, J = 6.9 Hz, 1H), 8.41 (s, 1H), 7.87 (s, 1H), 7.67-7.59 (m, 1H), 7.49-7.42 (m, 2H), 7.40 (br. s., 1H), 7.34 (d, J = 7.0 Hz, 1H), 6.14 (s, 2H), 4.57 (d, J = 5.6 Hz, 2H). |
| 169 | 5-{2-amino-[1,2,4]triazolo[1,5-a]pyridin-7-yl}-2-chloro-N-(3-phenylbutyl)pyridine-3-carboxamide | (3-phenylbutyl)amino | 421.1 | 8.86 (d, J = 2.2 Hz, 1H), 8.70 (br t, J = 5.3 Hz, 1H), 8.60 (d, J = 7.1 Hz, 1H), 8.20 (d, J = 2.2 Hz, 1H), 7.78 (s, 1H), 7.29 (br t, J = 7.8 Hz, 3H), 7.25-7.20 (m, 2H), 7.20-7.12 (m, 1H), 3.14 (q, J = 6.3 Hz, 2H), 2.86-2.77 (m, 1H), 1.79 (q, J = 7.3 Hz, 2H), 1.21 (d, J = 6.9 Hz, 3H) Note: unknown peak at 3.8 ppm. |
| 170 | 5-{2-amino-[1,2,4]triazolo[1,5-a]pyridin-7-yl}-2-chloro-N-{[2-fluoro-5-(trifluoromethyl)phenyl]methyl}pyridine-3-carboxamide | [2-fluoro-5-(trifluoromethyl)benzyl]amino | 465.1 | 9.36 (br. s., 1H), 8.91 (d, J = 2.4 Hz, 1H), 8.61 (d, J = 7.0 Hz, 1H), 8.34 (s, 1H), 7.84 (d, J = 6.3 Hz, 1H), 7.80 (s, 1H), 7.74 (d, J = 4.1 Hz, 1H), 7.45 (t, J = 9.2 Hz, 1H), 7.31 (dd, J = 7.0, 1.8 Hz, 1H), 6.10 (br. s., 2H), 4.58 (d, J = 5.6 Hz, 2H) |
| 171 | 5-{2-amino-[1,2,4]triazolo[1,5-a]pyridin-7-yl}-2-chloro-N-{[2-fluoro-5-(trifluoromethoxy)phenyl](deutero)methyl}pyridine-3-carboxamide | [2-fluoro-5-(trifluoromethoxy)phenyl](dideutero)methylamino | 483.0 | 9.28 (s, 1H), 8.94 (d, J = 2.2 Hz, 1H), 8.65 (d, J = 6.9 Hz, 1H), 8.38 (d, J = 2.2 Hz, 1H), 7.84 (s, 1H), 7.48 (d, J = 5.5 Hz, 1H), 7.37 (d, J = 7.2 Hz, 2H), 7.32 (d, J = 6.3 Hz, 1H), 6.10 (s, 2H). |

TABLE 3

Compounds in Table 1 were prepared in a similar fashion to example 16.

| Ex No | Name | R | M + H | 1H NMR (500 MHz, DMSO-d6) δ |
|---|---|---|---|---|
| 172 | 5-{2-amino-[1,2,4]triazolo[1,5-a]pyridin-7-yl}-N-(2-hydroxy-3-phenoxypropyl)-2,6-dimethylpyridine-3-carboxamide | -NH-CH₂-CH(OH)-CH₂-O-Ph | 433.1 | 8.60 (d, J = 6.8 Hz, 1H), 8.54 (br. s., 1H), 7.70 (s, 1H), 7.41 (s, 1H), 7.26 (t, J = 7.9 Hz, 2H), 6.95 (d, J = 6.9 Hz, 1H), 6.93-6.88 (m, 3H), 6.07 (br. s., 2H), 4.03-3.94 (m, 2H), 3.93-3.86 (m, 1H), 3.46 (m, 3H), 2.55-2.54 (s, 3H), 2.47 (s, 3H). |
| 173 | 5-{2-amino-[1,2,4]triazolo[1,5-a]pyridin-7-yl}-N-(2-hydroxy-3-phenylpropyl)-2,6-dimethylpyridine-3-carboxamide | -NH-CH₂-CH(OH)-CH₂-Ph | 417.2 | 8.59 (d, J = 6.7 Hz, 1H), 8.45 (br. s., 1H), 7.66 (s, 1H), 7.40 (s, 1H), 7.34-7.21 (m, 6H), 7.18-7.11 (m, 1H), 6.95 (dd, J = 6.8, 1.4 Hz, 1H), 6.05 (br. s., 2H), 3.35-3.27 (m, 1H), 3.22-3.12 (m, 2H), 2.63 (dd, J = 13.5, 7.6 Hz, 1H), 2.56-2.54 (br.s., 3H), 2.46 (s, 3H). |
| 174 | 5-{2-amino-[1,2,4]triazolo[1,5-a]pyridin-7-yl}-2,6-dimethyl-N-(3-phenylbutyl)pyridine-3-carboxamide | -NH-CH₂-CH₂-CH(CH₃)-Ph | 415.3 | 8.59 (d, J = 6.8 Hz, 1H), 8.42 (br. s., 1H), 7.57 (s, 1H), 7.40 (s, 1H), 7.31-7.20 (m, 4H), 7.19-7.12 (m, 1H), 6.95 (dd, J = 6.9, 1.4 Hz, 1H), 6.07 (br. s., 2H), 3.17-3.05 (m, 2H), 2.83-2.72 (m, 1H), 2.53 (s, 3H), 2.47 (s, 3H), 1.79 (q, J = 7.3 Hz, 2H), 1.21 (d, J = 6.9 Hz, 3H). |
| 175 | 5-{2-amino-[1,2,4]triazolo[1,5-a]pyridin-7-yl}-2,6-dimethyl-N-{2-[3-(trifluoromethoxy)phenyl]ethyl}pyridine-3-carboxamide | -NH-CH₂-CH₂-(3-OCF₃-C₆H₄) | 471.3 | 8.58 (br d, J = 6.7 Hz, 1H), 8.51 (br s, 1H), 7.50 (s, 1H), 7.43-7.39 (m, 1H), 7.36 (s, 1H), 7.29 (br d, J = 7.6 Hz, 1H), 7.21 (br s, 1H), 7.16 (br d, J = 7.6 Hz, 1H), 6.93 (br d, J = 6.7 Hz, 1H), 3.68-3.62 (m, 2H), 3.52 (br d, J = 6.1 Hz, 2H), 2.90 (br t, J = 6.6 Hz, 2H), 2.45 (s, 3H), 2.42 (s, 3H). |
| 176 | 5-{2-amino-[1,2,4]triazolo[1,5-a]pyridin-7-yl}-N-{[3-(cyclopropylmethoxy)phenyl]methyl}-2,6-dimethylpyridine-3-carboxamide | -NH-CH₂-(3-(cyclopropylmethoxy)-C₆H₄) | 443.3 | 8.96 (t, J = 6.3 Hz, 1H), 8.60 (d, J = 6.7 Hz, 1H), 7.70 (s, 1H), 7.42 (s, 1H), 7.23 (br t, J = 8.0 Hz, 1H), 6.96 (br d, J = 6.1 Hz, 1H), 6.91-6.84 (m, 2H), 6.80 (br d, J = 8.2 Hz, 1H), 6.04 (s, 2H), 4.43 (br d, J = 5.8 Hz, 2H), 3.78 (m, 2H), 2.56 (s, 3H), 2.47 (m, 3H), 1.19 (br s, 1H), 0.52 (br d, J = 7.0 Hz, 2H), 0.32-0.25 (m, 2H). |
| 177 | 5-{2-amino-[1,2,4]triazolo[1,5-a]pyridin-7-yl}-N-{[2-(cyclopentylmethoxy)-4,6-difluorophenyl]methyl}-2,6-dimethylpyridine-3-carboxamide | -NH-CH₂-(2-(cyclopentylmethoxy)-4,6-difluorophenyl) | 507.2 | 8.62-8.58 (m, 1H), 8.47 (br s, 1H), 7.57 (s, 1H), 7.37 (s, 1H), 6.97-6.87 (m, 1H), 6.84-6.71 (m, 2H), 6.04 (br s, 2H), 4.43-4.38 (m, 2H), 3.89 (br d, J = 6.7 Hz, 2H), 2.57 (s, 3H), 2.46 (s, 3H), 2.33-2.25 (m, 1H), 1.72 (br d, J = 7.6 Hz, 2H), 1.57-1.41 (m, 4H), 1.32 (td, J = 13.3, 7.0 Hz, 2H). |
| 178 | 5-{2-amino-[1,2,4]triazolo[1,5-a]pyridin-7-yl}-N-[(3R)-3-(4-chlorophenyl)-3-hydroxypropyl]-2,6-dimethylpyridine-3-carboxamide | -NH-CH₂-CH₂-CH(OH)-(4-Cl-C₆H₄) | 451.2 | 8.54 (d, J = 6.7 Hz, 1H), 8.44 (br. s., 1H), 7.53 (s, 1H), 7.36 (s, 1H), 7.33 (s, 4H), 6.94 (br d, J = 6.4 Hz, 1H), 5.99 (s, 2H), 4.61 (d, J = 4.9 Hz, 1H), 3.27 (d, J = 6.1 Hz, 2H), 2.53 (s, 3H), 2.44 (s, 3H), 1.87-1.79 (m, 2H). |

TABLE 3-continued

Compounds in Table 1 were prepared in a similar fashion to example 16.

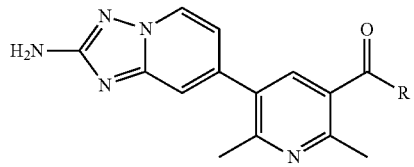

| Ex No | Name | R | M + H | 1H NMR (500 MHz, DMSO-d6) δ |
|---|---|---|---|---|
| 179 | 5-{2-amino-[1,2,4]triazolo[1,5-a]pyridin-7-yl}-N-[(3S)-3-(4-chlorophenyl)-3-hydroxypropyl]-2,6-dimethylpyridine-3-carboxamide | | 451.2 | (400 MHz) 8.60 (d, J = 6.8 Hz, 1H), 8.39 (t, J = 5.5 Hz, 1H), 7.61 (s, 1H), 7.41 (d, J = 1.1 Hz, 1H), 7.37 (s, 4H), 6.94 (dd, J = 6.8, 1.8 Hz, 1H), 6.06 (s, 2H), 5.37 (d, J = 4.5 Hz, 1H), 4.68-4.60 (m, 1H), 3.30-3.25 (m, 2H), 2.54 (s, 3H), 2.48 (s, 3H), 1.87-1.78 (m, 2H). |
| 180 | 5-{2-amino-[1,2,4]triazolo[1,5-a]pyridin-7-yl}-N-{[2-(cyclopentylmethoxy)-6-fluorophenyl]methyl}-2,6-dimethylpyridine-3-carboxamide | | 489.1 | 8.58 (br d, J = 6.6 Hz, 1H), 8.53 (br s, 1H), 7.57 (s, 1H), 7.37 (s, 1H), 7.28 (q, J = 8.0 Hz, 1H), 6.99-6.89 (m, 1H), 6.85 (br d, J = 8.3 Hz, 1H), 6.78 (br t, J = 8.8 Hz, 1H), 6.06 (br s, 2H), 4.46 (br d, J = 3.4 Hz, 2H), 3.88 (br d, J = 6.5 Hz, 2H), 2.55 (s, 3H), 2.46 (s, 3H), 2.36-2.23 (m, 1H), 1.71 (br d, J = 5.7 Hz, 2H), 1.51 (br s, 2H), 1.42 (br s, 2H), 1.36-1.26 (m, 2H). |
| 181 | 5-{2-amino-[1,2,4]triazolo[1,5-a]pyridin-7-yl}-N-{[2-fluoro-5-(trifluoromethoxy)phenyl]methyl}-2,6-dimethylpyridine-3-carboxamide | | 475.0 | 9.08 (br s, 1H), 8.61 (br d, J = 6.6 Hz, 1H), 7.72 (s, 1H), 7.42 (br s, 2H), 7.36 (br d, J = 6.7 Hz, 2H), 6.96 (br d, J = 6.8 Hz, 1H), 6.08 (br s, 2H), 4.51 (br d, J = 5.4 Hz, 2H), 2.55 (s, 3H), 2.49 (s, 3H). |
| 182 | 5-{2-amino-[1,2,4]triazolo[1,5-a]pyridin-7-yl}-N-{[3-(cyclopentylmethoxy)pyridin-2-yl]methyl}-2,6-dimethylpyridine-3-carboxamide | | 472.0 | 8.72 (br s, 1H), 8.59 (br d, J = 6.7 Hz, 1H), 8.05 (br d, J = 4.3 Hz, 1H), 7.73 (s, 1H), 7.46-7.35 (m, 2H), 7.26 (dd, J = 8.1, 4.8 Hz, 1H), 6.97 (br d, J = 6.9 Hz, 1H), 6.06 (br s, 2H), 4.56 (br d, J = 5.2 Hz, 2H), 3.95-3.72 (m, 2H), 2.58 (s, 3H), 2.47 (s, 3H), 2.40-2.25 (m, 1H), 1.76 (br d, J = 6.7 Hz, 2H), 1.57 (br s, 2H), 1.49 (br s, 2H), 1.40-1.28 (m, 2H). |
| 183 | 5-{2-amino-[1,2,4]triazolo[1,5-a]pyridin-7-yl}-N-{[2-(cyclopentylmethoxy)pyridin-3-yl]methyl}-2,6-dimethylpyridine-3-carboxamide | | 472.2 | 8.83 (t, J = 5.3 Hz, 1H), 8.59 (d, J = 6.7 Hz, 1H), 8.03 (d, J = 4.0 Hz, 1H), 7.74 (s, 1H), 7.61 (d, J = 7.0 Hz, 1H), 7.41 (s, 1H), 7.00-6.89 (m, 2H), 6.03 (s, 2H), 4.38 (d, J = 5.5 Hz, 2H), 4.17 (d, J = 7.0 Hz, 2H), 2.57 (s, 3H), 2.48 (s, 3H), 2.30 (dt, J = 14.6, 7.3 Hz, 1H), 1.72 (d, J = 7.6 Hz, 2H), 1.62-1.38 (m, 4H), 1.31 (dd, J = 12.1, 6.9 Hz, 2H). |
| 184 | 5-{2-amino-[1,2,4]triazolo[1,5-a]pyridin-7-yl}-N-{[2-(cyclopropylmethoxy)-3,5-difluorophenyl]methyl}-2,6-dimethylpyridine-3-carboxamide | | 479.1 | 8.98 (t, J = 5.6 Hz, 1H), 8.59 (d, J = 6.8 Hz, 1H), 7.75 (s, 1H), 7.42 (s, 1H), 7.19 (t, J = 8.5 Hz, 1H), 6.97 (d, J = 6.9 Hz, 2H), 6.06 (s, 2H), 4.53 (d, J = 5.6 Hz, 2H), 3.84 (d, J = 7.2 Hz, 2H), 2.56 (s, 3H), 2.48 (s, 3H), 1.25 (br. s., 1H), 0.53 (d, J = 6.8 Hz, 2H), 0.26 (d, J = 4.6 Hz, 2H). |

TABLE 3-continued

Compounds in Table 1 were prepared in a similar fashion to example 16.

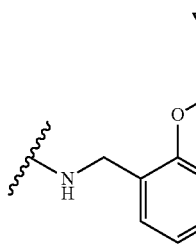

| Ex No | Name | R | M + H | 1H NMR (500 MHz, DMSO-d6) δ |
|---|---|---|---|---|
| 185 | 5-{2-amino-[1,2,4]triazolo[1,5-a]pyridin-7-yl}-N-{[2-(cyclopropylmethoxy)phenyl]methyl}-2,6-dimethylpyridine-3-carboxamide | 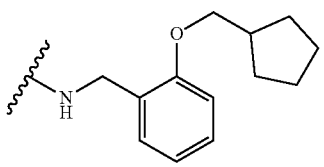 [SMILES: *NCc1ccccc1OCC1CCCC1] | 443.0 | 8.79 (t, J = 5.5 Hz, 1H), 8.59 (d, J = 7.0 Hz, 1H), 7.73 (s, 1H), 7.42 (s, 1H), 7.27-7.18 (m, 2H), 6.96 (t, J = 7.3 Hz, 2H), 6.91 (t, J = 7.5 Hz, 1H), 6.04 (s, 2H), 4.46 (d, J = 5.5 Hz, 2H), 3.92-3.81 (m, 2H), 2.58 (s, 3H), 2.48 (s, 3H), 1.22-1.18 (m, 1H), 0.53 (d, J = 7.3 Hz, 2H), 0.32 (d, J = 4.6 Hz, 2H). |
| 186 | 5-{2-amino-[1,2,4]triazolo[1,5-a]pyridin-7-yl}-N-{[2-(cyclopentylmethoxy)phenyl]methyl}-2,6-dimethylpyridine-3-carboxamide | 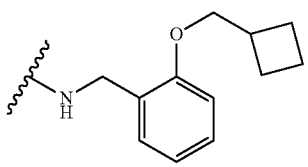 [SMILES: *NCc1ccccc1OCC1CCC1] | 471.1 | 8.77-8.70 (m, 1H), 8.60 (d, J = 6.7 Hz, 1H), 7.72 (s, 1H), 7.42 (s, 1H), 7.28-7.17 (m, 2H), 7.01-6.93 (m, 2H), 6.90 (t, J = 7.5 Hz, 1H), 6.04 (br. s., 2H), 4.44 (d, J = 5.2 Hz, 2H), 3.87 (d, J = 6.7 Hz, 2H), 2.57 (s, 3H), 2.48 (s, 3H), 2.35-2.26 (m, 1H), 1.76 (d, J = 6.7 Hz, 2H), 1.57 (d, J = 6.4 Hz, 2H), 1.53-1.43 (m, 2H), 1.35 (dd, J = 12.2, 6.7 Hz, 2H). |
| 187 | 5-{2-amino-[1,2,4]triazolo[1,5-a]pyridin-7-yl}-N-{[2-(cyclobutylmethoxy)pyridin-3-yl]methyl}-2,6-dimethylpyridine-3-carboxamide | 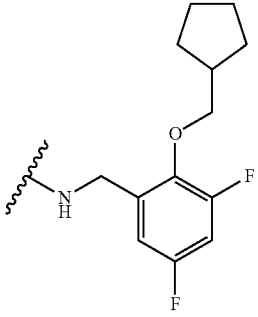 [SMILES: *NCc1cc(F)cc(F)c1OCC1CCCC1] | 457.9 | 8.88-8.80 (m, 1H), 8.60 (d, J = 7.0 Hz, 1H), 8.04 (d, J = 4.3 Hz, 1H), 7.76 (s, 1H), 7.62 (d, J = 7.0 Hz, 1H), 7.42 (s, 1H), 7.00-6.91 (m, 2H), 6.05 (s, 2H), 4.39 (d, J = 5.2 Hz, 2H), 4.27 (d, J = 6.4 Hz, 2H), 2.72 (d, J = 7.0 Hz, 1H), 2.58 (s, 3H), 2.49 (s, 3H), 2.10-1.97 (m, 2H), 1.84 (br. s., 4H). |
| 188 | 5-{2-amino-[1,2,4]triazolo[1,5-a]pyridin-7-yl}-N-{[2-(cyclopentylmethoxy)-3,5-difluorophenyl]methyl}-2,6-dimethylpyridine-3-carboxamide | 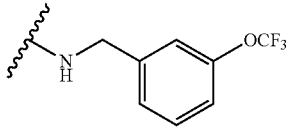 [SMILES: *NCc1cccc(OC(F)(F)F)c1] | 507.1 | 8.94 (t, J = 5.5 Hz, 1H), 8.58 (d, J = 7.0 Hz, 1H), 7.73 (s, 1H), 7.40 (s, 1H), 7.21-7.14 (m, 1H), 6.96 (d, J = 7.0 Hz, 2H), 6.02 (s, 2H), 4.49 (d, J = 5.5 Hz, 2H), 3.87 (d, J = 6.7 Hz, 2H), 2.55 (br. s., 3H), 2.47 (s, 3H), 2.29 (dq, J = 15.3, 7.6 Hz, 1H), 1.74 (d, J = 7.6 Hz, 2H), 1.62-1.43 (m, 4H), 1.32 (dd, J = 12.2, 6.4 Hz, 2H) |
| 189 | 5-{2-amino-[1,2,4]triazolo[1,5-a]pyridin-7-yl}-2,6-dimethyl-N-{[3-(trifluoromethoxy)phenyl]methyl}pyridine-3-carboxamide | 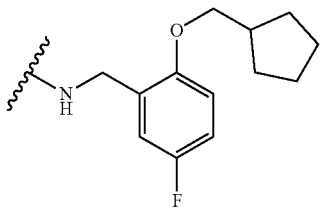 [SMILES: *NCc1cc(F)ccc1OCC1CCCC1] | 457.0 | 9.07 (t, J = 5.6 Hz, 1H), 8.59 (d, J = 7.0 Hz, 1H), 7.72 (s, 1H), 7.50-7.44 (m, 1H), 7.42-7.34 (m, 2H), 7.31 (br. s., 1H), 7.24 (d, J = 8.2 Hz, 1H), 6.95 (d, J = 6.7 Hz, 1H), 6.04 (s, 2H), 4.50 (d, J = 5.8 Hz, 2H), 2.55 (br. s., 3H), 2.48 (s, 3H). |
| 190 | 5-{2-amino-[1,2,4]triazolo[1,5-a]pyridin-7-yl}-N-{[2-(cyclopentylmethoxy)-5-fluorophenyl]methyl}-2,6-dimethylpyridine-3-carboxamide | | 489.1 | 8.81 (s, 1H), 8.60 (d, J = 6.7 Hz, 1H), 7.75 (s, 1H), 7.42 (s, 1H), 7.08-7.01 (m, 2H), 6.98 (dd, J = 13.4, 5.2 Hz, 2H), 6.05 (s, 2H), 4.43 (d, J = 5.5 Hz, 2H), 3.87 (d, J = 6.7 Hz, 2H), 2.58 (s, 3H), 2.49 (br. s., 3H), 2.35-2.27 (m, 1H), 1.76 (br. s., 2H), 1.63-1.44 (m, 4H), 1.35 (dd, J = 12.4, 6.9 Hz, 2H). |

TABLE 3-continued

Compounds in Table 1 were prepared in a similar fashion to example 16.

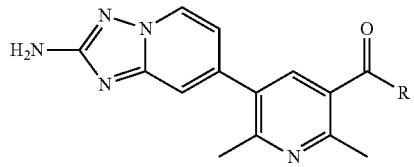

| Ex No | Name | R | M + H | 1H NMR (500 MHz, DMSO-d6) δ |
|---|---|---|---|---|
| 191 | 5-{2-amino-[1,2,4]triazolo[1,5-a]pyridin-7-yl}-N-{[2-fluoro-5-(trifluoromethoxy)phenyl](deutero)methyl}-2,6-dimethylpyridine-3-carboxamide | (D,D-CH-NH- linked to 2-F, 5-OCF3 phenyl) | 477.1 | 9.05 (s, 1H), 8.59 (d, J = 7.0 Hz, 1H), 7.70 (s, 1H), 7.44-7.31 (m, 4H), 6.96 (d, J = 7.0 Hz, 1H), 6.04 (s, 2H), 2.53 (s, 3H), 2.48 (s, 3H) |
| 192 | 5-{2-amino-[1,2,4]triazolo[1,5-a]pyridin-7-yl}-N-{[2-fluoro-5-(trifluoromethyl)phenyl]methyl}-2,6-dimethylpyridine-3-carboxamide | (CH2-NH- linked to 2-F, 5-CF3 phenyl) | 459.4 | 9.10 (br t, J = 5.6 Hz, 1H), 8.55 (d, J = 7.0 Hz, 1H), 7.76-7.68 (m, 2H), 7.66 (s, 1H), 7.42 (t, J = 9.2 Hz, 1H), 7.37 (s, 1H), 6.95 (br d, J = 6.7 Hz, 1H), 6.00 (s, 2H), 4.53 (br d, J = 5.8 Hz, 2H), 2.45 (s, 3H). Note: One CH3 under DMSO-d6 peak |

TABLE 4

Compunds in Table 1 were prepared in a similar fashion to example 3.

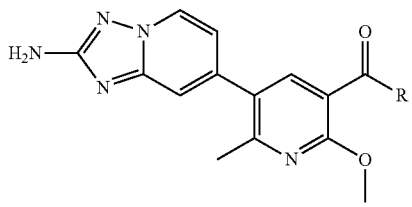

| Ex No | Name | R | M + H | 1H NMR (500 MHz, DMSO-d6) δ |
|---|---|---|---|---|
| 193 | 5-{2-amino-[1,2,4]triazolo-[1,5-a]pyridin-7-yl}-N-[(3S)-3-(4-chlorophenyl)-3-hydroxypropyl]-2-methoxy-6-methylpyridine-3-carboxamide | (NH-CH2CH2-CH(OH)- linked to 4-Cl phenyl) | 467.3 | 8.56 (d, J = 6.7 Hz, 1H), 8.46 (br. s., 1H), 8.01 (s, 1H), 7.40-7.31 (m, 5H), 6.91 (d, J = 6.7 Hz, 1H), 6.02 (s, 2H), 4.68 (br. s., 1H), 4.01 (s, 3H), 3.54-3.51 (m, 1H), 3.36 (d, J = 5.8 Hz, 2H), 2.46 (s, 3H), 1.94-1.76 (m, 2H). |
| 194 | 5-{2-amino-[1,2,4]triazolo-[1,5-a]pyridin-7-yl}-2-methoxy-6-methyl-N-{2-[2-(trifluoromethoxy)-phenyl]ethyl}pyridine-3-carboxamide | (NH-CH2CH2- linked to 2-OCF3 phenyl) | 487.3 | 8.55 (d, J = 7.0 Hz, 1H), 8.32 (t, J = 5.5 Hz, 1H), 7.97 (s, 1H), 7.49-7.42 (m, 1H), 7.39-7.27 (m, 4H), 6.89 (d, J = 6.7 Hz, 1H), 6.01 (s, 2H), 3.95 (s, 3H), 3.60-3.48 (m, 2H), 2.92 (t, J = 7.0 Hz, 2H), 2.44 (s, 3H). |
| 195 | 5-{2-amino-[1,2,4]triazolo-[1,5-a]pyridin-7-yl}-2-methoxy-6-methyl-N-{[2-(oxan-4-yloxy)phenyl]methyl}pyridine-3-carboxamide | (NH-CH2- linked to 2-(oxan-4-yloxy)phenyl) | 489.4 | 8.62-8.51 (m, 1H), 8.06 (s, 1H), 7.35 (s, 1H), 7.27-7.16 (m, 2H), 7.05 (d, J = 7.9 Hz, 1H), 6.93-6.83 (m, 2H), 6.02 (br. s., 2H), 4.66 (br. s., 1H), 4.50 (d, J = 5.8 Hz, 2H), 4.03 (s, 3H), 3.87-3.81 (m, 2H), 3.50 (br.s., 2H), 3.16 (br. s., 1H), 2.46 (s, 3H), 1.96 (br. s., 2H), 1.70-1.59 (m, 2H). |

TABLE 4-continued

Compunds in Table 1 were prepared in a similar fashion to example 3.

| Ex No | Name | R | M + H | 1H NMR (500 MHz, DMSO-d6) δ |
|---|---|---|---|---|
| 196 | 5-{2-amino-[1,2,4]triazolo-[1,5-a]pyridin-7-yl}-N-{[3-fluoro-5-(trifluoromethyl)-phenyl]methyl}-2-methoxy-6-methylpyridine-3-carboxamide | | 475.0 | 9.00 (br. s., 1H), 8.57 (d, J = 6.8 Hz, 1H), 8.01 (s, 1H), 7.60-7.52 (m, 2H), 7.49 (d, J = 9.5 Hz, 1H), 7.36 (s, 1H), 6.91 (d, J = 6.4 Hz, 1H), 6.05 (br. s., 2H), 4.59 (d, J = 5.9 Hz, 2H), 4.03 (s, 3H), 2.47 (s, 3H). |
| 197 | 5-{2-amino-[1,2,4]triazolo-[1,5-a]pyridin-7-yl}-N-{[2-fluoro-5-(trifluoromethyl)-phenyl]methyl}-2-methoxy-6-methylpyridine-3-carboxamide | | 475.0 | 8.99-8.87 (m, 1H), 8.54 (d, J = 6.7 Hz, 1H), 7.97 (s, 1H), 7.77-7.66 (m, 2H), 7.42 (t, J = 9.2 Hz, 1H), 7.34 (s, 1H), 6.90 (d, J = 6.1 Hz, 1H), 6.00 (s, 2H), 4.59 (d, J = 5.5 Hz, 2H), 4.02 (s, 3H), 2.45 (s, 3H). |
| 198 | 5-{2-amino-[1,2,4]triazolo-[1,5-a]pyridin-7-yl}-2-methoxy-6-methyl-N-{2-[3-(trifluoromethoxy)-phenyl]ethyl}pyridine-3-carboxamide | | 487.2 | 8.57 (d, J = 6.7 Hz, 1H), 8.29 (br s, 1H), 7.97 (s, 1H), 7.45 (t, J = 7.8 Hz, 1H), 7.34 (s, 1H), 7.31 (d, J = 7.8 Hz, 1H), 7.26-7.18 (m, 2H), 6.89 (br d, J = 6.7 Hz, 1H), 6.03 (s, 2H), 3.96 (s, 3H), 3.58-3.53 (m, 1H), 3.51-3.48 (m, 1H), 2.91 (br t, J = 6.9 Hz, 2H), 2.47-2.43 (m, 3H). |
| 199 | 5-{2-amino-[1,2,4]triazolo-[1,5-a]pyridin-7-yl}-2-methoxy-6-methyl-N-{[3-(trifluoromethyl)phenyl]methyl}pyridine-3-carboxamide | | 457.2 | 8.96 (br t, J = 6.1 Hz, 1H), 8.56 (d, J = 7.0 Hz, 1H), 8.01 (s, 1H), 7.69 (s, 1H), 7.66-7.55 (m, 3H), 7.36 (s, 1H), 6.91 (br d, J = 5.5 Hz, 1H), 6.02 (s, 2H), 4.59 (br d, J = 6.1 Hz, 2H), 4.03 (s, 3H), 2.48-2.45 (m, 3H). |
| 200 | 5-{2-amino-[1,2,4]triazolo-[1,5-a]pyridin-7-yl}-N-{[3-(cyclopropylmethoxy)-phenyl]methyl}-2-methoxy-6-methylpyridine-3-carboxamide | | 459.3 | 8.78 (br s, 1H), 8.58 (d, J = 6.7 Hz, 1H), 8.03 (s, 1H), 7.37 (s, 1H), 7.22 (br t, J = 7.9 Hz, 1H), 6.94-6.87 (m, 3H), 6.79 (br d, J = 7.9 Hz, 1H), 6.03 (s, 2H), 4.48 (br d, J = 5.8 Hz, 1H), 4.04 (s, 3H), 3.79 (d, J = 6.7 Hz, 2H), 3.49-3.43 (m, 1H), 2.46 (s, 3H), 1.20 (br s, 1H), 0.55 (br d, J = 7.6 Hz, 2H), 0.30 (br d, J = 4.6 Hz, 2H). |
| 201 | 5-{2-amino-[1,2,4]triazolo-[1,5-a]pyridin-7-yl}-N-{[2-fluoro-5-(trifluoromethoxy)-phenyl]methyl}-2-methoxy-6-methylpyridine-3-carboxamide | | 491.2 | 8.89 (br t, J = 5.8 Hz, 1H), 8.57 (d, J = 6.7 Hz, 1H), 7.99 (s, 1H), 7.36 (s, 2H), 7.34-7.31 (m, 2H), 6.91 (br d, J = 7.0 Hz, 1H), 6.03 (s, 2H), 4.56 (br d, J = 5.8 Hz, 2H), 4.03 (s, 3H), 2.46 (s, 3H). |
| 202 | 5-{2-amino-[1,2,4]triazolo-[1,5-a]pyridin-7-yl}-N-{[2-(cyclopentylmethoxy)-4,6-difluorophenyl]methyl}-2-methoxy-6-methylpyridine-3-carboxamide | | 523.4 | 8.61 (br d, J = 7.0 Hz, 1H), 8.28 (br t, J = 5.0 Hz, 1H), 8.03 (s, 1H), 7.39 (s, 1H), 6.99 (br d, J = 7.0 Hz, 1H), 6.83-6.73 (m, 2H), 4.49 (br d, J = 5.2 Hz, 2H), 3.98 (s, 3H), 3.93 (br d, J = 6.7 Hz, 2H), 3.61 (br s, 2H), 2.47-2.42 (m, 3H), 2.32 (dt, J = 14.6, 7.3 Hz, 1H), 1.76 (br s, 2H), 1.60-1.46 (m, 4H), 1.33 (br dd, J = 12.1, 6.6 Hz, 2H). |

TABLE 4-continued

Compunds in Table 1 were prepared in a similar fashion to example 3.

| Ex No | Name | R | M + H | 1H NMR (500 MHz, DMSO-d6) δ |
|---|---|---|---|---|
| 203 | 5-{2-amino-[1,2,4]triazolo-[1,5-a]pyridin-7-yl}-N-{[3-(cyclopentylmethoxy)-pyridin-2-yl]methyl}-2-methoxy-6-methylpyridine-3-carboxamide | | 487.9 | 9.25 (br s, 1H), 8.59 (d, J = 7.0 Hz, 1H), 8.19-8.16 (m, 2H), 7.45 (br d, J = 8.2 Hz, 1H), 7.38 (s, 1H), 7.32 (t, J = 6.8 Hz, 1H), 6.92 (br d, J = 7.0 Hz, 1H), 6.04 (s, 2H), 4.62 (br d, J = 4.3 Hz, 2H), 4.13 (s, 3H), 3.97 (br d, J = 6.7 Hz, 2H), 2.55 (s, 3H), 2.36 (br t, J = 7.5 Hz, 1H), 1.80 (br s, 2H), 1.63 (br s, 2H), 1.61-1.50 (m, 2H), 1.42-1.34 (m, 2H). |
| 204 | 5-{2-amino-[1,2,4]triazolo-[1,5-a]pyridin-7-yl}-N-{[3-(difluoromethoxy)phenyl]-methyl}-2-methoxy-6-methylpyridine-3-carboxamide | | 455.0 | 8.86 (t, J = 5.8 Hz, 1H), 8.56 (d, J = 7.0 Hz, 1H), 8.02 (s, 1H), 7.42-7.16 (m, 4H), 7.13 (s, 1H), 7.07-7.00 (m, 1H), 6.91 (d, J = 6.7 Hz, 1H), 6.02 (s, 2H), 4.52 (d, J = 5.8 Hz, 2H), 4.03 (s, 3H), 2.46 (s, 3H). |
| 205 | 5-{2-amino-[1,2,4]triazolo-[1,5-a]pyridin-7-yl}-2-methoxy-6-methyl-N-{1-[2-(trifluoromethoxy)phenyl]-ethyl}pyridine-3-carboxamide | | 487.1 | 8.67 (d, J = 7.6 Hz, 1H), 8.55 (d, J = 6.9 Hz, 1H), 7.90 (s, 1H), 7.63-7.57 (m, 1H), 7.39 (dd, J = 5.8, 3.6 Hz, 2H), 7.34 (s, 2H), 6.90 (d, J = 6.8 Hz, 1H), 6.04 (s, 2H), 5.37 (quin, J = 7.1 Hz, 1H), 4.02 (s, 3H), 2.45 (s, 3H), 1.44 (d, J = 6.9 Hz, 3H). |
| 206 | 5-{2-amino-[1,2,4]triazolo-[1,5-a]pyridin-7-yl}-N-{[2-(cyclopentylmethoxy)-5-fluorophenyl]methyl}-2-methoxy-6-methylpyridine-3-carboxamide | | 504.9 | 8.64 (t, J = 5.9 Hz, 1H), 8.52 (d, J = 6.8 Hz, 1H), 7.99 (s, 1H), 7.32 (s, 1H), 7.02-6.90 (m, 3H), 6.87 (d, J = 6.6 Hz, 1H), 6.00 (s, 2H), 4.42 (d, J = 5.9 Hz, 2H), 3.99 (s, 3H), 3.83 (d, J = 6.7 Hz, 2H), 2.42 (s, 3H), 2.27 (dt, J = 14.8, 7.3 Hz, 1H), 1.73 (d, J = 7.5 Hz, 2H), 1.61-1.42 (m, 4H), 1.31 (dd, J = 12.5, 6.7 Hz, 2H) |
| 207 | 5-{2-amino-[1,2,4]triazolo-[1,5-a]pyridin-7-yl}-N-{[2-(cyclopentylmethoxy)-phenyl]methyl}-2-methoxy-6-methylpyridine-3-carboxamide | | 487.0 | 8.61-8.53 (m, 2H), 8.06 (s, 1H), 7.37 (s, 1H), 7.25-7.16 (m, 2H), 6.98 (d, J = 8.4 Hz, 1H), 6.93-6.84 (m, 2H), 6.06 (s, 2H), 4.49 (d, J = 5.7 Hz, 2H), 4.03 (s, 3H), 3.91 (d, J = 6.6 Hz, 2H), 2.47 (s, 3H), 2.34 (dt, J = 14.6, 7.2 Hz, 1H), 1.80 (d, J = 7.1 Hz, 2H), 1.66-1.48 (m, 4H), 1.44-1.33 (m, 2H) |
| 208 | 5-{2-amino-[1,2,4]triazolo-[1,5-a]pyridin-7-yl}-N-{[2-(cyclopentylmethoxy)-3,5-difluorophenyl]methyl}-2-methoxy-6-methylpyridine-3-carboxamide | | 523.3 | 8.80 (t, J = 5.8 Hz, 1H), 8.55 (d, J = 6.7 Hz, 1H), 8.02 (s, 1H), 7.35 (s, 1H), 7.16 (t, J = 8.5 Hz, 1H), 6.91 (d, J = 6.7 Hz, 2H), 6.01 (s, 2H), 4.53 (d, J = 5.8 Hz, 2H), 4.03 (s, 3H), 3.88 (d, J = 6.7 Hz, 2H), 2.46 (s, 3H), 2.36-2.26 (m, 1H), 1.76 (d, J = 6.7 Hz, 2H), 1.64-1.45 (m, 4H), 1.34 (dd, J = 12.2, 6.7 Hz, 2H). |

TABLE 4-continued

Compunds in Table 1 were prepared in a similar fashion to example 3.

| Ex No | Name | R | M + H | 1H NMR (500 MHz, DMSO-d6) δ |
|---|---|---|---|---|
| 209 | 5-{2-amino-[1,2,4]triazolo-[1,5-a]pyridin-7-yl}-N-{[2-(cyclobutylmethoxy)-pyridin-3-yl]methyl}-2-methoxy-6-methyl-pyridine-3-carboxamide | | 474.0 | 8.68 (t, J = 5.8 Hz, 1H), 8.54 (d, J = 7.0 Hz, 1H), 8.06-7.97 (m, 2H), 7.55 (d, J = 7.0 Hz, 1H), 7.34 (s, 1H), 6.96-6.87 (m, 2H), 6.00 (s, 2H), 4.43 (d, J = 5.8 Hz, 2H), 4.27 (d, J = 6.1 Hz, 2H), 4.02 (s, 3H), 2.77-2.65 (m, 1H), 2.45 (s, 3H), 2.03 (d, J = 3.7 Hz, 2H), 1.94-1.73 (m, 4H). |
| 210 | 5-{2-amino-[1,2,4]triazolo-[1,5-a]pyridin-7-yl}-2-methoxy-6-methyl-N-{[3-(trifluoromethoxy)phenyl]-methyl}pyridine-3-carboxamide | | 473.0 | (400 MHz) 8.89 (t, J = 6.1 Hz, 1H), 8.59 (dd, J = 6.8, 0.7 Hz, 1H), 8.03 (s, 1H), 7.52-7.28 (m, 5H), 6.91 (dd, J = 6.8, 1.8 Hz, 1H), 6.04 (s, 2H), 4.57 (d, J = 6.1 Hz, 2H), 4.04 (s, 3H), 2.49 (s, 3H). |
| 211 | 5-{2-amino-[1,2,4]triazolo-[1,5-a]pyridin-7-yl}-2-methoxy-6-methyl-N-{[2-(trifluoromethoxy)phenyl]-methyl}pyridine-3-carboxamide | | 473.2 | (400 MHz) 8.83 (t, J = 6.2 Hz, 1H), 8.60 (dd, J = 6.8, 0.6 Hz, 1H), 8.07 (s, 1H), 7.51-7.38 (m, 5H), 6.92 (dd, J = 6.8, 2.0 Hz, 1H), 6.05 (s, 2H), 4.61 (d, J = 6.0 Hz, 2H), 4.06 (s, 3H), 2.50 (br, s., 3H). |
| 212 | 5-{2-amino-[1,2,4]triazolo-[1,5-a]pyridin-7-yl}-2-methoxy-6-methyl-N-{[2-(propan-2-yloxy)phenyl]-methyl}pyridine-3-carboxamide | | 447.0 | 8.57 (d, J = 6.4 Hz, 2H), 8.07 (s, 1H), 7.36 (s, 1H), 7.27-7.17 (m, 2H), 7.01 (d, J = 8.2 Hz, 1H), 6.95-6.81 (m, 2H), 6.03 (s, 2H), 4.72-4.60 (m, 1H), 4.46 (d, J = 5.8 Hz, 2H), 4.04 (s, 3H), 2.47 (s, 3H), 1.30 (d, J = 6.1 Hz, 6H). |
| 213 | 5-{2-amino-[1,2,4]triazolo-[1,5-a]pyridin-7-yl}-N-{[3-(cyclopentyloxy)pyridin-2-yl]methyl}-2-methoxy-6-methylpyridine-3-carboxamide | | 474.2 | 9.21 (br. s., 1H), 8.56 (d, J = 6.9 Hz, 1H), 8.15 (s, 1H), 8.13 (d, J = 3.9 Hz, 1H), 7.42 (d, J = 8.0 Hz, 1H), 7.36 (s, 1H), 7.30 (dd, J = 8.3, 5.0 Hz, 1H), 6.92 (d, J = 6.6 Hz, 1H), 6.01 (s, 2H), 4.92 (br. s., 1H), 4.55 (d, J = 4.7 Hz, 2H), 4.10 (s, 3H), 2.47 (s, 3H), 1.91 (br. s., 2H), 1.71 (br. s., 4H), 1.59 (br. s., 2H). |
| 214 | 5-{2-amino-[1,2,4]triazolo-[1,5-a]pyridin-7-yl}-N-{[2-(cyclobutylmethoxy)-6-fluorophenyl]methyl}-2-methoxy-6-methylpyridine-3-carboxamide | | 491.0 | 8.54 (d, J = 6.7 Hz, 1H), 8.35-8.27 (m, 1H), 8.03 (s, 1H), 7.36-7.24 (m, 2H), 6.89 (dd, J = 12.7, 8.1 Hz, 2H), 6.78 (t, J = 9.0 Hz, 1H), 6.00 (s, 2H), 4.55 (d, J = 5.2 Hz, 2H), 4.02 (d, J = 5.8 Hz, 2H), 3.98 (s, 3H), 2.74 (d, J = 6.1 Hz, 1H), 2.44 (s, 3H), 2.04 (d, J = 7.0 Hz, 2H), 1.91-1.80 (m, 4H). |
| 215 | 5-{2-amino-[1,2,4]triazolo-[1,5-a]pyridin-7-yl}-N-{[2-(cyclopropylmethoxy)-6-fluorophenyl]methyl}-2-methoxy-6-methylpyridine-3-carboxamide | | 477.3 | 8.58 (d, J = 6.8 Hz, 1H), 8.38 (t, J = 5.3 Hz, 1H), 8.07 (s, 1H), 7.36 (s, 1H), 7.32-7.24 (m, 1H), 6.88 (dd, J = 11.5, 7.7 Hz, 2H), 6.79 (t, J = 8.8 Hz, 1H), 6.06 (s, 2H), 4.58 (d, J = 5.4 Hz, 2H), 4.02 (s, 3H), 3.95 (d, J = 6.8 Hz, 2H), 2.46 (s, 3H), 1.27 (br. s., 1H), 0.57 (d, J = 6.7 Hz, 2H), 0.37 (d, J = 4.8 Hz, 2H). |

TABLE 4-continued

Compunds in Table 1 were prepared in a similar fashion to example 3.

| Ex No | Name | R | M + H | 1H NMR (500 MHz, DMSO-d6) δ |
|---|---|---|---|---|
| 216 | 5-{2-amino-[1,2,4]triazolo-[1,5-a]pyridin-7-yl}-N-{[2-(cyclopentyloxy)-5-fluoro-phenyl]methyl}-2-methoxy-6-methylpyridine-3-carboxamide | | 491.1 | 8.65 (t, J = 5.8 Hz, 1H), 8.58 (d, J = 6.7 Hz, 1H), 8.04 (s, 1H), 7.38 (br. s., 1H), 7.06-6.95 (m, 3H), 6.92 (d, J = 6.6 Hz, 1H), 4.85 (br. s., 1H), 4.41 (d, J = 5.7 Hz, 2H), 4.03 (s, 3H), 3.43 (br. s., 1H), 3.16 (s, 1H), 2.47 (s, 3H), 1.88 (br. s., 2H), 1.80-1.66 (m, 4H), 1.59 (br. s., 2H). |
| 217 | 5-{2-amino-[1,2,4]triazolo-[1,5-a]pyridin-7-yl}-N-{[2-(cyclopentyloxy)-6-fluoro-phenyl]methyl}-2-methoxy-6-methylpyridine-3-carboxamide | | 491.2 | 8.57 (d, J = 6.7 Hz, 1H), 8.29 (t, J = 5.3 Hz, 1H), 8.05 (s, 1H), 7.35 (br. s., 1H), 7.32-7.24 (m, 1H), 6.88 (dd, J = 17.9, 7.5 Hz, 2H), 6.76 (t, J = 8.9 Hz, 1H), 4.92 (br. s., 1H), 4.52 (d, J = 5.2 Hz, 2H), 4.00 (s, 3H), 3.17 (s, 1H), 2.46 (s, 3H), 1.99-1.87 (m, 2H), 1.82-1.64 (m, 4H), 1.58 (br. s., 2H). |
| 218 | 5-{2-amino-[1,2,4]triazolo-[1,5-a]pyridin-7-yl}-2-methoxy-6-methyl-N-(3-phenylbutyl)pyridine-3-carboxamide | | 431.0 | 8.58 (d, J = 6.7 Hz, 1H), 8.22-8.13 (m, 1H), 7.97 (s, 1H), 7.35 (s, 1H), 7.32-7.27 (m, 2H), 7.26-7.21 (m, 2H), 7.20-7.14 (m, 1H), 6.89 (d, J = 6.7 Hz, 1H), 6.03 (s, 2H), 4.01 (s, 3H), 3.24-3.14 (m, 2H), 2.84-2.73 (m, 1H), 2.46 (s, 3H), 1.81 (q, J = 7.1 Hz, 2H), 1.23 (d, J = 6.7 Hz, 3H). |
| 219 | 5-{2-amino-[1,2,4]triazolo-[1,5-a]pyridin-7-yl}-N-{[2-(cyclopentyloxy)phenyl]methyl}-2-methoxy-6-methylpyridine-3-carboxamide | | 473.1 | 8.58 (d, J = 6.7 Hz, 1H), 8.53 (t, J = 6.0 Hz, 1H), 8.07 (s, 1H), 7.37 (s, 1H), 7.26-7.18 (m, 2H), 6.99 (d, J = 8.2 Hz, 1H), 6.93-6.83 (m, 2H), 6.03 (s, 2H), 4.90 (br. s., 1H), 4.44 (d, J = 5.8 Hz, 2H), 4.04 (s, 3H), 2.48 (s, 3H), 2.00-1.86 (m, 2H), 1.83-1.67 (m, 4H), 1.61 (br. s., 2H). |
| 220 | 5-{2-amino-[1,2,4]triazolo-[1,5-a]pyridin-7-yl}-N-{[2-(cyclopentylmethoxy)-6-fluorophenyl]methyl}-2-methoxy-6-methylpyridine-3-carboxamide | | 505.3 | 8.57 (d, J = 6.7 Hz, 1H), 8.29 (br t, J = 5.2 Hz, 1H), 8.04 (s, 1H), 7.35 (s, 1H), 7.31-7.26 (m, 1H), 6.89 (t, J = 6.2 Hz, 2H), 6.79 (t, J = 8.9 Hz, 1H), 6.03 (s, 2H), 4.56 (br d, J = 5.2 Hz, 2H), 4.00-3.98 (m, 5H), 2.46 (s, 3H), 2.34 (dt, J = 14.6, 7.3 Hz, 1H), 1.79 (br d, J = 7.6 Hz, 2H), 1.62-1.48 (m, 4H), 1.36 (br dd, J = 12.2, 6.7 Hz, 2H). |
| 221 | 5-{2-amino-[1,2,4]triazolo-[1,5-a]pyridin-7-yl}-N-{[2-(cyclopropylmethoxy)phenyl]methyl}-2-methoxy-6-methylpyridine-3-carboxamide | | 459.1 | 8.61 (t, J = 5.8 Hz, 1H), 8.57 (d, J = 6.7 Hz, 1H), 8.07 (s, 1H), 7.37 (s, 1H), 7.26-7.16 (m, 2H), 6.97 (d, J = 8.2 Hz, 1H), 6.94-6.86 (m, 2H), 6.03 (s, 2H), 4.51 (d, J = 5.8 Hz, 2H), 4.04 (s, 3H), 3.95-3.86 (m, 2H), 2.47 (s, 3H), 1.33-1.20 (m, 1H), 0.65-0.52 (m, 2H), 0.40-0.31 (m, 2H). |

TABLE 4-continued

Compunds in Table 1 were prepared in a similar fashion to example 3.

| Ex No | Name | R | M + H | 1H NMR (500 MHz, DMSO-d6) δ |
|---|---|---|---|---|
| 222 | 5-{2-amino-[1,2,4]triazolo-[1,5-a]pyridin-7-yl}-N-{[2-fluoro-5-(trifluoromethoxy)-phenyl](deutero)methyl}-2-methoxy-6-methylpyridine-3-carboxamide | | 492.8 | 8.88 (s, 1H), 8.55 (d, J = 6.7 Hz, 1H), 7.98 (s, 1H), 7.38-7.30 (m, 4H), 6.90 (dd, J = 6.9, 1.7 Hz, 1H), 6.01 (s, 2H), 4.02 (s, 3H), 2.46 (s, 3H) |
| 223 | 5-{2-amino-[1,2,4]triazolo-[1,5-a]pyridin-7-yl}-2-methoxy-6-methyl-N-{1-[3-(trifluoromethoxy)-phenyl]ethyl}pyridine-3-carboxamide | | 487.3 | 8.65 (br d, J = 7.6 Hz, 1H), 8.57 (br d, J = 6.7 Hz, 1H), 7.90 (s, 1H), 7.51-7.39 (m, 3H), 7.36 (s, 1H), 7.24 (br d, J = 7.3 Hz, 1H), 6.91 (br d, J = 6.7 Hz, 1H), 6.04 (s, 2H), 5.18 (br t, J = 7.3 Hz, 1H), 4.03 (s, 3H), 2.47 (s, 3H), 1.48 (br d, J = 7.0 Hz, 3H). |

TABLE 5

Compounds in Table 1 were prepared in a similar fashion to example 82.

| Ex No | Name | R | M + H | 1H NMR (500 MHz, DMSO-d6) δ |
|---|---|---|---|---|
| 224 | 5-{2-amino-[1,2,4]triazolo-[1,5-a]pyridin-7-yl}-N-[(3R)-3-(4-chlorophenyl)-3-hydroxypropyl]-2-methyl-pyridine-3-carboxamide | | 437.2 | 8.91 (s, 1H), 8.61 (d, J = 7.0 Hz, 1H), 8.53 (br. s., 1H), 8.06 (s, 1H), 7.77 (s, 1H), 7.38 (s, 4H), 7.29 (d, J = 7.0 Hz, 1H), 6.05 (s, 2H), 4.67 (br. s., 1H), 3.46-3.43 (m, 1H), 3.33 (d, J = 5.8 Hz, 2H), 2.56 (s, 3H), 1.91-1.81 (m, 2H). |
| 225 | 5-{2-amino-[1,2,4]triazolo-[1,5-a]pyridin-7-yl}-N-[(3S)-3-(4-chlorophenyl)-3-hydroxypropyl]-2-methyl-pyridine-3-carboxamide | | 437.3 | 8.92 (s, 1H), 8.61 (d, J = 7.0 Hz, 1H), 8.52 (br. s., 1H), 8.06 (s, 1H), 7.77 (s, 1H), 7.38 (s, 4H), 7.29 (d, J = 7.0 Hz, 1H), 6.05 (s, 2H), 4.67 (br. s., 1H), 3.44-3.40 (m, 1H), 3.33 (d, J = 6.4 Hz, 2H), 2.56 (s, 3H), 1.92-1.79 (m, 2H). |
| 226 | 5-{2-amino-[1,2,4]triazolo-[1,5-a]pyridin-7-yl}-N-{[2-fluoro-5-(trifluoromethyl)-phenyl]methyl}-2-methyl-pyridine-3-carboxamide | | 445.0 | 9.18 (t, J = 5.5 Hz, 1H), 8.94 (d, J = 1.8 Hz, 1H), 8.61 (d, J = 7.0 Hz, 1H), 8.15 (d, J = 1.8 Hz, 1H), 7.81 (d, J = 5.5 Hz, 1H), 7.76 (s, 2H), 7.46 (t, J = 9.2 Hz, 1H), 7.30 (d, J = 7.0 Hz, 1H), 6.05 (s, 2H), 4.59 (d, J = 5.5 Hz, 2H), 2.54 (s, 3H). |
| 227 | 5-{2-amino-[1,2,4]triazolo-[1,5-a]pyridin-7-yl}-2-methyl-N-{2-[3-trifluoromethoxy)phenyl]ethyl}-pyridine-3-carboxamide | | 457.2 | 8.93 (s, 1H), 8.66-8.58 (m, 2H), 8.01 (s, 1H), 7.76 (s, 1H), 7.46 (t, J = 7.8 Hz, 1H), 7.34 (br d, J = 7.6 Hz, 1H), 7.28 (s, 1H), 7.27 (d, J = 5.6 Hz, 1H), 7.22 (br d, J = 7.3 Hz, 1H), 6.08 (s, |

TABLE 5-continued

Compounds in Table 1 were prepared in a similar fashion to example 82.

| Ex No | Name | R | M + H | 1H NMR (500 MHz, DMSO-d6) δ |
|---|---|---|---|---|
| | | | | 2H), 3.60-3.54 (m, 2H), 2.95 (br t, J = 6.7 Hz, 2H), 2.48-2.45 (m, 3H). |
| 228 | 5-{2-amino-[1,2,4]triazolo-[1,5-a]pyridin-7-yl}-N-{[2-(cyclopentylmethoxy)-4,6-difluorophenyl]methyl}-2-methylpyridine-3-carboxamide | | 493.2 | 8.97-8.91 (m, 1H), 8.68-8.59 (m, 2H), 8.05 (s, 1H), 7.77 (s, 1H), 7.36-7.28 (m, 1H), 6.87-6.74 (m, 2H), 4.48-4.42 (m, 2H), 3.93 (br d, J = 6.4 Hz, 2H), 2.61-2.53 (m, 3H), 2.37-2.27 (m, 1H), 1.77 (br d, J = 7.0 Hz, 2H), 1.57 (br s, 2H), 1.54-1.45 (m, 2H), 1.41-1.31 (m, 2H), 1.23 (s, 2H). |
| 229 | 5-{2-amino-[1,2,4]triazolo-[1,5-a]pyridin-7-yl}-N-{[2-fluoro-5-(trifluoromethoxy)phenyl]methyl}-2-methylpyridine-3-carboxamide | | 461.3 | 9.15 (br t, J = 5.5 Hz, 1H), 8.97 (s, 1H), 8.65 (br d, J = 6.7 Hz, 1H), 8.19 (s, 1H), 7.81 (br s, 1H), 7.46 (br d, J = 4.3 Hz, 1H), 7.38 (d, J = 6.7 Hz, 2H), 7.31 (br d, J = 6.7 Hz, 1H), 6.08 (br s, 2H), 4.57 (br d, J = 5.5 Hz, 2H), 2.57 (s, 3H). |
| 230 | 5-{2-amino-[1,2,4]triazolo-[1,5-a]pyridin-7-yl}-N-{[2-(cyclohexylmethoxy)phenyl]methyl}-2-methylpyridine-3-carboxamide | | 470.9 | 8.93 (s, 1H), 8.87 (br t, J = 5.2 Hz, 1H), 8.62 (d, J = 7.0 Hz, 1H), 8.17 (s, 1H), 7.78 (s, 1H), 7.30 (br t, J = 7.6 Hz, 2H), 7.23 (t, J = 7.8 Hz, 1H), 6.97 (d, J = 8.2 Hz, 1H), 6.93 (t, J = 7.6 Hz, 1H), 6.05 (s, 2H), 4.48 (br d, J = 5.2 Hz, 2H), 3.82 (br d, J = 6.1 Hz, 2H), 2.60 (s, 3H), 1.82 (br d, J = 12.8 Hz, 2H), 1.76 (br s, 1H), 1.70-1.60 (m, 3H), 1.26-1.05 (m, 5H). |
| 231 | 5-{2-amino-[1,2,4]triazolo-[1,5-a]pyridin-7-yl}-N-{[2-(cyclopentylmethoxy)pyridin-3-yl]methyl}-2-methylpyridine-3-carboxamide | | 458.1 | 9.01-8.89 (m, 2H), 8.64 (d, J = 6.7 Hz, 1H), 8.22 (s, 1H), 8.06 (d, J = 4.0 Hz, 1H), 7.81 (s, 1H), 7.68 (d, J = 7.0 Hz, 1H), 7.32 (d, J = 6.7 Hz, 1H), 7.04-6.93 (m, 1H), 6.07 (s, 2H), 4.44 (d, J = 5.5 Hz, 2H), 4.20 (d, J = 7.0 Hz, 2H), 2.60 (s, 3H), 2.39-2.28 (m, 1H), 1.77 (d, J = 7.0 Hz, 2H), 1.66-1.44 (m, 4H), 1.36 (dd, J = 12.2, 6.4 Hz, 2H). |
| 232 | 5-{2-amino-[1,2,4]triazolo-[1,5-a]pyridin-7-yl}-N-{[2-(cyclopentylmethoxy)-3,5-difluorophenyl]methyl}-2-methylpyridine-3-carboxamide | | 493.3 | 9.05 (br. s., 1H), 8.96 (s, 1H), 8.64 (d, J = 6.8 Hz, 1H), 8.22 (br. s., 1H), 7.81 (s, 1H), 7.32 (d, J = 6.8 Hz, 1H), 7.23 (t, J = 8.8 Hz, 1H), 7.04 (d, J = 8.2 Hz, 1H), 6.09 (s, 2H), 4.54 (d, J = 5.2 Hz, 2H), 3.90 (d, J = 6.8 Hz, 2H), 2.58 (s, 3H), 2.33 (dt, J = 14.7, 7.3 Hz, 1H), 1.78 (d, J = 6.2 Hz, 2H), 1.64-1.46 (m, 4H), 1.36 (d, J = 5.8 Hz, 2H). |

TABLE 5-continued

Compounds in Table 1 were prepared in a similar fashion to example 82.

| Ex No | Name | R | M + H | 1H NMR (500 MHz, DMSO-d6) δ |
|---|---|---|---|---|
| 233 | 5-{2-amino-[1,2,4]triazolo-[1,5-a]pyridin-7-yl}-N-{[2-(cyclobutylmethoxy)-pyridin-3-yl]methyl}-2-methylpyridine-3-carboxamide | | 444.0 | 9.01-8.91 (m, 2H), 8.63 (d, J = 6.9 Hz, 1H), 8.21 (s, 1H), 8.05 (d, J = 4.3 Hz, 1H), 7.80 (s, 1H), 7.67 (d, J = 7.1 Hz, 1H), 7.32 (d, J = 6.9 Hz, 1H), 7.02-6.95 (m, 1H), 6.08 (s, 2H), 4.42 (d, J = 5.5 Hz, 2H), 4.28 (d, J = 6.5 Hz, 2H), 2.78-2.69 (m, 1H), 2.59 (s, 3H), 2.04 (d, J = 6.6 Hz, 2H), 1.85 (br. s., 4H). |
| 234 | 5-{2-amino-[1,2,4]triazolo-[1,5-a]pyridin-7-yl}-2-methyl-N-{1-[3-trifluoromethoxy)phenyl]ethyl}-pyridine-3-carboxamide | | 457.1 | 9.08 (d, J = 7.7 Hz, 1H), 8.95 (s, 1H), 8.64 (d, J = 7.0 Hz, 1H), 8.15 (s, 1H), 7.81 (s, 1H), 7.55-7.42 (m, 2H), 7.39 (br. s., 1H), 7.32 (d, J = 7.0 Hz, 1H), 7.25 (d, J = 7.6 Hz, 1H), 6.09 (s, 2H), 5.22-5.14 (m, 1H), 1.48 (d, J = 7.0 Hz, 3H) [3 protons from one methyl group lost in water suppression]. |
| 235 | 5-{2-amino-[1,2,4]triazolo-[1,5-a]pyridin-7-yl}-N-{[2-(cyclopropylmethoxy)-3,5-difluorophenyl]methyl}-2-methylpyridine-3-carboxamide | | 465.0 | 9.10-9.00 (m, 1H), 8.96 (s, 1H), 8.64 (d, J = 7.0 Hz, 1H), 8.22 (s, 1H), 7.81 (s, 1H), 7.32 (d, J = 6.7 Hz, 1H), 7.22 (t, J = 8.5 Hz, 1H), 7.05 (d, J = 8.8 Hz, 1H), 6.07 (s, 2H), 4.58 (d, J = 5.5 Hz, 2H), 3.87 (d, J = 7.3 Hz, 2H), 2.59 (s, 3H), 1.24 (br. s., 1H), 0.55 (d, J = 7.0 Hz, 2H), 0.29 (d, J = 4.6 Hz, 2H). |
| 236 | 5-{2-amino-[1,2,4]triazolo-[1,5-a]pyridin-7-yl}-N-{[3-(cyclobutylmethoxy)-pyridin-2-yl]methyl}-2-methylpyridine-3-carboxamide | | 444.3 | 8.90 (s, 1H), 8.81 (t, J = 5.0 Hz, 1H), 8.60 (d, J = 7.0 Hz, 1H), 8.17 (s, 1H), 8.08 (d, J = 4.6 Hz, 1H), 7.75 (s, 1H), 7.41 (d, J = 8.2 Hz, 1H), 7.32-7.22 (m, 2H), 6.04 (s, 2H), 4.60 (d, J = 5.2 Hz, 2H), 4.02 (d, J = 6.4 Hz, 2H), 2.80-2.68 (m, 1H), 2.60 (s, 3H), 2.12-1.99 (m, 2H), 1.88 (br. s., 4H). |
| 237 | 5-{2-amino-[1,2,4]triazolo-[1,5-a]pyridin-7-yl}-2-methyl-N-({2-[(3-methylcyclopentyl)oxy]phenyl}methyl)pyridine-3-carboxamide | | 457.1 | 8.96 (s, 1H), 8.85 (br. s., 1H), 8.66 (d, J = 6.9 Hz, 1H), 8.19 (d, J = 7.0 Hz, 1H), 7.81 (br. s., 1H), 7.32 (dd, J = 15.0, 7.1 Hz, 2H), 7.28-7.17 (m, 1H), 6.99-6.87 (m, 2H), 4.95-4.78 (m, 1H), 4.51-4.38 (m, 2H), 3.36 (br. s., 1H), 2.61 (br. s., 3H), 2.34-1.67 (m, 5H), 1.49-1.06 (m, 3H), 1.04-0.91 (m, 3H). |
| 238 | 5-{2-amino-[1,2,4]triazolo-[1,5-a]pyridin-7-yl}-N-{[3-(cyclopropylmethoxy)-pyridin-2-yl]methyl}-2-methylpyridine-3-carboxamide | | 430.1 | 8.94 (s, 1H), 8.80 (br. s., 1H), 8.64 (d, J = 7.0 Hz, 1H), 8.20 (s, 1H), 8.10 (d, J = 4.6 Hz, 1H), 7.79 (s, 1H), 7.40 (d, J = 8.2 Hz, 1H), 7.34-7.23 (m, 2H), 6.07 (s, 2H), 4.63 (d, J = 5.2 Hz, 2H), 3.94 (d, J = 6.7 Hz, 2H), 2.62 (s, 3H), 1.27 (br. s., 1H), 0.58 (d, J = 7.6 Hz, 2H), 0.37 (d, J = 4.6 Hz, 2H). |

TABLE 5-continued

Compounds in Table 1 were prepared in a similar fashion to example 82.

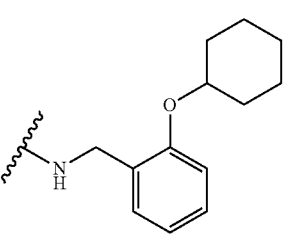 [SMILES: *NCc1ccccc1OC1CCCCC1]

| Ex No | Name | R | M + H | 1H NMR (500 MHz, DMSO-d6) δ |
|---|---|---|---|---|
| 239 | 5-{2-amino-[1,2,4]triazolo-[1,5-a]pyridin-7-yl}-N-{[2-(cyclohexyloxy)phenyl]-methyl}-2-methylpyridine-3-carboxamide | 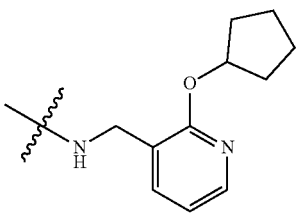 [SMILES: *NCc1cccnc1OC1CCCC1] | 457.0 | 8.94 (s, 1H), 8.86 (t, J = 5.5 Hz, 1H), 8.64 (d, J = 6.7 Hz, 1H), 8.22-8.11 (m, 1H), 7.80 (s, 1H), 7.31 (t, J = 6.0 Hz, 2H), 7.27-7.17 (m, 1H), 7.02 (d, J = 8.2 Hz, 1H), 6.92 (t, J = 7.3 Hz, 1H), 4.49 (d, J = 5.5 Hz, 2H), 4.43 (br. s., 1H), 3.52-3.44 (m, 1H), 2.61 (s, 3H), 1.88 (br. s., 2H), 1.71 (br. s., 2H), 1.64-1.25 (m, 7H). |
| 240 | 5-{2-amino-[1,2,4]triazolo-[1,5-a]pyridin-7-yl}-N-{[2-(cyclopentyloxy)-pyridin-3-yl]methyl}-2-methylpyridine-3-carboxamide | 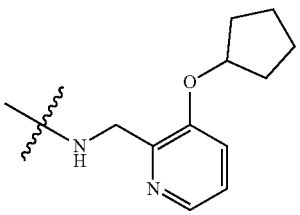 [SMILES: *NCc1ncccc1OC1CCCC1] | 444.2 | 8.96 (s, 1H), 8.93 (t, J = 5.3 Hz, 1H), 8.66 (d, J = 6.9 Hz, 1H), 8.21 (s, 1H), 8.07 (d, J = 4.6 Hz, 1H), 7.82 (s, 1H), 7.67 (d, J = 7.2 Hz, 1H), 7.33 (d, J = 6.9 Hz, 1H), 7.01-6.88 (m, 1H), 5.45 (br. s., 1H), 4.39 (d, J = 5.4 Hz, 2H), 3.90 (s, 1H), 3.16 (s, 1H), 2.60 (s, 3H), 1.92 (br. s., 2H), 1.80-1.65 (m, 4H), 1.58 (br. s., 2H). |
| 241 | 5-{2-amino-[1,2,4]triazolo-[1,5-a]pyridin-7-yl}-N-{[3-(cyclopentyloxy)-pyridin-2-yl]methyl}-2-methylpyridine-3-carboxamide | 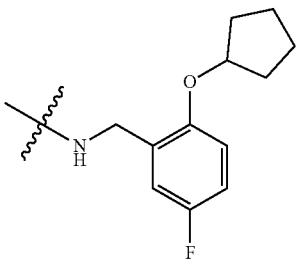 [SMILES: *NCc1cc(F)ccc1OC1CCCC1] | 444.2 | 8.94 (s, 1H), 8.80 (t, J = 5.3 Hz, 1H), 8.65 (d, J = 7.0 Hz, 1H), 8.18 (s, 1H), 8.08 (d, J = 4.5 Hz, 1H), 7.79 (s, 1H), 7.42 (d, J = 8.2 Hz, 1H), 7.34-7.23 (m, 2H), 6.10 (s, 2H), 4.93 (br. s., 1H), 4.57 (d, J = 5.4 Hz, 2H), 2.62 (s, 3H), 1.93 (d, J = 6.2 Hz, 2H), 1.83-1.69 (m, 4H), 1.66-1.54 (m, 2H). |
| 242 | 5-{2-amino-[1,2,4]triazolo-[1,5-a]pyridin-7-yl}-N-{[2-(cyclopentyloxy)-5-fluorophenyl]methyl}-2-methylpyridine-3-carboxamide | 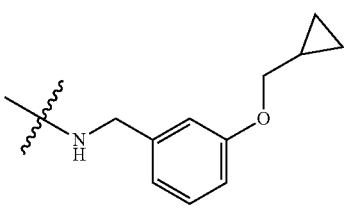 [SMILES: *NCc1cccc(OCC2CC2)c1] | 461.1 | 8.95 (d, J = 1.8 Hz, 1H), 8.88 (t, J = 5.6 Hz, 1H), 8.64 (d, J = 6.7 Hz, 1H), 8.19 (d, J = 1.8 Hz, 1H), 7.79 (s, 1H), 7.31 (d, J = 7.0 Hz, 1H), 7.10 (dd, J = 9.2, 2.7 Hz, 1H), 7.07-7.02 (m, 1H), 7.01-6.96 (m, 1H), 6.06 (s, 2H), 4.84 (br. s., 1H), 4.42 (d, J = 5.8 Hz, 2H), 2.59 (s, 3H), 1.89 (d, J = 5.8 Hz, 2H), 1.81-1.65 (m, 4H), 1.58 (br. s., 2H). |
| 243 | 5-{2-amino-[1,2,4]triazolo-[1,5-a]pyridin-7-yl}-N-{[3-(cyclopropylmethoxy)-phenyl]methyl}-2-methyl-pyridine-3-carboxamide | | 429.1 | 9.05 (t, J = 5.8 Hz, 1H), 8.94 (s, 1H), 8.62 (d, J = 7.0 Hz, 1H), 8.16 (d, J = 1.8 Hz, 1H), 7.79 (s, 1H), 7.31 (d, J = 5.8 Hz, 1H), 7.25 (t, J = 7.8 Hz, 1H), 6.97-6.88 (m, 2H), 6.81 (d, J = 9.2 Hz, 1H), 4.47 (d, J = 5.8 Hz, 2H), 3.80 (d, J = 7.0 Hz, 2H), 3.42 (d, J = 5.2 Hz, 1H), 3.16 (br. s., 1H), 2.58 (s, 3H), 1.20 (br. s., 1H), 0.59-0.48 (m, 2H), 0.29 (d, J = 5.2 Hz, 2H). |

TABLE 5-continued

Compounds in Table 1 were prepared in a similar fashion to example 82.

| Ex No | Name | R | M + H | 1H NMR (500 MHz, DMSO-d6) δ |
|---|---|---|---|---|
| 244 | 5-{2-amino-[1,2,4]triazolo-[1,5-a]pyridin-7-yl}-2-methyl-N-{[2-(1,1,2,2-tetrafluoroethoxy)phenyl]methyl}pyridine-3-carboxamide | | 475.1 | 9.07 (t, J = 5.6 Hz, 1H), 8.96 (d, J = 2.1 Hz, 1H), 8.64 (d, J = 6.1 Hz, 1H), 8.22 (d, J = 2.1 Hz, 1H), 7.81 (s, 1H), 7.60-7.50 (m, 1H), 7.45-7.37 (m, 2H), 7.36-7.29 (m, 2H), 7.03-6.73 (m, 1H), 6.07 (s, 2H), 4.54 (d, J = 5.5 Hz, 2H), 2.60 (s, 3H). |
| 245 | 5-{2-amino-[1,2,4]triazolo-[1,5-a]pyridin-7-yl}-N-{[2-(cyclopropylmethoxy)-6-fluorophenyl]methyl}-2-methylpyridine-3-carboxamide | | 447.2 | 8.91 (s, 1H), 8.69-8.59 (m, 2H), 8.05 (s, 1H), 7.76 (s, 1H), 7.33-7.24 (m, 2H), 6.86 (d, J = 8.3 Hz, 1H), 6.81 (t, J = 8.8 Hz, 1H), 6.08 (br. s., 2H), 4.53 (d, J = 4.2 Hz, 2H), 3.90 (d, J = 6.6 Hz, 2H), 2.56 (s, 3H), 0.84 (t, J = 6.2 Hz, 1H), 0.52 (d, J = 7.7 Hz, 2H), 0.33 (d, J = 4.5 Hz, 2H). |
| 246 | 5-{2-amino-[1,2,4]triazolo-[1,5-a]pyridin-7-yl}-2-methyl-N-{[3-(trifluoromethoxy)phenyl]methyl}-pyridine-3-carboxamide | | 442.9 | (400 MHz) 9.15 (t, J = 5.7 Hz, 1H), 8.97 (d, J = 2.1 Hz, 1H), 8.65 (d, J = 7.0 Hz, 1H), 8.21 (d, J = 2.1 Hz, 1H), 7.81 (s, 1H), 7.55-7.48 (m, 1H), 7.47-7.40 (m, 1H), 7.37 (br. s., 1H), 7.34-7.22 (m, 2H), 6.19-5.97 (m, 2H), 4.56 (d, J = 5.9 Hz, 2H), 2.58 (s, 3H). |
| 247 | 5-{2-amino-[1,2,4]triazolo-[1,5-a]pyridin-7-yl}-N-{[2-(cyclopentyloxy)-6-fluorophenyl]methyl}-2-methylpyridine-3-carboxamide | | 460.9 | 8.91 (s, 1H), 8.66-8.57 (m, 2H), 8.01 (s, 1H), 7.74 (s, 1H), 7.34-7.22 (m, 2H), 6.86 (d, J = 8.3 Hz, 1H), 6.78 (t, J = 8.8 Hz, 1H), 6.09 (s, 2H), 4.89 (br. s., 1H), 4.47 (d, J = 4.2 Hz, 2H), 2.59-2.52 (m, 3H), 1.97-1.83 (m, 2H), 1.81-1.61 (m, 4H), 1.54 (br. s., 2H). |
| 248 | 5-{2-amino-[1,2,4]triazolo-[1,5-a]pyridin-7-yl}-N-{[2-(cyclobutylmethoxy)-phenyl]-methyl}-2-methyl-pyridine-3-carboxamide | | 443.2 | 8.96 (s, 1H), 8.87 (t, J = 5.5 Hz, 1H), 8.65 (d, J = 7.0 Hz, 1H), 8.20 (s, 1H), 7.81 (s, 1H), 7.32 (br. s., 2H), 7.25 (t, J = 7.5 Hz, 1H), 7.00 (d, J = 8.2 Hz, 1H), 6.97-6.91 (m, 1H), 6.07 (s, 2H), 4.50 (d, J = 5.5 Hz, 2H), 4.00 (d, J = 6.4 Hz, 2H), 2.77 (d, J = 6.1 Hz, 1H), 2.61 (s, 3H), 2.14-2.02 (m, 2H), 1.90 (br. s., 4H). |
| 249 | 5-{2-amino-[1,2,4]triazolo-[1,5-a]pyridin-7-yl}-N-{[2-(cyclopentyloxy)phenyl]methyl}-2-methylpyridine-3-carboxamide | | 443.0 | 8.96 (d, J = 1.8 Hz, 1H), 8.83 (t, J = 5.5 Hz, 1H), 8.65 (d, J = 6.1 Hz, 1H), 8.18 (d, J = 1.8 Hz, 1H), 7.81 (s, 1H), 7.36-7.28 (m, 2H), 7.24 (t, J = 7.3 Hz, 1H), 7.00 (d, J = 7.9 Hz, 1H), 6.96-6.87 (m, 1H), 6.08 (s, 2H), 4.89 (br. s., 1H), 4.45 (d, J = 5.5 Hz, 2H), 2.61 (s, 3H), 1.97-1.85 (m, 2H), 1.83-1.66 (m, 4H), 1.59 (br. s., 2H). |

TABLE 5-continued

Compounds in Table 1 were prepared in a similar fashion to example 82.

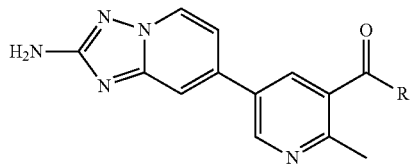

| Ex No | Name | R | M + H | 1H NMR (500 MHz, DMSO-d6) δ |
|---|---|---|---|---|
| 250 | 5-{2-amino-[1,2,4]triazolo-[1,5-a]pyridin-7-yl}-N-{[2-(cyclopropylmethoxy)-phenyl]methyl}-2-methyl-pyridine-3-carboxamide | | 429.2 | 8.96 (d, J = 1.6 Hz, 1H), 8.90 (t, J = 5.6 Hz, 1H), 8.65 (d, J = 7.0 Hz, 1H), 8.21 (d, J = 1.8 Hz, 1H), 7.82 (s, 1H), 7.32 (t, J = 6.9 Hz, 2H), 7.25-7.19 (m, 2H), 7.00-6.90 (m, 2H), 6.10 (br. s., 1H), 4.50 (d, J = 5.6 Hz, 2H), 3.89 (d, J = 6.7 Hz, 2H), 2.61 (s, 3H), 1.25 (d, J = 6.6 Hz, 1H), 0.60-0.52 (m, 2H), 0.39-0.30 (m, 2H). |
| 251 | 5-{2-amino-[1,2,4]triazolo-[1,5-a]pyridin-7-yl}-2-methyl-N-{1-[3-trifluoromethoxy)phenyl]ethyl}-pyridine-3-carboxamide | | 457.2 | 9.07 (d, J = 7.3 Hz, 1H), 8.94 (s, 1H), 8.63 (d, J = 6.7 Hz, 1H), 8.13 (br. s., 1H), 7.79 (s, 1H), 7.54-7.43 (m, 2H), 7.38 (br. s., 1H), 7.31 (d, J = 7.0 Hz, 1H), 7.24 (d, J = 7.6 Hz, 1H), 6.06 (br. s., 2H), 5.18 (t, J = 7.2 Hz, 1H), 3.56 (br. s., 3H), 1.48 (d, J = 6.7 Hz, 3H). |
| 252 | 5-{2-amino-[1,2,4]triazolo-[1,5-a]pyridin-7-yl}-N-{[2-fluoro-5-(trifluoromethoxy)phenyl](deutero)methyl}-2-methylpyridine-3-carboxamide | | 463.1 | 9.13 (s, 1H), 8.90 (br. s., 1H), 8.59 (d, J = 6.7 Hz, 1H), 8.13 (s, 1H), 7.74 (br. s., 1H), 7.38 (d, J = 4.6 Hz, 1H), 7.34-7.26 (m, 3H), 7.25-7.01 (m, 2H), 2.46 (br. s., 3H). |
| 253 | 5-{2-amino-[1,2,4]triazolo-[1,5-a]pyridin-7-yl}-N-{[2-(cyclopropylmethoxy)-3,5-difluorophenyl](deutero)methyl}-2-methylpyridine-3-carboxamide | | 467.2 | 9.08 (br s, 1H), 8.94 (br s, 1H), 8.65 (br s, 1H), 8.20 (br s, 1H), 7.80 (br s, 1H), 7.32 (br d, J = 6.8 Hz, 1H), 7.27-7.14 (m, 1H), 7.04 (br d, J = 8.3 Hz, 1H), 6.08 (br s, 2H), 3.91-3.81 (m, 2H), 2.61-2.54 (m, 3H), 1.23 (br s, 1H), 0.54 (br d, J = 7.3 Hz, 2H), 0.28 (br d, J = 4.5 Hz, 2H). |
| 254 | 5-{2-amino-[1,2,4]triazolo-[1,5-a]pyridin-7-yl}-N-{[2-chloro-5-(trifluoromethyl)-phenyl]methyl}-2-methyl-pyridine-3-carboxamide | | 461.3 | 9.23 (br s, 1H), 8.95 (br s, 1H), 8.63 (br d, J = 6.6 Hz, 1H), 8.19 (br s, 1H), 7.79-7.75 (m, 2H), 7.73 (br d, J = 9.8 Hz, 2H), 7.31 (br d, J = 7.0 Hz, 1H), 6.09 (br s, 2H), 4.63 (br d, J = 5.2 Hz, 2H), 2.57 (s, 3H). |
| 255 | 5-{2-amino-[1,2,4]triazolo-[1,5-a]pyridin-7-yl}-N-{1-[2-fluoro-5-(trifluoromethoxy)phenyl]ethyl}-2-methylpyridine-3-carboxamide | | 475.0 | 9.15 (br d, J = 7.1 Hz, 1H), 8.97 (br s, 1H), 8.65 (br d, J = 6.8 Hz, 1H), 8.16 (br s, 1H), 7.81 (br s, 1H), 7.47 (br s, 1H), 7.41-7.30 (m, 3H), 6.11 (br s, 2H), 5.35 (br t, J = 7.0 Hz, 1H), 2.50-2.47 (m, 3H), 1.48 (br d, J = 6.9 Hz, 3H). |

TABLE 6

Compounds in Table 1 were prepared in a similar fashion to example 17.

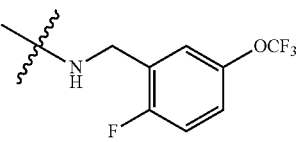 [SMILES: *NCc1cc(OC(F)(F)F)ccc1F]

| Ex No | Name | R | M + H | 1H NMR (500 MHz, DMSO-d6) δ |
|---|---|---|---|---|
| 256 | 5-{2-amino-[1,2,4]triazolo[1,5-a]pyridin-7-yl}-N-{[2-fluoro-5-(trifluoromethoxy)phenyl]methyl}-6-methylpyridine-3-carboxamide | 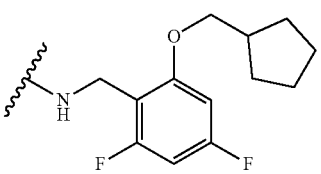 [SMILES: *NCc1c(F)cc(F)cc1OCC1CCCC1] | 461.2 | 9.30-9.25 (m, 1H), 8.96 (s, 1H), 8.62 (d, J = 6.7 Hz, 1H), 8.15 (s, 1H), 7.45 (s, 1H), 7.40-7.32 (m, 3H), 6.98 (br d, J = 5.8 Hz, 1H), 6.06 (s, 2H), 4.55 (br d, J = 5.2 Hz, 2H), 2.56-2.52 (m, 3H). |
| 257 | 5-{2-amino-[1,2,4]triazolo[1,5-a]pyridin-7-yl}-N-{[2-(cyclopentylmethoxy)-4,6-difluorophenyl]methyl}-6-methylpyridine-3-carboxamide | 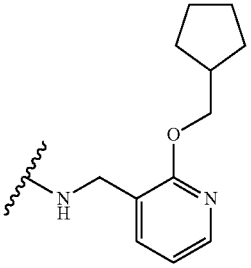 [SMILES: *NCc1cccnc1OCC1CCCC1] | 493.3 | 8.97-8.93 (m, 1H), 8.89 (s, 1H), 8.66-8.59 (m, 1H), 8.08 (s, 1H), 7.40 (s, 1H), 6.99-6.93 (m, 1H), 6.82-6.75 (m, 1H), 6.05 (br s, 2H), 4.46-4.41 (m, 2H), 3.88 (br d, J = 6.7 Hz, 2H), 2.55-2.53 (m, 3H), 2.30-2.21 (m, 1H), 1.76-1.65 (m, 2H), 1.56 (br s, 1H), 1.49 (br s, 2H), 1.47-1.39 (m, 2H), 1.38-1.24 (m, 2H). |
| 258 | 5-{2-amino-[1,2,4]triazolo[1,5-a]pyridin-7-yl}-N-{[2-(cyclopentylmethoxy)pyridin-3-yl]methyl}-6-methylpyridine-3-carboxamide | 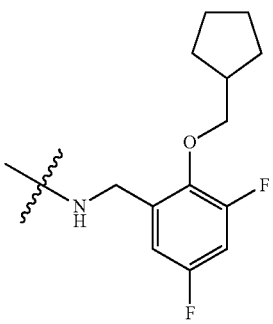 [SMILES: *NCc1cc(F)cc(F)c1OCC1CCCC1] | 458.0 | 9.05 (t, J = 6.1 Hz, 1H), 8.96 (s, 1H), 8.63 (br d, J = 6.7 Hz, 1H), 8.17 (s, 1H), 8.03 (br d, J = 3.7 Hz, 1H), 7.59 (br d, J = 7.3 Hz, 1H), 7.45 (br s, 1H), 6.98 (d, J = 6.8 Hz, 1H), 6.94 (t, J = 6.5 Hz, 1H), 6.07 (br s, 2H), 4.43 (br d, J = 5.5 Hz, 2H), 4.18 (d, J = 6.7 Hz, 2H), 2.54 (m, 3H), 2.30 (dq, J = 14.9, 7.3 Hz, 1H), 1.73 (br d, J = 7.0 Hz, 2H), 1.60-1.44 (m, 4H), 1.32 (br dd, J = 12.2, 6.7 Hz, 2H). |
| 259 | 5-{2-amino-[1,2,4]triazolo[1,5-a]pyridin-7-yl}-N-{[2-(cyclopentylmethoxy)-3,5-difluorophenyl]methyl}-6-methylpyridine-3-carboxamide | 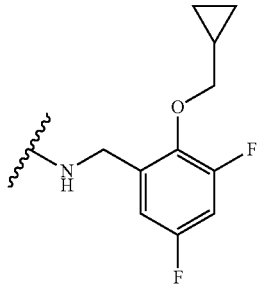 [SMILES: *NCc1cc(F)cc(F)c1OCC1CC1] | 493.3 | 9.21 (br. s., 1H), 8.96 (s, 1H), 8.62 (d, J = 6.6 Hz, 1H), 8.17 (s, 1H), 7.46 (br. s., 1H), 7.27-7.03 (m, 3H), 7.03-6.88 (m, 2H), 6.09 (br. s., 2H), 4.53 (d, J = 5.0 Hz, 2H), 3.17 (s, 3H), 2.30 (dd, J = 15.6, 7.7 Hz, 1H), 1.74 (br. s., 2H), 1.63-1.44 (m, 4H), 1.34 (d, J = 5.4 Hz, 2H). |
| 260 | 5-{2-amino-[1,2,4]triazolo[1,5-a]pyridin-7-yl}-N-{[2-(cyclopropylmethoxy)-3,5-difluorophenyl]methyl}-6-methylpyridine-3-carboxamide | | 465.2 | 9.23 (t, J = 5.6 Hz, 1H), 8.93 (s, 1H), 8.59 (d, J = 6.8 Hz, 1H), 8.15 (s, 1H), 7.44 (s, 1H), 7.15 (t, J = 8.5 Hz, 1H), 6.99 (d, J = 6.9 Hz, 1H), 6.92 (d, J = 9.1 Hz, 1H), 6.06 (s, 2H), 4.55 (d, J = 5.6 Hz, 2H), 3.71 (br. s., 2H), 2.52 (s, 3H), 1.19 (br. s., 1H), 0.58-0.45 (m, 2H), 0.24 (d, J = 4.7 Hz, 2H). |

TABLE 6-continued

Compounds in Table 1 were prepared in a similar fashion to example 17.

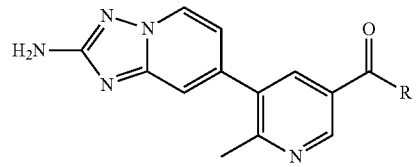

| Ex No | Name | R | M + H | 1H NMR (500 MHz, DMSO-d6) δ |
|---|---|---|---|---|
| 261 | 5-{2-amino-[1,2,4]triazolo[1,5-a]pyridin-7-yl}-N-{[2-(cyclobutylmethoxy)pyridin-3-yl]methyl}-6-methylpyridine-3-carboxamide | | 443.8 | 9.06 (t, J = 5.4 Hz, 1H), 8.89 (s, 1H), 8.55 (d, J = 6.8 Hz, 1H), 8.10 (s, 1H), 7.97 (d, J = 4.3 Hz, 1H), 7.53 (d, J = 7.0 Hz, 1H), 7.38 (s, 1H), 6.94 (d, J = 6.7 Hz, 1H), 6.92-6.86 (m, 1H), 6.02 (s, 2H), 4.37 (d, J = 5.3 Hz, 2H), 4.20 (d, J = 6.3 Hz, 2H), 2.64 (d, J = 6.3 Hz, 1H), 2.48 (s, 3H), 1.94 (d, J = 7.6 Hz, 2H), 1.82-1.71 (m, 4H). |
| 262 | 5-{2-amino-[1,2,4]triazolo[1,5-a]pyridin-7-yl}-N-{[2-(cyclopentylmethoxy)-5-fluorophenyl]methyl}-6-methylpyridine-3-carboxamide | | 474.9 | 9.06 (t, J = 5.4 Hz, 1H), 8.96 (s, 1H), 8.62 (d, J = 6.9 Hz, 1H), 8.18 (s, 1H), 7.46 (s, 1H), 7.07-6.91 (m, 4H), 6.09 (s, 2H), 4.46 (d, J = 5.5 Hz, 2H), 3.86 (d, J = 6.6 Hz, 2H), 2.55-2.54 (m, 3H), 2.29 (dt, J = 14.6, 7.3 Hz, 1H), 1.75 (d, J = 6.9 Hz, 2H), 1.62-1.44 (m, 4H), 1.41-1.26 (m, 2H). |
| 263 | 5-{2-amino-[1,2,4]triazolo[1,5-a]pyridin-7-yl}-N-{[2-(cyclopentylmethoxy)phenyl]methyl}-6-methylpyridine-3-carboxamide | | 457.1 | 9.07-8.90 (m, 1H), 8.63 (d, J = 6.6 Hz, 1H), 8.18 (br. s., 1H), 7.46 (br. s., 1H), 7.27-7.15 (m, 2H), 6.99 (t, J = 8.5 Hz, 2H), 6.89 (t, J = 7.2 Hz, 1H), 6.10 (br. s., 2H), 4.48 (d, J = 5.0 Hz, 2H), 3.89 (d, J = 6.4 Hz, 2H), 2.55 (s, 3H), 2.37-2.25 (m, 1H), 1.75 (br. s., 2H), 1.63-1.42 (m, 4H), 1.36 (d, J = 5.4 Hz, 2H). |

TABLE 7

Compounds in Table 1 were prepared in a similar fashion to example 13.

| Ex No | Name | R | M + H | 1H NMR (500 MHz, DMSO-d6) δ |
|---|---|---|---|---|
| 264 | 5-{2-amino-[1,2,4]triazolo[1,5-a]pyridin-7-yl}-N-{[2-(cyclopentyloxy)-5-fluorophenyl]methyl}-2-ethoxypyridine-3-carboxamide | | 491.2 | 8.74 (br. s., 1H), 8.68 (br. s., 1H), 8.59 (d, J = 6.7 Hz, 1H), 8.41 (br. s., 1H), 7.70 (br. s., 1H), 7.25 (d, J = 6.9 Hz, 1H), 7.13 (d, J = 9.2 Hz, 1H), 7.09-6.93 (m, 2H), 6.06 (br. s., 2H), 4.85 (br. s., 1H), 4.51 (q, J = 6.8 Hz, 2H), 4.43 (d, J = 5.6 Hz, 2H), 1.88 (br. s., 2H), 1.81-1.65 (m, 4H), 1.59 (br. s., 2H), 1.39 (t, J = 6.8 Hz, 3H). |
| 265 | 5-{2-amino-[1,2,4]triazolo[1,5-a]pyridin-7-yl}-2-ethoxy-N-({2-[(2,2,2-trifluoroethyl)sulfanyl]phenyl}methyl)pyridine-3-carboxamide | | 503.0 | 8.79 (t, J = 5.9 Hz, 1H), 8.76 (d, J = 2.2 Hz, 1H), 8.59 (d, J = 7.1 Hz, 1H), 8.45 (d, J = 2.4 Hz, 1H), 7.71 (s, 1H), 7.66-7.58 (m, 1H), 7.52-7.46 (m, 1H), 7.25 (dd, J = 7.0, 1.7 Hz, 1H), 6.05 (s, 2H), 4.75-4.63 (m, 2H), 4.59-4.45 (m, 2H), 4.06-3.96 (m, 2H), 1.39 (t, J = 7.0 Hz, 3H), 1.23 (s, 2H). |
| 266 | 5-{2-amino-[1,2,4]triazolo[1,5-a]pyridin-7-yl}-2-ethoxy-N-{[2-(propan-2-ylsulfanyl)phenyl]methyl}pyridine-3-carboxamide | | 463.1 | (600 MHz) δ 8.79-8.72 (m, 2H), 8.59 (d, J = 6.9 Hz, 1H), 8.46 (d, J = 2.4 Hz, 1H), 7.70 (d, J = 1.0 Hz, 1H), 7.46 (td, J = 9.2, 1.4 Hz, 2H), 7.32-7.22 (m, 3H), 6.04 (s, 2H), 4.62 (d, J = 5.9 Hz, 2H), 4.52 (q, J = 6.9 Hz, 2H), 3.48-3.41 (m, 1H), 1.43-1.37 (m, 3H), 1.30-1.25 (m, 6H). |
| 267 | 5-{2-amino-[1,2,4]triazolo[1,5-a]pyridin-7-yl}-N-{[2-(cyclopentyloxy)phenyl]methyl}-2-ethoxypyridine-3-carboxamide | | 473.1 | 8.73 (d, J = 2.4 Hz, 1H), 8.61-8.53 (m, 2H), 8.44 (d, J = 2.5 Hz, 1H), 7.69 (s, 1H), 7.31 (d, J = 7.2 Hz, 1H), 7.26-7.19 (m, 2H), 6.98 (d, J = 8.2 Hz, 1H), 6.89 (t, J = 7.4 Hz, 1H), 6.05 (s, 2H), 4.88 (br. s., 1H), 4.49 (q, J = 7.0 Hz, 2H), 4.45 (d, J = 5.8 Hz, 2H), 1.95-1.83 (m, 2H), 1.79-1.65 (m, 4H), 1.58 (br. s., 2H), 1.35 (t, J = 7.0 Hz, 3H). |
| 268 | 5-{2-amino-[1,2,4]triazolo[1,5-a]pyridin-7-yl}-N-{[2-(cyclobutylmethoxy)phenyl]methyl}-2-ethoxypyridine-3-carboxamide | | 472.9 | 8.73 (d, J = 2.5 Hz, 1H), 8.63-8.54 (m, 2H), 8.45 (d, J = 2.5 Hz, 1H), 7.69 (s, 1H), 7.32 (d, J = 7.3 Hz, 1H), 7.27-7.20 (m, 2H), 6.99 (d, J = 8.2 Hz, 1H), 6.91 (t, J = 7.4 Hz, 1H), 6.05 (s, 2H), 4.55-4.43 (m, 4H), 3.98 (d, J = 6.2 Hz, 2H) 2.79-2.68 (m, 1H), 2.05 (q, J = 7.2 Hz, 2H), 1.88 (br. s., 4H), 1.35 (t, J = 7.0 Hz, 3H). |
| 269 | 5-{2-amino-[1,2,4]triazolo[1,5-a]pyridin-7-yl}-2-ethoxy-N-[2-(2-phenoxyphenyl)ethyl]pyridine-3-carboxamide | | 495.3 | 8.70 (d, J = 2.4 Hz, 1H), 8.58 (d, J = 7.0 Hz, 1H), 8.35 (d, J = 2.4 Hz, 1H), 8.31 (t, J = 5.6 Hz, 1H), 7.66 (s, 1H), 7.40 (d, J = 7.1 Hz, 1H), 7.31 (t, J = 7.9 Hz, 2H), 7.28-7.19 (m, 2H), 7.14 (t, J = 7.4 Hz, 1H), 7.06 (t, J = 7.4 Hz, 1H), 6.91 (d, J = 7.9 Hz, 2H), 6.86 (d, J = 8.0 Hz, 1H), 4.42 (q, J = 7.0 Hz, 2H), 3.55-3.44 (m, 2H), 2.87 (t, J = 6.9 Hz, 2H), 1.27 (t, J = 7.0 Hz, 3H), 1.21 (s, 2H). |

TABLE 7-continued

Compounds in Table 1 were prepared in a similar fashion to example 13.

| Ex No | Name | R | M + H | 1H NMR (500 MHz, DMSO-d6) δ |
|---|---|---|---|---|
| 270 | 5-{2-amino-[1,2,4]triazolo[1,5-a]pyridin-7-yl}-2-ethoxy-N-({2-[2-(hydroxymethyl)benzenesulfonyl]phenyl}methyl)pyridine-3-carboxamide | | 559.2 | 8.83 (t, J = 5.9 Hz, 1H), 8.75 (d, J = 2.4 Hz, 1H), 8.59 (d, J = 7.0 Hz, 1H), 8.43 (d, J = 2.4 Hz, 1H), 8.06 (d, J = 7.9 Hz, 2H), 7.85-7.80 (m, 1H), 7.77 (t, J = 7.5 Hz, 2H), 7.72-7.56 (m, 4H), 7.24 (d, J = 6.9 Hz, 1H), 6.07 (s, 2H), 5.54 (t, J = 5.6 Hz, 1H), 4.63 (t, J = 5.9 Hz, 4H), 4.51 (q, J = 7.0 Hz, 2H), 1.40 (t, J = 7.0 Hz, 3H). |
| 271 | 5-{2-amino-[1,2,4]triazolo[1,5-a]pyridin-7-yl}-N-{[2-(difluoromethoxy)phenyl]methyl}-2-ethoxypyridine-3-carboxamide | | 454.9 | 8.81-8.73 (m, 2H), 8.60 (d, J = 7.0 Hz, 1H), 8.45 (d, J = 2.4 Hz, 1H), 7.72 (s, 1H), 7.51 (d, J = 7.4 Hz, 1H), 7.44-7.11 (m, 5H), 6.07 (s, 2H), 4.57 (d, J = 5.9 Hz, 2H), 4.52 (q, J = 7.0 Hz, 2H), 1.40 (t, J = 7.0 Hz, 3H). |
| 272 | 5-{2-amino-[1,2,4]triazolo[1,5-a]pyridin-7-yl}-N-{[2-(cyclopropylmethoxy)phenyl]methyl}-2-ethoxypyridine-3-carboxamide | | 459.2 | 8.75 (d, J = 2.4 Hz, 1H), 8.64 (t, J = 5.8 Hz, 1H), 8.59 (d, J = 7.0 Hz, 1H), 8.46 (d, J = 2.4 Hz, 1H), 7.71 (s, 1H), 7.33 (d, J = 7.3 Hz, 1H), 7.28-7.17 (m, 2H), 6.99 (d, J = 8.2 Hz, 1H), 6.06 (s, 2H), 4.55-4.48 (m, 4H), 3.90 (d, J = 6.7 Hz, 2H), 1.38 (t, J = 7.0 Hz, 3H), 0.84 (t, J = 6.7 Hz, 1H), 0.61-0.52 (m, 2H), 0.40-0.32 (m, 2H). |
| 273 | 5-{2-amino-[1,2,4]triazolo[1,5-a]pyridin-7-yl}-N-{[(1S,2S)-2-[(4-bromo-2-fluorophenoxy)methyl]cyclopropyl]methyl}-2-ethoxypyridine-3-carboxamide | | 555.1 | 8.74 (d, J = 2.1 Hz, 1H), 8.59 (d, J = 7.0 Hz, 1H), 8.41 (d, J = 2.2 Hz, 1H), 8.35 (t, J = 5.4 Hz, 1H), 7.69 (s, 1H), 7.43 (d, J = 10.9 Hz, 1H), 7.30-7.20 (m, 2H), 7.10 (t, J = 8.9 Hz, 1H), 6.06 (s, 2H), 4.48 (q, J = 7.0 Hz, 2H), 3.99-3.87 (m, 2H), 3.43-3.13 (m, 2H), 1.39 (t, J = 6.9 Hz, 3H), 1.30-1.07 (m, 2H), 0.68-0.53 (m, 2H). |
| 274 | 5-{2-amino-[1,2,4]triazolo[1,5-a]pyridin-7-yl}-2-ethoxy-N-{[1-(2-fluorophenyl)cyclopropyl]methyl}pyridine-3-carboxamide | | 447.2 | 8.73 (s, 1H), 8.60 (d, J = 6.9 Hz, 1H), 8.33 (s, 1H), 8.28 (br. s., 1H), 7.67 (s, 1H), 7.40 (t, J = 7.2 Hz, 1H), 7.30 (d, J = 5.6 Hz, 1H), 7.22-7.11 (m, 3H), 6.07 (s, 2H), 4.47 (q, J = 6.9 Hz, 2H), 3.54 (d, J = 5.6 Hz, 1H), 3.41 (br. s., 1H), 1.34 (t, J = 6.9 Hz, 3H), 1.01 (br. s., 2H), 0.80 (br. s., 2H). |
| 275 | 5-{2-amino-[1,2,4]triazolo[1,5-a]pyridin-7-yl}-2-ethoxy-N-[(2-{[2-(hydroxymethyl)phenyl]sulfanyl}phenyl)methyl]pyridine-3-carboxamide | | 526.9 | 8.77 (t, J = 5.8 Hz, 1H), 8.72 (d, J = 2.4 Hz, 1H), 8.57 (d, J = 7.0 Hz, 1H), 8.41 (d, J = 2.4 Hz, 1H), 7.68 (s, 1H), 7.53 (t, J = 6.7 Hz, 2H), 7.38-7.17 (m, 6H), 7.12 (d, J = 7.6 Hz, 1H), 7.03 (d, J = 7.6 Hz, 1H), 6.02 (s, 2H), 4.62-4.55 (m, 4H), 4.49 (q, J = 7.0 Hz, 2H), 1.37 (t, J = 7.0 Hz, 3H). |

TABLE 7-continued

Compounds in Table 1 were prepared in a similar fashion to example 13.

| Ex No | Name | R | M + H | 1H NMR (500 MHz, DMSO-d6) δ |
|---|---|---|---|---|
| 276 | 5-{2-amino-[1,2,4]triazolo[1,5-a]pyridin-7-yl}-N-[(3R)-3-(4-chlorophenyl)-3-hydroxypropyl]-2-ethoxypyridine-3-carboxamide | | 466.9 | 8.72 (d, J = 2.4 Hz, 1H), 8.57 (d, J = 7.0 Hz, 1H), 8.47-8.38 (m, 2H), 7.68 (s, 1H), 7.38 (s, 4H), 7.23 (d, J = 5.2 Hz, 1H), 6.03 (s, 2H), 5.55 (d, J = 4.6 Hz, 1H), 4.75-4.67 (m, 1H), 4.50 (q, J = 7.0 Hz, 2H), 3.16 (d, J = 5.2 Hz, 2H), 1.91-1.80 (m, 2H), 1.39 (t, J = 6.9 Hz, 3H). |
| 277 | 5-{2-amino-[1,2,4]triazolo[1,5-a]pyridin-7-yl}-2-ethoxy-N-[(2-phenoxyphenyl)methyl]pyridine-3-carboxamide | | 481.1 | 8.79-8.70 (m, 2H), 8.59 (d, J = 7.0 Hz, 1H), 8.39 (s, 1H), 7.69 (s, 1H), 7.52 (d, J = 7.4 Hz, 1H), 7.38 (t, J = 7.7 Hz, 2H), 7.33-7.28 (m, 1H), 7.24 (d, J = 6.2 Hz, 1H), 7.22-7.16 (m, 1H), 7.11 (t, J = 7.3 Hz, 1H), 6.99 (d, J = 7.9 Hz, 2H), 6.91 (d, J = 8.0 Hz, 1H), 6.06 (s, 2H), 4.55 (d, J = 5.8 Hz, 2H), 4.48 (q, J = 6.9 Hz, 2H), 1.36 (t, J = 7.0 Hz, 3H). |
| 278 | 5-{2-amino-[1,2,4]triazolo[1,5-a]pyridin-7-yl}-N-[(3S)-3-(4-chlorophenyl)-3-hydroxypropyl]-2-ethoxypyridine-3-carboxamide | | 467.2 | 8.73 (d, J = 2.4 Hz, 1H), 8.59 (d, J = 7.0 Hz, 1H), 8.42 (d, J = 2.4 Hz, 2H), 7.69 (s, 1H), 7.38 (s, 4H), 7.23 (d, J = 5.5 Hz, 1H), 6.03 (s, 2H), 5.51 (d, J = 4.6 Hz, 1H), 4.76-4.67 (m, 1H), 4.51 (q, J = 6.9 Hz, 2H), 3.17 (d, J = 5.5 Hz, 2H), 1.94-1.78 (m, 2H), 1.40 (t, J = 7.0 Hz, 3H). |
| 279 | 5-{2-amino-[1,2,4]triazolo[1,5-a]pyridin-7-yl}-N-(1-benzyl-1H-pyrazol-4-yl)-2-ethoxypyridine-3-carboxamide | | 455.3 | 10.32 (s, 1H), 8.76 (d, J = 1.9 Hz, 1H), 8.60 (d, J = 6.9 Hz, 1H), 8.41 (d, J = 1.9 Hz, 1H), 8.16 (s, 1H), 7.73 (s, 1H), 7.60 (s, 1H), 7.39-7.19 (m, 6H), 6.06 (s, 2H), 5.32 (s, 2H), 4.49 (q, J = 7.0 Hz, 2H), 1.38 (t, J = 7.0 Hz, 3H). |
| 280 | 5-{2-amino-[1,2,4]triazolo[1,5-a]pyridin-7-yl}-2-ethoxy-N-(3-phenylbutyl)pyridine-3-carboxamide | | 431.2 | 8.72 (d, J = 2.3 Hz, 1H), 8.59 (d, J = 7.0 Hz, 1H), 8.36 (d, J = 2.3 Hz, 1H), 8.24 (t, J = 5.2 Hz, 1H), 7.69 (s, 1H), 7.36-7.13 (m, 6H), 4.48 (q, J = 7.0 Hz, 2H), 3.42-3.13 (m, 2H), 2.90-2.78 (m, 1H), 1.82 (q, J = 7.0 Hz, 2H), 1.39 (t, J = 7.0 Hz, 3H), 1.24 (d, J = 6.9 Hz, 3H). Additional 2 protons not observed due to water suppression. |
| 281 | 5-{2-amino-[1,2,4]triazolo[1,5-a]pyridin-7-yl}-N-{[2-(cyclopropylmethoxy)-3,5-difluorophenyl]methyl}-2-ethoxypyridine-3-carboxamide | | 495.2 | 8.82 (t, J = 6.1 Hz, 1H), 8.78 (d, J = 2.6 Hz, 1H), 8.61 (d, J = 7.1 Hz, 1H), 8.43 (d, J = 2.6 Hz, 1H), 7.73 (d, J = 1.3 Hz, 1H), 7.29-7.19 (m, 2H), 7.08 (d, J = 9.0 Hz, 1H), 6.05 (s, 2H), 4.62 (d, J = 6.0 Hz, 2H), 4.54-4.50 (m, 2H), 3.90 (d, J = 7.2 Hz, 2H), 1.42 (t, J = 7.0 Hz, 3H), 1.26-1.22 (m, 1H), 0.64-0.53 (m, 2H), 0.34-0.28 (m, 2H) |

Example 282

5-(2-Amino-[1,2,4]triazolo[1,5-a]pyridin-7-yl)-N-(2-(cyclopropylmethoxy-d2)-3,5-difluorobenzyl)-2-(methoxy-d3)-6-methylnicotinamide

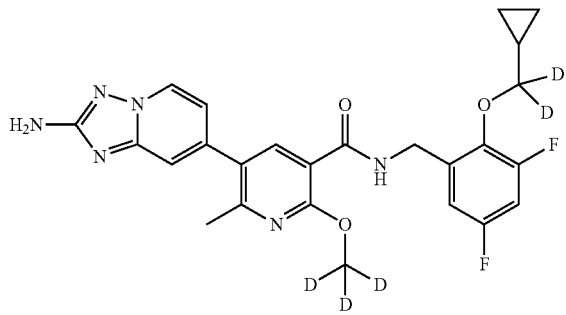 [SMILES: [2H]C([2H])([2H])Oc1nc(C)c(-c2ccn3nc(N)nc3c2)cc1C(=O)NCc1cc(F)cc(F)c1OC([2H])([2H])C1CC1]

282A: Cyclopropylmethanol-d2: To a mixture of cyclopropanecarboxylic acid (0.319 mL, 4 mmol) and sodium borodeuteride (0.385 g, 9.20 mmol) in THF (20 mL) at 0° C. was added iodine (1.015 g, 4.00 mmol) as a solution on 4 ml of THF over 45 min. The reaction mixture was stirred at rt for 18 h. The reaction was cooled back to 0° C. and was very carefully quenched with 1N HCl (10 ml). The resulting solution was partitioned between ethyl ether (50 ml) and 1.5M dibasic potassium phosphate solution (50 ml). The organic layer was washed with brine (50 ml), dried (MgSO$_4$) and concentrated to afford cyclopropylmethanol-d2 as a yellow liquid which was used as is in next step.

$^1$H NMR (400 MHz, CDCl$_3$) δ 1.15-1.00 (m, 1H), 0.60-0.45 (m, 2H), 0.27-0.14 (m, 2H).

282B: 2-(Cyclopropylmethoxy)-3,5-difluorobenzonitrile-d2: To a solution of 3,5-difluoro-2-hydroxybenzonitrile (400 mg, 2.58 mmol), cyclopropylmethanol-d2 (229 mg, 3.09 mmol) and triphenylphosphine (947 mg, 3.61 mmol) in THF (15 mL) at 0° C. was added DIAD (0.752 mL, 3.87 mmol). The reaction mixture was allowed to warm to rt and was stirred at rt for 3 d. The volatiles were removed in vacuo, and the residue was chromatographed on a 40 gm ISCO silica gel cartridge, eluting with a 0-50% EtOAc/Hex gradient. The pure fractions were concentrated to afford 2-(cyclopropylmethoxy)-3,5-difluorobenzonitrile-d2 (515 mg, 2.438 mmol, 95% yield) as a yellow oil which was used as is in the next step.

$^1$H NMR (400 MHz, DMSO-d6) δ 7.81 (ddd, J=11.7, 8.8, 3.1 Hz, 1H), 7.73-7.66 (m, 1H), 3.31 (s, 1H), 1.27-1.10 (m, 1H), 0.63-0.47 (m, 2H), 0.33-0.20 (m, 2H).

282C: 2-(Cyclopropylmethoxy)-3,5-difluorobenzylamine-d2: To a suspension of lithium aluminum hydride (367 mg, 9.68 mmol) in diethyl ether (25 mL) at 0° C. was added dropwise over 15 min a solution of 2-(cyclopropylmethoxy)-3,5-difluorobenzonitrile-d2 (511 mg, 2.419 mmol) in 5 ml of ether. After warming to rt, the reaction mixture was allowed to stir at rt ON. After re-cooling to 0° C., water (0.5 ml) was very carefully added to minimize gas evolution. 15% NaOH (0.5 ml) was added followed by water (1.5 ml).

After stirring 1 h, anhydrous magnesium sulfate was added. Filtration and concentration of the filtrate afforded 2-(cyclopropylmethoxy)-3,5-difluorobenzylamine-d2 (427 mg, 1.984 mmol, 82% yield) as a colorless oil which was carried forward without further purification.

$^1$H NMR (400 MHz, CDCl$_3$) δ 6.83 (dt, J=8.7, 2.2 Hz, 1H), 6.77-6.68 (m, 1H), 3.88 (s, 2H), 1.26-1.16 (m, 1H), 0.66-0.53 (m, 2H), 0.35-0.22 (m, 2H) NH2 protons missing.

282: A mixture of 5-(2-amino-[1,2,4]triazolo[1,5-a]pyridin-7-yl)-2-(methoxy-d3)-6-methylnicotinic acid (20 mg, 0.066 mmol), prepared as in Example 97, BOP (43.9 mg, 0.099 mmol), (2-(cyclopropylmethoxy-d2)-3,5-difluorophenyl)methanamine (14.24 mg, 0.066 mmol) and Hünig's base (0.058 mL, 0.331 mmol) in DMF (1.0 mL) was stirred at rt for 4 h. The reaction mixture was diluted to 75 mL with EtOAc, then washed with 10% LiCl (2×) and brine. The organic layer was dried over sodium sulfate, filtered and concentrated. The crude reaction mixture was purified by flash chromatography using a 4 g ISCO column, eluting with 0-100% EtOAc in hexanes, then 0-10% MeOH in DCM. An impurity remained, so the material was repurified by The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 4-minute hold at 100% B; Flow: 20 mL/min. Fractions containing the desired product were combined and dried via centrifugal evaporation. This afforded 5-(2-amino-[1,2,4]triazolo[1,5-a]pyridin-7-yl)-N-(2-(cyclopropylmethoxy-d2)-3,5-difluorobenzyl)-2-(methoxy-d3)-6-methylnicotinamide (9.3 mg, 0.019 mmol, 28% yield).

MS ESI m/z 500.3 (M+H)

$^1$H NMR (500 MHz, DMSO-d6) δ 8.83 (br t, J=5.8 Hz, 1H), 8.58 (d, J=6.7 Hz, 1H), 8.04 (s, 1H), 7.38 (s, 1H), 7.19 (br t, J=8.7 Hz, 1H), 7.00-6.88 (m, 2H), 6.04 (s, 2H), 4.60 (br d, J=5.8 Hz, 2H), 2.50-2.46 (m, 3H), 1.24 (br s, 1H), 0.56 (br d, J=7.9 Hz, 2H), 0.30 (br d, J=4.6 Hz, 2H)

TABLE 8

Compounds in Table 8 were prepared in a similar fashion to examples 90 and 282.

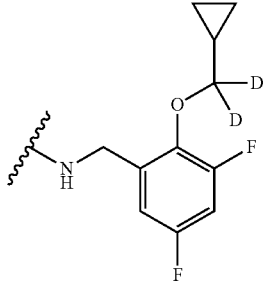 [SMILES: *NCc1cc(F)cc(F)c1OC([2H])([2H])C1CC1]

| Ex No | Name | R | M + H | 1H NMR (500 MHz, DMSO-d6) δ |
|---|---|---|---|---|
| 283 | 5-(2-amino-[1,2,4]triazolo[1,5-a]pyridin-7-yl)-N-(2-(cyclopropylmethoxy-d2)-3,5-difluorobenzyl)-2-(methoxy-H3)nicotinamide | 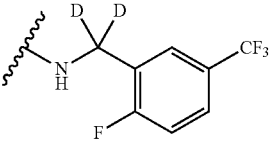 [SMILES: *NC([2H])([2H])c1cc(C(F)(F)F)ccc1F] | 486.1 | 1H NMR (500 MHz, DMSO-d6) δ 8.80 (t, J = 5.9 Hz, 1H), 8.75 (d, J = 2.6 Hz, 1H), 8.56 (d, J = 7.0 Hz, 1H), 8.44 (d, J = 2.5 Hz, 1H), 7.68 (d, J = 1.8 Hz, 1H), 7.23 (dd, J = 7.0, 2.0 Hz, 1H), 7.14 (ddd, J = 11.3, 8.4, 2.9 Hz, 1H), 7.01 (br d, J = 9.6 Hz, 1H), 5.89 (s, 2H), 4.62 (s, 2H), 1.24 (s, 1H), 0.62-0.52 (m, 2H), 0.35-0.25 (m, 2H). |
| 284 | 5-(2-amino-[1,2,4]triazolo[1,5-a]pyridin-7-yl)-N-((2-fluoro-5-(trifluoromethyl)phenyl)methyl-d2)-2-(methoxy-d3)nicotinamide | 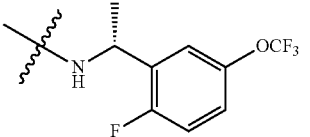 [SMILES: *N[C@H](C)c1cc(OC(F)(F)F)ccc1F] | 466.2 | 1H NMR (500 MHz, DMSO-d6) δ 8.88 (s, 1H), 8.76 (d, J = 2.6 Hz, 1H), 8.57 (d, J = 6.9 Hz, 1H), 8.40 (d, J = 2.6 Hz, 1H), 7.87-7.81 (m, 1H), 7.72 (br s, 1H), 7.68 (d, J = 1.3 Hz, 1H), 7.45 (t, J = 9.2 Hz, 1H), 7.22 (dd, J = 7.0, 1.9 Hz, 1H), 5.90 (s, 2H). |
| 285 | (R)-5-(2-amino-[1,2,4]triazolo[1,5-a]pyridin-7-yl)-N-(1-(2-fluoro-5-(trifluoromethoxy)phenyl)ethyl)-2-(methoxy-d3)nicotinamide | 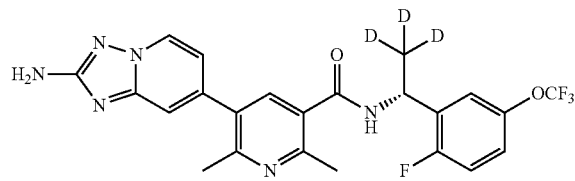 | 494.3 | 1H NMR (500 MHz, DMSO-d6) δ 8.88 (br d, J = 7.4 Hz, 1H), 8.77 (d, J = 2.2 Hz, 1H), 8.61 (d, J = 6.9 Hz, 1H), 8.31 (s, 1H), 7.73 (s, 1H), 7.55 (br d, J = 4.4 Hz, 1H), 7.41-7.31 (m, 2H), 7.26 (br d, J = 6.9 Hz, 1H), 6.40-5.80 (m, 2H), 5.36 (br t, J = 7.3 Hz, 1H), 1.47 (d, J = 6.9 Hz, 3H) |

Example 286

(R)-5-(2-amino-[1,2,4]triazolo[1,5-a]pyridin-7-yl)-N-(1-(2-fluoro-5-(trifluoromethoxy)phenyl)ethyl-2,2,2-d3)-2,6-dimethylnicotinamide 286A: (S,E)-N-(2-fluoro-5-(trifluoromethoxy)benzylidene)-2-methylpropane-2-sulfinamide: Titanium(IV) isopropoxide (5.69 mL, 19.22 mmol) was added to a THF (20 mL) solution of 2-fluoro-5-(trifluoromethoxy)benzaldehyde (2.0 g, 9.61 mmol) and (S)-(−)-2-methyl-2-propanesulfinamide (1.165 g, 9.61 mmol) at rt and stirred for 72 h. The reaction mixture was quenched by adding brine (10 mL) and hexanes (10 mL) at 0° C. The mixture was filtered through a pad of celite, and the pad was rinsed with ethyl acetate (2×10 mL). The combined organic solutions were dried over sodium sulfate, filtered and concentrated under reduced pressure to give crude product which was purified on a silica gel column with Hexanes/EtOAc (100/0 to 50/50) to give (S,E)-N-(2-fluoro-5-(trifluoromethoxy)benzylidene)-2-methylpropane-2-sulfinamide (2.827 g, 8.73 mmol, 91% yield).

MS ESI m/z 312.0 (M+H)

286B: (S)—N—((R)-1-(2-fluoro-5-(trifluoromethoxy)phenyl)ethyl-2,2,2-d3)-2-methylpropane-2-sulfinamide: To a solution of (S,E)-N-(2-fluoro-5-(trifluoromethoxy)benzylidene)-2-methylpropane-2-sulfinamide (2.827 g, 9.08 mmol) in THF (40 mL) was added methyl-d3-magnesium iodide, 1 M in Et₂O (13.62 mL, 13.62 mmol) dropwise at −40° C. The temperature was maintained at −40° C. for 6 h, then warmed to 23° C. and stirred for 12 h. The reaction mixture was concentrated to about 10 mL and quenched with saturated NH₄Cl solution (50 mL) at 0° C. The aqueous layer was extracted with EtOAc (50 mL×3). The combined organic phases were washed with brine (50 mL) and dried over Na₂SO₄. Filtration and concentration yielded crude product, (S)—N—((R)-1-(2-fluoro-5-(trifluoromethoxy)phenyl)ethyl-2,2,2-d3)-2-methylpropane-2-sulfinamide (3.2 g, 9.12 mmol, 100% yield).

MS ESI m/z 331.0 (M+H)

286C: (S)—N—((R)-1-(2-fluoro-5-(trifluoromethoxy)phenyl)ethyl-2,2,2-d3)-2-methylpropane-2-sulfinamide: (S)—N—((R)-1-(2-fluoro-5-(trifluoromethoxy)phenyl)ethyl-2,2,2-d3)-2-methylpropane-2-sulfinamide (3.2 g, 9.69 mmol) was separated by chiral HPLC. HPLC: Column: Phenomenex-prime S5-C18 4.6×50 mm; Gradient time: 3 min; Flow rate=4 ml/min; Solvent A=10% MeOH-90% Water-0.2% H3PO4; Solvent B=90% MeOH-10% water-0.2% H3PO4; Start % B=0; Final % B=100.

The fractions from peak 1 were collected as (S)—N—((R)-1-(2-fluoro-5-(trifluoromethoxy)phenyl)ethyl-2,2,2-d3)-2-methylpropane-2-sulfinamide (1.608 g, 4.84 mmol, 50% yield). HPLC: 99.5%, rt=2.557 min.

MS ESI m/z 331.1 (M+H)

The fractions from peak 2 were collected as (S)—N—((S)-1-(2-fluoro-5-(trifluoromethoxy)phenyl)ethyl-2,2,2-d3)-2-methylpropane-2-sulfinamide (0.97 g, 2.87 mmol, 30% yield). HPLC: 97.6%, rt=2.578 min.

MS ESI m/z 331.1 (M+H)

286D: (R)-1-(2-fluoro-5-(trifluoromethoxy)phenyl)ethan-2,2,2-d3-1-amine, HCl: A solution of (S)—N—((R)-1-(2-fluoro-5-(trifluoromethoxy)phenyl)ethyl-2,2,2-d3)-2-methylpropane-2-sulfinamide (1.608 g, 4.87 mmol) and HCl, 4 M in 1,4-dioxane (7.30 mL, 29.2 mmol) in THF (10 mL) was stirred at 23° C. for 1 h. The reaction mixture was concentrated and triturated in ether (10 mL). The solid was collected as (R)-1-(2-fluoro-5-(trifluoromethoxy)phenyl)ethan-2,2,2-d3-1-amine, HCl (996 mg, 3.79 mmol, 78% yield).

MS ESI m/z 227.1 (M+H)

$^1$H NMR (400 MHz, CDCl$_3$) δ 1.15-1.00 (m, 1H), 0.60-0.45 (m, 2H), 0.27-0.14 (m, 2H).

286: A mixture of 5-(2-amino-[1,2,4]triazolo[1,5-a]pyridin-7-yl)-2,6-dimethylnicotinic acid (15 mg, 0.053 mmol), as prepared in example 16, BOP (35.1 mg, 0.079 mmol), (R)-1-(2-fluoro-5-(trifluoromethoxy)phenyl)ethan-2,2,2-d3-1-amine, HCl (15.30 mg, 0.058 mmol) and Hünig's base (0.046 mL, 0.265 mmol) in DMF (1 mL) was stirred at rt ON. The reaction mixture was diluted to 2 mL with methanol, then filtered. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 17-57% B over 20 minutes, then a 4-minute hold at 100% B; Flow: 20 mL/min. Fractions containing the desired product were combined and dried via centrifugal evaporation. Afforded (R)-5-(2-amino-[1,2,4]triazolo[1,5-a]pyridin-7-yl)-N-(1-(2-fluoro-5-(trifluoromethoxy)phenyl)ethyl-2,2,2-d3)-2,6-dimethylnicotinamide (13.8 mg, 0.028 mmol, 53% yield).

MS ESI m/z 492.0 (M+H)

1H NMR (500 MHz, DMSO-d6) δ 8.87 (br d, J=7.4 Hz, 1H), 8.59 (d, J=6.8 Hz, 1H), 7.68 (s, 1H), 7.44 (br s, 1H), 7.42-7.27 (m, 3H), 6.94 (br d, J=6.8 Hz, 1H), 5.91 (s, 2H), 5.33 (br d, J=7.6 Hz, 1H), 2.50-2.48 (m, 6H)

TABLE 9

Compounds in Table 9 were prepared in a similar fashion to examples 16, 47, 79, 80, 87, 282 and, 286.

| Ex No | Name | R | M + H | 1H NMR (500 MHz, DMSO-d6) δ |
|---|---|---|---|---|
| 287 | 5-(2-amino-[1,2,4]triazolo[1,5-a]pyridin-7-yl)-N-(2-(cyclopropylmethoxy-d2)-3,5-difluorobenzyl)-2,6-dimethylnicotinamide | | 481.2 | 8.81 (br t, J = 5.6 Hz, 1H), 8.59 (d, J = 6.8 Hz, 1H), 7.75 (s, 1H), 7.41 (s, 1H), 7.25-7.08 (m, 1H), 7.03-6.92 (m, 2H), 5.92 (s, 2H), 4.56 (d, J = 5.7 Hz, 2H), 2.59 (s, 3H), 2.50-2.48 (m, 3H), 1.20 (bs, 1H), 0.61-0.49 (m, 2H), 0.38-0.21 (m, 2H) |
| 288 | 5-(2-amino-[1,2,4]triazolo[1,5-a]pyridin-7-yl)-N-((2-fluoro-5-(trifluoromethyl)phenyl)methyl-d2)-2,6-dimethylnicotinamide | | 461.1 | 9.00 (s, 1H), 8.57 (br d, J = 6.7 Hz, 1H), 7.75 (br d, J = 6.4 Hz, 1H), 7.72-7.64 (m, 2H), 7.49-7.31 (m, 2H), 6.91 (d, J = 6.7 Hz, 1H), 6.02 (br s, 2H), 2.46 (s, 3H), 2.44 (s, 3H) |
| 289 | (R)-5-(2-amino-[1,2,4]triazolo[1,5-a]pyridin-7-yl)-N-(1-(2-fluoro-5-(trifluoromethyl)phenyl)ethyl-2,2,2-d3)-2,6-dimethylnicotinamide | | 476.0 | 8.92 (br d, J = 7.4 Hz, 1H), 8.60 (d, J = 6.7 Hz, 1H), 7.83 (br d, J = 5.8 Hz, 1H), 7.77-7.63 (m, 2H), 7.50-7.36 (m, 2H), 6.94 (br d, J = 6.7 Hz, 1H), 5.93 (s, 2H), 5.37 (br d, J = 7.4 Hz, 1H), 2.50-2.48 (m, 6H) |

TABLE 9-continued

Compounds in Table 9 were prepared in a similar fashion to examples 16, 47, 79, 80, 87, 282 and, 286.

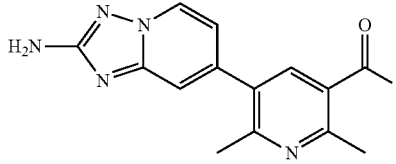

| Ex No | Name | R | M + H | 1H NMR (500 MHz, DMSO-d6) δ |
|---|---|---|---|---|
| 290 | 5-(2-amino-[1,2,4]triazolo[1,5-a]pyridin-7-yl)-N-(5-(cyclopropylmethoxy)-2-fluorobenzyl)-2,6-dimethylnicotinamide | 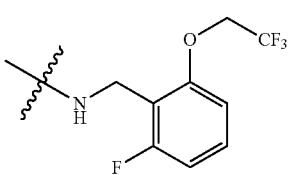 [SMILES: *NCc1c(F)cccc1OCC(F)(F)F] | 461.1 | 8.75 (br t, J = 5.8 Hz, 1H), 8.36 (d, J = 7.0 Hz, 1H), 7.45 (s, 1H), 7.18 (s, 1H), 6.86 (t, J = 9.3 Hz, 1H), 6.74 (d, J = 7.0 Hz, 1H), 6.71-6.68 (m, 1H), 6.64-6.56 (m, 1H), 5.80 (s, 2H), 4.23 (br d, J = 5.5 Hz, 2H), 3.51 (d, J = 7.0 Hz, 2H), 2.32 (s, 3H), 2.27-2.23 (m, 3H), 0.93 (br t, J = 7.3 Hz, 1H), 0.32-0.22 (m, 2H), 0.01 (q, J = 4.7 Hz, 2H) |
| 291 | 5-(2-amino-[1,2,4]triazolo[1,5-a]pyridin-7-yl)-N-(2-fluoro-6-(2,2,2-trifluoroethoxy)benzyl)-2,6-dimethylnicotinamide | 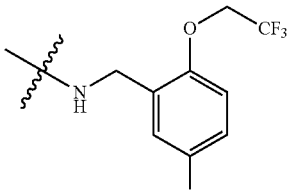 | 489.2 | 8.65-8.55 (m, 2H), 7.56 (s, 1H), 7.45-7.27 (m, 2H), 7.06-6.96 (m, 1H), 6.96-6.90 (m, 2H), 6.02 (s, 2H), 4.83-4.73 (m, 2H), 4.53-4.43 (m, 2H), 2.57 (s, 3H), 2.46 (s, 3H) |
| 292 | 5-(2-amino-[1,2,4]triazolo[1,5-a]pyridin-7-yl)-N-(5-fluoro-2-(2,2,2-trifluoroethoxy)benzyl)-2,6-dimethylnicotinamide | 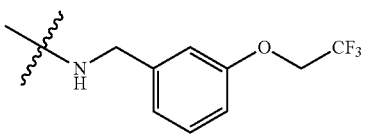 [SMILES: *NCc1cccc(OCC(F)(F)F)c1] | 489.1 | 9.08-8.86 (m, 1H), 8.63 (d, J = 6.8 Hz, 1H), 7.79 (s, 1H), 7.45 (s, 1H), 7.28-7.08 (m, 3H), 6.98 (br d, J = 6.7 Hz, 1H), 6.09 (s, 2H), 4.81 (q, J = 8.7 Hz, 2H), 4.46 (br d, J = 5.6 Hz, 2H), 2.60-2.54 (m, 6H) |
| 293 | 5-(2-amino-[1,2,4]triazolo[1,5-a]pyridin-7-yl)-2,6-dimethyl-N-(3-(2,2,2-trifluoroethoxy)benzyl)nicotinamide | 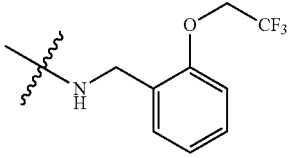 [SMILES: *NCc1ccccc1OCC(F)(F)F] | 471.1 | 8.98 (br t, J = 5.8 Hz, 1H), 8.62 (d, J = 7.0 Hz, 1H), 7.74 (s, 1H), 7.44 (s, 1H), 7.32 (t, J = 8.1 Hz, 1H), 7.08-6.99 (m, 2H), 6.99-6.93 (m, 2H), 6.06 (s, 1H), 4.74 (q, J = 8.9 Hz, 2H), 4.47 (d, J = 5.8 Hz, 2H), 2.65 (s, 3H), 2.47 (s, 3H) |
| 294 | 5-(2-amino-[1,2,4]triazolo[1,5-a]pyridin-7-yl)-2,6-dimethyl-N-(2-(2,2,2-trifluoroethoxy)benzyl)nicotinamide | 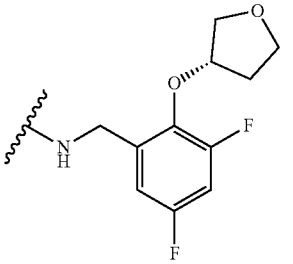 | 471.2 | 8.83 (br t, J = 5.5 Hz, 1H), 8.67 (br s, 1H), 7.77 (s, 1H), 7.46 (br s, 1H), 7.40-7.26 (m, 2H), 7.14 (d, J = 7.9 Hz, 1H), 7.06 (t, J = 7.5 Hz, 1H), 6.99 (d, J = 6.7 Hz, 1H), 6.08 (br s, 2H), 4.81 (q, J = 8.9 Hz, 2H), 4.49 (br d, J = 5.5 Hz, 2H), 2.56 (s, 6H) |
| 295 | (S)-5-(2-amino-[1,2,4]triazolo[1,5-a]pyridin-7-yl)-N-(3,5-difluoro-2-((tetrahydrofuran-3-yl)oxy)benzyl)-2,6-dimethylnicotinamide | | 495.2 | 8.80 (br t, J = 5.6 Hz, 1H), 8.58 (d, J = 6.8 Hz, 1H), 7.75 (s, 1H), 7.40 (s, 1H), 7.28-7.10 (m, 1H), 7.00 (d, J = 8.8 Hz, 1H), 6.95 (d, J = 7.0 Hz, 1H), 5.91 (s, 2H), 4.96 (br s, 1H), 4.55-4.44 (m, 2H), 4.01-3.85 (m, 2H), 3.85-3.68 (m, 2H), 2.58 (s, 3H), 2.49 (s, 3H), 2.18-2.09 (m, 2H) |

TABLE 9-continued

Compounds in Table 9 were prepared in a similar fashion to examples 16, 47, 79, 80, 87, 282 and, 286.

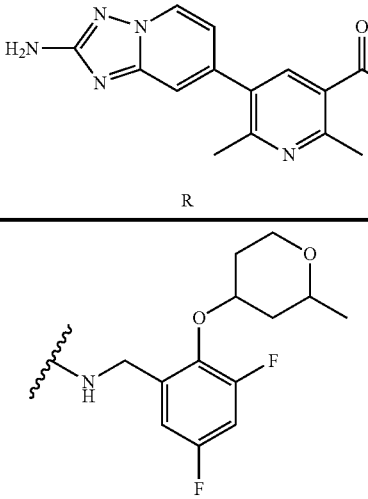

| Ex No | Name | R | M + H | 1H NMR (500 MHz, DMSO-d6) δ |
|---|---|---|---|---|
| 296 | 5-(2-amino-[1,2,4]triazolo[1,5-a]pyridin-7-yl)-N-(3,5-difluoro-2-((2-methyltetrahydro-2H-pyran-4-yl)oxy)benzyl)-2,6-dimethylnicotinamide | 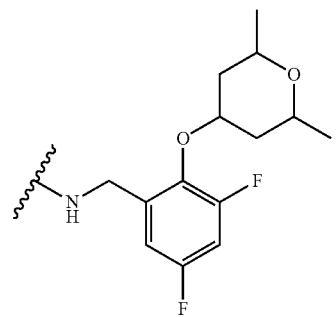 [SMILES: *NCc1cc(F)cc(F)c1OC1CC(C)OC(C)C1] | 523.2 | 8.97 (br t, J = 5.5 Hz, 1H), 8.60 (d, J = 7.0 Hz, 1H), 7.76 (s, 1H), 7.42 (s, 1H), 7.20 (br t, J = 8.7 Hz, 1H), 7.06-6.92 (m, 2H), 6.04 (s, 2H), 4.56-4.46 (m, 3H), 3.95-3.59 (m, 3H), 2.57 (br s, 3H), 2.50-2.47 (m, 3H), 1.95-1.84 (m, 1H), 1.76 (br s, 2H), 1.58-1.41 (m, 1H), 1.09 (d, J = 6.4 Hz, 3H) |
| 297 | 5-(2-amino-[1,2,4]triazolo[1,5-a]pyridin-7-yl)-N-(2-((2,6-dimethyltetrahydro-2H-pyran-4-yl)oxy)-3,5-difluorobenzyl)-2,6-dimethylnicotinamide | 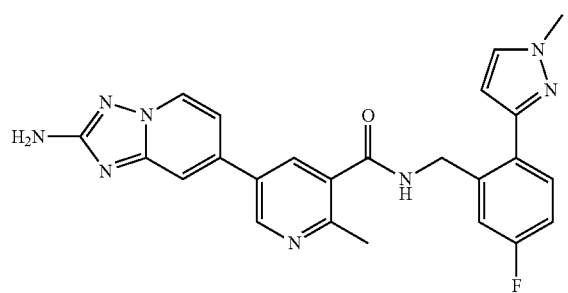 | 537.2 | 9.04-8.88 (m, 1H), 8.62 (d, J = 6.8 Hz, 1H), 7.83-7.74 (m, 1H), 7.44 (s, 1H), 7.24 (t, J = 8.9 Hz, 1H), 7.06-6.95 (m, 2H), 6.09 (s, 2H), 4.51 (br d, J = 5.4 Hz, 2H), 3.98-3.89 (m, 2H), 2.57-2.55 (m, 6H), 2.50-2.47 (m, 2H), 1.95-1.80 (m, 1H), 1.39 (br t, J = 11.7 Hz, 1H), 1.26 (q, J = 11.4 Hz, 1H), 1.16-1.05 (m, 6H) |

Example 298

5-(2-amino-[1,2,4]triazolo[1,5-a]pyridin-7-yl)-N-(5-fluoro-2-(1-methyl-1H-pyrazol-3-yl)benzyl)-2-methylnicotinamide 298A: Benzyl (2-bromo-5-fluorobenzyl)carbamate: To a mixture of (2-bromo-5-fluorophenyl)methanamine (1.00 g, 4.90 mmol) in THF (17 mL) was added N-(benzyloxycarbonyloxy)succinimide (1.832 g, 7.35 mmol) and TEA (1.708 mL, 12.25 mmol) and the resulting mixture was stirred at rt ON. The product was partitioned between EtOAc (90 mL) water (20 mL). The EtOAc layer was washed with brine, then dried over sodium sulfate, filtered and concentrated. The crude residue was purified using flash column chromatography on a 24 g ISCO column, eluting with 0-70% EtOAc in hexanes. Afforded benzyl (2-bromo-5-fluorobenzyl)carbamate (1.33 g, 3.74 mmol, 76% yield) as a colorless oil which became a crystalline white solid on a vacuum pump. The material was carried forward without further purification.

MS ESI m/z 338.2 (M+H)

298B: Tert-butyl (5-fluoro-2-(1-methyl-1H-pyrazol-3-yl)benzyl)carbamate: A mixture of tert-butyl (5-fluoro-2-(4,4,5,5-tetramethyl-1,3,2-dioxaborolan-2-yl)benzyl)carbamate (65 mg, 0.185 mmol), 3-bromo-1-methyl-1H-pyrazole (44.7 mg, 0.278 mmol) and PdCl$_2$(dppf)-CH$_2$Cl$_2$ adduct (7.56 mg, 9.25 μmol) in 1,4-dioxane (3 mL) was degassed by bubbling nitrogen through the mixture for 5 min. Tripotassium phosphate, 2M aq. (0.278 mL, 0.555 mmol) was added, the vial sealed tightly, and the reaction mixture then stirred at 100° C. for 10 min. The reaction mixture was concentrated onto Celite, then purified by column chromatography using a 12 g ISCO column and eluting with 0-70% EtOAc in hexanes. Afforded tert-butyl (5-fluoro-2-(1-methyl-1H-pyrazol-3-yl)benzyl)carbamate (23 mg, 0.075 mmol, 41% yield). Material was used in subsequent chemistry as is.

MS ESI m/z 206.1 (M+H)

298C: (5-fluoro-2-(1-methyl-1H-pyrazol-3-yl)phenyl)methanamine, HCl: To a solution of tert-butyl (5-fluoro-2-(1-methyl-1H-pyrazol-3-yl)benzyl)carbamate (23 mg, 0.075 mmol) in DCM (1 mL) was added HCl, 4M in 1,4-dioxane (0.621 mL, 2.486 mmol). The resulting solution was stirred 3 h at rt. The reaction mixture was concentrated to a solid, then used as—is in the next step. Afforded 5-fluoro-2-(1- methyl-1H-pyrazol-3-yl)phenyl)methanamine, HCl (20 mg, 0.074 mmol, 99% crude yield.

MS ESI m/z 206.1 (M+H)

298: A mixture of 5-(2-amino-[1,2,4]triazolo[1,5-a]pyridin-7-yl)-2-methylnicotinic acid (15 mg, 0.056 mmol), as prepared in example 5, BOP (37.0 mg, 0.084 mmol), (5-fluoro-2-(1-methyl-1H-pyrazol-3-yl)phenyl)methanamine, HCl (16.16 mg, 0.067 mmol), Hünig's base (0.049 mL, 0.279 mmol) and DMF (1.0 mL) was stirred at rt for 2 d. The mixture was dissolved in MeOH (2 mL), then filtered. The crude reaction mixture was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. Afforded 5-(2-amino-[1,2,4]triazolo[1,5-a]pyridin-7-yl)-N-(5-fluoro-2-(1-methyl-1H-pyrazol-3-yl)benzyl)-2-methylnicotinamide (21.5 mg, 0.047 mmol, 85% yield).

MS ESI m/z 457.4 (M+H)

1H NMR (500 MHz, DMSO-d6) δ 9.01-8.95 (m, 2H), 8.65 (d, J=6.7 Hz, 1H), 8.19 (s, 1H), 7.79 (d, J=11.0 Hz, 2H), 7.61 (dd, J=8.4, 6.3 Hz, 1H), 7.33-7.26 (m, 2H), 7.17 (t, J=8.3 Hz, 1H), 6.57 (d, J=1.8 Hz, 1H), 6.05 (s, 2H), 4.76 (br d, J=5.5 Hz, 2H), 3.91 (s, 3H), 2.60 (s, 3H).

TABLE 10

Compounds in Table 10 were prepared in a similar fashion to examples 16, 47, 79, 80, 87, 282, 286, 287, and 298.

| Ex No | Name | R | M + H | 1H NMR (500 MHz, DMSO-d6) δ |
|---|---|---|---|---|
| 299 | (R)-5-(2-amino-[1,2,4]triazolo[1,5-a]pyridin-7-yl)-N-(1-(2-fluoro-5-(trifluoromethoxy)phenyl)ethyl-2,2,2-d3)-2-methylnicotinamide | CD3, 2-F, 5-OCF3 phenyl ethyl | 478.3 | 9.10 (d, J = 7.5 Hz, 1H), 8.98 (d, J = 2.3 Hz, 1H), 8.66 (d, J = 6.9 Hz, 1H), 8.18 (d, J = 2.3 Hz, 1H), 7.82 (d, J = 1.2 Hz, 1H), 7.49 (br d, J = 3.9 Hz, 1H), 7.41-7.30 (m, 3H), 6.10 (s, 2H), 5.35 (d, J = 7.5 Hz, 1H), 2.51 (s, 3H) |
| 300 | (S)-5-(2-amino-[1,2,4]triazolo[1,5-a]pyridin-7-yl)-N-(1-(2-fluoro-5-(trifluoromethoxy)phenyl)ethyl-2,2,2-H3)-2-methylnicotinamide | CD3, 2-F, 5-OCF3 phenyl ethyl | 478.3 | 9.11 (br d, J = 7.6 Hz, 1H), 8.99 (d, J = 1.8 Hz, 1H), 8.67 (d, J = 7.0 Hz, 1H), 8.18 (d, J = 1.8 Hz, 1H), 7 83 (s, 1H), 7.50 (br d, J = 4.3 Hz, 1H), 7.42-7.29 (m, 3H), 6.09 (s, 2H), 5.36 (br d, J =7.3 Hz, 1H), 2.55 (s, 3H) |
| 301 | 5-(2-amino-[1,2,4]triazolo[1,5-a]pyridin-7-yl)-N-(3,5-difluoro-2-isobutoxybenzyl)-2-methylnicotinamide | 3,5-difluoro-2-isobutoxybenzyl | 467.2 | 9.05 (br t, J = 5.6 Hz, 1H), 8.98 (d, J = 1.9 Hz, 1H), 8.66 (d, J = 7.0 Hz, 1H), 8.25 (d, J = 1.9 Hz, 1H), 7.84 (s, 1H), 7.34 (dd, J = 6.9, 1.5 Hz, 1H), 7.30-7.20 (m, 1H), 7.07 (br d, J = 8.8 Hz, 1H), 6.10 (s, 2H), 4.56 (br d, J = 5.6 Hz, 2H), 3.82 (d, J = 6.3 Hz, 2H), 2.61 (s, 3H), 2.07 (dquin, J = 13.2, 6.6 Hz, 1H), 1.03 (d, J = 6.7 Hz, 6H) |
| 302 | (S)-5-(2-amino-[1,2,4]triazolo[1,5-a]pyridin-7-yl)-N-(1-(2-fluoro-5-(trifluoromethyl)phenyl)ethyl-2,2,2-H3)-2-methylnicotinamide | CD3, 2-F, 5-CF3 phenyl ethyl | 462.4 | 9.04 (br d, J = 7.4 Hz, 1H), 8.96 (d, J = 2.2 Hz, 1H), 8.63 (d, J = 7.0 Hz, 1H), 8.14 (d, J = 2.2 Hz, 1H), 7.88 (br d, J = 5.1 Hz, 1H), 7.78 (s, 1H), 7.76-7.69 (m, 1H), 7.46 (t, J = 9.3 Hz, 1H), 7.29 (dd, J = 7.0, 1.9 Hz, 1H), 5.94 (s, 2H), 5.42 (d, J = 7.4 Hz, 1H), 2.55 (s, 3H) |
| 303 | (R)-5-(2-amino-[1,2,4]triazolo[1,5-a]pyridin-7-yl)-N-(1-(2-fluoro-5-(trifluoromethyl)phenyl)ethyl-2,2,2-H3)-2-methylnicotinamide | CD3, 2-F, 5-CF3 phenyl ethyl | 462.4 | 9.15 (d, J = 7.5 Hz, 1H), 8.99 (d, J = 2.3 Hz, 1H), 8.67 (d, J = 7.0 Hz, 1H), 8.18 (d, J = 2.2 Hz, 1H), 7.94-7.85 (m, 1H), 7.82 (d, J = 1.3 Hz, 1H), 7.75 (br dd, J = 7.5, 3.7 Hz, 1H), 7.48 (t, J = 9.2 Hz, 1H), 7.32 (dd, J = 7.0, 1.9 Hz, 1H), 6.10 (s, 2H), 5.39 (d, J = 7.5 Hz, 1H), 3.32 (s, 5H), 2.54 (s, 3H) |

US 12,157,733 B2
213                                                                    214
TABLE 10-continued Compounds in Table 10 were prepared in a similar fashion to examples 16, 47, 79, 80, 87, 282, 286, 287, and 298.

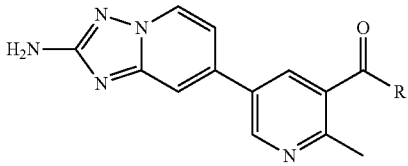

| Ex No | Name | R | M + H | 1H NMR (500 MHz, DMSO-d6) δ |
|---|---|---|---|---|
| 304 | 5-(2-amino-[1,2,4]triazolo[1,5-a]pyridin-7-yl)-N-(6-(cyclopropylmethoxy)-2,3-difluorbenzyl)-2-methylnicotinamide | 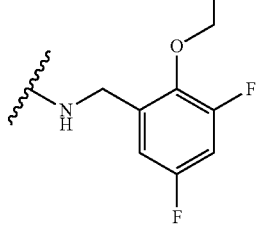 | 465.2 | 8.99-8.82 (m, 1H), 8.65-8.56 (m, 2H), 8.03 (d, J = 2.1 Hz, 1H), 7.71 (s, 1H), 7.34-7.21 (m, 2H), 6.83 (br d, J = 9.3 Hz, 1H), 5.90 (s, 2H), 4.56 (br d, J = 4.5 Hz, 2H), 3.96-3.85 (m, 2H), 2.56 (s, 3H), 1.14-0.95 (m, 1H), 0.58-0.45 (m, 2H), 0.38-0.25 (m, 2H) |
| 305 | 5-(2-amino-[1,2,4]triazolo[1,5-a]pyridin-7-yl)-N-(2-isobutoxbenzyl)-2-methylnicotinamide | 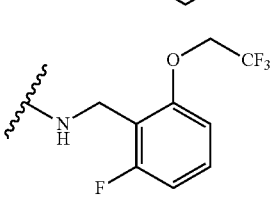 | 431.1 | 8.97 (d, J = 2.0 Hz, 1H), 8.90 (br t, J = 5.6 Hz, 1H), 8.66 (d, J = 7.0 Hz, 1H), 8.21 (d, J = 2.0 Hz, 1H), 7.82 (s, 1H), 7.37-7.29 (m, 2H), 7.25 (br t, J = 7.4 Hz, 1H), 6.99 (d, J = 8.0 Hz, 1H), 6.95 (t, J = 7.4 Hz, 1H), 6.10 (s, 2H), 4.52 (br d, J = 5.6 Hz, 2H), 3.81 (d, J = 6.3 Hz, 2H), 2.62 (s, 3H), 2.08 (dquin, J = 13.1, 6.5 Hz, 1H), 1.03 (d, J = 6.6 Hz, 6H) |
| 306 | 5-(2-amino-[1,2,4]triazolo[1,5-a]pyridin-7-yl)-N-(2-fluoro-6-(2,2,2-(trifluoromethoxy)benzyl)-2-methylnicotinamide | 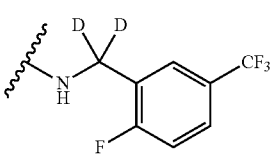 [SMILES: *NC([2H])([2H])c1cc(C(F)(F)F)ccc1F] | 475.1 | 8.93 (d, J = 1.8 Hz, 1H), 8.73-8.60 (m, 2H), 8.05 (d, J = 2.1 Hz, 1H), 7.76 (s, 1H), 7.43-7.25 (m, 2H), 7.11-7.02 (m, 1H), 6.97 (t, J = 8.7 Hz, 1H), 4.90-4.79 (m, 2H), 4.60-4.48 (m, 2H), 2.56(s, 3H) NH2 protons not observed |
| 307 | 5-(2-amino-[1,2,4]triazolo[1,5-a]pyridin-7-yl)-N-((2-fluoro-5-(trifluoromethyl)phenyl)methyl-H2)-2-methylnicotinamide | 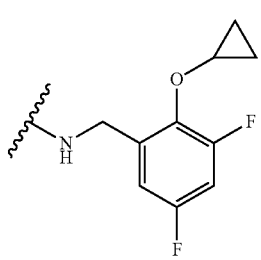 [SMILES: *NCc1cc(F)cc(F)c1OC1CC1] | 447.2 | 9.16 (s, 1H), 8.96 (s, 1H), 8.64 (br d, J = 7.0 Hz, 1H), 8.17 (s, 1H), 7,84 (br d, J = 5.5 Hz, 1H), 7.81-7.73 (m, 2H), 7 48 (br t, J = 9.2 Hz, 1H), 7.31 (br d, J = 6.7 Hz, 1H), 6.07 (s, 2H), 2.56 (s, 3H) |
| 308 | 5-(2-amino-[1,2,4]triazolo[1,5-a]pyridin-7-yl)-N-(2-(cyclopropoxy)-3,5-difluorbenzyl)-2-methylnicotinamide | 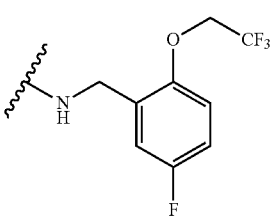 [SMILES: *NCc1cc(F)ccc1OCC(F)(F)F] | 451.0 | 9.03 (br t, J = 5.6 Hz, 1H), 8.96 (s, 1H), 8.64 (d, J =7.0 Hz, 1H), 8.21 (s, 1H), 7.80 (s, 1H), 7.37-7.21 (m, 2H), 7.06 (br d, J = 8.9 Hz, 1H), 6.06 (s, 2H), 4.45 (br d, J = 5.5 Hz, 2H), 4.21 (br d, J = 2.7 Hz, 1H), 2.59 (s, 3H), 0.83 (br s, 2H), 0.68-0.56 (m, 2H) |
| 309 | 5-(2-amino-[1,2,4]triazolo[1,5-a]pyridin-7-yl)-N-(5-fluoro-2-(2,2,2-(trifluoroethoxy)benzyl)-2-methylnicotinamide | | 475.1 | 9.04-8.91 (m, 2H), 8.65 (d, J = 6.7 Hz, 1H), 8.24 (s, 1H), 7.82 (s, 1H), 7.33 (br d, J = 7.0 Hz, 1H), 7.23-7.11 (m, 3H), 6.07 (s, 2H), 4.81 (q, J = 8.9 Hz, 2H),4.50 (br d, J = 5.8 Hz, 2H), 2.61 (s, 3H) |

TABLE 10-continued

Compounds in Table 10 were prepared in a similar fashion to examples 16, 47, 79, 80, 87, 282, 286, 287, and 298.

| Ex No | Name | R | M + H | 1H NMR (500 MHz, DMSO-d6) δ |
|---|---|---|---|---|
| 310 | (S)-5-(2-amino-[1,2,4]triazolo[1,5-a]pyridin-7-yl)-2-methyl-N-(1-(3-(trifluoromethoxy)phenyl)ethyl-2,2,2-H3)nicotinamide | | 460.3 | 9.06 (br d, J = 7.6 Hz, 1H), 8.96 (s, 1H), 8.64 (d, J = 7.0 Hz, 1H), 8.15 (s, 1H), 7.81 (s, 1H), 7.55-7.43 (m, 2H), 7.40 (br s, 1H), 7.32 (br d, J = 6.7 Hz, 1H), 7.25 (br d, J = 7.6 Hz, 1H), 6.07 (s, 2H), 5.18 (br d, J = 7.6 Hz, 1H), 2.51 (s, 3H) |
| 311 | (R)-5-(2-amino-[1,2,4]triazolo[1,5-a]pyridin-7-yl)-2-methyl-N-(1-(3-(trifluoromethoxy)phenyl)ethyl-2,2,2-H3)nicotinamide | | 460.2 | 9.05 (br d, J = 7.6 Hz, 1H), 8.97 (s, 1H), 8.65 (br d, J = 6.7 Hz, 1H), 8.16 (br s, 1H), 7.82 (s, 1H), 7.55-7.44 (m, 2H), 7.41 (br s, 1H), 7.32 (br d, J = 6.7 Hz, 1H), 7.26 (br d, J = 7.6 Hz, 1H), 6.08 (s, 2H), 5.19 (br d, J = 7.6 Hz, 1H), 2.51 (s, 3H) |
| 312 | 5-(2-amino-[1,2,4]triazolo[1,5-a]pyridin-7-yl)-2-methyl-N-(2-(2,2,2-(trifluoroethoxy)benzyl)nicotinamide | | 457.0 | 8.98-8.96 (m, 1H), 8.94 (t, J = 6.0 Hz, 1H), 8.66 (d, J = 7.0 Hz, 1H), 8.22 (d, J = 1.8 Hz, 1H), 7.83 (s, 1H), 7.39 (br d, J = 7.3 Hz, 1H), 7.36-7.29 (m, 2H), 7.15 (d, J = 8.2 Hz, 1H), 7.09 (t, J = 7.5 Hz, 1H), 6.02 (s, 2H), 4.83 (q, J = 8.9 Hz, 2H), 4.52 (d, J = 5.5 Hz, 2H), 2.62 (s, 3H) |
| 313 | 5-(2-amino-[1,2,4]triazolo[1,5-a]pyridin-7-yl)-2-methyl-N-(3-(2,2,2-(trifluoroethoxy)benzyl)nicotinamide | | 457.1 | 9.08 (br t, J = 5.8 Hz, 1H), 8.97 (d, J =2.1 Hz, 1H), 8.65 (d, J = 7.0 Hz, 1H), 8.21 (s, 1H), 7.83 (s, 1H), 7.39-7.22 (m, 1H), 7.08 (s, 1H), 7.08 (d, J = 6.6 Hz, 2H), 6.99 (br d, J = 9.2 Hz, 1H), 6.08 (s, 2H), 4.77 (q, J = 8.9 Hz, 2H), 4.51 (br d, J = 5.8 Hz, 2H), 2.61 (s, 3H) |
| 314 | 5-(2-amino-[1,2,4]triazolo[1,5-a]pyridin-7-yl)-N-(3,5-difluoro-2-((tetrahydro-2H-pyran-3-yl)oxy)benzyl)-2-methylnicotinamide | | 495.2 | 9.05-9.01 (m, 1H), 8.98 (s, 1H), 8.65 (d, J = 7.0 Hz, 1H), 8.25 (d, J = 2.1 Hz, 1H), 7.83 (s, 1H), 7.34 (dd, J = 7.0, 1.5 Hz, 1H), 7.29-7.19 (m, 1H), 7.07 (br d, J = 9.2 Hz, 1H), 6.08 (s, 2H), 4.66-4.53 (m, 2H), 4.15 (br s, 1H), 3.78 (br d, J = 11.6 Hz, 1H), 3.65-3.52 (m, 2H), 2.61 (s, 3H), 2.57-2.54 (m, 1H), 2.06-1.97 (m, 1H), 1.96-1.79 (m, 2H), 1.58-1.45 (m, 1H) |
| 315 | 5-(2-amino-[1,2,4]triazolo[1,5-a]pyridin-7-yl)-N-(2-((2,6-dimethyltetrahydro-2H-pyran-4-yl)oxy)-3,5-difluorobenzyl)-2-methylnicotinamide | | 523.2 | 9.14-9.01 (m, 1H), 8.98 (s, 1H), 8.66 (d, J = 7.0 Hz, 1H), 8.33-8.16 (m, 1H), 7.83 (s, 1H), 7.34 (d, J = 7.1 Hz, 1H), 7.30-7.21 (m, 1H), 7.09 (br d, J = 6.1 Hz, 1H), 6.11 (s, 2H), 4.61-4.48 (m, 3H), 3.97 (br dd, J = 10.9, 6.0 Hz, 1H), 3.91 (s, 1H), 3.55-3.42 (m, 2H), 2.64-2.58 (m, 3H), 1.41 (br t, J = 11.7 Hz, 1H), 1.28 (q, J = 11.3 Hz, 1H), 1.17-1.06 (m, 6H) |

TABLE 10-continued

Compounds in Table 10 were prepared in a similar fashion to examples 16, 47, 79, 80, 87, 282, 286, 287, and 298.

| Ex No | Name | R | M + H | 1H NMR (500 MHz, DMSO-d6) δ |
|---|---|---|---|---|
| 316 | 5-(2-amino-[1,2,4]triazolo[1,5-a]pyridin-7-yl)-N-(3,5-difluoro-2((2-methyltetrahydro-2H-pyran-4-yl)oxy)benzyl)-2-methylnicotinamide | | 509.2 | 9.07 (br t, J = 5.5 Hz, 1H), 8.98 (br s, 1H), 8.67 (br d, J = 5.8 Hz, 1H), 8.24 (s, 1H), 7.83 (br s, 1H), 7.33 (br d, J = 7.0 Hz, 1H), 7.24 (br t J = 8.5 Hz, 1H), 7.08 (br d, J = 8.9 Hz, 1H), 6.08 (br s, 2H), 4.57 (br d, J = 5.8 Hz, 2H), 4.53 (br s, 1H), 3.98-3.81 (m, 2H), 3.81-3.72 (m, 1H), 2.60 (s, 3H), 1.92 (br d, J = 13.7 Hz, 1H), 1.79 (br s, 2H), 1.67-1.45 (m, 1H), 1.11 (d, J = 6.1 Hz, 3H) |
| 317 | 5-(2-amino-[1,2,4]triazolo[1,5-a]pyridin-7-yl)-N-(3,5-difluoro-2-((tetrahydrofuran-3-yl)oxy)benzyl)-2-methylnicotinamide | | 481.2 | 9.05-9.01 (m, 1H), 8.98 (s, 1H), 8.65 (d, J = 7.0 Hz, 1H), 8.25 (d, J = 1.8 Hz, 1H), 7.83 (s, 1H), 7.34 (d, J = 7.1 Hz, 1H), 7.30-7.24 (m, 1H), 7.08 (br d, J = 8.9 Hz, 1H), 6.08 (br s, 2H), 4.98 (br s, 1H), 4.58-4.47 (m, 2H), 4.06-3.89 (m, 2H), 3.86-3.69 (m, 2H), 2.61 (s, 3H), 2.19-2.07 (m, 2H) |
| 318 | (R)-5-(2-amino-[1,2,4]triazolo[1,5-a]pyridin-7-yl)-N-(1-(2-fluoro-5-(trifluoromethoxy)phenyl)ethyl-N,2-dimethylnicotinamide | | 489.2 | 9.02-8.89 (m, 1H), 8.62 (br d, J = 6.8 Hz, 1H), 8.30-7.87 (m, 1H), 7.81 (s, 1H), 7.55 (br d, J = 3.8 Hz, 1H), 7.43 (br d, J = 8.9 Hz, 2H), 7.31 (br d, J = 6.8 Hz, 1H), 6.07 (s, 2H), 2.88 (br s, 1H), 2.59 (s, 3H), 2.45-2.25 (m, 3H), 1.61 (br d, J = 6.9 Hz, 3H) |
| 319 | 5-(2-amino-[1,2,4]triazolo[1,5-a]pyridin-7-yl)-N-(1-benzyl-1H-imidazol-4-yl)-2-methylnicotinamide | | 425.1 | 10.99 (s, 1H), 8.93 (d, J = 2.3 Hz, 1H), 8.62 (d, J = 7.0 Hz, 1H), 8.24 (d, J = 2.5 Hz, 1H), 7.82 (s, 1H), 7.68 (s, 1H), 7.47-7.27 (m, 7H), 5.20 (s, 2H), 2.59 (s, 3H). |

TABLE 11

Compounds in Table 11 were prepared in a similar fashion to examples 86 and 286.

| Ex No | Name | R | M + H | 1H NMR (500 MHz, DMSO-d6) δ |
|---|---|---|---|---|
| 320 | (R)-5-(2-amino-[1,2,4]triazolo[1,5-a]pyridin-7-yl)-2-ethyl-N-(1-(2-fluoro-5-(trifluoromethoxy)phenyl)ethyl)nicotinamide | | 489.2 | 9.04 (br d, J = 7.4 Hz, 1H), 8.99 (s, 1H), 8.62 (d, J = 7.0 Hz, 1H), 8.10 (s, 1H), 7.78 (s, 1H), 7.47 (d, J = 6.5 Hz, 1H), 7.39-7.27 (m, 3H), 5.38 (quin, J = 7.1 Hz, 1H), 2.91-2.74 (m, 2H), 1.50 (d, J = 7.0 Hz, 3H), 1.18 (t, J = 7.5 Hz, 3H) NH2 protons not observed |

TABLE 11-continued

Compounds in Table 11 were prepared in a similar fashion to examples 86 and 286.

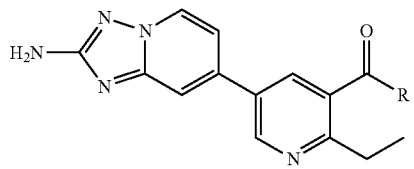

| Ex No | Name | R | M + H | 1H NMR (500 MHz, DMSO-d6) δ |
|---|---|---|---|---|
| 321 | (S)-5-(2-amino-[1,2,4]triazolo[1,5-a]pyridin-7-yl)-2-ethyl-N-(1-(2-fluoro-5-(trifluoromethoxy)phenyl)ethyl)nicotinamide | | 489.1 | 9.05-9.02 (m, 1H), 9.00 (s, 1H), 8.63 (d, J = 7.0 Hz, 1H), 8.11 (s, 1H), 7.78 (s, 1H), 7.48 (br s, 1H), 7.40-7.27 (m, 3H), 5.38 (quin, J = 7.0 Hz, 1H), 2.93-2.74 (m, 2H), 1.50 (d, J = 7.0 Hz, 3H), 1.18 (t, J = 7.5 Hz, 3H) NH2 protons not observed |
| 322 | 5-(2-amino-[1,2,4]triazolo[1,5-a]pyridin-7-yl)-2-ethyl-N-(2-fluoro-5-(trifluoromethyl)benzyl)nicotinamide | | 459.2 | 9.21 (br t, J = 5.6 Hz, 1H), 9.01 (s, 1H), 8.65 (d, J = 6.7 Hz, 1H), 8.16 (s, 1H), 7.86-7.73 (m, 3H), 7.49 (t, J = 9.2 Hz, 1H), 7.32 (br d, J = 7.0 Hz, 1H), 6.08 (s, 2H), 4.62 (br d, J = 5.5 Hz, 2H), 2.89 (q, J = 7.6 Hz, 2H), 1.19 (t, J = 7.5 Hz, 3H) |

TABLE 12

Compounds in Table 12 were prepared in a similar fashion to examples 96 and 97.

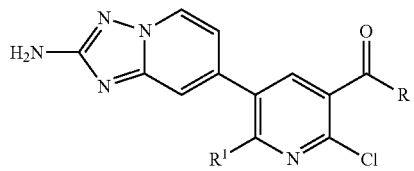

| Ex No | Name | R | R¹ | M + H | 1H NMR (500 MHz, DMSO-d6) δ |
|---|---|---|---|---|---|
| 323 | (R)-5-(2-amino-[1,2,4]triazolo[1,5-a]pyridin-7-yl)-2-chloro-N-(1-(2-fluoro-5-(trifluoromethoxy)phenyl)ethyl)-6-methylnicotinamide | | Me | 508.9 | 9.22 (br d, J = 7.3 Hz, 1H), 8.68 (br d, J = 6.7 Hz, 1H), 7.85 (s, 1H), 7.49 (br s, 2H), 7.40-7.30 (m, 2H), 7.03 (br d, J = 5.5 Hz, 1H), 5.31 (br t, J = 7.0 Hz, 1H), 2.57-2.55 (m, 3H), 1.45 (br d, J = 7.0 Hz, 3H) NH2 protons not observed |
| 324 | (R)-5-(2-amino-[1,2,4]triazolo[1,5-a]pyridin-7-yl)-2-chloro-N-(1-(2-fluoro-5-(trifluoromethoxy)phenyl)ethyl)nicotinamide | | H | 495.0 | 9.28 (d, J = 7.4 Hz, 1H), 8.96 (d, J = 2.2 Hz, 1H), 8.67 (d, J = 6.9 Hz, 1H), 8.38 (d, J = 2.5 Hz, 1H), 7.87 (s, 1H), 7.51 (br d, J = 3.6 Hz, 1H), 7.42-7.28 (m, 3H), 6.12 (s, 2H), 5.34 (t, J = 7.2 Hz, 1H), 1.47 (d, J = 7.2 Hz, 3H) |

Example 325

(R)-5-(2-amino-[1,2,4]triazolo[1,5-a]pyridin-7-yl)-N-(1-(2-fluoro-5-(trifluoromethoxy)phenyl)ethyl)-2-methoxy-N,6-dimethylnicotinamide

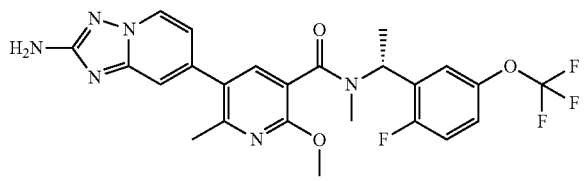 [SMILES: COc1nc(C)c(-c2ccn3nc(N)nc3c2)cc1C(=O)N(C)[C@H](C)c1cc(OC(F)(F)F)ccc1F]

325A: (S,E)-N-(2-fluoro-5-(trifluoromethoxy)benzylidene)-2-methylpropane-2-sulfinamide: Titanium(V) isopropoxide (5.69 mL, 19.22 mmol) was added to a THF (20 mL) solution of 2-fluoro-5-(trifluoromethoxy)benzaldehyde (2.0 g, 9.61 mmol) and (S)-(−)-2-methyl-2-propanesulfinamide (1.165 g, 9.61 mmol) at rt and stirred for 24 h. The reaction mixture was quenched by adding brine (10 mL) and hexanes (10 mL) at 0° C. The mixture was filtered through a pad of celite and rinsed with ethyl acetate (2×75 mL). The combined organic solutions were dried over sodium sulfate, decanted (TiO$_2$ precipitated out of the organic layer) and concentrated under reduced pressure to give crude product which was purified on a silica gel column with Hexanes/EtOAc (100/0 to 50/50) to give (S,E)-N-(2-fluoro-5-(trifluoromethoxy)benzylidene)-2-methylpropane-2-sulfinamide (1.92 g, 6.11 mmol, 64% yield) as a colorless oil.

$^1$H NMR (400 MHz, DMSO-d6) δ 8.68 (s, 1H), 7.93 (d, J=5.7 Hz, 1H), 7.75-7.57 (m, 2H), 1.31-1.16 (m, 9H).

325B: (S)—N—((R)-1-(2-fluoro-5-(trifluoromethoxy)phenyl)ethyl)-2-methylpropane-2-sulfinamide: To a solution of (S,E)-N-(2-fluoro-5-(trifluoromethoxy)benzylidene)-2-methylpropane-2-sulfinamide (1.92 g, 6.17 mmol) in THF (30 mL) was added methylmagnesium bromide (2.70 mL, 8.11 mmol) dropwise at −65° C. The temperature was maintained for 8 h, then the reaction mixture was warmed to 23° C. and stirred 12 h. The reaction mixture was concentrated to about 10 mL and quenched with saturated NH$_4$Cl solution at 0° C. The aqueous layer was extracted with EtOAc (50 mL×3). The combined organic phases were washed with brine (50 mL) and dried over Na$_2$SO$_4$. Filtration and concentration yielded a crude product, (S)—N—((R)-1-(2-fluoro-5-(trifluoromethoxy)phenyl)ethyl)-2-methylpropane-2-sulfinamide (1.49 g, 4.32 mmol, 70% yield), containing ~30% of the S,S-isomer.

MS ESI m/z 328.3 (M+H)

The material was further purified by chiral HPLC. Conditions: Column: (R.R)Whelko-o1 (3×25 cm, 10 um); Column Temp. 345 0° C.; Back Pressure: 100 bar; Flow rate: 180 mL/min; Mobile Phase: CO2/IPA=95:5; Injection Volume: 3.75 mL (15 mg/ml); Injection Program: Stacked (2.5 min/per cycle); Detector Wavelength: 220 nm; Sample Solvent: MEOH/IPA=1:1 (V:V).

The fractions from peak 1 (retention time=5.68 min) were collected as (S)—N—((R)-1-(2-fluoro-5-(trifluoromethoxy)phenyl)ethyl)-2-methylpropane-2-sulfinamide (820 mg, 2.480 mmol, 55% yield), crystalline white solid.

The fractions from peak 2 (retention time=6.69 min) were collected as (S)—N—((S)-1-(2-fluoro-5-(trifluoromethoxy)phenyl)ethyl)-2-methylpropane-2-sulfinamide (350 mg, 1.037 mmol, 23% yield), a colorless oil.

Each isomer was carried into deprotection separately.

325C: (R)-1-(2-fluoro-5-(trifluoromethoxy)phenyl)ethan-1-amine, HCl: To a solution of (S)—N—((R)-1-(2-fluoro-5-(trifluoromethoxy)phenyl)ethyl)-2-methylpropane-2-sulfinamide (820 mg, 2.505 mmol) in THF (5 mL) was added HCl, 4 M in dioxane (3.76 mL, 15.03 mmol). After stirring 1 h at rt, the reaction mixture was concentrated and triturated in ether (20 mL). The solid was collected as (R)-1-(2-fluoro-5-(trifluoromethoxy)phenyl)ethan-1-amine, HCl (555 mg, 2.031 mmol, 81% yield). The material was carried forward without further purification.

MS ESI m/z 223.9 (M+H)

325D: tert-butyl (R)-(1-(2-fluoro-5-(trifluoromethoxy)phenyl)ethyl)carbamate: A mixture of (R)-1-(2-fluoro-5-(trifluoromethoxy)phenyl)ethan-1-amine, HCl (200 mg, 0.770 mmol), BOC-anhydride (0.268 mL, 1.155 mmol) and Et$_3$N (0.376 mL, 2.70 mmol) in THF (10 mL) was stirred at rt ON. The reaction mixture was partitioned between EtOAc (30 mL) and water (20 mL). The organic layer was washed with brine (20 mL), dried (MgSO$_4$) and concentrated to afford a solid. The crude product was was chromatographed on a 12 gm ISCO silica gel cartridge, eluting with a 0-40% EtOAc/Hex gradient. The pure fractions were concentrated to afford tert-butyl (R)-(1-(2-fluoro-5-(trifluoromethoxy)phenyl)ethyl)carbamate (230 mg, 0.711 mmol, 92% yield) as a white solid.

MS ESI m/z 268.1 (M−C(CH3)3+H)

325E: (R)-1-(2-fluoro-5-(trifluoromethoxy)phenyl)-N-methylethan-1-amine: To a suspension of LAH (162 mg, 4.27 mmol) in diethyl ether (4 mL) at 0° C. was added dropwise over 5 min a solution of tert-butyl (R)-(1-(2-fluoro-5-(trifluoromethoxy)phenyl)ethyl)carbamate (230 mg, 0.711 mmol) in diethyl ether (4 mL). The reaction mixture was allowed to warm to rt and stir ON. THF (5 ml) was added and the reaction was heated to 50° C. for 8 h. After cooling to 0° C. and with extreme care, water (0.3 mL), followed by 15% NaOH (0.3 mL) and water (0.9 mL) were added. After stirring the suspension 1 h, anhydrous magnesium sulfate was added and the mixture was filtered. The filtrate was concentrated to afford (R)-1-(2-fluoro-5-(trifluoromethoxy)phenyl)-N-methylethan-1-amine (149 mg, 0.628 mmol, 88% yield) as a colorless oil. The material was carried forward without further purification.

MS ESI m/z 238.4 (M+H)

325: A mixture of 5-(2-amino-[1,2,4]triazolo[1,5-a]pyridin-7-yl)-2-methoxy-6-methylnicotinic acid (20 mg, 0.067 mmol), made as in example 3, (R)-1-(2-fluoro-5-(trifluoromethoxy)phenyl)-N-methylethan-1-amine (23.78 mg, 0.100 mmol), BOP (32.5 mg, 0.074 mmol) and Et$_3$N (0.028 mL, 0.200 mmol) in DMF (0.3 mL) was agitated at rt for 3 d. The reaction was filtered and purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 25 minutes, then a 6-minute hold at 100% B; Flow: 20 mL/min. Fractions containing the desired product were combined and dried via centrifugal evaporation to afford (R)-5-(2-amino-[1,2,4]triazolo[1,5-a]pyridin-7-yl)-N-(1-(2-fluoro-5-(trifluoromethoxy)phenyl)ethyl)-2-methoxy-N,6-dimethylnicotinamide (14.4 mg, 0.027 mmol, 40% yield).

MS ESI m/z 519.4 (M+H)

$^1$H NMR (500 MHz, DMSO-d$_6$) δ 8.55 (br d, J=6.7 Hz, 1H), 7.63-7.48 (m, 1H), 7.46-7.25 (m, 4H), 6.96-6.82 (m,

1H), 6.03-5.81 (m, 1H), 5.13-4.86 (m, 1H), 3.93 (br s, 3H), 2.84-2.60 (m, 3H), 2.45 (s, 3H), 1.57 (br d, J=6.4 Hz, 3H).

Example 326

5-(2-Amino-[1,2,4]triazolo[1,5-a]pyridin-7-yl)-N-(3-fluoro-2-(pyrrolidin-1-ylmethyl)benzyl)-2-methoxy-6-methylnicotinamide

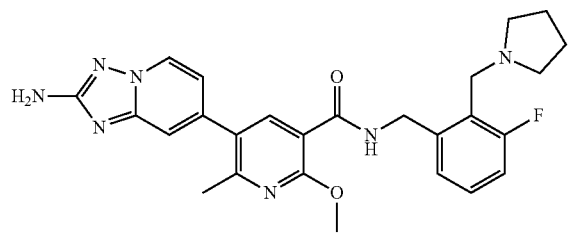 [SMILES: COc1nc(C)c(-c2ccn3nc(N)nc3c2)cc1C(=O)NCc1cccc(F)c1CN1CCCC1]

326A: 3-fluoro-2-(pyrrolidin-1-ylmethyl)benzonitrile: A solution of 2-(bromomethyl)-3-fluorobenzonitrile (250 mg, 1.168 mmol), pyrrolidine (0.288 mL, 3.50 mmol) and Et₃N (0.488 mL, 3.50 mmol) in acetonitrile (6 mL) was stirred at rt for 16 h. The reaction mixture was partitioned between EtOAc (30 ml) and water (30 ml). The organic layer was washed with brine (30 mL), dried over anhydrous sodium sulfate and concentrated to afford 3-fluoro-2-(pyrrolidin-1-ylmethyl)benzonitrile (235 mg, 1.151 mmol, 99% yield) as a yellow oil.

1H NMR (400 MHz, CDCl₃) δ 7.47 (dd, J=7.6, 0.9 Hz, 1H), 7.35 (td, J=7.9, 5.3 Hz, 1H), 7.32-7.27 (m, 1H), 3.87 (d, J=1.7 Hz, 2H), 2.83-2.46 (m, 4H), 1.86-1.73 (m, 4H).

326B: (3-Fluoro-2-(pyrrolidin-1-ylmethyl)phenyl)methanamine: To a suspension of LAH (175 mg, 4.60 mmol) in diethyl ether (10 mL) at 0° C. was added (3-fluoro-2-(pyrrolidin-1-ylmethyl)phenyl)methanamine as a solution in diethyl ether (10 mL) dropwise over five min. The reaction mixture was allowed to warm to rt and stirred ON. The reaction mixture was cooled to 0° C. and water (0.1 mL) was added carefully. 15% NaOH (0.1 mL) and water (0.3 mL) were added sequentially and the resulting mixture was allowed to stir at rt for 1 h. Anhydrous magnesium sulfate was added and the suspension was filtered and the filter cake washed with EtOAc (20 mL). The filtrate was concentrated to afford (3-fluoro-2-(pyrrolidin-1-ylmethyl)phenyl)methanamine (223 mg, 1.071 mmol, 93% yield) as an amber oil.

1H NMR (400 MHz, CDCl₃) δ 7.20 (td, J=7.8, 5.6 Hz, 1H), 7.07 (d, J=7.0 Hz, 1H), 6.93 (ddd, J=9.7, 8.3, 1.2 Hz, 1H), 3.83 (s, 2H), 3.70 (d, J=2.4 Hz, 2H), 2.53 (td, J=5.5, 1.5 Hz, 4H), 1.80-1.65 (m, 4H).

326: A mixture of 5-(2-amino-[1,2,4]triazolo[1,5-a]pyridin-7-yl)-2-methoxy-6-methylnicotinic acid (15 mg, 0.050 mmol), made as in example 3, (3-fluoro-2-(pyrrolidin-1-ylmethyl)phenyl)methanamine (12.53 mg, 0.060 mmol), BOP (24.38 mg, 0.055 mmol) and Et₃N (0.021 mL, 0.150 mmol) in DMF (0.3 mL) was agitated at rt for 3 d. The reaction was filtered and purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 3-43% B over 20 minutes, then a 4-minute hold at 100% B; Flow: 20 mL/min. Fractions containing the desired product were combined and dried via centrifugal evaporation to afford 5-(2-Amino-[1,2,4]triazolo[1,5-a]pyridin-7-yl)-N-(3-fluoro-2-(pyrrolidin-1-ylmethyl)benzyl)-2-methoxy-6-methylnicotinamide (25.1 mg, 0.051 mmol, 99% yield).

MS ESI m/z 490.0 (M+H)

1H NMR (500 MHz, DMSO-d6) δ 9.18 (t, J=5.9 Hz, 1H), 8.60 (d, J=6.9 Hz, 1H), 8.01 (s, 1H), 7.58-7.48 (m, 1H), 7.38 (br d, J=7.2 Hz, 2H), 7.31-7.25 (m, 1H), 6.94 (d, J=6.9 Hz, 1H), 4.75-4.47 (m, 4H), 4.05 (s, 3H), 3.25-3.17 (m, 2H), 2.46 (s, 3H), 2.08 (br s, 2H), 1.90 (br s, 2H) NH2 missing and 2 protons are buried under the water peak.

TABLE 13

Compounds in Table 13 were prepared in a similar fashion to examples 2, 3, 5, 6, 9, 81, 84, 96, 97, and 286.

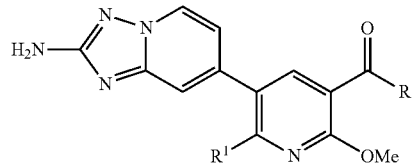

| Ex No | Name | R | R¹ | M + H | 1H NMR (500 MHz, DMSO-d6) δ |
|---|---|---|---|---|---|
| 327 | 5-(2-amino-[1,2,4]triazlo[1,5-a]pyridin-7-yl)-N-(2-isobutoxybenzyl)-2-methoxy-6-methylnicotinamide | | Me | 461.1 | 8.63-8.56 (m, 2H), 8.08 (s, 1H), 7.38 (s, 1H), 7.23 (br s, 2H), 6.98 (br d, J = 8.4 Hz, 1H), 6.94-6.88 (m, 2H), 6.06 (s, 2H), 4.52 (br d, J = 5.7 Hz, 2H), 4.04 (s, 3H), 3.82 (br d, J = 6.3 Hz, 2H), 2.57-2.54 (m, 3H), 2.08 (dt, J = 13.1, 6.6 Hz, 1H), 1.04 (br d, J = 6.65 Hz, 6H) |

TABLE 13-continued

Compounds in Table 13 were prepared in a similar fashion to examples 2, 3, 5, 6, 9, 81, 84, 96, 97, and 286.

| Ex No | Name | R | R¹ | M + H | 1H NMR (500 MHz, DMSO-d6) δ |
|---|---|---|---|---|---|
| 328 | 5-(2-amino-[1,2,4]triazlo[1,5-a]pyridin-7-yl)-N-(2-fluoro-6-(2,2,2-trifluoroethoxy)benzyl)-2-methoxy-6-methylnicotinamide | | Me | 505.2 | 8.55 (br d, J = 6.7 Hz, 1H), 8.38 (br t, J = 5.5 Hz, 1H), 8.12-7.98 (m, 1H), 7.39-7.31 (m, 2H), 7.12-6.97 (m, 1H), 6.96-6.87 (m, 2H), 6.02 (br s, 2H), 4.89-4.76 (m, 2H), 4.57 (br d, J = 5.2 Hz, 2H), 4.00 (s, 3H), 2.46-2.45 (s, 3H) |
| 329 | 5-(2-amino-[1,2,4]triazolo[1,5-a]pyridin-7-yl)-N-(5-fluoro-2-(trifluoromethoxy)benzyl)-2-methoxy-6-methylnicotinamide | | Me | 491.0 | 8.79 (br t, J = 5.8 Hz, 1H), 8.54 (br d, J = 6.8 Hz, 1H), 8.03 (s, 1H), 7.40 (br s, 1H), 7.35 (s, 1H), 7.30-7.13 (m, 2H), 6.94 (br d, J = 6.8 Hz, 1H), 4.57 (br d, J = 5.9 Hz, 2H), 4.05 (s, 3H), 2.49-2.44 (m, 3H) NH₂ protons not observed |
| 330 | 5-(2-amino-[1,2,4]triazlo[1,5-a]pyridin-7-yl)-N-(2-isopropoxymethyl)benzyl)-2-methoxy-6-methylnicotinamide | | Me | 461.1 | 8.67 (t, J = 6.5 Hz, 1H), 8.63 (d, J = 6.8 Hz, 1H), 8.06 (s, 1H), 7 43 (s, 1H), 7.37-7.21 (m, 5H), 7.08-6.96 (m, 2H), 4.62-4.53 (m, 4H), 4.03 (s, 3H), 3.79-3.57 (m, 1H), 2.49-2.46 (m, 3H), 1.16 (d, J = 6.1 Hz, 6H) |
| 331 | 5-(2-amino-[1,2,4]triazlo[1,5-a]pyridin-7-yl)-N-((2-fluoro-5-(trifluoromethyl)phenyl)methyl-d2)-2-methoxy-6-methylnicotinamide | | Me | 477.2 | 8.91 (s, 1H), 8.57 (d, J = 6.7 Hz, 1H), 7.99 (s, 1H), 7.78 (br d, J = 6.1 Hz, 1H), 7.73 (br s, 1H), 7.45 (t, J = 9.2 Hz, 1H), 7.37 (s, 1H), 6.91 (br d, J = 7.0 Hz, 1H), 6.03 (s, 2H), 4.04 (s, 3H), 2.48 (s, 3H) |
| 332 | 5-(2-amino-[1,2,4]triazlo[1,5-a]pyridin-7-yl)-2-methoxy-6-methyl-N-(2-(2,2,2-trifluoroethoxy)benzyl)nicotinamide | | Me | 487.2 | 8.64 (t, J = 6.7 Hz, 1H), 8,59 (d, J = 7.0 Hz, 1H), 8.08 (s, 1H), 7.38 (s, 1H), 7.34-7.25 (m, 2H), 7.14 (d, J = 8.5 Hz, 1H), 7.04 (t, J = 7.3 Hz, 1H), 6.92 (br d, J = 8.2 Hz, 1H), 6.05 (s, 2H), 4.84 (q, J = 8.9 Hz, 2H), 4.53 (br d, J = 6.1 Hz, 2H), 4.05 (s, 3H), 2.50-2.48 (m, 3H) |
| 333 | 5-(2-amino-[1,2,4]triazlo[1,5-a]pyridin-7-yl)-N-(3,5-difluoro-2-isobutoxybenzyl)-2-methoxy-6-methylnicotinamide | | Me | 497.3 | 8.84 (br t, J = 6.0 Hz, 1H), 8.55 (d, J = 6.8 Hz, 1H), 8.03 (s, 1H), 7.35 (s, 1H), 7.23-7.09 (m, 1H), 6.96-6.89 (m, 2H), 6.03 (s, 2H), 4.54 (br d, J = 5.9 Hz, 2H), 4.03 (s, 3H), 3.77 (s, 2H), 2.48-2.45 (m, 3H), 2.03 (dquin, J = 13.0, 6.6 Hz, 1H), 0.99 (d, J = 6.7 Hz, 6H) |
| 334 | 5-(2-amino-[1,2,4]triazlo[1,5-a]pyridin-7-yl)-2-methoxy-6-methyl-N-(3-(2,2,2-trifluoroethoxy)benzyl)nicotinamide | | Me | 487.1 | 8.80 (br t, J = 6.1 Hz, 1H), 8.59 (d, J = 7 0 Hz, 1H), 8.05 (s, 1H), 7.39 (s, 1H), 7.31 (t, J = 8.1 Hz, 1H), 7.04 (s, 1H), 7.03 (d, J = 6.6 Hz, 1H), 6.99-6.88 (m, 2H), 6.05 (s, 2H), 4.75 (q, J = 9.1 Hz, 2H), 4.52 (br d, J = 6.1 Hz, 2H), 4.05 (s, 3H), 2.49 (s, 3H) |

TABLE 13-continued

Compounds in Table 13 were prepared in a similar fashion to examples 2, 3, 5, 6, 9, 81, 84, 96, 97, and 286.

| Ex No | Name | R | R¹ | M + H | 1H NMR (500 MHz, DMSO-d6) δ |
|---|---|---|---|---|---|
| 335 | 5-(2-amino-[1,2,4]triazlo[1,5-a]pyridin-7-yl)-2-methoxy-6-methyl-N-((3-(trifluoromethyl)phenyl)methyl-d2)-nicotinamide | [NH-CD2-C6H4-CF3 (3-position)] | Me | 459.2 | 8.93 (s, 1H), 8.59 (d, J = 7.0 Hz, 1H), 8.03 (s, 1H), 7.72 (s, 1H), 7.70-7.56 (m, 3H), 7.38 (s, 1H), 6.92 (br d, J = 6.7 Hz, 1H), 6.05 (s, 2H), 4.05 (s, 3H), 2.49 (s, 3H) |
| 336 | 5-(2-amino-[1,2,4]triazlo[1,5-a]pyridin-7-yl)-N-(3-chloro-2-fluoro-5-(trifluoromethyl)benzyl)-2-methoxy-6-methylnicotinamide | [NH-CH2-C6H2(F)(Cl)(CF3)] | Me | 509.3 | 9.06-8.90 (m, 1H), 8.58 (d, J = 6.7 Hz, 1H), 8.00 (s, 2H), 7.76 (br d, J = 4.3 Hz, 1H), 7.37 (s, 1H), 6.92 (br d, J = 5.8 Hz, 1H), 4.64 (br d, J = 5.5 Hz, 2H), 4.05 (s, 3H), 2.50-2.46 (m, 3H) NH2 protons not observed |
| 337 | 5-(2-amino-[1,2,4]triazlo[1,5-a]pyridin-7-yl)-N-(2-fluoro-5-methoxybenzyl)-2-methoxy-6-methylnicotinamide | [NH-CH2-C6H3(F)(OMe)] | Me | 437.2 | 8.79 (br t, J = 5.8 Hz, 1H), 8.59 (d, J = 7.0 Hz, 1H), 8.03 (s, 1H), 7.39 (s, 1H), 7.17-7.08 (m, 1H), 6.97-6.91 (m, 2H), 6.89-6.81 (m, 1H), 4.53 (br d, J = 6.1 Hz, 2H), 4.04 (s, 3H), 3.72 (s, 3H), 2.48 (s, 3H) NH2 protons not observed |
| 338 | 5-(2-amino-[1,2,4]triazolo[1,5-a]pyridin-7-yl)-N-(6-(cyclopropylmethoxy)-2,3-difluorobenzyl)-2-methoxynicotinamide | [NH-CH2-C6H2(F)(F)(OCH2-cyclopropyl)] | H | 481.3 | 8.76 (d, J = 2.4 Hz, 1H), 8.59 (d, J = 7.0 Hz, 1H), 8.53 (br t, J = 5.3 Hz, 1H), 8.46 (d, J = 2.4 Hz, 1H), 7.70 (s, 1H), 7.31 (q, J = 9.5 Hz, 1H), 7.23 (br d, J = 5.5 Hz, 1H), 6.85 (br d, J = 7.6 Hz, 1H), 6.04 (s, 2H), 4.61 (br d, J = 5.2 Hz, 2H), 4.03 (s, 3H), 3.93 (d, J = 7.0 Hz, 2H), 1.27 (br s, 1H), 0.57 (br d, J = 6.7 Hz, 2H), 0.36 (br d, J = 4.0 Hz, 2H) |
| 339 | 5-(2-amino-[1,2,4]triazlo[1,5-a]pyridin-7-yl)-N-(5-fluoro-2-(2,2,2-trifluoroethoxy)benzyl)-2-methoxynicotinamide | [NH-CH2-C6H3(F)(OCH2CF3)] | H | 491.2 | 8.88-8.75 (m, 2H), 8.61 (d, J = 7.0 Hz, 1H), 8.48 (d, J = 2.1 Hz, 1H), 7.73 (s, 1H), 7.26 (br d, J = 6.7 Hz, 1H), 7.21-7.11 (m, 3H), 6.05 (s, 2H), 4.83 (q, J = 8.7 Hz, 2H), 4.52 (br d, J = 5.8 Hz, 2H), 4.07 (s, 3H) |
| 340 | 5-(2-amino-[1,2,4]triazlo[1,5-a]pyridin-7-yl)-N-(2-isobutoxybenzyl)-2-methoxynicotinamide | [NH-CH2-C6H4(O-iBu)] | H | 446.9 | 8.77-8.68 (m, 2H), 8.57 (d, J = 6.9 Hz, 1H), 8.46 (d, J = 2.4 Hz, 1H), 7.68 (s, 1H), 7.31-7.19 (m, 3H), 6.97 (d, J = 8.0 Hz, 1H), 6.91 (t, J = 7.5 Hz, 1H), 6.04 (s, 2H), 4.52 (br d, J = 5.8 Hz, 2H), 4.03 (s, 3H), 3.80 (br d, J = 6.3 Hz, 2H), 2.06 (dt, J = 13.1, 6.5 Hz, 1H), 1.02 (d, J = 6.7 Hz, 6H) |

TABLE 13-continued

Compounds in Table 13 were prepared in a similar fashion to examples 2, 3, 5, 6, 9, 81, 84, 96, 97, and 286.

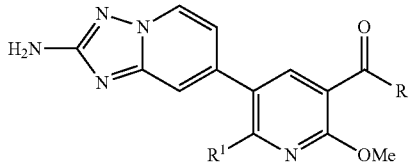

| Ex No | Name | R | R¹ | M + H | 1H NMR (500 MHz, DMSO-d6) δ |
|---|---|---|---|---|---|
| 341 | 5-(2-amino-[1,2,4]triazlo[1,5-a]pyridin-7-yl)-N-(3,5-difluoro-2-isobutoxybenzyl)-2-methoxynicotinamide | 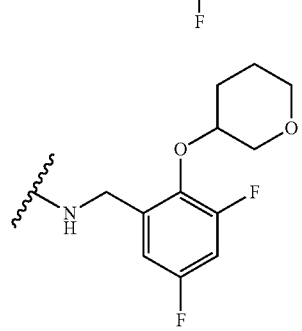 | H | 484.0 | 8.91 (t, J = 6.0 Hz, 1H), 8.80 (d, J = 2.4 Hz, 1H), 8.61 (d, J = 6.9 Hz, 1H), 8.47 (d, J = 2.5 Hz, 1H), 7.74 (s, 1H), 7.31-7.18 (m, 2H), 7.02 (br d, J = 8.8 Hz, 1H), 6.07 (s, 2H), 4.58 (d, J = 5.9 Hz, 2H), 4.06 (s, 3H), 3.82 (d, J = 6.3 Hz, 2H), 2.07 (dquin, J = 13.2, 6.6 Hz, 1H), 1.03 (d, J = 6.7 Hz, 6H) |
| 342 | 5-(2-amino-[1,2,4]triazlo[1,5-a]pyridin-7-yl)-N-(3,5-difluoro-2-((tetrahydro-2H-pyran-3-yl)oxy)benzyl)-2-methoxynicotinamide | 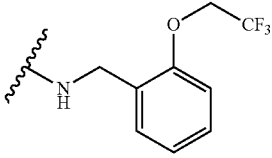 [SMILES: *NCc1ccccc1OCC(F)(F)F] | H | 511.2 | 8.91 (br t, J = 6.0 Hz, 1H), 8.78 (d, J = 2.4 Hz, 1H), 8.60 (d, J = 7.0 Hz, 1H), 8.47 (d, J = 2.4 Hz, 1H), 7.72 (s, 1H), 7.30-7.11 (m, 4H), 7.11-6.99 (m, 2H), 4.67-4.55 (m, 2H), 4.17 (br s, 1H), 4.06 (s, 3H), 3.76 (br d, J = 10.1 Hz, 1H), 3.67-3.47 (m, 2H), 2.05-1.98 (m, 1H), 1.94-1.82 (m, 2H), 1.67-1.47 (m, 1H) |
| 343 | 5-(2-amino-[1,2,4]triazlo[1,5-a]pyridin-7-yl)-2-methoxy-N-(2-(2,2,2-trifluoroethoxy)benzyl)nicotinamide | 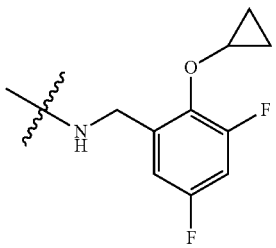 [SMILES: *NCc1cc(F)cc(F)c1OC1CC1] | H | 473.3 | 8.79 (d, J = 2.4 Hz, 1H), 8 74 (br t, J = 5.8 Hz, 1H), 8.61 (d, J = 7.0 Hz, 1H), 8.49 (d, J = 2.4 Hz, 1H), 7.72 (s, 1H), 7.35 (br d, J = 7.6 Hz, 1H), 7.33-7.28 (m, 1H), 7.26 (dd, J = 7.0, 1.5 Hz, 1H), 7.14 (d, J = 8.2 Hz, 1H), 7.06 (t, J = 7.5 Hz, 1H), 6.05 (s, 2H), 4.84 (q, J = 8.9 Hz, 2H), 4.54 (br d, J = 6.1 Hz, 2H), 4.06 (s, 3H) |
| 344 | 5-(2-amino-[1,2,4]triazlo[1,5-a]pyridin-7-yl)-N-(2-cyclopropoxy-3,5-difluorobenzyl)-2-methoxynicotinamide | 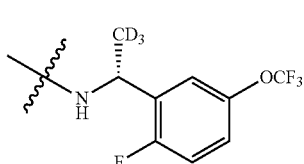 [SMILES: *N[C@@H](c1cccc(OC(F)(F)F)c1)C([2H])([2H])[2H]] | H | 467.1 | 8.91 (br t, J = 6.0 Hz, 1H), 8.78 (d, J = 2.4 Hz, 1H), 8.60 (d, J = 7.0 Hz, 1H), 8.45 (d, J = 2.4 Hz, 1H), 7.72 (s, 1H), 7.31-7.19 (m, 2H), 7.01 (br d, J = 8 5 Hz, 1H), 6.04 (s, 2H), 4.47 (br d, J = 6.1 Hz, 2H), 4.22 (br d, J = 3.1 Hz, 1H), 4.06 (s, 3H), 0.85 (br s, 2H), 0.71-0.54 (m, 2H) |
| 345 | (R)-5-(2-amino-[1,2,4]triazlo[1,5-a]pyridin-7-yl)-N-(1-(2-fluoro-5-trifluoromethoxy)phenyl)ethyl-2,2,2-d3)-2-methoxynicotinamide | 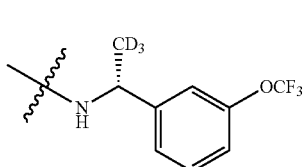 | H | 449.1 | 8.89 (br d, J = 7.6 Hz, 1H), 8.78 (d, J = 2.4 Hz, 1H), 8.60 (d, J = 6.7 Hz, 1H), 8.32 (d, J = 2.4 Hz, 1H), 7.73 (s, 1H), 7.55 (br s, 1H), 7.41-7.32 (m, 2H), 7.26 (br d, J = 5.2 Hz, 1H), 6.05 (s, 2H), 5.35 (br d, J = 7.6 Hz, 1H), 4.04 (s, 3H) |
| 346 | (R)-5-(2-amino-[1,2,4]triazlo[1,5-a]pyridin-7-yl)-2-methoxy-N-(1-(3-(trifluoromethoxy)phenyl)ethyl-2,2,2-d3)nicotinamide |  | H | 476.1 | 8.74 (d, J = 2.5 Hz, 1H), 8.65 (d, J = 7.9 Hz, 1H), 8.56 (d, J = 7.0 Hz, 1H), 8.32 (d, J = 2.6 Hz, 1H), 7.69 (d, J = 1.4 Hz, 1H), 7.53-7.44 (m, 2H), 7.42 (s, 1H), 7.22 (dd, J = 7.0, 2.0 Hz, 2H), 5.90 (s, 2H), 5.20 (d, J = 7.9 Hz, 1H). |

TABLE 13-continued

Compounds in Table 13 were prepared in a similar fashion to examples 2, 3, 5, 6, 9, 81, 84, 96, 97, and 286.

| Ex No | Name | R | R¹ | M + H | 1H NMR (500 MHz, DMSO-d6) δ |
|---|---|---|---|---|---|
| 347 | (S)-5-(2-amino-[1,2,4]triazlo[1,5-a]pyridin-7-yl)-N-(1-(2-fluoro-5-trifluoromethyl)phenyl)ethyl-2,2,2-d3)-2-methoxynicotinamide | | H | 478.2 | 8.97 (d, J = 7.6 Hz, 1H), 8.77 (d, J = 2.4 Hz, 1H), 8.60 (d, J = 7.0 Hz, 1H), 8.31 (d, J = 2.4 Hz, 1H), 7.94 (br d, J = 5.8 Hz, 1H), 7.72 (s, 2H), 7.47 (t, J = 9.3 Hz, 1H), 7.26 (br d, J = 7.0 Hz, 1H), 6.04 (s, 2H), 5.40 (br d, J = 7.6 Hz, 1H), 4.03 (s, 3H) |
| 348 | 5-(2-amino-[1,2,4]triazlo[1,5-a]pyridin-7-yl)-N-(2-isopropoxymethyl)benzyl)-2-methoxynicotinamide | | H | 447.3 | 8.75 (d, J = 2.5 Hz, 1H), 8.65 (br t, J = 5.7 Hz, 1H), 8.57 (d, J = 7.0 Hz, 1H), 8.45 (d, J = 2.5 Hz, 1H), 7.69 (s, 1H), 7.40 (br d, J = 7.3 Hz, 1H), 7.37 (br d, J = 7.3 Hz, 1H), 7.33-7.21 (m, 3H), 5.91 (s, 2H), 4.61 (d, J = 5.9 Hz, 2H), 4.59 (s, 2H), 4.05 (s, 3H), 3.71 (dt, J = 12.2, 6.1 Hz, 1H), 1.18 (d, J = 6.1 Hz, 6H) |
| 349 | 5-(2-amino-[1,2,4]triazlo[1,5-a]pyridin-7-yl)-N-((2-fluoro-5-trifluoromethyl)phenyl)methyl-d2)-2-methoxynicotinamide | | H | 463.0 | 9.01 (s, 1H), 8.79 (s, 1H), 8.60 (d, J = 7.0 Hz, 1H), 8.42 (s, 1H), 7.84 (br d, J = 6.4 Hz, 1H), 7.78-7.69 (m, 2H), 7.47 (t, J = 9.2 Hz, 1H), 7.25 (br d, J = 7.0 Hz, 1H), 6.05 (s, 2H), 4.05 (s, 3H) |
| 350 | 5-(2-amino-[1,2,4]triazlo[1,5-a]pyridin-7-yl)-N-(3,5-difluoro-2-((tetrahydro-2H-pyran-3-yl)oxy)benzyl)-2-methoxy-6-methylnicotinamide | | Me | 525.3 | 8.81 (t, J = 6.0 Hz, 1H), 8.59 (d, J = 6.7 Hz, 1H), 8.06 (s, 1H), 7.38 (s, 1H), 7.24-7.18 (m, 1H), 6.99-6.90 (m, 2H), 6.05 (s, 2H), 4.65-4.55 (m, 2H), 4.16 (br s, 1H), 4.05 (s, 3H), 3.78-3.73 (m, 1H), 3.67-3.51 (m, 2H), 2.50-2.48 (m, 3H), 2.01 (br dd, J = 8.9, 4.9 Hz, 1H), 1.93-1.83 (m, 2H), 1.54-1.47 (m, 2H) |
| 351 | (S)-5-(2-amino-[1,2,4]triazlo[1,5-a]pyridin-7-yl)-N-(3,5-difluoro-2-((tetrahydrofuran-3-yl)oxy)benzyl)-2-methoxy-6-methylnicotinamide | | Me | 511.1 | 8.81 (br t, J = 5.8 Hz, 1H), 8.60 (br d, J = 7.0 Hz, 1H), 8.05 (s, 1H), 7.39 (br s, 1H), 7.24 (br t, J = 8.7 Hz, 1H), 6.97 (d, J = 8.5 Hz, 1H), 6.93 (d, J = 6.9 Hz, 1H), 6.05 (br s, 2H), 4.99 (br s, 1H), 4.66-4.45 (m, 2H), 4.06 (s, 3H), 4.02-3.89 (m, 2H), 3.86-3.77 (m, 1H), 3.73 (dd, J = 10.5, 3.8 Hz, 1H), 2.49 (s, 3H), 2.19-2.07 (m, 2H) |
| 352 | 5-(2-amino-[1,2,4]triazlo[1,5-a]pyridin-7-yl)-N-(3,5-difluoro-2-((2-methyltetrahydro-2H-pyran-4-yl)oxy)benzyl)-2-methoxy-6-methylnicotinamide | | Me | 539.4 | 8.92-8.78 (m, 1H), 8.57 (br d, J = 6.7 Hz, 1H), 8.04 (s, 1H), 7.37 (s, 1H), 7.19 (br t, J = 8.7 Hz, 1H), 7.01-6.88 (m, 1H), 6.03 (s, 2H), 4.62-4.49 (m, 2H), 4.05 (s, 3H), 3.95-3.71 (m, 2H), 2.58-2.54 (s, 6H), 1.90 (br d, J = 16.5 Hz, 2H), 1.78 (br s, 1H), 1.51 (br t, J = 12.5 Hz, 1H), 1.10 (br d, J = 6.1 Hz, 3H) |

TABLE 13-continued

Compounds in Table 13 were prepared in a similar fashion to examples 2, 3, 5, 6, 9, 81, 84, 96, 97, and 286.

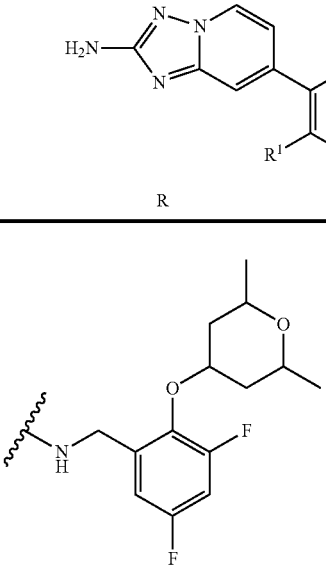

| Ex No | Name | R | R¹ | M + H | 1H NMR (500 MHz, DMSO-d6) δ |
|---|---|---|---|---|---|
| 353 | 5-(2-amino-[1,2,4]triazlo[1,5-a]pyridin-7-yl)-N-(2-((2,6-dimethyltetrahydro-2H-pyran-4-yl)oxy)3,5-difluorobenzyl)-2-methoxy-6-methylnicotinamide | 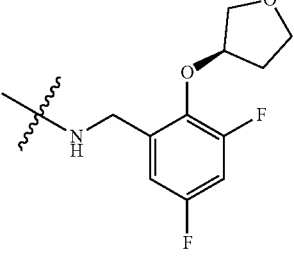 | Me | 553.2 | 8.89-8.74 (m, 1H), 8.59 (d, J = 6.7 Hz, 1H), 8.04 (s, 1H), 7.38 (s, 1H), 7.22 (br t, J = 9.2 Hz, 1H), 6.98 (d, J = 8.5 Hz, 1H), 6.92 (d, J = 6.7 Hz, 1H), 6.04 (s, 2H), 4.56 (br d, J = 5.5 Hz, 3H), 4.06 (s, 3H), 4.01-3.90 (m, 2H), 2.56 (s, 3H), 1.94-1.86 (m, 2H), 1.42 (br t, J = 12.2 Hz, 2H), 1.17-1.07 (m, 6H) |
| 354 | (R)-5-(2-amino-[1,2,4]triazlo[1,5-a]pyridin-7-yl)-N-(3,5-difluoro-2-((tetrahydrofuran-3-yl)oxy)benzyl)-2-methoxy-6-methylnicotinamide | 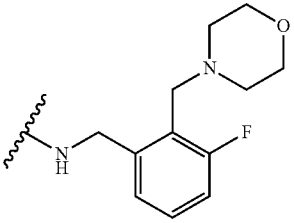 [SMILES: *NCc1cccc(F)c1CN1CCOCC1] | Me | 511.1 | 8.69 (br t, J = 5.9 Hz, 1H), 8.56 (d, J = 6.9 Hz, 1H), 8.05 (s, 1H), 7.36 (s, 1H), 7.27-7.12 (m, 1H), 6.99 (br d, J = 8.7 Hz, 1H), 6.90 (dd, J = 6.9, 1.6 Hz, 1H), 5.91 (s, 2H), 4.99 (br s, 1H), 4.61-4.47 (m, 2H), 4.07 (s, 3H), 4.04-3.89 (m, 2H), 3.87-3.71 (m, 2H), 2.49 (s, 3H), 2.21-2.10 (m, 2H) |
| 355 | 5-(2-amino-[1,2,4]triazlo[1,5-a]pyridin-7-yl)-N-(3-fluoro-2-(morpholinomethyl)benzyl)-2-methoxy-6-methylnicotinamide | 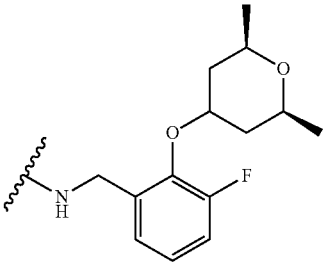 [SMILES: *NCc1cccc(F)c1OC1C[C@@H](C)O[C@@H](C)C1] | Me | 506.2 | 8.64 (br t, J = 5.9 Hz, 1H), 8.52 (d, J = 6.9 Hz, 1H), 7.98 (s, 1H), 7.34-7.26 (m, 2H), 7.20 (d, J = 7.4 Hz, 1H), 7.05 (t, J = 8.8 Hz, 1H), 6.89 (dd, J = 6.9, 1.8 Hz, 1H), 5.85 (s, 2H), 4.68 (d, J = 6.0 Hz, 2H), 4.00 (s, 3H), 2.45 (s, 3H), 2.37 (br s, 4H) Four morpholine protons buried under water peak |
| 356 | 5-(2-amino-[1,2,4]triazlo[1,5-a]pyridin-7-yl)-N-(2-(((2R,6S)-2,6-dimethyltetrahydro-2H-pyran-4-yl)oxy)3-fluorobenzyl)-2-methoxy-6-methylnicotinamide | 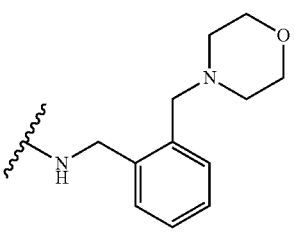 [SMILES: *NCc1ccccc1CN1CCOCC1] | Me | 535.4 | 8.74 (br d, J = 5.8 Hz, 1H), 8.60 (d, J = 7.0 Hz, 1H), 8.06 (s, 1H), 7.39 (s, 1H), 7.21-7.04 (m, 3H), 6.92 (br d, J = 7.0 Hz, 1H), 6.05 (s, 2H), 4.63 (br s, 1H), 4.58 (br d, J = 5.8 Hz, 2H), 4.06 (s, 3H), 3.97 (br dd, J = 11.1, 5.6 Hz, 2H), 2.57-2.54 (m, 3H), 1.90 (br d, J = 13.7 Hz, 2H), 1.43 (br t, J = 12.8 Hz, 2H), 1.17-1.08 (m, 6H) |
| 357 | 5-(2-amino-[1,2,4]triazlo[1,5-a]pyridin-7-yl)-2-methoxy-6-methyl-N-(2-(morpholinomethyl)benzyl)nicotinamide | | Me | 488.3 | 8.55 (br d, J = 6.6 Hz, 2H), 8.02 (s, 1H), 7.38 (d, J = 7.7 Hz, 1H), 7.34 (s, 1H), 7.32-7.20 (m, 3H), 6.90 (dd, J = 6.8, 1.6 Hz, 1H), 5.89 (s, 2H), 4.67 (d, J = 5.8 Hz, 2H), 4.03 (s, 3H), 3.61-3.47 (m, 6H), 2.49-2.46 (m, 3H), 2.44-2.32 (m, 4H) |

TABLE 13-continued

Compounds in Table 13 were prepared in a similar fashion to examples 2, 3, 5, 6, 9, 81, 84, 96, 97, and 286.

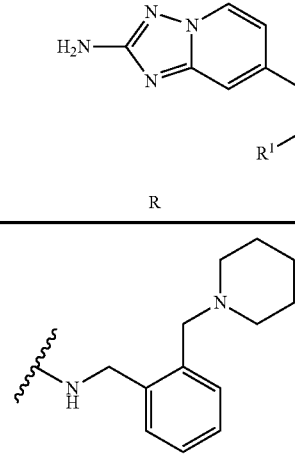

| Ex No | Name | R | R¹ | M + H | 1H NMR (500 MHz, DMSO-d6) δ |
|---|---|---|---|---|---|
| 358 | 5-(2-amino-[1,2,4]triazlo[1,5-a]pyridin-7-yl)-2-methoxy-6-methyl-N-(2-(piperidin-1-ylmethyl)benzyl)nicotinamide | 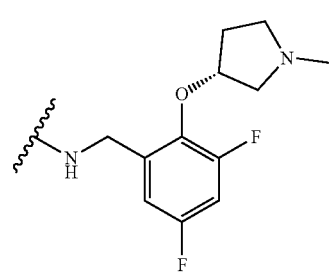 [SMILES: *NCc1cc(F)cc(F)c1O[C@@H]1CCN(C)C1] | Me | 486.1 | 8.69 (t, J = 6.1 Hz, 1H), 8.56 (d, J = 6.9 Hz, 1H), 7.98 (s, 1H), 7.37-7.30 (m, 2H), 7.29-7.14 (m, 3H), 6.90 (dd, J = 6.6, 1.4 Hz, 1H), 6.23-5.90 (m, 2H), 4.62 (d, J = 5.8 Hz, 2H), 4.00 (s, 3H), 2.46 (s, 3H), 2.31 (br s, 4H), 1.46-1.32 (m, 6H) piperidine benzyl methylene group buried under water peak |
| 359 | (R)-5-(2-amino-[1,2,4]triazlo[1,5-a]pyridin-7-yl)-N-(3,5-difluoro-2-((1-methylpyrrolidin-3-yl)oxy)benzyl)-2-methoxy-6-methylnicotinamide | 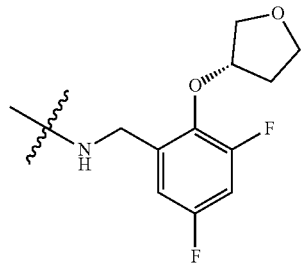 [SMILES: *NCc1cc(F)cc(F)c1O[C@H]1CCOC1] | Me | 524.3 | 8.91 (br s, 1H), 8.67 (d, J = 6.9 Hz, 1H), 8.04 (s, 1H), 7.47 (s, 1H), 7.36-7.07 (m, 3H), 7.03 (br d, J = 7.2 Hz, 2H), 5.17-4.93 (m, 1H), 4.68-4.46 (m, 2H), 4.07 (s, 3H), 4.02-3.64 (m, 2H), 3.56-3.12 (m, 2H), 3.09-2.80 (m, 3H), 2.50 (s, 3H), 2.41-2.04 (m, 2H) |
| 360 | (S)-5-(2-amino-[1,2,4]triazlo[1,5-a]pyridin-7-yl)-N-(3,5-difluoro-2-((tetrahydrofuran-3-yl)oxy)benzyl)-2-methoxynicotinamide | 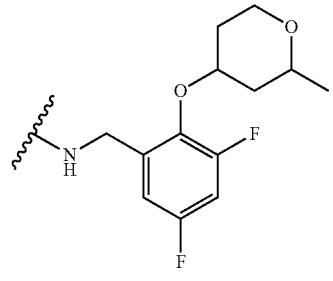 [SMILES: *NCc1cc(F)cc(F)c1OC1CCOC(C)C1] | H | 497.2 | 8.92 (br t, J = 6.0 Hz, 1H), 8.76 (d, J = 2.4 Hz, 1H), 8.58 (d, J = 7.0 Hz, 1H), 8.45 (d, J = 2.4 Hz, 1H), 7.70 (s, 1H), 7.29-7.18 (m, 2H), 7.01 (br d, J = 9.2 Hz, 1H), 6.03 (s, 2H), 4.99 (br s, 1H), 4.59-4.46 (m, 2H), 4.06 (s, 3H), 4.02-3.88 (m, 2H), 3.87-3.77 (m, 1H), 3.76-3.59 (m, 1H), 2.19-2.10 (m, 2H) |
| 361 | 5-(2-amino-[1,2,4]triazlo[1,5-a]pyridin-7-yl)-N-(3,5-difluoro-2-((2-methyltetrahydro-2H-pyran-4-yl)oxy)benzyl)-2-methoxynicotinamide | 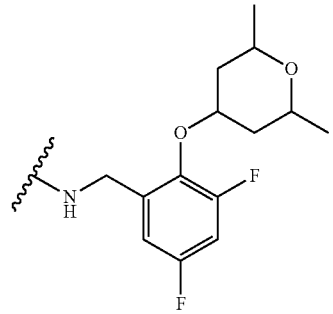 [SMILES: *NCc1cc(F)cc(F)c1OC1CC(C)OC(C)C1] | H | 525.2 | 8.94 (br t, J = 6.0 Hz, 1H), 8.77 (d, J = 2.4 Hz, 1H), 8.59 (d, J = 7.0 Hz, 1H), 8.45 (d, J = 2.4 Hz, 1H), 7.71 (s, 1H), 7.26 (d, J = 7.2 Hz, 1H), 7.23-7.18 (m, 1H), 7.02 (br d, J = 8.5 Hz, 1H), 6.03 (s, 2H), 4.58 (br d, J = 5.8 Hz, 2H), 4.53 (br s, 1H), 4.06 (s, 3H), 3.95-3.81 (m, 2H), 3.81-3.74 (m, 1H), 1.91 (br d, J = 14.0 Hz, 1H), 1.79 (br s, 2H), 1.58-1.47 (m, 1H), 1.11 (d, J = 6.1 Hz, 3H) |
| 362 | 5-(2-amino-[1,2,4]triazlo[1,5-a]pyridin-7-yl)-N-(2-((2,6-dimethyltetrahydro-2H-pyran-4-yl)oxy)3,5-difluorobenzyl)-2-methoxynicotinamide | | H | 539.2 | 8.98-8.85 (m, 1H), 8.80 (d, J = 2.1 Hz, 1H), 8.61 (d, J = 7.0 Hz, 1H), 8.46 (s, 1H), 7.73 (s, 1H), 7.30-7.19 (m, 2H), 7.04 (br d, J = 8.5 Hz, 1H), 6.05 (s, 2H), 4.63-4.51 (m, 3H), 4.07 (s, 3H), 3.97 (br dd, J = 11.3, 6.1 Hz, 2H), 1.90 (br d, J = 14.0 Hz, 2H), 1.43 (br t, J = 11.7 Hz, 2H), 1.17-1.09 (m, 6H) |

TABLE 13-continued

Compounds in Table 13 were prepared in a similar fashion to examples 2, 3, 5, 6, 9, 81, 84, 96, 97, and 286.

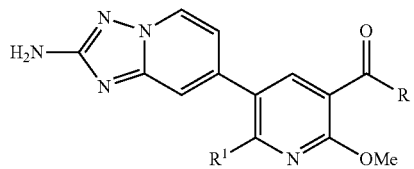

| Ex No | Name | R | R¹ | M + H | 1H NMR (500 MHz, DMSO-d6) δ |
|---|---|---|---|---|---|
| 363 | (R)-5-(2-amino-[1,2,4]triazlo[1,5-a]pyridin-7-yl)-N-(3,5-difluoro-2-((tetrahydrofuran-3-yl)oxy)benzyl)-2-methoxynicotinamide | | H | 497.1 | 8.84-8.72 (m, 2H), 8.58 (d, J = 7.0 Hz, 1H), 8.46 (d, J = 2.4 Hz, 1H), 7.70 (s, 1H), 7.32-7.13 (m, 2H), 7.04 (br d, J = 9.3 Hz, 1H), 5.91 (s, 2H), 5.00 (br s, 1H), 4.63-4.50 (m, 2H), 4.08 (s, 3H), 4.03-3.87 (m, 2H), 3.87-3.74(m, 2H), 2.23-2.10 (m, 2H) |
| 364 | 5-(2-amino-[1,2,4]triazlo[1,5-a]pyridin-7-yl)-N-(3,5-difluoro-2-(oxetan-3-yloxy)benzyl)-2-methoxynicotinamide | | H | 483.3 | 8.92 (br t, J = 5.8 Hz, 1H), 8.78 (d, J = 2.4 Hz, 1H), 8.59 (d, J = 6.7 Hz, 1H), 8.45 (d, J = 2.1 Hz, 1H), 7.72 (s, 1H), 7.31-7.18 (m, 2H), 7.03 (br d, J = 8.5 Hz, 1H), 6.04 (s, 2H), 5.17 (br s, 1H), 4.83 (t, J = 6.9 Hz, 2H), 4.74 (br t, J = 6.1 Hz, 2H), 4.55 (br d, J = 5.8 Hz, 2H), 4.06 (s, 3H) |
| 365 | 5-(2-amino-[1,2,4]triazlo[1,5-a]pyridin-7-yl)-N-(3-fluoro-2-(morpholinomethyl)benzyl)-2-methoxynicotinamide | | H | 492.4 | 8.85 (br t, J = 5.2 Hz, 1H), 8.77 (d, J = 2.2 Hz, 1H), 8.59 (d, J = 7.2 Hz, 1H), 8.42 (d, J = 2.5 Hz, 1H), 7.72 (s, 1H), 7.38-7.30 (m, 1H), 7.29-7.20 (m, 2H), 7.09 (br t, J = 8.9 Hz, 1H), 6.04 (s, 2H), 4.72 (d, J = 6.1 Hz, 2H), 4.02 (s, 3H), 3.60 (br s, 2H), 3.49 (br s, 4H), 2.39 (br s, 4H). |
| 366 | 5-(2-amino-[1,2,4]triazlo[1,5-a]pyridin-7-yl)-2-methoxy-6-methyl-N-((3-(2,2,2-trifluoroethoxy)pyridin-2-yl)methyl)nicotinamide | | Me | 488.3 | 9.28-9.20 (m, 1H), 8.59 (d, J = 6.7 Hz, 1H), 8.30 (d, J = 4.6 Hz, 1H), 8.19 (s, 1H), 7.62 (d, J = 8.2 Hz, 1H), 7.47-7.33 (m, 2H), 6.93 (br d, J = 6.7 Hz, 1H), 6.05 (s, 2H), 4.93 (q, J = 8.9 Hz, 2H), 4.65 (d, J = 4.6 Hz, 2H), 4.13 (s, 3H), 2.50 (s, 3H) |
| 367 | 5-(2-amino-[1,2,4]triazlo[1,5-a]pyridin-7-yl)-N-(2-fluoro-5-(trifluoromethoxy)benzyl)-2-methoxy-N-methyl-d3)nicotinamide | | H | 494.2 | 8.80-8.67 (m, 1H), 8.63-8.55 (m, 1H), 8.25-8.06 (m, 1H), 7.80-7.61 (m, 1H), 7.48-7.16 (m, 4H), 6.04 (s, 2H), 4.01 (s, 3H), NH2 protons not observed, rotamers seen |

Example 368

5-(2-Amino-[1,2,4]triazolo[1,5-a]pyridin-7-yl)-6-chloro-N-(2-fluoro-5-(trifluoromethoxy)benzyl)nicotinamide

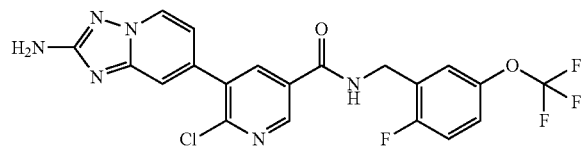 [SMILES: Nc1nc2cc(-c3cc(C(=O)NCc4cc(OC(F)(F)F)ccc4F)cnc3Cl)ccn2n1]

368A: Methyl 6-chloro-5-(2-(di-(tert-butyl carbamoyl)amino)-[1,2,4]triazolo[1,5-a]pyridin-7-yl)nicotinate: To the stirred crude 2-(di-(tert-butyl carbamoyl)amino)-[1,2,4]triazolo[1,5-a]pyridin-7-yl)boronic acid (234 mg, 0.618 mmol), prepared as in example 13, was added methyl 6-chloro-5-iodonicotinate (175 mg, 0.588 mmol) and 1,1'-bis(di-tert-butylphosphino)ferrocene palladium dichloride (19.17 mg, 0.029 mmol) and the mixture was degassed by bubbling nitrogen through the mixture for 5 min 2M $K_3PO_4$ (aq) (0.882 mL, 1.765 mmol) was quickly added and the reaction mixture heated at 85° C. for 15 min. The reaction mixture was concentrated onto Celite. The material was purified by flash chromatography using a 40 g ISCO silica column and eluting with 0-100% EtOAc in hexanes. The fractions containing the product were concentrated to afforded methyl 6-chloro-5-(2-(di-(tert-butyl carbamoyl)amino)-[1,2,4]triazolo[1,5-a]pyridin-7-yl)nicotinate (295 mg, 0.527 mmol, 90% yield) as a brown solid.

MS ESI m/z 504.1 (M+H)

368B: Methyl 5-(2-amino-[1,2,4]triazolo[1,5-a]pyridin-7-yl)-6-chloronicotinate: A stirred mixture of methyl 6-chloro-5-(2-(di-(tert-butyl carbamoyl)amino)-[1,2,4]triazolo[1,5-a]pyridin-7-yl)nicotinate (295 mg, 0.570 mmol) in TFA (5 mL) was stirred at rt for 45 min. The reaction mixture was concentrated to an oil. The oil was suspended in water, basified with 1.5M $K_2HPO_4$ solution. The solution was extracted with EtOAc (2x). The combined EtOAc layers were washed with brine and dried over sodium sulfate. The mixture was filtered and concentrated to afford methyl 5-(2-amino-[1,2,4]triazolo[1,5-a]pyridin-7-yl)-6-chloronicotinate (111 mg, 0.342 mmol, 60% yield) as a free base. The crude material was carried on without further purification.

MS ESI m/z 304.0 (M+H)

368C: 5-(2-amino-[1,2,4]triazolo[1,5-a]pyridin-7-yl)-6-chloronicotinic acid, lithium salt: To a mixture of methyl 5-(2-amino-[1,2,4]triazolo[1,5-a]pyridin-7-yl)-6-chloronicotinate (111 mg, 0.349 mmol) in tetrahydrofuran (2.5 mL) was added a solution of lithium hydroxide monohydrate (17.59 mg, 0.419 mmol) in water (1.5 mL), and the resulting mixture was stirred ON at rt. The reaction mixture was concentrated to a solid and used as—is in the next step. Obtained 5-(2-amino-[1,2,4]triazolo[1,5-a]pyridin-7-yl)-6-chloronicotinic acid, lithium salt (100 mg, 0.338 mmol, 97% yield) as a tan solid.

MS ESI m/z 290.2 (M+H)

368: A mixture of 5-(2-amino-[1,2,4]triazolo[1,5-a]pyridin-7-yl)-6-chloronicotinic acid, lithium salt (15 mg, 0.052 mmol), (2-fluoro-5-(trifluoromethoxy)phenyl)methanamine, HCl (13.74 mg, 0.056 mmol), BOP (34.4 mg, 0.078 mmol) and Hünig's base (0.045 mL, 0.259 mmol) in DMF (1 mL) was stirred at rt for 3 d. The reaction mixture was diluted to 2 mL with methanol, then filtered. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 19-59% B over 20 minutes, then a 4-minute hold at 100% B; Flow: 20 mL/min. Fractions containing the desired product were combined and dried via centrifugal evaporation to afford 5-(2-amino-[1,2,4]triazolo[1,5-a]pyridin-7-yl)-6-chloro-N-(2-fluoro-5-(trifluoromethoxy)benzyl)nicotinamide (7.1 mg, 0.014 mmol, 27% yield).

MS ESI m/z 481.1 (M+H)

1H NMR (500 MHz, DMSO-d6) δ 9.39 (t, J=6.2 Hz, 1H), 8.92 (d, J=2.1 Hz, 1H), 8.68 (d, J=6.7 Hz, 1H), 8.40 (d, J=2.1 Hz, 1H), 7.57 (s, 1H), 7.44 (br d, J=5.2 Hz, 1H), 7.37 (br d, J=7.0 Hz, 2H), 7.07 (br d, J=5.5 Hz, 1H), 6.13 (s, 2H), 4.58 (br d, J=5.2 Hz, 2H).

TABLE 14

Compounds in Table 14 were prepared in a similar fashion to example 368.

| Ex No | Name | R | M + H | 1H NMR (500 MHz, DMSO-d6) δ |
|---|---|---|---|---|
| 369 | 5-(2-amino-[1,2,4]triazolo[1,5-a]pyridin-7-yl)-6-chloro-N-(5-fluoro-2-(trifluoromethoxy)benzyl)nicotinamide | | 481.0 | 9.39 (br s, 1H), 8.89 (d, J = 1.8 Hz, 1H), 8.64 (d, J = 7.0 Hz, 1H), 8.38 (s, 1H), 7.55 (s, 1H), 7.44 (br s, 1H), 7.38-7.20 (m, 2H), 7.08 (br d, J = 7.0 Hz, 1H), 6.10 (s, 2H), 4.56 (br d, J = 5.5 Hz, 2H) |

TABLE 14-continued

Compounds in Table 14 were prepared in a similar fashion to example 368.

| Ex No | Name | R | M + H | 1H NMR (500 MHz, DMSO-d6) δ |
|---|---|---|---|---|
| 370 | (R)-5-(2-amino-[1,2,4]triazolo[1,5-a]pyridin-7-yl)-6-chloro-N-(1-(2-(trifluoromethoxy)phenyl)ethyl)nicotinamide | *N(H)-CH(CH₃)-(2-OCF₃-phenyl)* | 477.1 | 9.07 (br d, J = 7.2 Hz, 1H), 8.88 (d, J = 1.9 Hz, 1H), 8.63 (d, J = 6.9 Hz, 1H), 8.38 (s, 1H), 7.68-7.59 (m, 1H), 7.54 (s, 1H), 7.44-7.30 (m, 3H), 7.05 (br d, J = 6.9 Hz, 1H), 5.97 (s, 2H), 5.46 (quin, J = 7.1 Hz, 1H), 1.49 (d, J = 7.1 Hz, 3H) |
| 371 | (S)-5-(2-amino-[1,2,4]triazolo[1,5-a]pyridin-7-yl)-6-chloro-N-(1-(2-fluoro-5-(trifluoromethoxy)phenyl)ethyl)nicotinamide | *N(H)-CH(CH₃)-(2-F,5-OCF₃-phenyl)* | 495.1 | 9.27 (br d, J = 7.0 Hz, 1H), 8.91 (s, 1H), 8.70 (br d, J = 7.0 Hz, 1H), 8.43 (s, 1H), 7.60 (s, 1H), 7.49 (br s, 1H), 7.40-7.33 (m, 2H), 7.15-7.06 (m, 1H), 5.40 (br t, J = 7.0 Hz, 1H), 1.54 (br d, J = 7.0 Hz, 3H) NH₂ protons not observed |
| 372 | 5-(2-amino-[1,2,4]triazolo[1,5-a]pyridin-7-yl)-6-chloro-N-(2-(trifluoromethoxy)benzyl)nicotinamide | *N(H)-CH₂-(2-OCF₃-phenyl)* | 462.9 | 9.32-9.14 (m, 1H), 8.92 (d, J = 1.9 Hz, 1H), 8.65 (d, J = 6.8 Hz, 1H), 8.40 (d, J = 1.9 Hz, 1H), 7.60-7.49 (m, 2H), 7.46-7.34 (m, 3H), 7.05 (br d, J = 6.8 Hz, 1H), 5.98 (s, 2H), 4.60 (br d, J = 5.5 Hz, 2H) |
| 373 | 5-(2-amino-[1,2,4]triazolo[1,5-a]pyridin-7-yl)-6-chloro-N-(2-fluoro-5-(trifluoromethyl)benzyl)nicotinamide | *N(H)-CH₂-(2-F,5-CF₃-phenyl)* | 465.1 | 9.46-9.33 (m, 1H), 8.92 (d, J = 1.8 Hz, 1H), 8.67 (d, J = 6.7 Hz, 1H), 8.40 (d, J = 2.1 Hz, 1H), 7.82 (br d, J = 5.2 Hz, 1H), 7.76 (br s, 1H), 7.60-7.53 (m, 1H), 7.47 (br t, J = 9.0 Hz, 1H), 7.07 (br d, J = 6.7 Hz, 1H), 6.13 (s, 2H), 4.63 (br d, J = 5.2 Hz, 2H) |

Example 374

(S)—N-(1-(2-fluoro-5-(trifluoromethoxy)phenyl)ethyl)-2-methoxy-5-(2-(methylamino)imidazo[1,2-b]-pyridazin-6-yl)nicotinamide

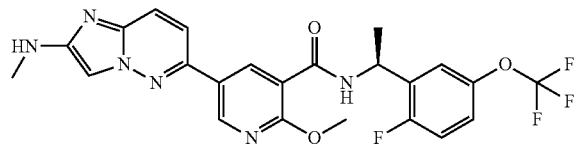 [SMILES: CNc1cn2nc(-c3cnc(OC)c(C(=O)N[C@@H](C)c4cc(OC(F)(F)F)ccc4F)c3)ccc2n1]

374A: Bis-Boc-7-bromo-[1,2,4]triazolo[1,5-a]pyridin-2-amine: DMAP (2.294 g, 18.78 mmol) and BOC-anhydride (27.2 mL, 117 mmol) in acetonitrile (100 mL) were added to a mixture of 7-bromo-[1,2,4]triazolo[1,5-a]pyridin-2-amine (10 g, 46.9 mmol) in DCM (100 mL). The resulting mixture was stirred ON at rt. The reaction mixture was pre-absorbed on Celite and purified by column chromatography using a 220 gm ISCO silica gel cartridge, eluting with a 0-100% EtOAc/Hex gradient. The pure fractions were concentrated to afford bis-Boc-7-bromo-[1,2,4]triazolo[1,5-a]pyridin-2-amine (17.88 g, 43.3 mmol, 92% yield) as a white solid.

$^1$H NMR (400 MHz, CDCl$_3$) δ 8.40 (d, J=7.2 Hz, 1H), 7.90 (d, J=1.5 Hz, 1H), 7.16 (dd, J=7.2, 2.1 Hz, 1H), 1.47 (s, 18H).

374B: Tert-butyl (7-bromo-[1,2,4]triazolo[1,5-a]pyridin-2-yl)carbamate: A mixture of bis-tert-butyl (7-bromo-[1,2,4]triazolo[1,5-a]pyridin-2-yl)carbamate (532 mg, 1.287 mmol) and NaOH, 1M (2.57 mL, 2.57 mmol) in MeOH (10 mL) was stirred at rt for 24 h. The product had precipitated out of solution. The product was filtered off, washed with methanol and then diethyl ether to afford tert-butyl (7-bromo-[1,2,4]triazolo[1,5-a]pyridin-2-yl)carbamate (379 mg, 1.150 mmol, 89% yield) as a white solid.

MS ESI m/z 312.3 (M+H).

374C: Tert-butyl (7-bromo-[1,2,4]triazolo[1,5-a]pyridin-2-yl)(methyl)carbamate: To a solution of tert-butyl (7-bromo-[1,2,4]triazolo[1,5-a]pyridin-2-yl)carbamate (200 mg, 0.639 mmol) in THF (5 mL) was added sodium hydride (51.1 mg, 1.277 mmol). The resulting mixture was stirred 10 min before iodomethane (0.060 mL, 0.958 mmol) was added and the resulting mixture was stirred 4 h at rt. The reaction mixture was partitioned between EtOAc (100 mL) and water (20 mL). The EtOAc layer was washed with 10% aq. LiCl (2×) and brine. The solution was dried over sodium sulfate, then filtered and concentrated. The crude material was purified by flash chromatography, eluting with 0-100% EtOAc in hexanes to afford tert-butyl (7-bromo-[1,2,4]triazolo[1,5-a]pyridin-2-yl)(methyl)carbamate (199 mg, 0.547 mmol, 86% yield) as a white solid.

MS ESI m/z 413.1 (M+H)

374D: (2-(Methyl(tert-butyl carbamoyl)amino)-[1,2,4]triazolo[1,5-a]pyridin-7-yl)boronic acid: A mixture of tert-butyl (7-bromo-[1,2,4]triazolo[1,5-a]pyridin-2-yl)(methyl)carbamate (111 mg, 0.339 mmol), bis(pinacolato)diboron (129 mg, 0.509 mmol), potassium acetate (100 mg, 1.018 mmol) and PdCl$_2$(dppf)-CH$_2$Cl$_2$ adduct (27.7 mg, 0.034 mmol) was heated at 100° C. for 75 min. The reaction mixture was cooled to rt and carried directly into the next step. 374E: Methyl 5-(2-((tert-butoxycarbonyl)(methyl)amino)-[1,2,4]triazolo[1,5-a]pyridin-7-yl)-2-methoxynicotinate: To the stirred crude mixture containing (2-(methyl(tert-butyl carbamoyl)amino)-[1,2,4]triazolo[1,5-a]pyridin-7-yl)boronic acid was added methyl 5-bromo-2-methoxynicotinate (85 mg, 0.345 mmol) and 1,1'-bis(di-tert-butylphosphino)ferrocene palladium dichloride (11.26 mg, 0.017 mmol). The mixture was degassed by bubbling nitrogen through the mixture for 5 min. 2M K$_3$PO$_4$ (aq) (0.518 mL, 1.036 mmol) was quickly added and the reaction mixture heated at 100° C. for 25 min. The material was purified by flash chromatography using a 40 g ISCO column and eluting with 0-100% EtOAc in hexanes. Fractions containing the product were concentrated to afford methyl 5-(2-((tert-butoxycarbonyl)(methyl)amino)-[1,2,4]triazolo[1,5-a]pyridin-7-yl)-2-methoxynicotinate (118 mg, 0.271 mmol, 78% yield) as a crystalline beige solid.

MS ESI m/z 414.5 (M+H)

374F: 5-(2-((Tert-butoxycarbonyl)(methyl)amino)-[1,2,4]triazolo[1,5-a]pyridin-7-yl)-2-methoxynicotinic acid, lithium salt: To a mixture of methyl 5-(2-((tert-butoxycarbonyl)(methyl)amino)-[1,2,4]triazolo[1,5-a]pyridin-7-yl)-2-methoxynicotinate (118 mg, 0.285 mmol) in tetrahydrofuran (3 mL) was added a solution of lithium hydroxide monohydrate (14.37 mg, 0.342 mmol) in water (1.5 mL), and the resulting mixture was stirred ON at rt. The reaction mixture was concentrated to afford 5-(2-((tert-butoxycarbonyl)(methyl)amino)-[1,2,4]triazolo[1,5-a]pyridin-7-yl)-2-methoxynicotinic acid, lithium salt as a tan solid. The crude material was used as—is in the next step.

MS ESI m/z 400.5 (M+H).

374: A mixture of 5-(2-((tert-butoxycarbonyl)(methyl)amino)imidazo[1,2-b]pyridazin-6-yl)-2-methoxynicotinic acid, lithium salt (15 mg, 0.038 mmol), BOP (24.92 mg, 0.056 mmol), (S)-1-(2-fluoro-5-(trifluoromethoxy)phenyl)ethan-1-amine, HCl (10.73 mg, 0.041 mmol) and Hünig's base (0.033 mL, 0.188 mmol) in DMF (1 mL) was stirred at rt ON. The mixture was partitioned between EtOAc (75 mL) and 10% aq. LiCl (20 mL). The EtOAc layer was washed one additional time with 10% aq. LiCl and brine. The solution was dried over sodium sulfate, filtered and concentrated. The crude residue was dissolved in TFA (2 mL) and stirred for 30 min. The reaction mixture was concentrated to an oil, then dissolved in DMSO (2 mL) and purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-70% B over 25 minutes, then a 2-minute hold at 100% B; Flow: 20 mL/min. Fractions containing the desired product were combined and dried via centrifugal evaporation to afford (S)—N-(1-(2-fluoro-5-(trifluoromethoxy)phenyl)ethyl)-2-methoxy-5-(2-(methylamino)imidazo[1,2-b]pyridazin-6-yl)nicotinamide (12.5 mg, 0.025 mmol, 65% yield).

MS ESI m/z 506.3 (M+H)

1H NMR (500 MHz, DMSO-d6) δ 8.89 (br d, J=7.6 Hz, 1H), 8.77 (d, J=2.4 Hz, 1H), 8.65 (d, J=7.0 Hz, 1H), 8.31 (d, J=2.4 Hz, 1H), 7.74 (s, 1H), 7.55 (br d, J=4.3 Hz, 1H), 7.41-7.32 (m, 2H), 7.26 (dd, J=7.0, 1.5 Hz, 1H), 6.66-6.31 (m, 1H), 5.37 (quin, J=7.2 Hz, 1H), 4.03 (s, 3H), 2.84 (d, J=4.6 Hz, 3H), 1.48 (d, J=7.0 Hz, 3H)

Example 375

(R)—N-(1-(2-fluoro-5-(trifluoromethoxy)phenyl)
ethyl)-2-methyl-5-(2-((methyl-d3)amino)-[1,2,4]
triazolo[1,5-a]pyridin-7-yl)nicotinamide

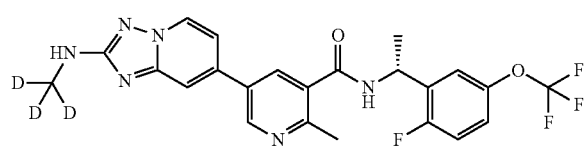 [SMILES: [2H]C([2H])([2H])Nc1nc2cc(-c3cnc(C)c(C(=O)N[C@H](C)c4cc(OC(F)(F)F)ccc4F)c3)ccn2n1]

(R)—N-(1-(2-fluoro-5-(trifluoromethoxy)phenyl)ethyl)-2-methyl-5-(2-((methyl-d3)amino)-[1,2,4]triazolo[1,5-a]pyridin-7-yl)nicotinamide: Prepared in a similar fashion as example 374. A mixture of 5-(2-((tert-butoxycarbonyl)(methyl-d3)amino)-[1,2,4]triazolo[1,5-a]pyridin-7-yl)-2-methylnicotinic acid (22 mg, 0.057 mmol), BOP (37.8 mg, 0.085 mmol), (R)-1-(2-fluoro-5-(trifluoromethoxy)phenyl)ethan-1-amine, HCl (16.26 mg, 0.063 mmol), and Hünig's base (0.050 mL, 0.285 mmol) in DMF (1 mL) was stirred at rt over the weekend. The crude reaction mixture was partitioned between EtOAc (75 mL) and 10% aq. LiCl (20 mL). The organics were washed 10% aq. LiCl and brine. The solution was dried over sodium sulfate, filtered and concentrated. The crude residue was loaded onto a 4 g ISCO column and purified by flash chromatography To afford 25 mg of the Boc-protected compound. This material was dissolved in TFA (2 mL) and stirred for 1 h. The reaction mixture was concentrated and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-59% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. Afforded (R)—N-(1-(2-fluoro-5-(trifluoromethoxy)phenyl)ethyl)-2-methyl-5-(2-((methyl-d3)amino)-[1,2,4]triazolo[1,5-a]pyridin-7-yl)nicotinamide (3.6 mg, 7.02 μmol, 12% yield).

MS ESI m/z 492.4 (M+H).

1H NMR (500 MHz, DMSO-d6) δ 9.05-8.92 (m, 2H), 8.68 (br d, J=6.8 Hz, 1H), 8.14 (s, 1H), 7.81 (br s, 1H), 7.49 (br s, 1H), 7.39-7.28 (m, 3H), 6.35 (br s, 1H), 5.47-5.31 (m, 1H), 2.52 (br s, 3H), 1.51 (d, J=7.0 Hz, 3H).

Example 376

5-(2-amino-[1,2,4]triazolo[1,5-a]pyridin-7-yl)-N-(2-(3,3-difluoropyrrolidine-1-carbonyl)-5-fluorobenzyl)-2-methoxynicotinamide

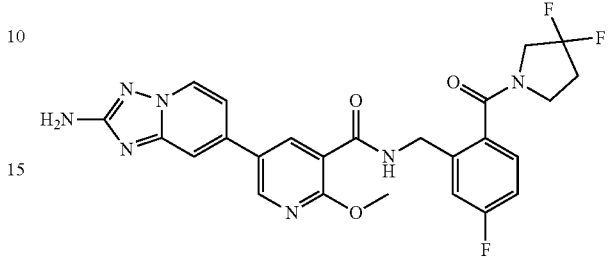

376A: 2-(3,3-difluoropyrrolidine-1-carbonyl)-5-fluorobenzonitrile: A mixture of 2-bromo-5-fluorobenzonitrile (750 mg, 3.75 mmol), 3,3-difluoropyrrolidine, HCl (673 mg, 4.69 mmol), Pd(OAc)$_2$ (21.05 mg, 0.094 mmol), bis(2-diphenylphosphinophenyl)ether [DPEPhos] (202 mg, 0.375 mmol) and cesium hydroxide monohydrate (7241 mg, 43.1 mmol) in toluene (10 mL) was degassed by bubbling nitrogen through the mixture for 5 min. Chloroform (0.907 mL, 11.25 mmol) was added, the vial sealed tightly, and the reaction mixture was stirred at 80° C. over the weekend. The crude reaction mixture was concentrated onto Celite, then purified by column chromatography using a 40 g ISCO silica gel column, eluting with 0-70% EtOAc in hexanes. Afforded 2-(3,3-difluoropyrrolidine-1-carbonyl)-5-fluorobenzonitrile (422 mg, 1.643 mmol, 44% yield) as a yellow oil which became a crystalline solid.

MS ESI m/z 255.0 (M+H).

376B: (2-(aminomethyl)-4,6-difluorophenyl)(3,3-difluoropyrrolidin-1-yl)methanone: A mixture of 2-(3,3-difluoropyrrolidine-1-carbonyl)-3,5-difluorobenzonitrile (81 mg, 0.298 mmol) and Pd/C (15.83 mg, 0.015 mmol) in acetic acid (3 mL) at rt was stirred briskly under 1 atm of hydrogen at rt over the weekend. The reaction mixture was filtered through a 45 micron nylon filter, and the filter was rinsed with MeOH. The filtrate was partitioned between EtOAc and sat. sodium bicarbonate. The organics were washed with brine, dried over sodium sulfate, then concentrated and co-evaporated from EtOAc/heptane thrice. Drying afforded (2-(aminomethyl)-4,6-difluorophenyl)(3,3-difluoropyrrolidin-1-yl)methanone (55 mg, 0.197 mmol, 66% yield) as a white solid. The material was carried forward without further purification.

MS ESI m/z 277.3 (M+H).

376: A mixture of 5-(2-amino-[1,2,4]triazolo[1,5-a]pyridin-7-yl)-2-methoxynicotinic acid (15 mg, 0.053 mmol), BOP (34.9 mg, 0.079 mmol), (2-(aminomethyl)-4-fluorophenyl)(3,3-difluoropyrrolidin-1-yl)methanone (16.30 mg, 0.063 mmol), Hünig's base (0.046 mL, 0.263 mmol) and DMF (1.0 mL) was stirred at rt ON. The reaction mixture was concentrated under reduced pressure then diluted to 2 mL with methanol and filtered. The reaction mixture was concentrated and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-59% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. Afforded 5-(2-amino-[1,2,4]triazolo[1,5-a]pyridin-7-yl)-N-(2-(3,3-difluoropyrrolidine-1-carbonyl)-5-fluorobenzyl)-2-methoxynicotinamide (7.0 mg, 0.013 mmol, 25% yield).

MS ESI m/z 526.3 (M+H).

$^1$H NMR (500 MHz, DMSO-d6) δ 8.95 (br d, J=7.6 Hz, 1H), 8.79 (s, 1H), 8.60 (d, J=6.7 Hz, 1H), 8.47 (d, J=2.1 Hz, 1H), 7.71 (br s, 1H), 7.47-7.42 (m, 1H), 7.31 (br t, J=7.5 Hz, 1H), 7.26-7.17 (m, 2H), 6.04 (s, 2H), 4.53-4.48 (m, 2H), 4.06 (s, 3H), 3.97-3.89 (m, 2H), 3.78-3.66 (m, 1H), 3.51-3.42 (m, 1H), 2.47-2.36 (m, 2H).

TABLE 15

Compounds in Table 15 were prepared in a similar fashion to example 376.

| Ex No | Name | R | R¹ | M + H | 1H NMR (500 MHz, DMSO-d6) δ |
|---|---|---|---|---|---|
| 377 | 5-(2-amino-[1,2,4]triazolo[1,5-a]pyridin-7-yl)-N-(2-(3,3-difluoropyrrolidine-1-carbonyl)benzyl)-2-methoxynicotinamide | 2-(3,3-difluoropyrrolidine-1-carbonyl)benzyl-NH- | H | 508.2 | 8.98-8.87 (m, 1H), 8.75 (d, J = 2.5 Hz, 1H), 8.58 (d, J = 6.9 Hz, 1H), 8.46 (d, J = 2.5 Hz, 1H), 7.68 (s, 1H), 7.49 (br t, J = 6.6 Hz, 1H), 7.44 (br d, J = 4.4 Hz, 1H), 7.35 (br d, J = 4.4 Hz, 2H), 7.23 (br d, J = 7.2 Hz, 1H), 6.02 (s, 2H), 4.49 (br t, J = 5.1 Hz, 2H), 4.04 (s, 3H), 3.98-3.83 (m, 2H), 3.81-3.69 (m, 1H), 3.68-3.63 (m, 1H), 2.47-2.29 (m, 2H). |
| 378 | 5-(2-amino-[1,2,4]triazolo[1,5-a]pyridin-7-yl)-N-(2-(3,3-difluoropyrrolidine-1-carbonyl)-3-fluorobenzyl)-2-methoxynicotinamide | 2-(3,3-difluoropyrrolidine-1-carbonyl)-3-fluorobenzyl-NH- | H | 526.3 | 9.00-8.94 (m, 1H), 8.76 (s, 1H), 8.58 (d, J = 6.7 Hz, 1H), 8.46 (s, 1H), 7.69 (br s, 1H), 7.50 (br d, J = 7.3 Hz, 1H), 7.35-7.31 (m, 1H), 7.28-7.20 (m, 2H), 6.02 (s, 2H), 4.56 (br dd, J = 15.1, 6.9 Hz, 1H), 4.38 (br dd, J = 15.7, 5.3 Hz, 1H), 4.05 (s, 3H), 4.03-3.80 (m, 2H), 3.43 (br s, 1H), 3.17 (br d, J = 4.0 Hz, 1H), 2.48-2.36 (m, 2H) |
| 379 | 5-(2-amino-[1,2,4]triazolo[1,5-a]pyridin-7-yl)-2-methoxy-N-(2-(pyrrolidine-1-carbonyl)benzyl)nicotinamide | 2-(pyrrolidine-1-carbonyl)benzyl-NH- | H | 473.3 | 8.78 (br t, J = 5.9 Hz, 1H), 8.75 (d, J = 2.6 Hz, 1H), 8.57 (d, J = 7.1 Hz, 1H), 8.48 (d, J = 2.6 Hz, 1H), 7.67 (d, J = 1.3 Hz, 1H), 7.47 (d, J = 7.6 Hz, 1H), 7.40 (td, J = 7.4, 1.6 Hz, 1H), 7.35-7.26 (m, 2H), 7.21 (dd, |

TABLE 15-continued

Compounds in Table 15 were prepared in a similar fashion to example 376.

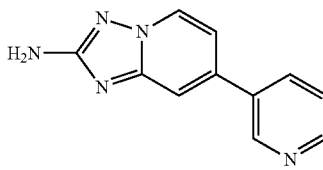

| Ex No | Name | R | R¹ | M + H | 1H NMR (500 MHz, DMSO-d6) δ |
|---|---|---|---|---|---|
| | | | | | J = 7.0, 1.9 Hz, 1H), 5.90 (s, 2H), 4.50 (d, J = 6.0 Hz, 2H), 4.06 (s, 3H), 3.51 (t, J = 6.9 Hz, 2H), 3.17 (t, J = 6.7 Hz, 2H), 1.92-1.81 (m, 2H), 1.80-1.71 (m, 2H). |
| 380 | 5-(2-amino-[1,2,4]triazolo[1,5-a]pyridin-7-yl)-N-(2-(3,3-difluoropyrrolidine-1-carbonyl)-3,5-difluorobenzyl)-2-methoxy-6-methylnicotinamide | 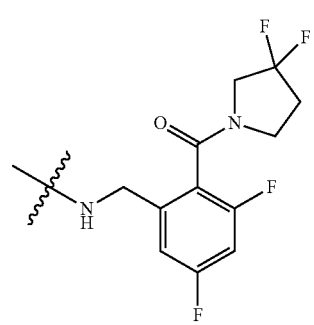 | Me | 558.0 | 8.93-8.86 (m, 1H), 8.59 (d, J = 6.8 Hz, 1H), 8.04 (s, 1H), 7.39-7.27 (m, 2H), 7.16 (t, J = 8.8 Hz, 1H), 6.90 (d, J = 6.9 Hz, 1H), 6.05 (s, 2H), 4.59-4.48 (m, 1H), 4.43-4.33 (m, 1H), 4.11-4.04 (m, 3H), 4.02-3.87 (m, 1H), 3.84-3.57 (m, 2H), 3.55-3.48 (m, 1H), 3.45-3.35 (m, 1H), 3.23-3.13 (m, 1H), 2.48 (s, 3H) |
| 381 | 5-(2-amino-[1,2,4]triazolo[1,5-a]pyridin-7-yl)-N-(2-(3,3-difluoropyrrolidine-1-carbonyl)-5-fluorobenzyl)-2-methoxy-6-methylnicotinamide | | Me | 540.4 | 8.89 (br d, J = 6.4 Hz, 1H), 8.63 (br d, J = 6.7 Hz, 1H), 8.05 (s, 1H), 7.42 (br d, J = 5.8 Hz, 2H), 7.27-7.21 (m, 2H), 7.19-7.13 (m, 2H), 7.06 (s, 1H), 7.01 (br d, J = 6.7 Hz, 1H), 4.50-4.43 (m, 2H), 4.05 (s, 3H), 3.94-3.88 (m, 1H), 2.48-2.44 (m, 5H), 2.38 (br dd, J = 13.7, 6.1 Hz, 2H) |
| 382 | 5-(2-amino-[1,2,4]triazolo[1,5-a]pyridin-7-yl)-N-(2-(3,3-difluoropyrrolidine-1-carbonyl)-3-fluorobenzyl)-2-methoxy-6-methylnicotinamide | 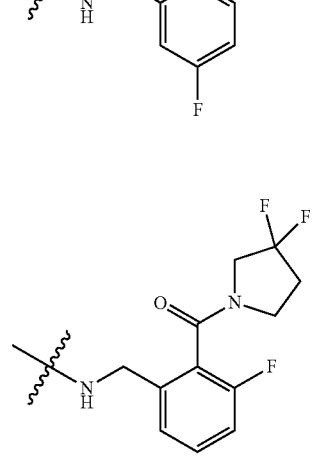 | Me | 540.4 | 8.91-8.84 (m, 1H), 8.59 (br d, J = 6.7 Hz, 1H), 8.06 (s, 1H), 7.53-7.42 (m, 1H), 7.37 (br s, 1H), 7.34-7.21 (m, 2H), 6.90 (br d, J = 6.7 Hz, 1H), 6.04 (br s, 2H), 4.60-4.52 (m, 1H), 4.36 (br d, J = 10.7 Hz, 1H), 4.08-3.91 (m, 4H), 3.72 (br d, J = 12.5 Hz, 1H), 2.50-2.48 (m, 3H), 2.48-2.34 |

TABLE 15-continued

Compounds in Table 15 were prepared in a similar fashion to example 376.

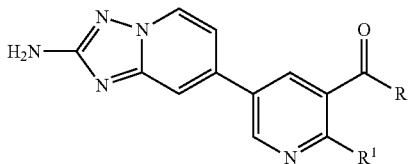

| Ex No | Name | R | R¹ | M + H | 1H NMR (500 MHz, DMSO-d6) δ |
|---|---|---|---|---|---|
| | | | | | (m, 3H), 1.82 (br s, 1H) |

TABLE 16

Compounds in Table 16 were prepared in a similar fashion to example 3.

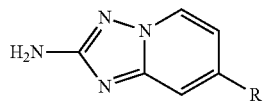

| Ex No | Name | R | M + H | 1H NMR (500 MHz, DMSO-d6) δ |
|---|---|---|---|---|
| 383 | (R)-6-(2-amino-[1,2,4]triazolo[1,5-a]pyridin-7-yl)-N-(1-(2-fluoro-5-(trifluoromethoxy)phenyl)ethyl-2,2,2-d3)-3-methoxy-pyrazine-2-carboxamide | | 495.1 | 9.31 (br d, J = 7.6 Hz, 1H), 9.13 (s, 1H), 8.65 (d, J = 7.0 Hz, 1H), 8.12 (s, 1H), 7.62 (br d, J = 7.0 Hz, 1H), 7.55 (br s, 1H), 7.42-7.34 (m, 2H), 6.12 (s, 2H), 5.34 (br d, J = 7.9 Hz, 1H), 4.01 (s, 3H) |
| 384 | 6-(2-amino-[1,2,4]triazolo[1,5-a]pyridin-7-yl)-N-(2-fluoro-5-(trifluoromethoxy)benzyl)-3-methoxy-pyrazine-2-carboxamide | | 478.1 | 9.44-9.35 (m, 1H), 9.15 (s, 1H), 8.64 (d, J = 7.0 Hz, 1H), 8.16 (s, 1H), 7.65 (br d, J = 7.0 Hz, 1H), 7.49-7.17 (m, 3H), 6.11 (s, 2H), 4.58 (br d, J = 5.8 Hz, 2H), 4.02 (s, 3H) |
| 385 | 6-(2-amino-[1,2,4]triazolo[1,5-a]pyridin-7-yl)-3-methoxy-N-(3-phenylbutyl)pyrazine-2-carboxamide | | 418.1 | 9.10 (s, 1H), 8.72-8.67 (m, 1H), 8.65 (d, J = 7.0 Hz, 1H), 8.13 (s, 1H), 7.63 (br d, J = 7.0 Hz, 1H), 7.36-7.13 (m, 5H), 6.11 (s, 2H), 4.00 (s, 3H), 3.23-3.13 (m, 2H), 2.87-2.80 (m, 1H), 1.83 (q, J = 7.1 Hz, 2H), 1.30-1.21 (m, 3H) |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 386 | 6-(2-amino-[1,2,4]triazolo[1,5-a]pyridin-7-yl)-N-(2-fluoro-5-(trifluoromethoxy)benzyl)-3-methoxy-pyridazine-4-carboxamide | | 478.1 | 9.23 (br s, 1H), 8.67 (br d, J = 7.0 Hz, 1H), 8.49 (s, 1H), 8.10 (s, 1H), 7.69 (br d, J = 7.0 Hz, 1H), 7.47 (br s, 1H), 7.39 (br d, J = 7.0 Hz, 2H), 6.15 (br s, 1H), 4.58 (br d, J = 5.8 Hz, 2H), 4.19 (s, 3H) 1 NH proton not observed |
| 387 | 6-(2-amino-[1,2,4]triazolo[1,5-a]pyridin-7-yl)-3-methoxy-N-(3-phenylbutyl)pyridazine-4-carboxamide | | 418.2 | 8.66 (d, J = 7.0 Hz, 1H), 8.56 (br t, J = 5.2 Hz, 1H), 8.38 (s, 1H), 8.08 (s, 1H), 7.68 (br d, J = 7.0 Hz, 1H), 7.39-7.13 (m, 5H), 6.14 (s, 2H), 4.16 (s, 3H), 3.21-3.14 (m, 2H), 2.87-2.79 (m, 1H), 1.82 (q, J = 7.3 Hz, 2H), 1.25 (br d, J = 7.0 Hz, 3H) |
| 388 | 2-(2-amino-[1,2,4]triazolo[1,5-a]pyridin-7-yl)-N-(2-fluoro-5-(trifluoromethoxy)benzyl)-5-methoxy-isonicotinamide | | 477.1 | 9.08 (br t, J = 5.6 Hz, 1H), 8.68 (s, 1H), 8.59 (d, J = 7.0 Hz, 1H), 8.19 (s, 1H), 7.98 (s, 1H), 7.59 (br d, J = 7.0 Hz, 1H), 7.44 (br d, J = 4.3 Hz, 1H), 7.37 (br d, J = 7.6 Hz, 2H), 6.07 (s, 2H), 4.57 (br d, J = 5.8 Hz, 2H), 4.05 (s, 3H) |
| 389 | (R)-2-(2-amino-[1,2,4]triazolo[1,5-a]pyridin-7-yl)-N-(1-(2-fluoro-5-(trifluoromethoxy)phenyl)ethyl)-5-methoxy-isonicotinamide | | 491.1 | 9.04 (br d, J = 7.6 Hz, 1H), 8.67 (s, 1H), 8.64 (br d, J = 7.0 Hz, 1H), 8.14 (s, 1H), 8.04 (br s, 1H), 7.67 (br d, J = 7.0 Hz, 1H), 7.53 (br s, 1H), 7.41-7.34 (m, 2H), 5.35 (br t, J = 7.2 Hz, 1H), 4.03 (s, 3H), 1.46 (br d, J = 7.0 Hz, 3H) NH protons not observed |
| 390 | 2-(2-amino-[1,2,4]triazolo[1,5-a]pyridin-7-yl)-5-methoxy-N-(3- | | 417.2 | 8.68 (br d, J = 6.7 Hz, 1H), 8.65 (s, 1H), 8.39 (br s, 1H), 8.17 (s, 1H), 8.06 (s, 1H), 7.73 (br d, J = 6.1 Hz, 1H), 7.38-7.15 (m, 5H), 4.03 (s, 3H), 3.17 (br s, |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| | phenylbutyl) isonicotinamide | | | 2H), 2.86-2.78 (m, 1H), 1.82 (q, J = 7.1 Hz, 2H), 1.25 (br d, J = 7.3 Hz, 3H), 2 NH protons not observed |
| 391 | 2-(2-amino-[1,2,4]triazolo[1,5-a]pyridin-7-yl)-N-(2-fluoro-5-(trifluoromethyl)benzyl)-5-methoxy-isonicotinamide | | 461.1 | 9.11 (t, J = 5.6 Hz, 1H), 8.68 (s, 1H), 8.66 (d, J = 6.7 Hz, 1H), 8 21 (s, 1H), 7.82 (d, J = 6.4 Hz, 1H), 7.78-7.71 (m, 1H), 7.67 (d, J = 6.7 Hz, 1H), 7.47 (t, J = 9.2 Hz, 1H), 4.61 (d, J = 5.8 Hz, 2H), 4.05 (s, 3H). |
| 392 | (R)-2-(2-amino-[1,2,4]triazolo[1,5-a]pyridin-7-yl)-N-(1-(2-fluoro-5-(trifluoromethoxy)phenyl)ethyl)-5-methylisonicotinamide | | 475.0 | 9.18 (d, J = 7.3 Hz, 1H), 8.65 (d, J = 7.0 Hz, 1H), 8.63 (s, 1H), 8.10 (s, 1H), 8.08 (s, 1H), 7.68 (d, J = 7.0 Hz, 1H), 7.49 (d, J = 4.0 Hz, 1H), 7.41-7.31 (m, 2H), 7.24-6.97 (m, 1H), 5.36 (quin, J = 7.2 Hz, 1H), 2.28 (s, 3H), 1.48 (d, J = 6.7 Hz, 3H) |
| 393 | 2-(2-amino-[1,2,4]triazolo[1,5-a]pyridin-7-yl)-5-methyl-N-(3-phenylbutyl)isonicotinamide | | 401.2 | 8.59 (m, 2H), 8.56 (s, 1H), 8.06 (s, 1H), 7.98 (s, 1H), 7.64 (d, J = 6.7 Hz, 1H), 7.34-7.29 (m, 2H), 7.29-7.24 (m, 2H), 7.23-7.15 (m, 1H), 3.26-3.07 (m, 2H), 2.91-2.72 (m, 1H), 2.35 (s, 3H), 1.83 (q, J = 6.8 Hz, 2H), 1.24 (d, J = 6.7 Hz, 3H |
| 394 | 2-(2-amino-[1,2,4]triazolo[1,5-a]pyridin-7-yl)-N-(2-fluoro-5-(trifluoromethoxy)benzyl)-5-methylisonicotinamide | | 461.1 | 9.22 (t, J = 5.6 Hz, 1H), 8.66-8.60 (m, 2H), 8.10 (s, 1H), 8.07 (s, 1H), 7.65 (d, J = 7.0 Hz, 1H), 7.46 (d, J = 4.6 Hz, 1H), 7.39 (s, 1H), 7.38 (s, 1H), 4.56 (d, J = 5.5 Hz, 2H), 2.35 (s, 3H) |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 395 | (R)-2-(2-amino-[1,2,4]triazolo[1,5-a]pyridin-7-yl)-N-(3-(4-chlorophenyl)-3-hydroxypropyl)-5-methylisonicotinamide | | 437.0 | 8.62 (s, 1H), 8.55 (s, 1H), 8.53 (d, J = 7.0 Hz, 1H), 7.94 (s, 1H), 7.79 (s, 1H), 7.56 (d, J = 7.0 Hz, 1H), 7.34 (s, 4H), 3.36-3.25 (m, 2H), 2.30 (s, 3H), 1.93-1.81 (m, 2H) |
| 396 | (R)-2-(2-amino-[1,2,4]triazolo[1,5-a]pyridin-7-yl)-N-(1-(2-fluoro-5-(trifluoromethyl)phenyl)ethyl)-5-methylisonicotinamide | | 495.1 | 9.32 (d, J = 7.0 Hz, 1H), 8.59 (s, 1H), 8.55 (d, J = 6.7 Hz, 1H), 7.97 (s, 1H), 7.92 (s, 1H), 7.77 (d, J = 5.5 Hz, 1H), 7.73-7.66 (m, 1H), 7.59 (d, J = 7.0 Hz, 1H), 7.41 (t, J = 9.2 Hz, 1H), 5.38-5.30 (m, 1H), 2.23 (s, 3H), 1.48 (d, J = 6.7 Hz, 3H) |
| 397 | (S)-2-(2-amino-[1,2,4]triazolo[1,5-a]pyridin-7-yl)-N-(3-(4-chlorophenyl)-3-hydroxypropyl)-5-methylisonicotinamide | | 374.2 | 8.64-8.59 (m, 1H), 8.55 (s, 1H), 8.53 (d, J = 7.0 Hz, 1H), 7.94 (s, 1H), 7.79 (s, 1H), 7.57 (d, J = 7.0 Hz, 1H), 7.34 (s, 4H), 3.31 (q, J = 6.2 Hz, 2H), 2.30 (s, 3H), 1.92-1.82 (m, 2H) |
| 398 | 2-(2-amino-[1,2,4]triazolo[1,5-a]pyridin-7-yl)-N-(2-fluoro-5-(trifluoromethyl)benzyl)-5-methylisonicotinamide | | 445.1 | 9.23 (t, J = 5.6 Hz, 1H), 8.68-8.59 (m, 2H), 8.09 (s, 1H), 8.06 (s, 1H), 7.83 (d, J = 6.1 Hz, 1H), 7.77 (d, J = 3.4 Hz, 1H), 7.65 (d, J = 6.7 Hz, 1H), 7.49 (t, J = 9.2 Hz, 1H), 4.61 (d, J = 5.5 Hz, 2H), 2.35 (s, 3H) |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 399 | 4-(2-amino-[1,2,4]triazolo[1,5-a]pyridin-7-yl)-N-(2-fluoro-5-(trifluoromethoxy)benzyl)-5-methyl-picolinamide | | 461.1 | 9.48 (t, J = 6.1 Hz, 1H), 8.63 (s, 1H), 8.61 (d, J = 7.0 Hz, 1H), 7.89 (s, 1H), 7.44 (s, 1H), 7.34-7.29 (m, 3H), 6.95 (d, J = 6.7 Hz, 1H), 6.09 (s, 1H), 4.55 (d, J = 6.1 Hz, 2H), 2.36 (s, 3H) |
| 400 | 4-(2-amino-[1,2,4]triazolo[1,5-a]pyridin-7-yl)-5-methyl-N-(3-phenylbutyl)picolinamide | | 401.2 | 8.78 (t, J = 6.0 Hz, 1H), 8.61 (d, J = 6.7 Hz, 1H), 8.58 (s, 1H), 7.85 (s, 1H), 7.43 (s, 1H), 7.31-7.25 (m, 2H), 7.25-7.20 (m, 2H), 7.19-7.13 (m, 1H), 6.94 (d, J = 6.7 Hz, 1H), 6.09 (s, 2H), 3.20 (td, J = 19.7, 13.2 Hz, 2H), 2.80-2.68 (m, 1H), 2.35 (s, 3H), 1.87-1.77 (m, 2H), 1.20 (d, J = 6.7 Hz, 3H) |
| 401 | (S)-6-(2-amino-[1,2,4]triazolo[1,5-a]pyridin-7-yl)-N-(3-(4-chlorophenyl)-3-hydroxypropyl)-3-methyl-picolinamide | | 437.1 | 8.90 (t, J = 5.0 Hz, 1H), 8.59 (d, J = 7.0 Hz, 1H), 8.18 (s, 1H), 8.15 (d, J = 8.2 Hz, 1H), 7.85 (d, J = 8.2 Hz, 1H), 7.74 (d, J = 7.0 Hz, 1H), 7.43-7.31 (m, 4H), 6.06 (s, 2H), 4.71 (d, J = 4.0 Hz, 1H), 3.37 (q, J = 6.6 Hz, 2H), 2.56 (s, 3H), 1.96-1.80 (m, 2H) |
| 402 | (R)-6-(2-amino-[1,2,4]triazolo[1,5-a]pyridin-7-yl)-N-(3-(4-chlorophenyl)-3-hydroxypropyl)-3-methyl-picolinamide | | 437.1 | 8.90 (t, J = 5.2 Hz, 1H), 8.59 (d, J = 6.7 Hz, 1H), 8.19 (s, 1H), 8.15 (d, J = 7.9 Hz, 1H), 7.85 (d, J = 8.2 Hz, 1H), 7.75 (d, J = 7.0 Hz, 1H), 7.43-7.31 (m, 4H), 6.06 (s, 2H), 4.75-4.67 (m, 1H), 3.37 (q, J = 6.3 Hz, 2H), 2.56 (s, 3H), 1.97-1.79 (m, 2H). |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 403 | (R)-6-(2-amino-[1,2,4]triazolo[1,5-a]pyridin-7-yl)-N-(1-(2-fluoro-5-(trifluoromethoxy)phenyl)ethyl)-3-methyl-picolinamide | | 475.1 | 9.19 (d, J = 8.2 Hz, 1H), 8.54 (d, J = 6.7 Hz, 1H), 8.12-8.06 (m, 2H), 7.85 (d, J = 8.2 Hz, 1H), 7.71 (d, J = 7.6 Hz, 1H), 7.51-7.46 (m, 1H), 7.35-7.26 (m, 2H), 6.00 (s, 2H), 5.37-5.29 (m, 1H), 2.38 (s, 3H), 1.49 (d, J = 7.0 Hz, 3H) |
| 404 | 6-(2-amino-[1,2,4]triazolo[1,5-a]pyridin-7-yl)-3-methyl-N-(3-phenylbutyl)picolinamide | | 401.2 | 8.64 (t, J = 5.0 Hz, 1H), 8.48 (d, J = 6.7 Hz, 1H), 8.02 (s, 1H), 7.99 (d, J = 8.5 Hz, 1H), 7.80 (d, J = 9.2 Hz, 1H), 7.66 (d, J = 7.6 Hz, 1H), 7.26-7.16 (m, 4H), 7.12-7.05 (m, 1H), 3.25-3.12 (m, 3H), 2.44 (s, 3H), 1.86-1.76 (m, 2H), 1.18 (d, J = 6.7 Hz, 3H) |
| 405 | 6-(2-amino-[1,2,4]triazolo[1,5-a]pyridin-7-yl)-N-(2-fluoro-5-(trifluoromethoxy)benzyl)-3-methyl-picolinamide | | 461.1 | 9.40 (t, J = 6.1 Hz, 1H), 8.54 (d, J = 7.0 Hz, 1H), 8.16 (s, 1H), 8.13 (d, J = 7.9 Hz, 1H), 7.87 (d, J = 8.2 Hz, 1H), 7.75 (d, J = 5.5 Hz, 1H), 7.39-7.24 (m, 3H), 6.01 (s, 2H), 4.56 (d, J = 6.1 Hz, 2H), 2.54 (s, 3H) |
| 406 | (R)-6-(2-amino-[1,2,4]triazolo[1,5-a]pyridin-7-yl)-N-(1-(2-fluoro-5-(trifluoromethoxy)phenyl)ethyl)-3-methoxy-picolinamide | | 491.1 | 9.13 (d, J = 7.6 Hz, 1H), 8.57 (d, J = 7.0 Hz, 1H), 8.22 (d, J = 8.9 Hz, 1H), 8.01 (s, 1H), 7.70 (d, J = 8.9 Hz, 1H), 7.63 (d, J = 7.0 Hz, 1H), 7.55 (s, 1H), 7.41-7.30 (m, 2H), 5.32 (t, J = 7.2 Hz, 1H), 3.87 (s, 3H), 1.45 (d, J = 7.0 Hz, 3H) |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 407 | (R)-2-(2-amino-[1,2,4]triazolo[1,5-a]pyridin-7-yl)-N-(1-(2-fluoro-5-(trifluoromethoxy)phenyl)ethyl)-5-methyl-pyrimidine-4-carboxamide | | 476.1 | 9.44 (d, J = 7.9 Hz, 1H), 8.95 (s, 1H), 8.67 (d, J = 7.0 Hz, 1H), 8.43 (s, 1H), 7.91 (d, J = 7.0 Hz, 1H), 7.60-7.52 (m, 1H), 7.43-7.30 (m, 2H), 5.41 (quin, J = 7.0 Hz, 1H), 2.41 (s, 3H), 1.55 (d, J = 6.7 Hz, 3H) |
| 408 | (R)-2-(2-amino-[1,2,4]triazolo[1,5-a]pyridin-7-yl)-N-(3-(4-chlorophenyl)-3-hydroxy-propyl)-5-methyl-pyrimidine-4-carboxamide | | 438.1 | 9.14 (t, J= 5.2 Hz, 1H), 8.94 (s, 1H), 8.64 (d, J = 7.0 Hz, 1H), 8.47 (s, 1H), 7.92 (d, J = 7.0 Hz, 1H), 7.42-7.36 (m, 4H), 6.13 (s, 2H), 4.75-4.66 (m, 1H), 3.36-3.32 (m, 2H), 2.55 (s, 3H), 1.96-1.85 (m, 2H) |
| 409 | (R)-2-(2-amino-[1,2,4]triazolo[1,5-a]pyridin-7-yl)-N-(1-(2-fluoro-5-(trifluoromethyl)phenyl)ethyl)-5-methyl-pyrimidine-4-carboxamide | | 460.1 | 9.51 (d, J = 7.9 Hz, 1H), 8.96 (s, 1H), 8.70 (d, J = 6.7 Hz, 1H), 8.44 (s, 1H), 7.98 (d, J = 5.8 Hz, 1H), 7.91 (d, J = 6.7 Hz, 1H), 7.79-7.70 (m, 1H), 7.48 (t, J = 9.2 Hz, 1H), 5.47 (quin, J = 7.2 Hz, 1H), 2.42 (s, 3H), 1.57 (d, J = 7.0 Hz, 3H) |
| 410 | (S)-2-(2-amino-[1,2,4]triazolo[1,5-a]pyridin-7-yl)-N-(3-(4-chlorophenyl)-3-hydroxy-propyl)-5-methyl-pyrimidine-4-carboxamide | | 438.1 | 9.14 (t, J = 5.5 Hz, 1H), 8.94 (s, 1H), 8.64 (d, J = 7.0 Hz, 1H), 8.47 (s, 1H), 7.92 (d, J = 7.0 Hz, 1H), 7.43-7.35 (m, 4H), 4.74-4.66 (m, 1H), 3.37-3.31 (m, 2H), 2.55 (s, 3H), 1.95-1.86 (m, 2H) |

TABLE 16-continued

Compounds in Table 16 were prepared in a similar fashion to example 3.

| Ex No | Name | R | M + H | 1H NMR (500 MHz, DMSO-d6) δ |
|---|---|---|---|---|
| 411 | (S)-2-(2-amino-[1,2,4]triazolo[1,5-a]pyridin-7-yl)-5-methyl-N-(3-phenylbutyl)pyrimidine-4-carboxamide | 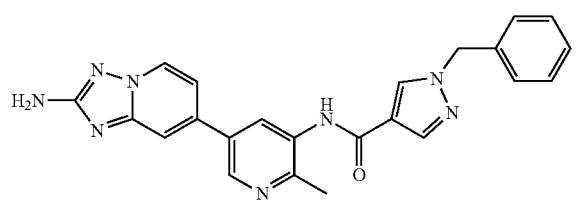 | 402.2 | 9.04 (t, J = 5.5 Hz, 1H), 8.93 (s, 1H), 8.65 (d, J = 7.0 Hz, 1H), 8.48 (s, 1H), 7.92 (d, J = 7.0 Hz, 1H), 7.34-7.24 (m, 4H), 7.22-7.13 (m, 1H), 6.13 (s, 2H), 3.35-3.30 (m, 2H), 2.86-2.75 (m, 1H), 2.52 (s, 3H), 1.87 (q, J = 6.9 Hz, 2H), 1.26 (d, J = 7.0 Hz, 3H) |

Example 412

N-(5-(2-amino-[1,2,4]triazolo[1,5-a]pyridin-7-yl)-2-methylpyridin-3-yl)-1-benzyl-1H-pyrazole-4-carboxamide 412A: 7-(5-amino-6-methylpyridin-3-yl)-N,N-di-tert-butyl carbamoyl-[1,2,4]triazolo[1,5-a]pyridin-2-amine: A stirred mixture of (2-(di-tert-butyl carbamoyl-amino)-[1,2,4]triazolo[1,5-a]pyridin-7-yl)boronic acid (1.83 g, 4.84 mmol), prepared as in example 3, and 1,1'-bis(diphenylphosphino)ferrocene-palladium(II)dichloride dichloromethane complex (0.198 g, 0.242 mmol) in 1,4-dioxane (16 mL) was degassed by bubbling nitrogen through the mixture for 5 min 2M K₃PO₄ (aq) (7.26 mL, 14.52 mmol) was quickly added and the reaction mixture heated to 100° C. for 30 min. After cooling to rt, the reaction mixture was concentrated directly onto Celite. Using a 40 g ISCO silica gel cartridge, the crude residue was purified by chromatography, eluting with a 0-100% EtOAc in hexanes. The pure fractions were concentrated to afford a solid that was triturated with 1:1 ether:hexane. Filtration and drying afforded 7-(5-amino-6-methylpyridin-3-yl)-N,N-di-tert-butyl carbamoyl-[1,2,4]triazolo[1,5-a]pyridin-2-amine (1.49 g, 3.31 mmol, 69% yield) as a cream colored solid.

MS ESI m/z 441.2 (M+H).

412B: 1-Benzyl-N-(5-(2-(bis-tert-butyl carbamoylamino)-[1,2,4]triazolo[1,5-a]pyridin-7-yl)-2-methylpyridin-3-yl)-1H-pyrazole-4-carboxamide: A solution of 7-(5-amino-6-methylpyridin-3-yl)-N,N-di-tert-butyl carbamoyl-[1,2,4]triazolo[1,5-a]pyridin-2-amine (40 mg, 0.091 mmol), 1-benzyl-1H-pyrazole-4-carboxylic acid (22.03 mg, 0.109 mmol), 1-propanephosphonic anhydride (0.081 ml, 0.136 mmol) [50% DMF solution] and Hünig's base (0.048 mL, 0.272 mmol) in DMF (1.5 mL) was stirred ON at 50° C. The reaction mixture was diluted to 75 mL with EtOAc, then washed with water, 10% aq. LiCl (2×) and brine. The organics were dried over sodium sulfate, then filtered and concentrated. The crude residue was loaded onto a 12 g column and purified by flash chromatography, eluting with 0-100% EtOAc in hexanes, Afforded 1-benzyl-N-(5-(2-(bis-tert-butyl carbamoylamino)-[1,2,4]triazolo[1,5-a]pyridin-7-yl)-2-methylpyridin-3-yl)-1H-pyrazole-4-carboxamide (51 mg, 0.073 mmol, 81% yield).

MS ESI m/z 625.5 (M+H).

412: To a solution of 1-benzyl-N-(5-(2-(bis-tert-butyl carbamoylamino)-[1,2,4]triazolo[1,5-a]pyridin-7-yl)-2-methylpyridin-3-yl)-1H-pyrazole-4-carboxamide (51 mg, 0.082 mmol) in DCM (1 mL) was added TFA. The resulting solution was stirred 30 min at rt. The reaction mixture was concentrated, then redissolved in methanol. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to afford N-(5-(2-amino-[1,2,4]triazolo[1,5-a]pyridin-7-yl)-2-methylpyridin-3-yl)-1-benzyl-1H-pyrazole-4-carboxamide (12.1 mg, 0.029 mmol, 35% yield).

MS ESI m/z 425.4 (M+H).

¹H NMR (500 z, DMSO-d6) δ 9.84 (s, 1H), 8.77 (s, 1H), 8.60 (brd, J=6.7 Hz, 1H), 8.45 (s, 1H), 8.13 (s, 1H), 8.08 (s, 1H), 7.71 (s, 1H), 7.41-7.29 (m, 5H), 7.25 (brd, J=6.4 Hz, 1H), 5.41 (s, 2H), 3.65-3.521 (m, 2H), 2.49-2.45 (m, 3H).

TABLE 17

Compounds in Table 17 were prepared in a similar fashion to example 412.

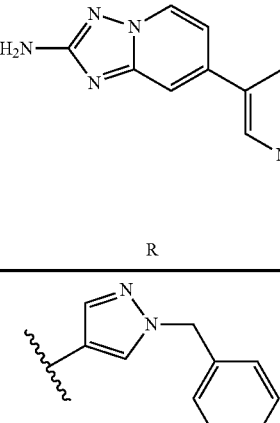

| Ex No | Name | R | R¹ | M + H | 1H NMR (500 MHz, DMSO-d6) δ |
|---|---|---|---|---|---|
| 413 | N-(5-(2-amino-[1,2,4]triazolo[1,5-a]pyridin-7-yl)-2-methoxypyridin-3-yl)-1-benzyl-1H-pyrazole-4-carboxamide | 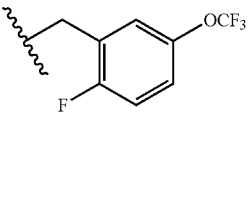 [SMILES: *Cc1cc(OC(F)(F)F)ccc1F] | OMe | 441.3 | 9.49 (s, 1H), 8.57 (d, J = 7.0 Hz, 1H), 8.50 (s, 1H), 8.45 (s, 1H), 8.42 (s, 1H), 8.08 (s, 1H), 7.61 (s, 1H), 7.40-7.27 (m, 5H), 7.22-7.16 (m, 1H), 6.01 (s, 2H), 5.39 (s, 2H), 3.98 (s, 3H) |
| 414 | N-(5-(2-amino-[1,2,4]triazolo[1,5-a]pyridin-7-yl)-2-methoxypyridin-3-yl)-2-(2-fluoro-5-(trifluoromethoxy)phenyl)acetamide | 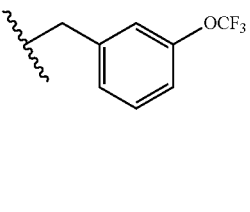 [SMILES: *Cc1cccc(OC(F)(F)F)c1] | OMe | 477.1 | 9.88 (s, 1H), 8.68 (s, 1H), 8.55 (d, J = 6.9 Hz, 1H), 8.34 (d, J = 1.9 Hz, 1H), 7.54 (s, 1H), 7.47 (br d, J = 4.7 Hz, 1H), 7.33 (br d, J = 7.7 Hz, 2H), 7.11 (dd, J = 6.9, 1.7 Hz, 1H), 6.02 (s, 2H), 4.02 (s, 3H), 3.96 (s, 2H) |
| 415 | N-(5-(2-amino-[1,2,4]triazolo[1,5-a]pyridin-7-yl)-2-methoxypyridin-3-yl)-2-(3-(trifluoromethoxy)phenyl)acetamide | 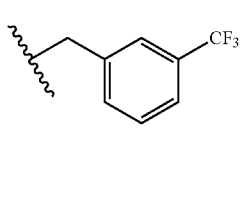 [SMILES: *Cc1cccc(C(F)(F)F)c1] | OMe | 459.1 | 9.64 (s, 1H), 8.66 (s, 1H), 8.53 (d, J = 7.0 Hz, 1H), 8.33 (d, J = 2.1 Hz, 1H), 7.52 (s, 1H), 7.49-7.44 (m, 1H), 7.41-7.33 (m, 2H), 7.23 (br d, J = 8.4 Hz, 1H), 7.11 (dd, J = 6.9, 1.6 Hz, 1H), 5.86 (s, 2H), 4.02 (s, 3H), 3.88 (d, J = 6.2 Hz, 2H) |
| 416 | N-(5-(2-amino-[1,2,4]triazolo[1,5-a]pyridin-7-yl)-2-methoxypyridin-3-yl)-2-(3-(trifluoromethyl)phenyl)acetamide | | OMe | 443.1 | 9.86 (s, 1H), 8.64 (s, 1H), 8.53 (d, J = 7.2 Hz, 1H), 8.32 (d, J = 2.2 Hz, 1H), 7.71 (s, 1H), 7.62 (br d, J = 12.1 Hz, 2H), 7.57 (br d, J = 7.4 Hz, 1H), 7.53 (s, 1H), 7.12 (dd, J = 7.2, 1.4 Hz, 1H), 5.99 (s, 2H), 3.99 (s, 3H), 3.92 (s, 2H) |

TABLE 17-continued

Compounds in Table 17 were prepared in a similar fashion to example 412.

| Ex No | Name | R | R¹ | M + H | 1H NMR (500 MHz, DMSO-d6) δ |
|---|---|---|---|---|---|
| 417 | N-(5-(2-amino-[1,2,4]triazolo[1,5-a]pyridin-7-yl)-2-methoxypyridin-3-yl)-2-(2-(trifluoromethoxy)phenyl)acetamide | 2-OCF₃-phenyl-CH₂- | OMe | 459.2 | 9.84 (s, 1H), 8.68 (s, 1H), 8.55 (d, J = 7.2 Hz, 1H), 8.35 (s, 1H), 7.53 (s, 1H), 7.49 (br d, J = 7.2 Hz, 1H), 7.45-7.32 (m, 3H), 7.13-7.07 (m, 1H), 6.02 (s, 2H), 4.02 (s, 3H), 3.95 (s, 2H) |
| 418 | N-(5-(2-amino-[1,2,4]triazolo[1,5-a]pyridin-6-yl)-2-methoxypyridin-3-yl)-2-(2-fluoro-5-(trifluoromethoxy)phenyl)acetamide | 4-F-2-(CH₂-)-OCF₃-phenyl | OMe | 477.1 | 9.69 (s, 1H), 8.77 (s, 1H), 8.58 (br s, 1H), 8.24 (s, 1H), 7.65 (d, J = 10.2 Hz, 1H), 7.47 (br d, J = 5.2 Hz, 1H), 7.41 (d, J = 9.1 Hz, 1H), 7.33 (br d, J = 6.9 Hz, 2H), 5.90 (s, 2H), 4.02 (s, 4H), 3.95 (s, 2H) |
| 419 | N-(5-(2-amino-[1,2,4]triazolo[1,5-a]pyridin-7-yl)-2-methylpyridin-3-yl)-2-fluoro-5-(trifluoromethoxy)benzamide | 5-OCF₃-2-F-phenyl | Me | 447.3 | 10.36 (s, 1H), 8.83 (s, 1H), 8.67 (br d, J = 6.6 Hz, 1H), 8.37 (s, 1H), 7.77 (br s, 2H), 7.70-7.63 (m, 1H), 7.61-7.52 (m, 1H), 7.32 (br d, J = 6.3 Hz, 1H), 2.54 (s, 3H) NH2 protons are observed |
| 420 | N-(5-(2-amino-[1,2,4]triazolo[1,5-a]pyridin-7-yl)-2-methylpyridin-3-yl)-2-(2-fluoro-5-(trifluoromethoxy)phenyl)acetamide | 5-OCF₃-2-F-phenyl-CH₂- | Me | 461.2 | 9.96 (s, 1H), 8.71 (s, 1H), 8.60 (d, J = 7.0 Hz, 1H), 8.23-8.19 (m, 1H), 7.66 (s, 1H), 7.50 (br d, J = 5.2 Hz, 1H), 7.36 (br d, J = 6.7 Hz, 2H), 7.19 (br d, J = 6.1 Hz, 1H), 3.91 (s, 2H), 2.50-2.47 (m, 3H) NH₂ protons not observed |

Example 421

5-(2-amino-[1,2,4]triazolo[1,5-a]pyridin-7-yl)-N-(3-(4-fluorophenyl)-2-hydroxy-2-methylpropyl)-2-methylnicotinamide

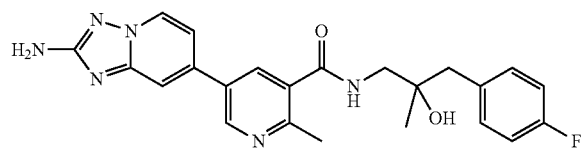 [SMILES: Cc1ncc(-c2ccn3nc(N)nc3c2)cc1C(=O)NCC(C)(O)Cc1ccc(F)cc1]

421A: Tert-butyl (3-(4-fluorophenyl)-2-hydroxy-2-methylpropyl)carbamate: To a 50 mL round-bottomed flask charged with tert-butyl (2-oxopropyl)carbamate (0.173 g, 1 mmol) in THF (1.5 mL) to give a colorless solution was added (4-fluorobenzyl)magnesium chloride (4.00 mL, 1.000 mmol) dropwise. The resultant clear mixture was stirred at rt for 120 min. The reaction was quenched with saturated $NH_4Cl$ solution and the mixture was diluted with EtOAc. The layers were separated. The organic layer was washed with brine, dried with $Na_2SO_4$ and concentrated. The residue was directly used in the next deprotection step.

421B: 1-amino-3-(4-fluorophenyl)-2-methylpropan-2-ol 2,2,2-trifluoroacetate: A 50 mL round-bottomed flask was charged with tert-butyl (3-(4-fluorophenyl)-2-hydroxy-2-methylpropyl)carbamate (0.283 g, 1 mmol) in $CH_2Cl_2$ (2 mL) to give a colorless suspension. TFA (1 mL, 12.98 mmol) was added. The resulted tan yellow solution was stirred at rt for 30 min. The volatiles were stripped off to afford the desired product as a tan oil which was carried forward without further purification.

MS ESI m/z 166.0 (M–$H_2O$).

421: A mixture of 5-(2-amino-[1,2,4]triazolo[1,5-a]pyridin-7-yl)-2-methylnicotinic acid (26.9 mg, 0.1 mmol), BOP (66.3 mg, 0.150 mmol), 1-amino-3-(4-fluorophenyl)-2-methylpropan-2-ol 2,2,2-trifluoroacetate (44.6 mg, 0.150 mmol) and Hünig's base (0.087 mL, 0.500 mmol) in DMF (0.5 mL) was stirred at rt over the weekend. The mixture was diluted with MeOH and filtered. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-46% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. Afforded 5-(2-amino-[1,2,4]triazolo[1,5-a]pyridin-7-yl)-N-(3-(4-fluorophenyl)-2-hydroxy-2-methylpropyl)-2-methylnicotinamide (3.7 mg, 8.26 μmol, 8% yield).

MS ESI m/z 435.3 (M+H).

1H NMR (500 MHz, DMSO-d6) δ 8.91 (d, J=2.4 Hz, 1H), 8.60 (d, J=7.0 Hz, 1H), 8.35 (d, J=6.3 Hz, 1H), 8.12 (d, J=2.4 Hz, 1H), 7.76 (s, 1H), 7.31 (td, J=7.5, 6.7, 3.8 Hz, 3H), 7.07 (t, J=8.7 Hz, 2H), 5.91 (s, 2H), 2.83-2.69 (m, 2H), 2.60 (s, 2H), 2.55 (s, 3H), 1.05 (s, 3H).

Example 422

(5-(2-amino-[1,2,4]triazolo[1,5-a]pyridin-7-yl)-2-methoxypyridin-3-yl)(3-((4-fluorophenyl)(hydroxy)methyl)piperidin-1-yl)methanone 422A: Tert-butyl 3-((4-fluorophenyl)(hydroxy)methyl)piperidine-1-carboxylate: In a 50 mL oven-dried round-bottomed flask was added tert-butyl 3-formylpiperidine-1-carboxylate (457 mg, 2.143 mmol) in THF (4 mL) to give a colorless solution. (4-Fluorophenyl)magnesium bromide (2.250 mL, 2.250 mmol) was added dropwise at rt. The mixture was stirred at rt for 30 min. The reaction was quenched with saturated $NH_4Cl$ solution and diluted with EtOAc. The layers were separated. The organic layer was dried and concentrated to the crude product as a colorless dense oil (766 mg, 86% purity). The crude material was carried forward without further purification.

MS ESI m/z 332.2 (M+Na).

422B: (4-fluorophenyl)(piperidin-3-yl)methanol 2,2,2-trifluoroacetate: In a 50 mL round-bottomed flask was added tert-butyl 3-((4-fluorophenyl)(hydroxy)methyl)piperidine-1-carboxylate (254 mg, 0.706 mmol) in $CH_2Cl_2$ (2 mL) to give a colorless solution. TFA (1 mL, 12.98 mmol) was added. The resulted tan yellow solution was stirred at rt for 30 min. The volatiles were stripped off to afford the desired product as a tan oil, which was used in the next coupling steps.

MS ESI m/z 210.0 (M+H).

422: A mixture of 5-(2-amino-[1,2,4]triazolo[1,5-a]pyridin-7-yl)-2-methylnicotinic acid (26.9 mg, 0.1 mmol), BOP (66.3 mg, 0.150 mmol), (4-fluorophenyl)(piperidin-3-yl)methanol 2,2,2-trifluoroacetate (35.6 mg, 0.110 mmol) and Hünig's base (0.087 mL, 0.500 mmol) in DMF (0.5 mL) was stirred at rt ON. The reaction mixture was concentrated and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-47% B over 25 minutes, then a 6-minute hold at 100% B; Flow Rate: 20 mL/min; Column Temperature: 25 C. Fraction collection was triggered by MS signals. Fractions containing the desired product were combined and dried via centrifugal evaporation. Afforded (5-(2-amino-[1,2,4]triazolo[1,5-a]pyridin-7-yl)-2-methoxypyridin-3-yl)(3-((4-fluorophenyl)(hydroxy)methyl)piperidin-1-yl)methanone (6.3 mg, 0.013 mmol, 130% yield) as a mixture of diastereomers.

MS ESI m/z 461.3 (M+H).

1H NMR (500 MHz, DMSO-d6) δ 8.96-8.79 (m, 1H), 8.73-8.56 (m, 1H), 8.12-7.63 (m, 2H), 7.27 (br s, 1H), 7.51-7.01 (m, 3H), 6.96-6.53 (m, 1H), 5.93 (br d, J=11.9 Hz, 2H), 5.38-4.01 (m, 2H), 3.68-3.16 (m, 2H), 3.10-2.60 (m, 3H), 2.38-1.99 (m, 2H), 1.89-1.14 (m, 5H). NMR complicated by diastereomers and rotamers.

TABLE 18

Compounds in Table 18 were prepared in a similar fashion to example 422.

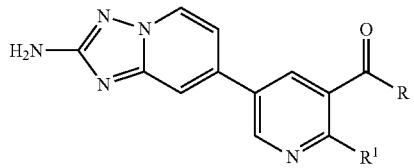

| Ex No | Name | R | R¹ | M + H | 1H NMR (500 MHz, DMSO-d6) δ |
|---|---|---|---|---|---|
| 423 | (5-(2-amino-[1,2,4]triazolo[1,5-a]pyridin-7-yl)-2-methylpyridin-3-yl)(3-((4-fluorophenyl)(hydroxy)methyl)piperidin-1-yl)methanone | | Me | 461.3 | 8.74-8.46 (m, 2H), 8.17-7.86 (m, 1H), 7.82-7.31 (m, 2H), 7.28-7.03 (m, 3H), 7.00-6.64 (m, 1H), 5.89 (br d, J = 9.2 Hz, 2H), 4.59-3.78 (m, 4H), 3.68-3.22 (m, 2H), 3.08-2.59 (m, 3H), 2.23-1.14 (m, 5H). NMR complicated by diastereomers, rotamers. |
| 424 | (5-(2-amino-[1,2,4]triazolo[1,5-a]pyridin-7-yl)-2-methoxypyridin-3-yl)(3-(phenylthio)piperidin-1-yl)methanone | | OMe | 461.2 | 8.82-8.57 (m, 2H), 8.31-7.64 (m, 3H), 7.59-7.28 (m, 3H), 7.20-6.80 (m, 4H), 4.58-3.77 (m, 3H), 3.50-2.94 (m, 2H), 2.92-2.71 (m, 3H), 2.09 (br d, J = 14.0 Hz, 1H), 1.98-1.42 (m, 3H). NMR complicated by rotamers. |
| 425 | (5-(2-amino-[1,2,4]triazolo[1,5-a]pyridin-7-yl)-2-methoxypyridin-3-yl)(2-phenylmorpholino)methanone | | OMe | 431.1 | 8.31-8.21 (m, 2H), 8.20-8.16 (m, 2H), 7.53 (br s, 2H), 7.43-7.32 (m, 2H), 7.10 (dd, J = 7.4, 4.9 Hz, 1H), 6.21 (br d, J = 7.6 Hz, 1H), 5.22 (br t, J = 6.9 Hz, 1H), 5.09 (br s, 1H), 4.10-4.01 (m, 1H), 3.68-3.11 (m, 6H), 2.67-2.57 (m, 1H), 2.47-2.41 (m, 1H), 2.34 (br s, 1H). NMR complicated by rotamers |

TABLE 18-continued

Compounds in Table 18 were prepared in a similar fashion to example 422.

| Ex No | Name | R | R¹ | M + H | 1H NMR (500 MHz, DMSO-d6) δ |
|---|---|---|---|---|---|
| 426 | tert-butyl (3-(5-(2-amino-[1,2,4]triazolo[1,5-a]pyridin-7-yl)-2-methoxynicotinamido)cyclohexyl)carbamate | | OMe | 482.1 | 8.77-8.71 (m, 1H), 8.60 (d, J = 6.7 Hz, 1H), 8.44-8.30 (m, 1H), 8.27-8.11 (m, 1H), 7.72 (s, 1H), 7.36-7.20 (m, 1H), 6.97-6.74 (m, 1H), 6.05 (s, 2H), 4.10-3.97 (m, 3H), 3.86-3.07 (m, 2H), 2.12-1.47 (m, 5H), 1.9 (s, 9H), 1.36-1.04 (m, 3H). NMR complicated by diastereomers. |
| 427 | 1-(1-(5-(2-amino-[1,2,4]triazolo[1,5-a]pyridin-7-yl)-2-methoxynicotinoyl)piperidin-3-yl)-2-phenylethan-1-one | | OMe | 471.2 | 8.71 (br s, 1H), 8.66-8.52 (m, 1H), 8.24-8.00 (m, 1H), 7.73 (br s, 1H), 7.38-6.93 (m, 6H), 6.04 (br s, 2H), 4.62-4.18 (m, 1H), 4.03-3.67 (m, 4H), 3.51-2.66 (m, 4H), 2.21-1.28 (m, 5H) NMR complicated by rotamers |
| 428 | (5-(2-amino-[1,2,4]triazolo[1,5-a]pyridin-7-yl)-2-methoxypyridin-3-yl)(2-benzylmorpholino)methanone | | OMe | 445.1 | 8.70 (br d, J = 19.5 Hz, 1H), 8.59 (br d, J = 7.0 Hz, 1H), 8.13 (br s, 1H), 7.72 (br d, J = 9.8 Hz, 1H), 7.35-7.28 (m, 2H), 7.27-7.20 (m, 2H), 7.19-6.95 (m, 2H), 4.33 (br d, J = 11.3 Hz, 1H), 4.00-3.86 (m, 3H), 3.86-3.57 (m, 3H), 3.18 (br s, 1H), 3.03-2.57 (m, 4H). NH2 protons not observed. |

Example 429

(R)-(((5-(2-amino-[1,2,4]triazolo[1,5-a]pyridin-7-yl)-2-methylnicotinoyl)(1-(2-fluoro-5-(trifluoromethoxy)phenyl)ethyl)carbamoyl)oxy)methyl 3-methoxy-4-(phosphonooxy)benzoate, TFA

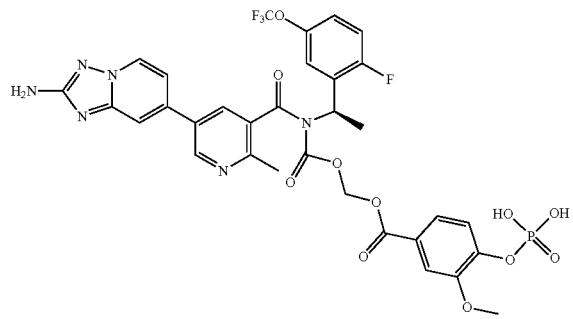 [SMILES: COc1cc(C(=O)OCOC(=O)N(C(=O)c2cc(-c3ccn4nc(N)nc4c3)cnc2C)[C@H](C)c2cc(OC(F)(F)F)ccc2F)ccc1OP(=O)(O)O]

429A: Methyl 4-((bis(benzyloxy)phosphoryl)oxy)-3-methoxybenzoate: To a solution of methyl 4-hydroxy-3-methoxybenzoate (5.00 g, 27.4 mmol) in dichloromethane (50 mL) was added dibenzyl N,N-diisopropylphosphoramidite (13.83 mL, 41.2 mmol) followed by 1H-tetrazole (0.45 M in acetonitrile) (122 mL, 41.2 mmol) and the mixture stirred at rt for 8 h. The reaction was cooled at 0° C. and $H_2O_2$ (8.41 mL, 274 mmol) was added. The mixture was then stirred at rt for 2 h. The reaction was concentrated to remove the acetonitrile and the obtained aqueous layer was diluted and extracted with ethyl acetate (3×100 mL). The combined organic layer was washed with brine, dried over anhydrous sodium sulfate, filtered and concentrated to get a colorless oil. The crude material was purified by silica gel chromatography, eluting with ethyl acetate in hexane. The product was eluted at 30% ethyl acetate in hexane to give methyl 4-((bis(benzyloxy)phosphoryl)oxy)-3-methoxybenzoate (10.600 g, 20.61 mmol, 75% yield) as a colorless oil.

MS ESI m/z 443.2 (M+H).

429B: 4-((Bis(benzyloxy)phosphoryl)oxy)-3-methoxybenzoic acid: To a biphasic mixture of methyl 4-((bis(benzyloxy)phosphoryl)oxy)-3-methoxybenzoate (5.00 g, 9.72 mmol) in tetrahydrofuran (50 mL) and water (25 mL) at 0° C. was added LiOH (0.466 g, 19.44 mmol). The reaction mixture was stirred at 0° C. for 1 h. The organic solvent was concentrated under vacuum at 30° C. The aqueous layer was extracted with ethyl acetate (2×50 mL). The aqueous layer was acidified with 1.5 N HCl solution (adjusted to pH-1) and extracted with ethyl acetate (3×50 mL). The organic layer was washed with brine solution, dried over anhydrous $Na_2SO_4$ and concentrated in vacuo at 30° C. to give the crude product as a colorless oil. The crude product was purified by silica gel chromotography eluting with 40% ethyl acetate in hexane to give 4-((bis(benzyloxy)phosphoryl)oxy)-3-methoxybenzoic acid (3.900 g, 8.92 mmol, 92% yield) as a of white solid.

MS ESI m/z 429.1 (M+H).

429C: (R)-5-bromo-N-(1-(2-fluoro-5-(trifluoromethoxy)phenyl)ethyl)-2-methylnicotinamide: To a round bottom flask charged with 5-bromo-2-methylnicotinic acid (1.329 g, 6.15 mmol) in dichloromethane (30.8 ml) was added (R)-1-(2-fluoro-5-(trifluoromethoxy)phenyl)ethan-1-amine, HCl (1.677 g, 6.46 mmol), Hünig's base (3.22 ml, 18.45 mmol) and BOP (2.86 g, 6.46 mmol). The reaction mixture was stirred at rt over the weekend. The reaction mixture was poured into a separatory funnel containing half-saturated aqueous ammonium chloride and dichloromethane. The aqueous layer was extracted with dichloromethane (2×). The organics were washed with saturated aqueous sodium bicarbonate and brine. The combined organics were dried over anhydrous sodium sulfate, filtered and concentrated in vacuo. The crude solid was purified by silica gel column chromatography on an Isco system (40 g column, 0-50% EtOAc/Hex).

1H NMR (400 MHz, $CDCl_3$) δ 8.62 (d, J=2.2 Hz, 1H), 7.79 (d, J=2.3 Hz, 1H), 7.25-7.08 (m, 3H), 6.18 (br d, J=8.2 Hz, 1H), 5.42 (quin, J=7.3 Hz, 1H), 2.58 (s, 3H), 1.63 (d, J=7.1 Hz, 3H).

429D: Chloromethyl (R)-(5-bromo-2-methylnicotinoyl)(1-(2-fluoro-5-(trifluoromethoxy)phenyl)ethyl)carbamate:

To a stirred solution of (R)-5-bromo-N-(1-(2-fluoromethoxy)phenyl)ethyl)-2-methylnicotinamide (1.00 g, 2.374 mmol) in THF (15 mL), was added NaH (0.475 g, 11.87 mmol). After being stirred at rt for 5 min, chloromethyl carbonochloridate (0.633 mL, 7.12 mmol) was added. The reaction mixture was stirred at rt for 12 h. The reaction mixture was partitioned between water and ethyl acetate. The organic layer was washed with brine solution, dried over anhydrous sodium sulphate, filtered and concentrated under vacuum to give the crude product as light yellow oil. The crude product was purified using by silica gel column chromatography, eluting with 35% ethyl acetate in pet. ether as eluent. The fractions containing product were concentrated using high vacuum at 30° C. to give chloromethyl (R)-(5-bromo-2-methylnicotinoyl)(1-(2-fluoro-5-(trifluoromethoxy)phenyl)ethyl)carbamate (0.970 g, 1.851 mmol, 78% yield) as a colorless oil.

MS ESI m/z 513.0 (M+H).

429E: 7-Bromo-2-((bis-tert-butoxycarbonyl)amino)-[1,2,4]triazolo[1,5-a]pyridine: To a stirred solution of 7-bromo-[1,2,4]triazolo[1,5-a]pyridin-2-amine (5.00 g, 23.47 mmol) in dichloromethane (50 mL) cooled to 0° C. was slowly added TEA (16.36 mL, 117 mmol), DMAP (5.73 g, 46.9 mmol) and Boc-anhydride (16.35 mL, 70.4 mmol). The reaction mixture was stirred at rt for 12 h. The reaction mixture was partitioned between water and DCM (200 mL). The organic layer was washed with water, saturated brine solution, dried over anhydrous sodium sulphate, filtered and concentrated under vacuum to give the crude product as light yellow solid. The crude product was purified by silica gel chromatography (35% ethyl acetate in hexane as eluent). The fractions containing product were concentrated at 40° C. to give 7bromo-2-((bis-tert-butoxycarbonyl)amino)-[1,2,4]triazolo[1,5-a]pyridine (8.00 g, 18.58 mmol, 79% yield) as an off white solid.

MS ESI m/z 413.2 (M+H).

429F: (2-((Bis-tert-butoxycarbonyl)amino)-[1,2,4]triazolo[1,5-a]pyridin-7-yl)boronic acid: To a stirred solution of 7-bromo-2-((bis-tert-butoxycarbonyl)amino)-[1,2,4]triazolo[1,5-a]pyridine (1.000 g, 2.420 mmol) in 1,4-dioxane (15 mL) was added bis(pinacolato)diboron (0.922 g, 3.63 mmol), potassium acetate (0.712 g, 7.26 mmol) and $PdCl_2$(dppf)-$CH_2Cl_2$ adduct (0.198 g, 0.242 mmol). The reaction mixture was sparged with $N_2$ for 5 min. The reaction mixture was heated at 100° C. for 2 h. The reaction mixture was partitioned between water and ethyl acetate. The organic layer was washed with brine solution, dried over anhydrous sodium sulphate, filtered and concentrated under vacuum to give crude product (1.168 g, 2.378 mmol, 98% crude yield)

as a dark brown semi-solid. The material was carried forward without further purification.

MS ESI m/z 379.4 (M+H).

429G: Tert-butyl (R)-(tert-butoxycarbonyl)(7-(5-(((chloromethoxy)carbonyl)(1-(2-fluoro-5-(trifluoromethoxy)phenyl)ethyl)carbamoyl)-6-methylpyridin-3-yl)-[1,2,4]triazolo[1,5-a]pyridin-2-yl)carbamate: To a stirred solution of crude (2-((bis-tert-butoxycarbonyl)amino)-[1,2,4]triazolo[1,5-a]pyridin-7-yl)boronic acid (0.989 g, 1.830 mmol) were added chloromethyl (R)-(5-bromo-2-methylnicotinoyl)(1-(2-fluoro-5-(trifluoromethoxy)phenyl)ethyl)carbamate (1.000 g, 1.830 mmol) and PdCl$_2$(dppf)-CH$_2$Cl$_2$ adduct (0.075 g, 0.091 mmol). The reaction mixture was sparged with N$_2$ for 10 min. Potassium carbonate (0.506 g, 3.66 mmol) was added and the reaction mixture was stirred at 50° C. for 12 h. The reaction mixture was partitioned between water and ethyl acetate. The organic layer was washed with brine solution, dried over anhydrous sodium sulphate, filtered and concentrated under vacuum to give crude product as a dark brown oil. The crude product was purified using RP HPLC (mobile phase A: 10 mM ammonium acetate in water; mobile phase B: acetonitrile; flow rate: 17 mL/min.). The fraction was concentrated using high vacuum at 30° C. The residue was dissolved in a mixture of acetonitrile and water, frozen and lyophilized for 12 h to give tert-butyl (R)-(tert-butoxycarbonyl)(7-(5-(((chloromethoxy)carbonyl)(1-(2-fluoro-5-(trifluoromethoxy)phenyl)ethyl)carbamoyl)-6-methylpyridin-3-yl)-[1,2,4]triazolo[1,5-a]pyridin-2-yl)carbamate (0.450 g, 0.581 mmol, 32% yield) as an off white solid.

MS ESI m/z 767.2 (M+H).

429H: (((5-(2-(bis(tert-butoxycarbonyl)amino)-[1,2,4]triazolo[1,5-a]pyridin-7-yl)-2-methylnicotinoyl)((R)-1-(2-fluoro-5-(trifluoromethoxy)phenyl)ethyl)carbamoyl)oxy)methyl 4-(((benzyloxy)(hydroxy)phosphoryl)oxy)-3-methoxybenzoate: To a solution of tert-butyl (R)-(tert-butoxycarbonyl)(7-(5-(((chloromethoxy)carbonyl)(1-(2-fluoro-5-(trifluoromethoxy)phenyl)ethyl)carbamoyl)-6-methylpyridin-3-yl)-[1,2,4]triazolo[1,5-a]pyridin-2-yl)carbamate (0.200 g, 0.261 mmol) in DMF (2 mL) was added 4-((bis(benzyloxy)phosphoryl)oxy)-3-methoxybenzoic acid (0.134 g, 0.313 mmol), DIPEA (0.455 mL, 2.61 mmol) and sodium iodide (0.059 g, 0.391 mmol). The reaction mixture was stirred at 50° C. for 12 h. The reaction mixture was partitioned between water and ethyl acetate. The organic layer was washed with brine solution, dried over anhydrous sodium sulfate, filtered and concentrated under vacuum to give crude product as light yellow oil. The crude product was purified using reverse phase HPLC (mobile phase A: 10 mM ammonium acetate in water; mobile phase B: acetonitrile; flow rate: 17 mL/min.). The fractions containing product were concentrated using high vacuum at 30° C. The residue was dissolved in a mixture of acetonitrile and water, frozen and lyophilized for 12 h to give (((5-(2-(bis(tert-butoxycarbonyl)amino)-[1,2,4]triazolo[1,5-a]pyridin-7-yl)-2-methylnicotinoyl)((R)-1-(2-fluoro-5-(trifluoromethoxy)phenyl)ethyl)carbamoyl)oxy)methyl 4-(((benzyloxy)(hydroxy)phosphoryl)oxy)-3-methoxybenzoate (0.110 g, 0.097 mmol, 37% yield) as an off-white solid. MS ESI m/z 1069.8 (M+H).

429: To a stirred solution of (((5-(2-(bis(tert-butoxycarbonyl)amino)-[1,2,4]triazolo[1,5-a]pyridin-7-yl)-2-methylnicotinoyl)((R)-1-(2-fluoro-5-(trifluoromethoxy)phenyl)ethyl)carbamoyl)oxy)methyl 4-(((benzyloxy)(hydroxy)phosphoryl)oxy)-3-methoxybenzoate (0.100 g, 0.094 mmol) in 1,2-dichloroethane (2.00 mL), was added TFA (0.360 mL, 4.68 mmol) and anisole (0.255 mL, 2.339 mmol) at 0° C.

The reaction mixture was stirred at 50° C. for 2 h. The reaction mixture was concentrated under vacuum at 30° C. to give the crude product as a light brown oil. The crude product was washed with diethyl ether and decanted. The solid was dried under high vacuum at 30° C. for 30 min. The solid was dissolved in a mixture of acetonitrile and water, frozen and lyophilized for 12 h to give (R)-(((5-(2-amino-[1,2,4]triazolo[1,5-a]pyridin-7-yl)-2-methylnicotinoyl)(1-(2-fluoro-5-(trifluoromethoxy)phenyl)ethyl)carbamoyl)oxy)methyl 3-methoxy-4-(phosphonooxy)benzoate, TFA (0.070 g, 0.077 mmol, 82% yield) as an off-white solid.

MS ESI m/z 779.2 (M+H).

1H NMR (500 MHz, DMSO-d6) δ 8.02 (d, J=2.0 Hz, 1H), 7.61-7.51 (m, 3H), 7.34-7.32 (m, 3H), 7.31-6.98 (m, 4H), 6.11 (d, J=6.8 Hz, 1H), 5.73 (q, J=6.2 Hz, 2H), 3.65 (s, 3H), 2.52-2.49 (m, 3H), 1.82 (d, J=6.8 Hz, 3H), 4 exchangeable protons not observed.

What is claimed is:
1. A compound of formula (III), or salt thereof,

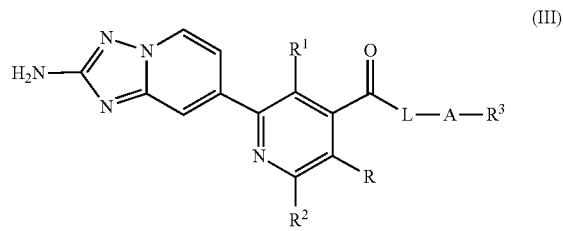

wherein
$R^1$ is H, $C_{1-4}$ alkyl, $C_{1-4}$ haloalkyl, $C_{1-4}$ deuteroalkyl, or halo;
$R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;
R is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or N ($R^a$)$_2$;
$R^a$ is H, $C_{1-4}$ alkyl, $C_{1-4}$ deuteroalkyl, or $C_{3-6}$ cycloalkyl;

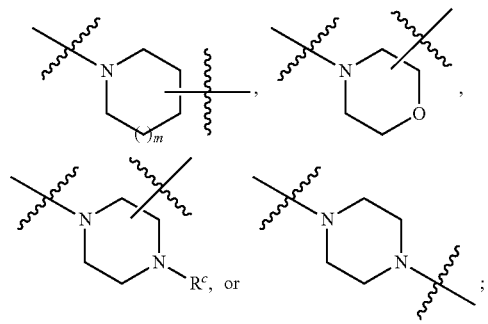

L is —NR$^b$,
R$^b$ is H;
R$^c$ is $C_{1-3}$ alkyl, or $C_{1-3}$ haloalkyl;
A is $C_{1-6}$ alkyl substituted with 0-1 OH;
$R^3$ is phenyl substituted with 0-3 $R^4$;
$R^4$ is halo, $C_{1-6}$ alkyl, $C_{1-6}$ ($C_{1-6}$ alkoxy) alkyl, $C_{1-6}$ ($C_{6-10}$ aryl) alkyl, $C_{1-6}$ alkoxy, $C_{1-6}$ ($C_{3-7}$ cycloalkyl) alkoxy, $C_{1-6}$ deuteroalkyl, $C_{1-6}$ deuteroalkoxy, $C_{1-6}$ ($C_{3-7}$ cycloalkyl) deuteroalkoxy, $C_{1-6}$ haloalkyl, $C_{1-6}$ haloalkoxy, $C_{3-7}$ cycloalkoxy, $C_{3-7}$ cycloalkyl, $C_{6-10}$ aryl, $C_{6-10}$ aryloxy, 5-or 6-membered heteroaryl, —S—$C_{1-6}$alkyl, —S—$C_{1-6}$ haloalkyl, —S—$C_{6-10}$ aryl, —$SO_2$—$C_{1-6}$ alkyl, —$SO_2$—$C_{6-10}$ aryl, —$SO_2$-heterocycle, —O—heterocycle, —(CO)-hetercycle, —$(CH_2)$n-hetercycle, or O—C(O)—$N(R^a)_2$, wherein each heterocycle is independently a 3-10 membered ring having 1-4 heteroatoms selected from the group consisting of N, O, and S, and wherein each heterocycle, aryl, or heteroaryl is substituted with 0-2 $R^5$;

$R^5$, at each occurrence, is independently $C_{1-4}$ alkyl, halo, =O, or $C_{1-4}$ hydroxyalkyl;

n is 1-3; and m is 0 or 1.

2. The compound of claim 1, or salt thereof, wherein
$R^1$ is H, $C_{1-4}$ alkyl, $C_{1-4}$ haloalkyl, $C_{1-4}$ deuteroalkyl, or halo;
$R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;
R is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or N $(R^a)_2$:
$R^a$ is H, $C_{1-4}$ alkyl, $C_{1-4}$ deuteroalkyl, or $C_{3-6}$ cycloalkyl;
L is-NH,

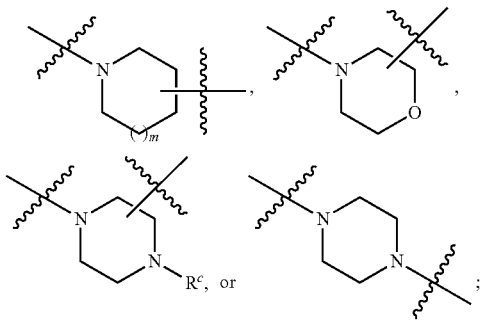

$R^c$ is $C_{1-3}$ alkyl, or $C_{1-3}$ haloalkyl;
A is $C_{1-6}$ alkyl substituted with 0-1 OH;
$R^3$ is phenyl substituted with 0-3 $R^4$;
$R^4$ is halo, $C_{1-6}$ alkyl, $C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-7}$ cycloalkoxy, $C_{3-7}$ cycloalkyl, $C_{6-10}$ aryl, $C_{6-10}$ aryloxy, —S—$C_{1-6}$alkyl, —S—$C_{1-6}$ haloalkyl, —S—$C_{6-10}$ aryl, —$SO_2$—$C_{1-6}$ alkyl, —$SO_2$—$C_{6-10}$ aryl, —$SO_2$-heterocycle, —O—heterocycle, or —$(CH_2)$ n-hetercycle, O—C(O)—$N(R^a)_2$, wherein each heterocycle is independently a 3-10 membered ring having 1-4 heteroatoms selected from the group consisting of N, O, and S, and wherein each heterocycle or aryl is substituted with 0-2 $R^5$;

$R^5$, at each occurrence, is independently $C_{1-4}$ alkyl, halo, =O, or $C_{1-4}$ hydroxyalkyl; and m is 0 or 1.

3. The compound of claim 2, or salt thereof, wherein A is $C_{1-4}$ alkyl substituted with 0-1 OH.

4. The A compound of claim 3, or salt thereof, wherein $R^1$ is H, or $C_{1-4}$ alkyl;
$R^2$ is H, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $NH_2$;
R is H, Cl, F, Br, $C_{1-4}$ alkyl, $C_{1-4}$ alkoxy, cyclopropyl, or $NR^a_2$,
$R^a$ is H, $C_{1-4}$ alkyl, or $C_{1-4}$ deuteroalkyl.

5. The A compound of claim 4, or salt thereof, wherein $R^4$ is halo, $C_{1-6}$ alkyl, $C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{3-7}$ cycloalkoxy, or $C_{3-7}$ cycloalkyl.

6. A compound or salt thereof, wherein the compound is selected from the group consisting of
2-(2-amino-[1,2,4] triazolo [1,5-a] pyridin-7-yl)-N-(2-fluoro-5-(trifluoromethoxy) benzyl)-5-methoxyisonicotinamide;
(R)-2-(2-amino-[1,2,4] triazolo [1,5-a] pyridin-7-yl)-N-(1-(2-fluoro-5-(trifluoromethoxy) phenyl) ethyl)-5-methoxyisonicotinamide;
2-(2-amino-[1,2,4] triazolo [1,5-a] pyridin-7-yl)-5-methoxy-N-(3-phenylbutyl) isonicotinamide;
2-(2-amino-[1,2,4] triazolo [1,5-a] pyridin-7-yl)-N-(2-fluoro-5-(trifluoromethyl) benzyl)-5-methoxyisonicotinamide;
(R)-2-(2-amino-[1,2,4] triazolo [1,5-a] pyridin-7-yl)-N-(1-(2-fluoro-5-(trifluoromethoxy) phenyl) ethyl)-5-methylisonicotinamide;
2-(2-amino-[1,2,4] triazolo [1,5-a] pyridin-7-yl)-5-methyl-N-(3-phenylbutyl) isonicotinamide;
2-(2-amino-[1,2,4] triazolo [1,5-a] pyridin-7-yl)-N-(2-fluoro-5-(trifluoromethoxy) benzyl)-5-methylisonicotinamide;
(R)-2-(2-amino-[1,2,4] triazolo [1,5-a] pyridin-7-yl)-N-(3-(4-chlorophenyl)-3-hydroxypropyl)-5-methylisonicotinamide;
(R)-2-(2-amino-[1,2,4] triazolo [1,5-a] pyridin-7-yl)-N-(1-(2-fluoro-5-(trifluoromethyl) phenyl) ethyl)-5-methylisonicotinamide;
(S)-2-(2-amino-[1,2,4] triazolo [1,5-a] pyridin-7-yl)-N-(3-(4-chlorophenyl)-3-hydroxypropyl)-5-methylisonicotinamide;
2-(2-amino-[1,2,4] triazolo [1,5-a] pyridin-7-yl)-N-(2-fluoro-5-(trifluoromethyl) benzyl)-5-methylisonicotinamide; and
2-{2-Amino-[1,2,4] triazolo [1,5-a] pyridin-7-yl}-N-(3-phenylbutyl) pyridine-4-carboxamide.

* * * * *